US009169471B2

(12) United States Patent
Holliger et al.

(10) Patent No.: US 9,169,471 B2

(45) Date of Patent: Oct. 27, 2015

(54) ENZYMES

(75) Inventors: Philipp Holliger, Cambridge (GB); Christopher Cozens, Cambridge (GB); Vitor B. Pinheiro, Cambridge (GB); Alexander I. Taylor, Cambridge (GB)

(73) Assignee: Medical Research Council, Swindon (GB)

( * ) Notice: Subject to any disclaimer, the term of this patent is extended or adjusted under 35 U.S.C. 154(b) by 0 days.

(21) Appl. No.: 13/695,377

(22) PCT Filed: Apr. 14, 2011

(86) PCT No.: PCT/GB2011/000583

§ 371 (c)(1), (2), (4) Date: Oct. 30, 2012

(87) PCT Pub. No.: WO2011/135280

PCT Pub. Date: Nov. 3, 2011

(65) Prior Publication Data

US 2013/0130320 A1 May 23, 2013

Related U.S. Application Data

(60) Provisional application No. 61/396,008, filed on May 20, 2010.

(30) Foreign Application Priority Data

Apr. 30, 2010 (GB) .................................. 1007384.9

(51) Int. Cl.

| | |
|---|---|
| *C12N 15/00* | (2006.01) |
| *C12N 9/14* | (2006.01) |
| *C12N 9/12* | (2006.01) |
| *C12P 19/34* | (2006.01) |

(52) U.S. Cl.

CPC ............ *C12N 9/1241* (2013.01); *C12N 9/1247* (2013.01); *C12P 19/34* (2013.01)

(58) Field of Classification Search

CPC .......................... C12N 9/1247; C12N 15/1027

USPC .......................................... 435/183; 530/350

See application file for complete search history.

(56) References Cited

FOREIGN PATENT DOCUMENTS

| | | | |
|---|---|---|---|
| EP | 1350841 | A2 | 10/2003 |
| WO | 0220735 | A2 | 3/2002 |
| WO | 2009131919 | A2 | 10/2009 |
| WO | 2011135280 | A2 | 11/2011 |

OTHER PUBLICATIONS

International Search Report and Written Opinion issued regarding PCT/GB2011/000583, with an international filing date of Apr. 14, 2011, and mailed from the International Searching Authority on Jul. 11, 2011.

Brown, et al., "Unlocking the Sugar "Steric Gate" of DNA Polymerases", Biochemistry, Feb. 2011, pp. 1135-1142, vol. 50, No. 7, American Chemical Society, United States of America.

Loakes, et al., "Evolving a Polymerase for Hydrophobic Base Analogues", Journal of the American Chemical Society, Oct. 2009, pp. 14827-14837, vol. 131, No. 41, American Chemical Society, United States of America.

Loakes, et al., "Polymerase engineering: towards the encoded synthesis of unnatural biopolymers", Chemical Communications, Jan. 2009, pp. 4619-4631, No. 31, Royal Society of Chemistry, United Kingdom.

Ong, et al., "Directed Evolution of DNA Polymerase, RNA Polymerase and Reverse Transcriptase Activity in a Single Polypeptide", Journal of Molecular Biology, pp. 537-550, vol. 361, No. 3, Elsevier, The Netherlands.

Patel, et al., "Multiple Amino Acid Substitutions Allow DNA Polymerases to Synthesize RNA", Journal of Biological Chemistry, Dec. 2000, pp. 40266-40272, vol. 275, No. 51, The American Society for Biochemistry and Molecular Biology, Inc., United States of America.

Ramsey, et al., "CyDNA: Synthesis and Replication of Highly Cy-Dye Substituted DNA by an Evolved Polymerase", Journal of the American Chemical Society, Apr. 2010, pp. 5096-5104, vol. 132, No. 14, American Chemical Society, United States of America.

*Primary Examiner* — Maryam Monshipouri

(74) *Attorney, Agent, or Firm* — Wiley Rein LLP

(57) ABSTRACT

The invention relates to a nucleic acid polymerase capable of producing a non-DNA nucleotide polymer from a DNA nucleotide polymer template, said polymerase comprising amino acid sequence having at least 36% identity to the amino acid sequence of SEQ ID NO:1, wherein said amino acid sequence is mutated relative to the amino acid sequence of SEQ ID NO:1 at one or more residues of the thumb region, said residues selected from: amino acids 651 to 679 (patch 10A); wherein said amino acid sequence is mutated relative to the amino acid sequence of SEQ ID NO:1 at residue E664. In one embodiment said polymerase comprises the mutations Y409G and E664K. In one embodiment said polymerase comprises amino acid sequence corresponding to SEQ ID NO:12. The invention also relates to A nucleic acid polymerase capable of reverse transcribing a HNA nucleotide polymer into a DNA nucleotide polymer, said polymerase comprising amino acid sequence having at least 36% identity to the amino acid sequence of SEQ ID NO:1, wherein said amino acid sequence is mutated relative to the amino acid sequence of SEQ ID NO:1 at residue I521.

6 Claims, 33 Drawing Sheets

Figure 3
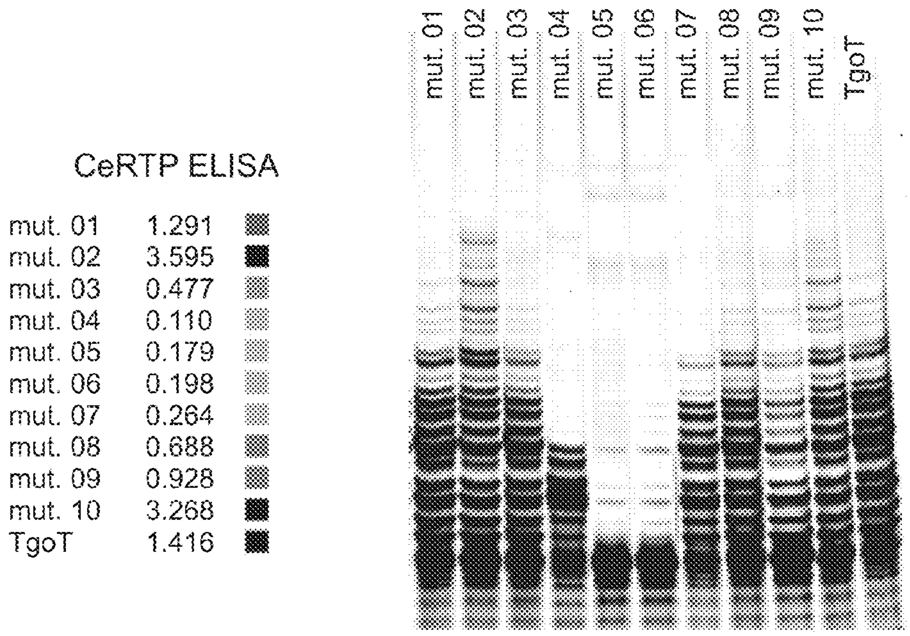
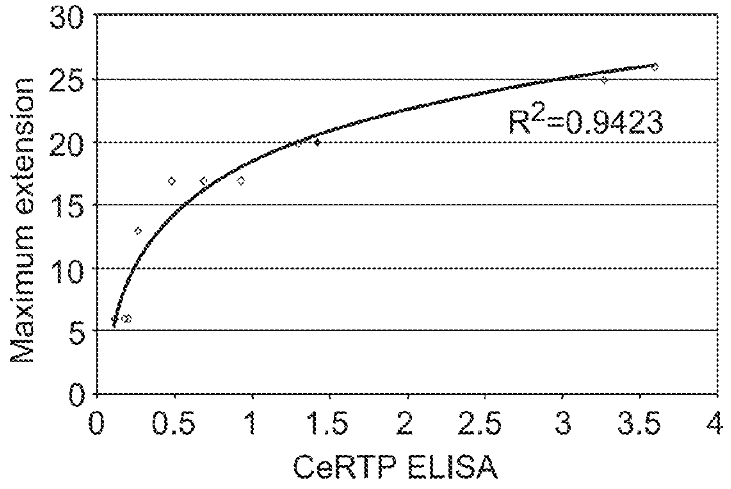
CeRTP ELISA
| mut. 01 | 1.291 |
| mut. 02 | 3.595 |
| mut. 03 | 0.477 |
| mut. 04 | 0.110 |
| mut. 05 | 0.179 |
| mut. 06 | 0.198 |
| mut. 07 | 0.264 |
| mut. 08 | 0.688 |
| mut. 09 | 0.928 |
| mut. 10 | 3.268 |
| TgoT | 1.416 |

Figure 5

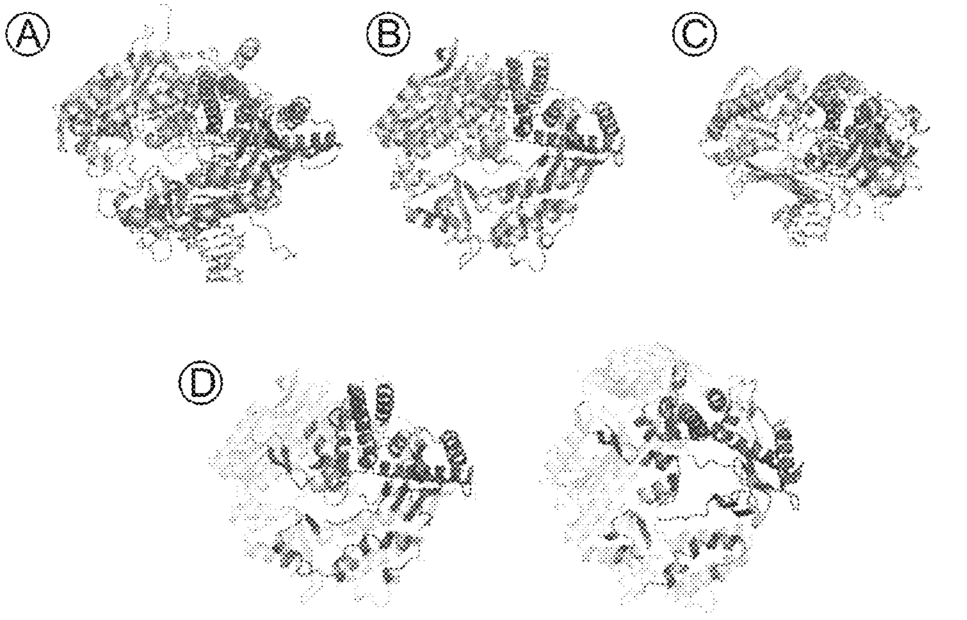

MILDTDYITEDGKPVIRIFKKENGEFKIDYKRNFEPYIYALLKDDSAIEDVKK
ITAERHGTTVRVVRAEKVKKKFLGRPIEVWKLYFTHPQDQPAIRDKIKEHPAV
VDIYEYDIPFAKRYLIDKGLIPMEGDEELKMLAFAIATLYHEGEEFAEGPILM
ISYADEEGARVITWKNIDLPYVDVVSTEKEMIKRFLKVVKEKDPDVLITYNGD
NFDFAYLKKRSEKLGVKFILGREGSEPKIQRMGDRFAVEVKGRIHFDLYPVIR
RTINLPTYTLEAVYEAIFGQPKEKVYAEEIAQAWETGEGLERVARYSMEDAKV
TYELGKEFFPMEAQLSRLVGQSLWDVSRSSTGNLVEWFLLRKAYERNELAPNK
PDERELARRRESYAGGYVKEPERGLWENIVYLDFRSLYPSIIITHNVSPDTLN
REGCEEYDVAPQVGHKFCKDFPGFIPSLLGDLLEERQKVKKKMKATIDPIEKK
LLDYRQRLIKILANSFYGYYGYAKARWYCKECAESVTAWGRQYIETTIREIEE
KFGFKVLYADTDGFFATIPGADAETVKKKAKEFLDYINAKLPGLLELEYEGFY
KRGFFVTKKKYAVIDEEDKITTRGLEIVRRDWSEIAKETQARVLEAILKHGDV
EEAVRIVKEVTEKLSKYEVPPEKLVIYEQITRDLKDYKATGPHVAVAKRLAAR
GIKIRPGTVISYIVLKGSGRIGDRAIPFDEFDPAKHKYDAEYYIENQVLPAVE
RILRAFGYRKEDLRYQKTRQVGLGAWLKPKT

Figure 8
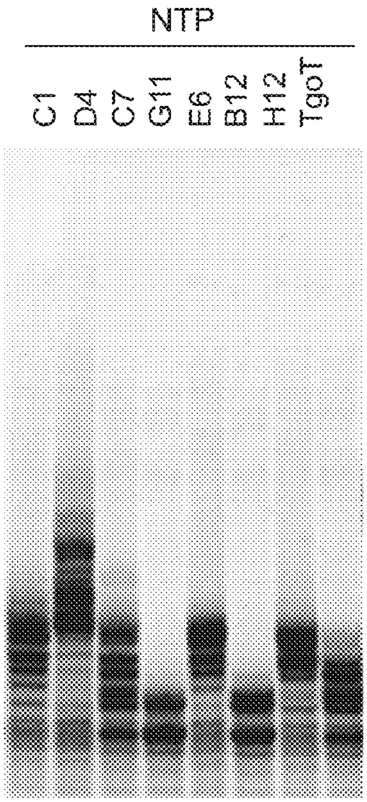
Figure 9
A
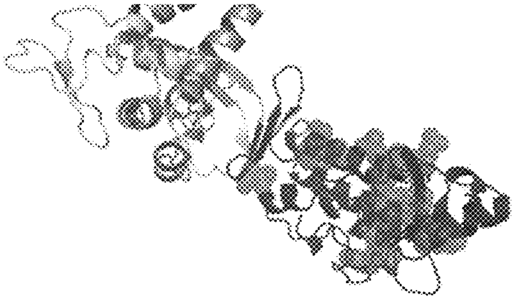
B
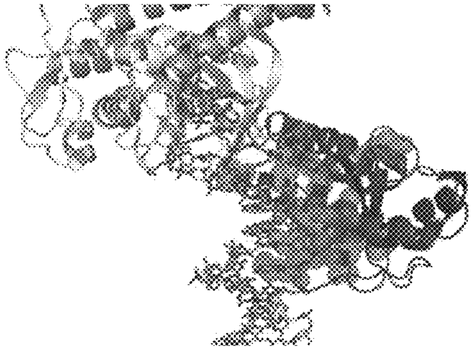

Figure 12
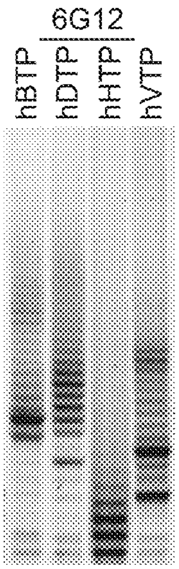
Figure 13
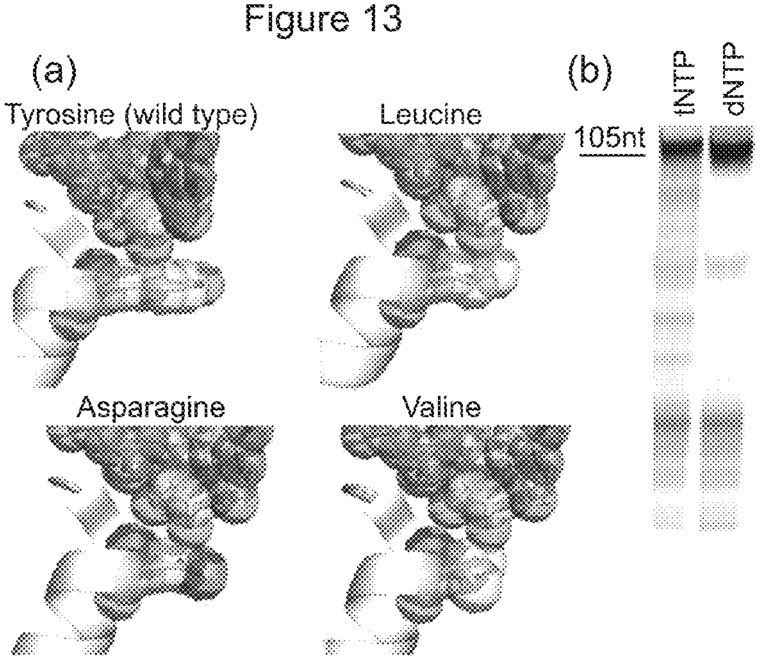
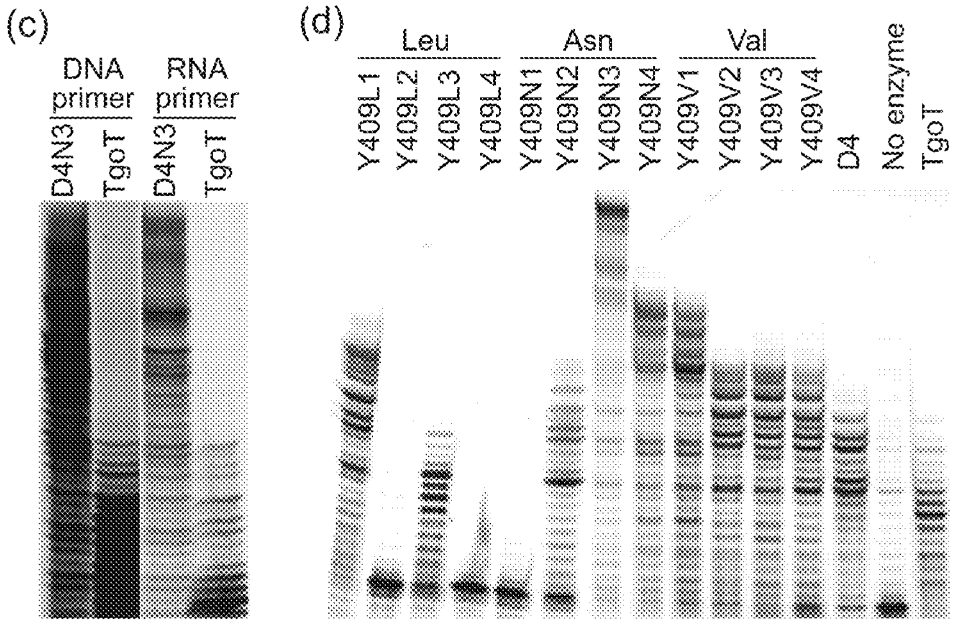

TN 664x RNA N10 plate 1

| | 1 | 2 | 3 | 4 | 5 | 6 | 7 | 8 | 9 | 10 | 11 | 12 |
|---|---|---|---|---|---|---|---|---|---|---|---|---|
| A | 0.054 | 0.065 | 0.075 | 0.082 | 0.074 | 0.079 | 0.068 | 0.058 | 0.092 | 0.102 | 0.100 | 0.365 |
| B | 0.709 | 0.079 | 0.080 | 0.078 | 0.047 | 0.067 | 0.058 | 0.082 | 0.070 | 0.078 | 0.089 | 1.461 |
| C | 0.071 | 0.061 | 0.061 | 0.065 | 0.070 | 0.104 | 0.331 | 0.068 | 1.456 | 0.070 | 0.084 | 2.587 |
| D | 0.062 | 0.123 | 0.056 | 0.829 | 0.053 | 0.075 | 0.061 | 0.058 | 0.063 | 2.260 | 0.076 | 0.099 |
| E | 0.048 | 0.057 | 0.048 | 0.041 | 0.997 | 0.111 | 0.050 | 0.101 | 0.061 | 0.080 | 0.060 | 0.070 |
| F | 0.160 | 0.074 | 0.085 | 0.051 | 0.049 | 0.066 | 0.054 | 0.076 | 0.048 | 0.071 | 0.059 | 0.076 |
| G | 0.053 | 0.040 | 1.411 | 0.068 | 0.071 | 0.079 | 0.049 | 0.058 | 0.048 | 0.057 | 0.066 | 0.201 |
| H | 0.058 | 0.045 | 0.077 | 0.138 | 0.050 | 0.060 | 0.057 | 0.096 | 0.056 | 0.077 | 0.418 | 0.072 |

Endpoint

Lm1 450
Lm2 650

Automix: Off
Calibrate: On

Plate Last Read:
15:59 05/02/2010

Wavelength Combination:!Lm1-!Lm2
Mean Temperature: 27.5
Data Mode: Absorbance
Reader: 340PC384 ROM v1.16 Feb04 2003

< 0.1 < 0.2 < 0.4 < 0.5
< 0.7 < 0.8 <= 1.0 > 1.0

TN664Q(TNQ)

TN664K(TNK)

Figure 29
a.
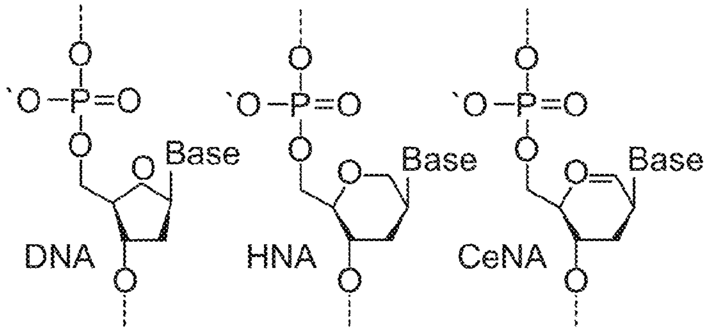
DNA HNA CeNA
b.
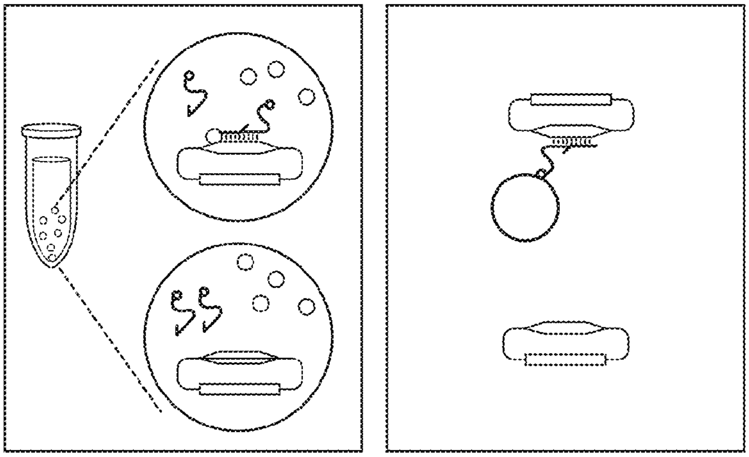
c.
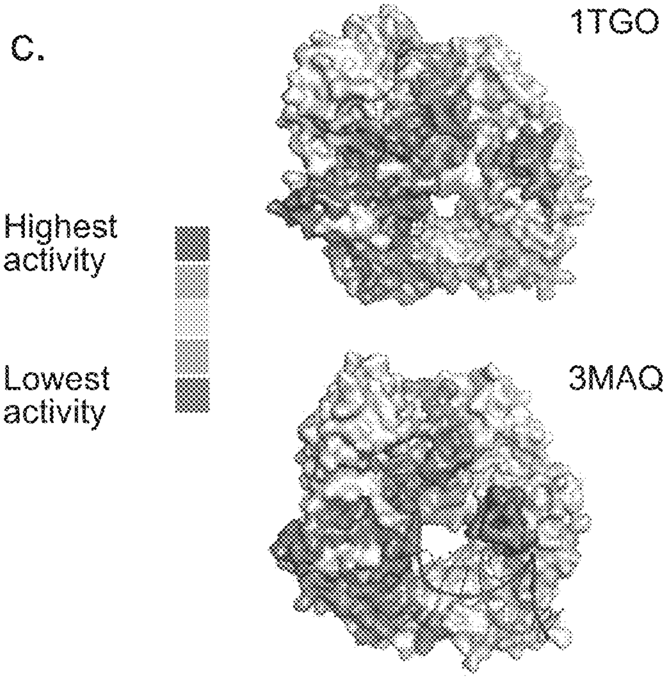

Figure 33
a.
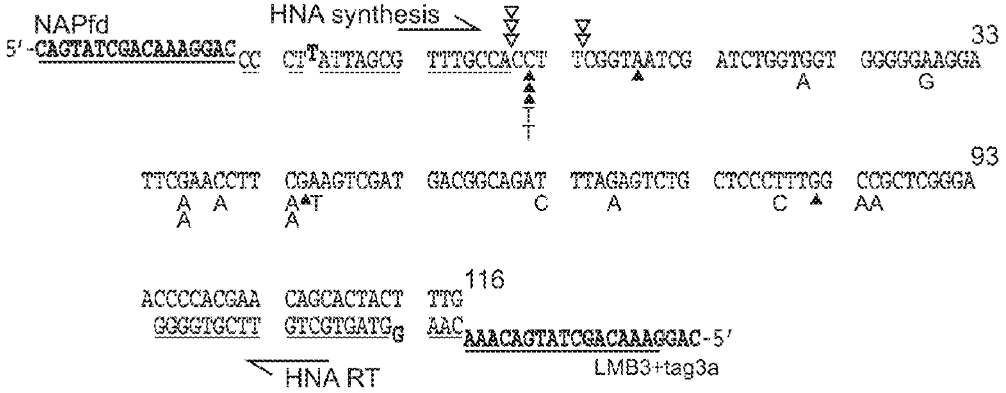
b.
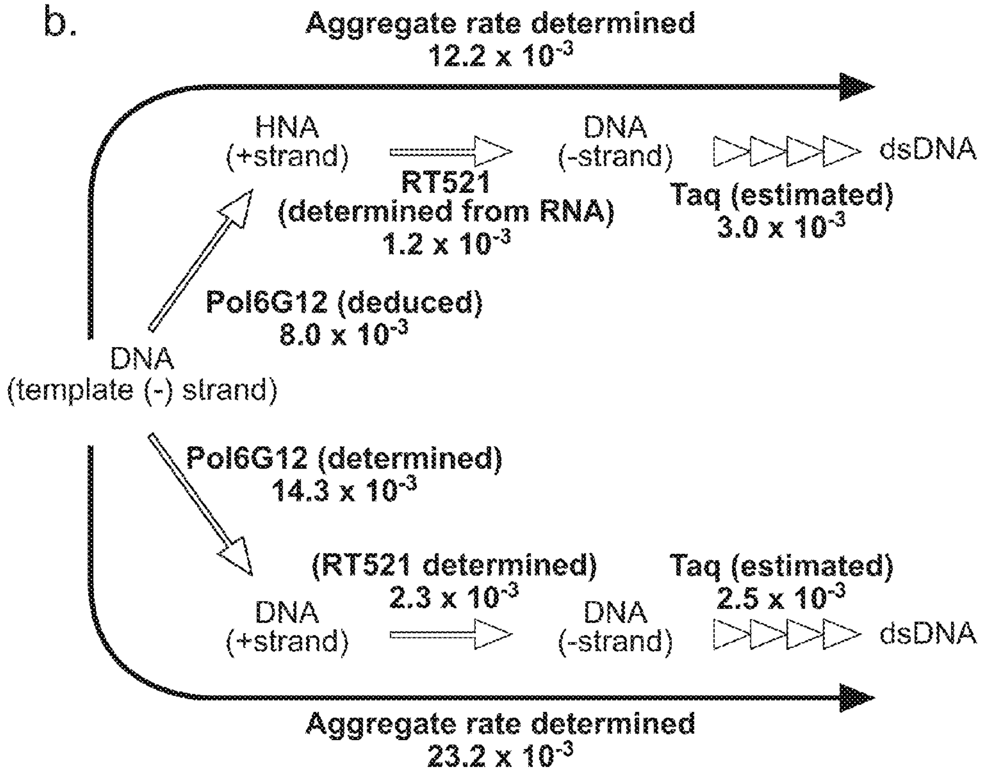

PCR can only succeed if both outnesting tags are present in the system. Sequencing of the amplified products can check that both the synthesis and the RT mismatches are present and could only be generated by extension of the synthesis primer followed by extension against it by the RT primer.

Figure 36
a.
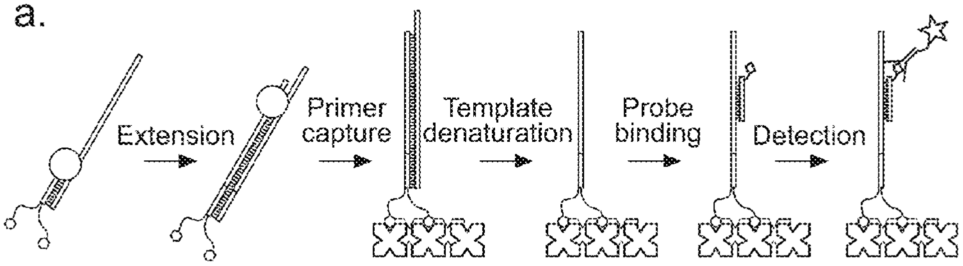
b.
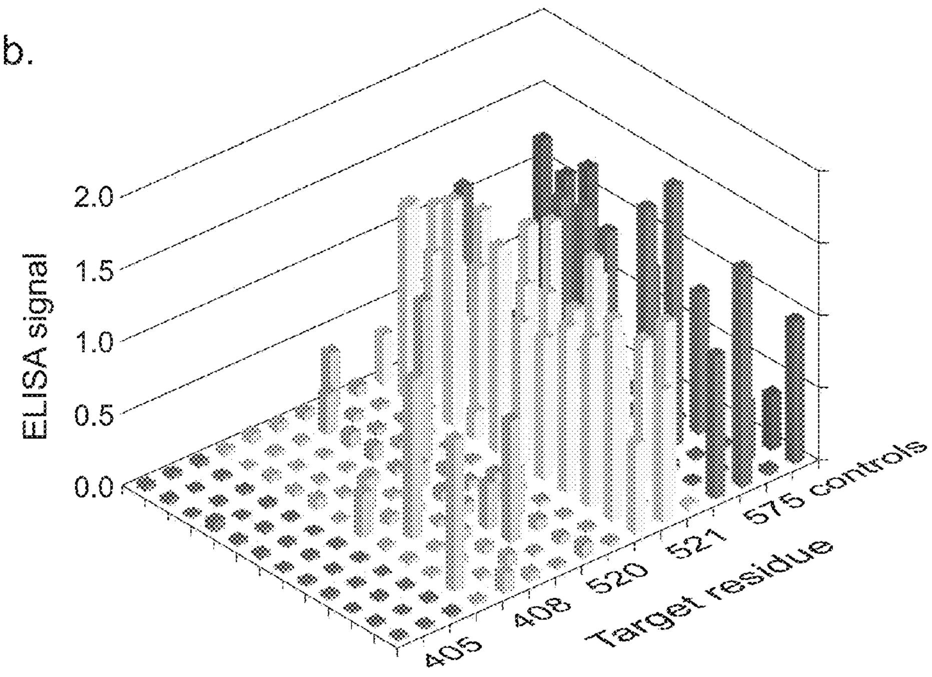

Figure 37

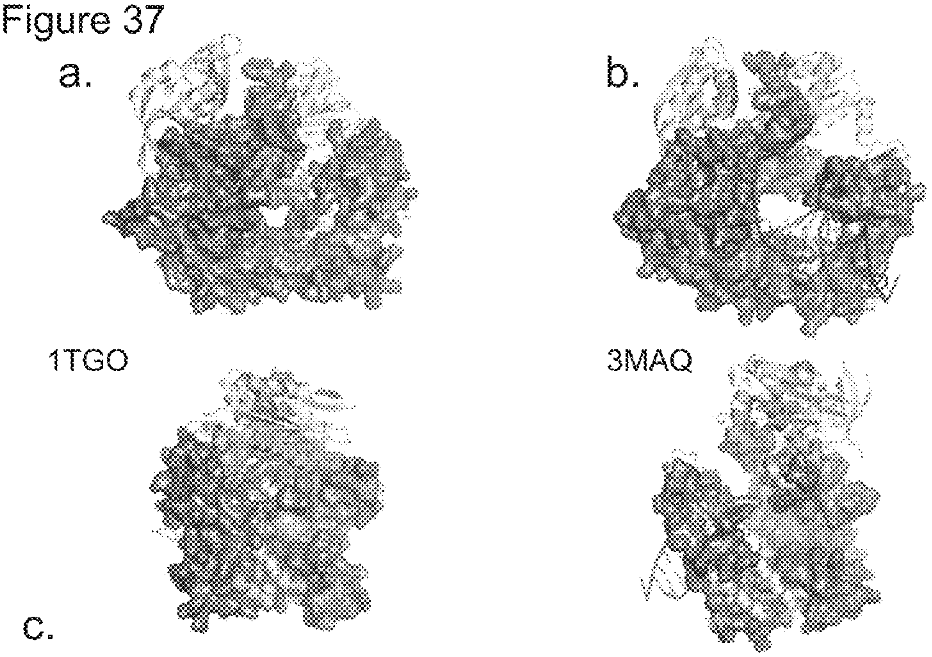

MILDTDYITE DGKPVIRIFK KENGEFKIDY DRNFEPYIYA LLKDDSAIED VKKITAERHG 60

TTVRVVRAEK VKKKFLGRPI EVWKLYFTHP QDCPAIRDKI KEHPAVVDIY EYDIPFAKRY 120

LIDKGLIPME GDEELKMLAF AIATLYHEGE EFAEGPILMI SYADEEGARV ITWKNIDLPY 180

VDVVSTEKEM IKRFLKVVKE KDPDVLITYN GDNFDFAYLK KRSEKLGVKF ILGREGSEPK 240
Motif 1

IQRMGDRFAV EVKGRIHFDL YPVIRRTINL PTYTLEAVYE AIFGQPKEKV YAEEIAQAWE 300
Motif 2

TGEGLERVAR YSMEDAKVTY ELGKEFFPME AQLSRLVGQS LWDVSRSSTG NLVEWFLLRK 360
Motif 3 Motif 4

AYERNELAPN KPDERELARR RESYAGGYVK EPERGLWENI VYLDFRSLYP SIIITHNVSP 420
Motif A- Motif A Motif A+

DTLNREGCEE YDVAPQVGHK FCKDFPGFIP SLLGDLLEER QKVKKKMKAT IDPIEKKLLD 480
Motif 5 Motif B-

YRQRLIKILA NSFYGYYGYA KARWYCKECA ESVTAWGRQY IETTIREIEE KFGFKVLYAD 540
Motif B Motif 6- Motif 6+ Motif C TDGFFATIPG ADAETVKKKA KEFLDYINAK LPGLLELEYE GFYKRGFFVT KKKYAVIDEE 600
Motif C+ Motif 7 Motif 8 Motif 9

DKITTRGLEI VRRDWSEIAK ETQARVLEAT LKHGDVEEAV RIVKEVTEKL SKYEVPPEKL 660
Motif 10A

VIYEQITRDL KDYKATGPHV AVAKRLAARG IKIRPGTVIS YIVLKGSGRI GDRAIPFDEF 720
Motif 10B Motif 11

DPAKHKYDAE YYIENQVLPA VERILRAFGY RKEDLRYQKT RQVGLGAWLK PKT 773
Motif 12

Figure 43
a.
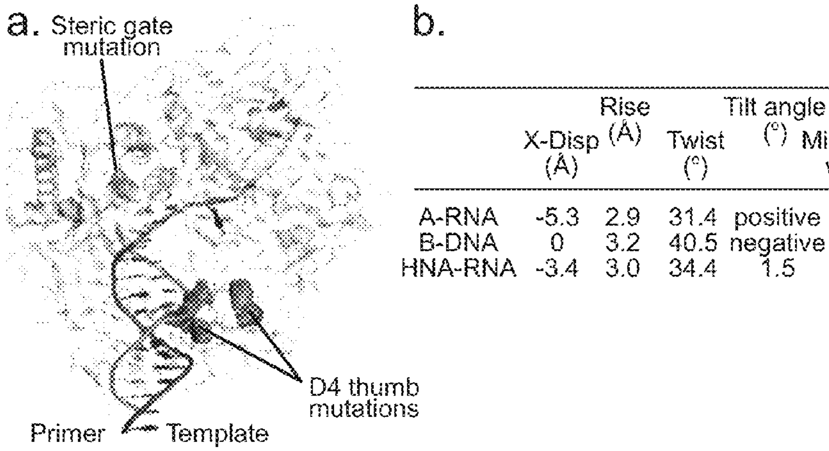
b.
| | X-Disp (Å) | Rise (Å) | Twist (°) | Tilt angle (°) | Minor groove width (Å) |
|---|---|---|---|---|---|
| A-RNA | -5.3 | 2.9 | 31.4 | positive | 11.0 |
| B-DNA | 0 | 3.2 | 40.5 | negative | 5.7 |
| HNA-RNA | -3.4 | 3.0 | 34.4 | 1.5 | 10.0 |
c.
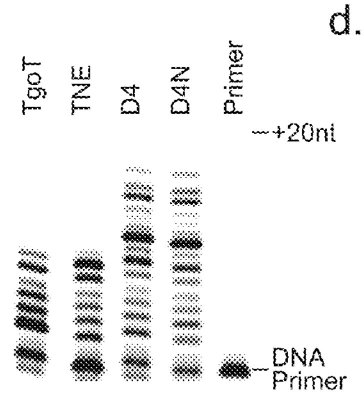
d.
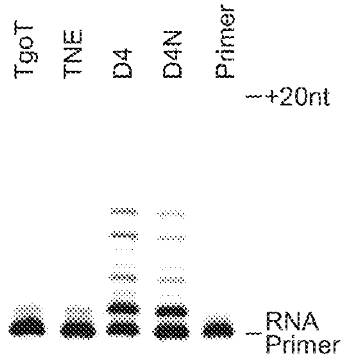
Figure 44
a.
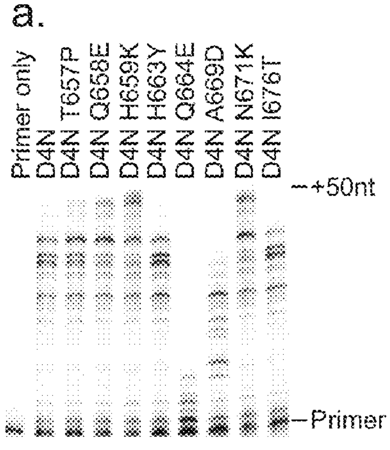
b.
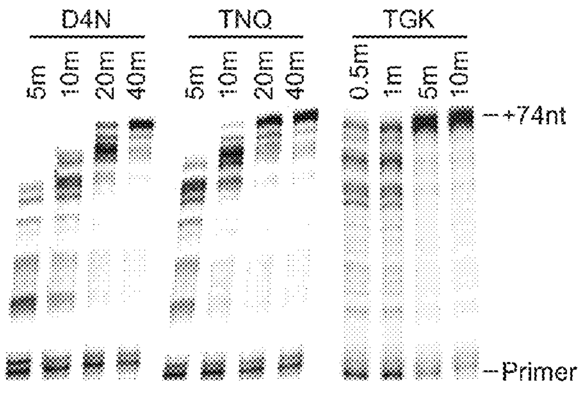

Figure 52

Table S1. Steric gate residues described in the literature in DNA polymerase families A, B, C, X, Y and the RT family.

| Family | Polymerase | Residue | Mutant | Reference |
|---|---|---|---|---|
| A | *E.coli* Pol I | E | A, Q, D | (5) |
| | *T. aquataicus* Pol I | E | A | (12) |
| B | RB69 gp43 | Y | A, V | (4) |
| | φ29 | Y | V | (9) |
| | Vent | Y | V | (10) |
| C | *G. kaustophilus* polC | H | (predicted) | (45) |
| X | *H. sapiens* pol λ | Y | G | (46) |
| Y | *E. colil* UmuC | FY | A | (47) |
| | E. coli DinB | FF | A, V | (48) |
| | *S. solfataricus* Dbh | F | V | (49) |
| RT | HIV-1 RT | Y | A, V | (11, 50) |
| | M-MULV RT | F | A | (7) |
| | MMTV | F | A, V | (51) |

SEQUENCE LISTING

<160> NUMBER OF SEQ ID NOS: 70

<210> SEQ ID NO 1
<211> LENGTH: 773
<212> TYPE: PRT
<213> ORGANISM: Thermococcus gorgonarius

<400> SEQUENCE: 1

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
```

```
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735
```

```
Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 2
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 2

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320
```

-continued

```
Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735
```

```
Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 3
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 3

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320
```

```
Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Gln Val Pro
                645                 650                 655

Pro Lys Lys Leu Val Ile Asn Gln Gln Ile Thr Arg Glu Leu Arg Asp
            660                 665                 670

Tyr Lys Ala Lys Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
```

740 745 750

Glu Asp Leu Arg Tyr Gln Lys Thr Arg Gln Val Gly Leu Gly Ala Trp
755 760 765

Leu Lys Pro Lys Thr
770

<210> SEQ ID NO 4
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 4

Met Ile Leu Asp Thr Asp Tyr Ile Thr Glu Asp Gly Lys Pro Val Ile
1 5 10 15

Arg Ile Phe Lys Lys Glu Asn Gly Glu Phe Lys Ile Asp Tyr Asp Arg
20 25 30

Asn Phe Glu Pro Tyr Ile Tyr Ala Leu Leu Lys Asp Asp Ser Ala Ile
35 40 45

Glu Asp Val Lys Lys Ile Thr Ala Glu Arg His Gly Thr Thr Val Arg
50 55 60

Val Val Arg Ala Glu Lys Val Lys Lys Lys Phe Leu Gly Arg Pro Ile
65 70 75 80

Glu Val Trp Lys Leu Tyr Phe Thr His Pro Gln Asp Gln Pro Ala Ile
85 90 95

Arg Asp Lys Ile Lys Glu His Pro Ala Val Val Asp Ile Tyr Glu Tyr
100 105 110

Asp Ile Pro Phe Ala Lys Arg Tyr Leu Ile Asp Lys Gly Leu Ile Pro
115 120 125

Met Glu Gly Asp Glu Glu Leu Lys Met Leu Ala Phe Ala Ile Ala Thr
130 135 140

Leu Tyr His Glu Gly Glu Glu Phe Ala Glu Gly Pro Ile Leu Met Ile
145 150 155 160

Ser Tyr Ala Asp Glu Glu Gly Ala Arg Val Ile Thr Trp Lys Asn Ile
165 170 175

Asp Leu Pro Tyr Val Asp Val Val Ser Thr Glu Lys Glu Met Ile Lys
180 185 190

Arg Phe Leu Lys Val Val Lys Glu Lys Asp Pro Asp Val Leu Ile Thr
195 200 205

Tyr Asn Gly Asp Asn Phe Asp Phe Ala Tyr Leu Lys Lys Arg Ser Glu
210 215 220

Lys Leu Gly Val Lys Phe Ile Leu Gly Arg Glu Gly Ser Glu Pro Lys
225 230 235 240

Ile Gln Arg Met Gly Asp Arg Phe Ala Val Glu Val Lys Gly Arg Ile
245 250 255

His Phe Asp Leu Tyr Pro Val Ile Arg Arg Thr Ile Asn Leu Pro Thr
260 265 270

Tyr Thr Leu Glu Ala Val Tyr Glu Ala Ile Phe Gly Gln Pro Lys Glu
275 280 285

Lys Val Tyr Ala Glu Glu Ile Ala Gln Ala Trp Glu Thr Gly Glu Gly
290 295 300

Leu Glu Arg Val Ala Arg Tyr Ser Met Glu Asp Ala Lys Val Thr Tyr
305 310 315 320

Glu Leu Gly Lys Glu Phe Phe Pro Met Glu Ala Gln Leu Ser Arg Leu

-continued

```
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Gln Val Pro
                645                 650                 655

Pro Lys Glu Leu Val Ile Tyr Ala Glu Ile Thr Arg Pro Leu Gln Asp
            660                 665                 670

Tyr Lys Ala Arg Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Val Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750
```

```
Glu Asp Leu Arg Tyr Gln Lys Thr Arg Gln Val Gly Leu Gly Ala Trp
        755                 760                 765

Leu Lys Pro Lys Thr
    770


<210> SEQ ID NO 5
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 5

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335
```

```
Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Gln Val Pro
                645                 650                 655

Pro Gln Gln Leu Ala Ile Tyr Gln Pro Ile Thr Arg Ala Leu Gln Asp
            660                 665                 670

Tyr Lys Ala Lys Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Lys Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750
```

```
Glu Asp Leu Arg Tyr Gln Lys Thr Arg Gln Val Gly Leu Gly Ala Trp
        755                 760                 765

Leu Lys Pro Lys Thr
    770


<210> SEQ ID NO 6
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 6

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335
```

```
Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Thr Gln His Leu Val Ile His Gln Gln Ile Thr Arg Ala Leu Asn Asp
            660                 665                 670

Tyr Lys Ala Ile Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
```

```
        755                 760                 765

Leu Lys Pro Lys Thr
    770


<210> SEQ ID NO 7
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 7

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
```

```
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Gln Val Pro
                645                 650                 655

Pro Gln Gln Leu Val Ile Tyr Gln Lys Ile Thr Lys Gln Leu His Glu
            660                 665                 670

Tyr Lys Ala Arg Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Arg His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765
```

Leu Lys Pro Lys Thr
770

<210> SEQ ID NO 8
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 8

Met Ile Leu Asp Thr Asp Tyr Ile Thr Glu Asp Gly Lys Pro Val Ile
1 5 10 15

Arg Ile Phe Lys Lys Glu Asn Gly Glu Phe Lys Ile Asp Tyr Asp Arg
20 25 30

Asn Phe Glu Pro Tyr Ile Tyr Ala Leu Leu Lys Asp Asp Ser Ala Ile
35 40 45

Glu Asp Val Lys Lys Ile Thr Ala Glu Arg His Gly Thr Thr Val Arg
50 55 60

Val Val Arg Ala Glu Lys Val Lys Lys Lys Phe Leu Gly Arg Pro Ile
65 70 75 80

Glu Val Trp Lys Leu Tyr Phe Thr His Pro Gln Asp Gln Pro Ala Ile
85 90 95

Arg Asp Lys Ile Lys Glu His Pro Ala Val Val Asp Ile Tyr Glu Tyr
100 105 110

Asp Ile Pro Phe Ala Lys Arg Tyr Leu Ile Asp Lys Gly Leu Ile Pro
115 120 125

Met Glu Gly Asp Glu Glu Leu Lys Met Leu Ala Phe Ala Ile Ala Thr
130 135 140

Leu Tyr His Glu Gly Glu Glu Phe Ala Glu Gly Pro Ile Leu Met Ile
145 150 155 160

Ser Tyr Ala Asp Glu Glu Gly Ala Arg Val Ile Thr Trp Lys Asn Ile
165 170 175

Asp Leu Pro Tyr Val Asp Val Val Ser Thr Glu Lys Glu Met Ile Lys
180 185 190

Arg Phe Leu Lys Val Val Lys Glu Lys Asp Pro Asp Val Leu Ile Thr
195 200 205

Tyr Asn Gly Asp Asn Phe Asp Phe Ala Tyr Leu Lys Lys Arg Ser Glu
210 215 220

Lys Leu Gly Val Lys Phe Ile Leu Gly Arg Glu Gly Ser Glu Pro Lys
225 230 235 240

Ile Gln Arg Met Gly Asp Arg Phe Ala Val Glu Val Lys Gly Arg Ile
245 250 255

His Phe Asp Leu Tyr Pro Val Ile Arg Arg Thr Ile Asn Leu Pro Thr
260 265 270

Tyr Thr Leu Glu Ala Val Tyr Glu Ala Ile Phe Gly Gln Pro Lys Glu
275 280 285

Lys Val Tyr Ala Glu Glu Ile Ala Gln Ala Trp Glu Thr Gly Glu Gly
290 295 300

Leu Glu Arg Val Ala Arg Tyr Ser Met Glu Asp Ala Lys Val Thr Tyr
305 310 315 320

Glu Leu Gly Lys Glu Phe Phe Pro Met Glu Ala Gln Leu Ser Arg Leu
325 330 335

Val Gly Gln Ser Leu Trp Asp Val Ser Arg Ser Ser Thr Gly Asn Leu
340 345 350

```
Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Gln Val Pro
                645                 650                 655

Ser Glu Gln Leu Val Ile Tyr His Gln Ile Thr Arg Pro Leu Lys Glu
            660                 665                 670

Tyr Arg Ala Met Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765
```

Leu Lys Pro Lys Thr
770

<210> SEQ ID NO 9
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 9

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350
```

-continued

```
Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Ser
                645                 650                 655

Gln Gln Gln Leu Val Ile Tyr Gln Gln Ile Thr Lys Glu Leu Ser Glu
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
```

770

<210> SEQ ID NO 10
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 10

Met Ile Leu Asp Thr Asp Tyr Ile Thr Glu Asp Gly Lys Pro Val Ile
1 5 10 15

Arg Ile Phe Lys Lys Glu Asn Gly Glu Phe Lys Ile Asp Tyr Asp Arg
20 25 30

Asn Phe Glu Pro Tyr Ile Tyr Ala Leu Leu Lys Asp Asp Ser Ala Ile
35 40 45

Glu Asp Val Lys Lys Ile Thr Ala Glu Arg His Gly Thr Thr Val Arg
50 55 60

Val Val Arg Ala Glu Lys Val Lys Lys Lys Phe Leu Gly Arg Pro Ile
65 70 75 80

Glu Val Trp Lys Leu Tyr Phe Thr His Pro Gln Asp Gln Pro Ala Ile
85 90 95

Arg Asp Lys Ile Lys Glu His Pro Ala Val Val Asp Ile Tyr Glu Tyr
100 105 110

Asp Ile Pro Phe Ala Lys Arg Tyr Leu Ile Asp Lys Gly Leu Ile Pro
115 120 125

Met Glu Gly Asp Glu Glu Leu Lys Met Leu Ala Phe Ala Ile Ala Thr
130 135 140

Leu Tyr His Glu Gly Glu Glu Phe Ala Glu Gly Pro Ile Leu Met Ile
145 150 155 160

Ser Tyr Ala Asp Glu Glu Gly Ala Arg Val Ile Thr Trp Lys Asn Ile
165 170 175

Asp Leu Pro Tyr Val Asp Val Val Ser Thr Glu Lys Glu Met Ile Lys
180 185 190

Arg Phe Leu Lys Val Val Lys Glu Lys Asp Pro Asp Val Leu Ile Thr
195 200 205

Tyr Asn Gly Asp Asn Phe Asp Phe Ala Tyr Leu Lys Lys Arg Ser Glu
210 215 220

Lys Leu Gly Val Lys Phe Ile Leu Gly Arg Glu Gly Ser Glu Pro Lys
225 230 235 240

Ile Gln Arg Met Gly Asp Arg Phe Ala Val Glu Val Lys Gly Arg Ile
245 250 255

His Phe Asp Leu Tyr Pro Val Ile Arg Arg Thr Ile Asn Leu Pro Thr
260 265 270

Tyr Thr Leu Glu Ala Val Tyr Glu Ala Ile Phe Gly Gln Pro Lys Glu
275 280 285

Lys Val Tyr Ala Glu Glu Ile Ala Gln Ala Trp Glu Thr Gly Glu Gly
290 295 300

Leu Glu Arg Val Ala Arg Tyr Ser Met Glu Asp Ala Lys Val Thr Tyr
305 310 315 320

Glu Leu Gly Lys Glu Phe Phe Pro Met Glu Ala Gln Leu Ser Arg Leu
325 330 335

Val Gly Gln Ser Leu Trp Asp Val Ser Arg Ser Ser Thr Gly Asn Leu
340 345 350

Val Glu Trp Phe Leu Leu Arg Lys Ala Tyr Glu Arg Asn Glu Leu Ala

```
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Cys Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Gln Val Pro
                645                 650                 655

Pro Gln Pro Leu Val Ile Tyr Gln Lys Ile Thr Lys Glu Leu Asn Asp
            660                 665                 670

Tyr Arg Ala Ile Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770
```

<210> SEQ ID NO 11
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 11

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365
```

```
Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Ser Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Gln Ser Ile Leu Gly Ala Phe Gly Tyr His Arg
            740                 745                 750

Gly Asp Leu Lys Tyr Gln Lys Ser Gln Gln Met Gly Leu Gly Ala Trp
        755                 760                 765

Leu Lys Pro Lys Thr
    770
```

<210> SEQ ID NO 12
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 12

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365
```

-continued

```
Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Ala Thr Lys Lys
            580                 585                 590

Lys Tyr Ala Val Ile Asp Glu Glu Asp Lys Ile Thr Thr Arg Gly Leu
        595                 600                 605

Lys Met Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Gln Leu Val Ile Tyr Gln Pro Ile Thr Lys Gln Leu His Asp
            660                 665                 670

Tyr Arg Ala Arg Gly Pro His Val Ser Val Ala Lys Arg Leu Ala Ala
        675                 680                 685

Arg Gly Ile Lys Ile Arg Pro Gly Thr Val Ile Ser Tyr Ile Val Pro
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Gly Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770
```

<210> SEQ ID NO 13
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 13

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
```

```
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Glu Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Gln Val Pro
                645                 650                 655

Thr Lys Gln Leu Val Ile Tyr Gln Glu Ile Thr Lys Glu Leu Arg Asp
            660                 665                 670

Tyr Lys Ala Arg Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770
```

<210> SEQ ID NO 14

<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 14

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380
```

```
Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Arg Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770
```

<210> SEQ ID NO 15
<211> LENGTH: 773

-continued

<212> TYPE: PRT
<213> ORGANISM: Artificial Sequence
<220> FEATURE:
<223> OTHER INFORMATION: Mutated SEQ ID NO:1 according to the invention

<400> SEQUENCE: 15

Met Ile Leu Asp Thr Asp Tyr Ile Thr Glu Asp Gly Lys Pro Val Ile
1 5 10 15

Arg Ile Phe Lys Lys Glu Asn Gly Glu Phe Lys Ile Asp Tyr Asp Arg
20 25 30

Asn Phe Glu Pro Tyr Ile Tyr Ala Leu Leu Lys Asp Asp Ser Ala Ile
35 40 45

Glu Asp Val Lys Lys Ile Thr Ala Glu Arg His Gly Thr Thr Val Arg
50 55 60

Val Val Arg Ala Glu Lys Val Lys Lys Lys Phe Leu Gly Arg Pro Ile
65 70 75 80

Glu Val Trp Lys Leu Tyr Phe Thr His Pro Gln Asp Gln Pro Ala Ile
85 90 95

Arg Asp Lys Ile Lys Glu His Pro Ala Val Val Asp Ile Tyr Glu Tyr
100 105 110

Asp Ile Pro Phe Ala Lys Arg Tyr Leu Ile Asp Lys Gly Leu Ile Pro
115 120 125

Met Glu Gly Asp Glu Glu Leu Lys Met Leu Ala Phe Ala Ile Ala Thr
130 135 140

Leu Tyr His Glu Gly Glu Glu Phe Ala Glu Gly Pro Ile Leu Met Ile
145 150 155 160

Ser Tyr Ala Asp Glu Glu Gly Ala Arg Val Ile Thr Trp Lys Asn Ile
165 170 175

Asp Leu Pro Tyr Val Asp Val Val Ser Thr Glu Lys Glu Met Ile Lys
180 185 190

Arg Phe Leu Lys Val Val Lys Glu Lys Asp Pro Asp Val Leu Ile Thr
195 200 205

Tyr Asn Gly Asp Asn Phe Asp Phe Ala Tyr Leu Lys Lys Arg Ser Glu
210 215 220

Lys Leu Gly Val Lys Phe Ile Leu Gly Arg Glu Gly Ser Glu Pro Lys
225 230 235 240

Ile Gln Arg Met Gly Asp Arg Phe Ala Val Glu Val Lys Gly Arg Ile
245 250 255

His Phe Asp Leu Tyr Pro Val Ile Arg Arg Thr Ile Asn Leu Pro Thr
260 265 270

Tyr Thr Leu Glu Ala Val Tyr Glu Ala Ile Phe Gly Gln Pro Lys Glu
275 280 285

Lys Val Tyr Ala Glu Glu Ile Ala Gln Ala Trp Glu Thr Gly Glu Gly
290 295 300

Leu Glu Arg Val Ala Arg Tyr Ser Met Glu Asp Ala Lys Val Thr Tyr
305 310 315 320

Glu Leu Gly Lys Glu Phe Phe Pro Met Glu Ala Gln Leu Ser Arg Leu
325 330 335

Val Gly Gln Ser Leu Trp Asp Val Ser Arg Ser Ser Thr Gly Asn Leu
340 345 350

Val Glu Trp Phe Leu Leu Arg Lys Ala Tyr Glu Arg Asn Glu Leu Ala
355 360 365

Pro Asn Lys Pro Asp Glu Arg Glu Leu Ala Arg Arg Arg Glu Ser Tyr
370 375 380

```
Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Gln Val Pro
                645                 650                 655

Pro Gln Gln Leu Val Ile Tyr Gln Pro Ile Thr Lys His Leu Arg Asp
            660                 665                 670

Tyr Lys Ala Lys Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770
```

<210> SEQ ID NO 16
<211> LENGTH: 768
<212> TYPE: PRT

<213> ORGANISM: Artificial Sequence
<220> FEATURE:
<223> OTHER INFORMATION: Mutated SEQ ID NO:1 according to the invention

<400> SEQUENCE: 16

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
```

```
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Leu Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Ala Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Gln Asp Val Gln Arg Ile Leu Arg Ala Phe Gly Tyr Lys Asn
            740                 745                 750

Gly Asp Leu Arg Cys Gln Lys Thr Ile Arg Arg Ala Trp Gly Arg Gly
        755                 760                 765
```

<210> SEQ ID NO 17
<211> LENGTH: 751
<212> TYPE: PRT
<213> ORGANISM: Artificial Sequence
<220> FEATURE:
<223> OTHER INFORMATION: Mutated SEQ ID NO:1 according to the invention -continued

<400> SEQUENCE: 17

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415
```

```
Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Tyr Val Leu Asp Asp Ser Glu Gly Leu Trp Leu Gln
            740                 745                 750
```

<210> SEQ ID NO 18
<211> LENGTH: 756
<212> TYPE: PRT
<213> ORGANISM: Artificial Sequence
<220> FEATURE:
<223> OTHER INFORMATION: Mutated SEQ ID NO:1 according to the invention

<400> SEQUENCE: 18

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30
```

```
Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445
```

```
Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Gln Met Ile Leu Arg Ala Phe Gly Tyr Gln Lys
            740                 745                 750

Asp Asp Leu Arg
        755
```

<210> SEQ ID NO 19
<211> LENGTH: 2319
<212> TYPE: DNA
<213> ORGANISM: Artificial Sequence
<220> FEATURE:
<223> OTHER INFORMATION: DNA sequence to SEQ ID NO: 2

<400> SEQUENCE: 19

```
atgatcctcg atacagacta cataactgag gatggaaagc ccgtcatcag gatcttcaag      60

aaggagaacg gcgagttcaa aatagactac gacagaaact ttgagccata catctacgcg     120

ctcttgaagg acgactctgc gattgaggac gtcaagaaga taactgccga gaggcacggc     180

actaccgtta gggttgtcag ggccgagaaa gtgaagaaga agttcctagg caggccgata     240

gaggtctgga agctctactt cactcacccc caggaccagc ccgcaatcag ggacaagata     300
```

```
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gcgatcgcga cgctctatca cgagggcgag gagttcgccg aagggcctat cctgatgata    480
agctacgccg acgaggaagg ggcgcgcgtt attacctgga agaatatcga ccttccctat    540
gttgacgtcg tttccaccga gaaggagatg ataaagcgct tcctcaaggt cgtcaaggaa    600
aaggatcccg acgtcctcat aacctacaac ggcgacaact tcgacttcgc ctacctcaag    660
aagcgctccg agaagctcgg agtcaagttc atcctcggaa gggaagggag cgagccgaaa    720
atccagcgca tgggcgatcg ctttgcggtg gaggtcaagg gaaggattca cttcgacctc    780
taccccgtca ttaggagaac gattaacctc cccacttaca cccttgaggc agtatatgaa    840
gccatctttg gacagccgaa ggagaaggtc tacgctgagg agatagcgca ggcctgggaa    900
acgggcgagg gattagaaag ggtggcccgc tactcgatgg aggacgcaaa ggtaacctat    960
gaactcggaa aagaattctt ccctatggaa gcccagctct cgcgcctcgt aggccagagc   1020
ctctgggatg tatctcgctc gagtaccgga aacctcgtcg agtggttttt gctgaggaag   1080
gcctacgaga ggaatgaact tgcaccaaac aagccggacg agagggagct ggcaagaaga   1140
agggagagct acgcgggtgg atacgtcaag gagcccgaaa ggggactgtg ggagaacatc   1200
gtgtatctgg acttccgctc cctgtatcct tcgataataa tcacccataa cgtctcccct   1260
gatacactca acagggaggg ttgtgaggag tacgacgtgg ctcctcaggt aggccataag   1320
ttctgcaagg acttccccgg cttcatccca agcctcctcg gtgacctctt ggaggagaga   1380
cagaaggtaa agaagaagat gaaggccact atagacccaa tcgagaagaa actcctcgat   1440
tacaggcaac gactgatcaa aatccttgct aatagcttct acggttacta cggctatgca   1500
aaggcccgct ggtactgcaa ggagtgcgcc gagagcgtta ccgcttgggg caggcagtac   1560
atcgagacta cgataaggga aatagaggag aaatttggct ttaaagtcct ctacgcggac   1620
acagatggat tttcgcaac aatacctgga gcggacgccg aaaccgtcaa aaagaaggca   1680
aaggagttcc tggactacat caacgccaaa ctgcccggcc tgctcgaact cgaatacgag   1740
ggcttctaca agcgcggctt cttcgtgacg aagaagaagt acgcggttat agacgaggag   1800
gacaagataa cgacgcgcgg gcttgaaata gttaggcgtg actggagcga gatagcgaag   1860
gagacgcagg cgagggttct tgaggcgata ctaaagcacg gtgacgttga agaagcggta   1920
aggattgtca aagaggttac ggagaagctg agcaagtacg aggttccacc ggagaagctg   1980
gtcatctacg agcagataac ccgcgacctg aaggactaca aggccaccgg gccgcatgtg   2040
gctgttgcaa aacgcctcgc cgcaaggggg ataaaaatcc ggcccggaac ggtcataagc   2100
tacatcgtgc tcaaaggctc gggaaggatt ggggacaggg ctataccctt tgacgaattt   2160
gacccggcaa agcacaagta cgatgcagaa tactacatcg agaaccaggt tcttccagct   2220
gtggagagga ttctgagggc ctttggttac cgtaaagaag atttaaggta tcagaaaacg   2280
cggcaggttg gcttgggggc gtggctaaaa cctaagaca                          2319
```

<210> SEQ ID NO 20
<211> LENGTH: 2319
<212> TYPE: DNA
<213> ORGANISM: Artificial Sequence
<220> FEATURE:
<223> OTHER INFORMATION: DNA sequence to SEQ ID NO: 3

<400> SEQUENCE: 20

-continued

```
atgatcctcg atacagacta cataactgag gatggaaagc ccgtcatcag gatcttcaag     60
aaggagaacg gcgagttcaa aatagactac gacagaaact ttgagccata catctacgcg    120
ctcttgaagg acgactctgc gattgaggac gtcaagaaga taactgccga gaggcacggc    180
actaccgtta gggttgtcag ggccgagaaa gtgaagaaga agttcctagg caggccgata    240
gaggtctgga agctctactt cactcacccc caggaccagc ccgcaatcag ggacaagata    300
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gcgatcgcga cgctctatca cgagggcgag gagttcgccg aagggcctat cctgatgata    480
agctacgccg acgaggaagg ggcgcgcgtt attacctgga agaatatcga ccttccctat    540
gttgacgtcg tttccaccga gaaggagatg ataaagcgct tcctcaaggt cgtcaaggaa    600
aaggatcccg acgtcctcat aacctacaac ggcgacaact tcgacttcgc ctacctcaag    660
aagcgctccg agaagctcgg agtcaagttc atcctcggaa gggaagggag cgagccgaaa    720
atccagcgca tgggcgatcg ctttgcggtg gaggtcaagg gaaggattca cttcgacctc    780
taccccgtca ttaggagaac gattaacctc cccacttaca cccttgaggc agtatatgaa    840
gccatctttg gacagccgaa ggagaaggtc tacgctgagg agatagcgca ggcctgggaa    900
acgggcgagg gattagaaag ggtggcccgc tactcgatgg aggacgcaaa ggtaacctat    960
gaactcggaa aagaattctt ccctatggaa gcccagctct cgcgcctcgt aggccagagc   1020
ctctgggatg tatctcgctc gagtaccgga aacctcgtcg agtggttttt gctgaggaag   1080
gcctacgaga ggaatgaact tgcaccaaac aagccggacg agagggagct ggcaagaaga   1140
agggagagct acgcgggtgg atacgtcaag gagcccgaaa ggggactgtg ggagaacatc   1200
gtgtatctgg acttccgctc cctgtatcct tcgataataa tcacccataa cgtctcccct   1260
gatacactca acagggaggg ttgtgaggag tacgacgtgg ctcctcaggt aggccataag   1320
ttctgcaagg acttccccgg cttcatccca agcctcctcg gtgacctctt ggaggagaga   1380
cagaaggtaa agaagaagat gaaggccact atagacccaa tcgagaagaa actcctcgat   1440
tacaggcaac gactgatcaa aatccttgct aatagcttct acggttacta cggctatgca   1500
aaggcccgct ggtactgcaa ggagtgcgcc gagagcgtta ccgcttgggg caggcagtac   1560
atcgagacta cgataaggga aatagaggag aaatttggct ttaaagtcct ctacgcggac   1620
acagatggat tttcgcaac aatacctgga gcggacgccg aaaccgtcaa aaagaaggca   1680
aaggagttcc tggactacat caacgccaaa ctgcccggcc tgctcgaact cgaatacgag   1740
ggcttctaca agcgcggctt cttcgtgacg aagaagaagt acgcggttat agacgaggag   1800
gacaagataa cgacgcgcgg gcttgaaata gttaggcgtg actggagcga gatagcgaag   1860
gagacgcagg cgagggttct tgaggcgata ctaaagcacg gtgacgttga agaagcggta   1920
aggattgtca aagaggttac ggagaagctg agcaagtacc aggttccacc gaagaagctg   1980
gtcatcaacc agcagataac cagagagctg cgggactaca aggccaaggg gccgcatgtg   2040
gctgttgcaa aacgcctcgc cgcaaggggg ataaaaatcc ggcccggaac ggtcataagc   2100
tacatcgtgc tcaaaggctc gggaaggatt ggggacaggg ctataccctt tgacgaattt   2160
gacccggcaa agcacaagta cgatgcagaa tactacatcg agaaccaggt tcttccagct   2220
gtggagagga ttctgagggc ctttggttac cgtaaagaag atttaaggta tcagaaaacg   2280
cggcaggttg gcttgggggc gtggctaaaa cctaagaca                           2319
```

<210> SEQ ID NO 21
<211> LENGTH: 2322
<212> TYPE: DNA
<213> ORGANISM: Artificial Sequence
<220> FEATURE:
<223> OTHER INFORMATION: DNA Sequence to SEQ ID NO: 4

<400> SEQUENCE: 21

```
atgatcctcg atacagacta cataactgag gatggaaagc ccgtcatcag gatcttcaag     60

aaggagaacg gcgagttcaa aatagactac gacagaaact ttgagccata catctacgcg    120

ctcttgaagg acgactctgc gattgaggac gtcaagaaga taactgccga gaggcacggc    180

actaccgtta gggttgtcag ggccgagaaa gtgaagaaga agttcctagg caggccgata    240

gaggtctgga agctctactt cactcacccc caggaccagc ccgcaatcag ggacaagata    300

aaggagcatc ctgccgttgt ggacatctac gagtacgaca tccccttcgc gaagcgctac    360

ctcatagaca aaggcttaat cccgatggag ggcgacgagg aacttaagat gctcgccttc    420

gcgatcgcga cgctctatca cgagggcgag gagttcgccg aagggcctat cctgatgata    480

agctacgccg acgaggaagg ggcgcgcgtt attacctgga agaatatcga ccttccctat    540

gttgacgtcg tttccaccga gaaggagatg ataaagcgct tcctcaaggt cgtcaaggaa    600

aaggatcccg acgtcctcat aacctacaac ggcgacaact tcgacttcgc ctacctcaag    660

aagcgctccg agaagctcgg agtcaagttc atcctcggaa gggaagggag cgagccgaaa    720

atccagcgca tgggcgatcg ctttgcggtg gaggtcaagg gaaggattca cttcgacctc    780

taccccgtca ttaggagaac gattaacctc cccacttaca cccttgaggc agtatatgaa    840

gccatctttg gacagccgaa ggagaaggtc tacgctgagg agatagcgca ggcctgggaa    900

acgggcgagg gattagaaag ggtggcccgc tactcgatgg aggacgcaaa ggtaacctat    960

gaactcggaa aagaattctt ccctatggaa gcccagctct cgcgcctcgt aggccagagc   1020

ctctgggatg tatctcgctc gagtaccgga aacctcgtcg agtggttttt gctgaggaag   1080

gcctacgaga ggaatgaact tgcaccaaac aagccggacg agagggagct ggcaagaaga   1140

agggagagct acgcgggtgg atacgtcaag gagcccgaaa ggggactgtg ggagaacatc   1200

gtgtatctgg acttccgctc cctgtatcct tcgataataa tcacccataa cgtctcccct   1260

gatacactca acagggaggg ttgtgaggag tacgacgtgg ctcctcaggt aggccataag   1320

ttctgcaagg acttccccgg cttcatccca agcctcctcg gtgacctctt ggaggagaga   1380

cagaaggtaa agaagaagat gaaggccact atagacccaa tcgagaagaa actcctcgat   1440

tacaggcaac gactgatcaa aatccttgct aatagcttct acggttacta cggctatgca   1500

aaggcccgct ggtactgcaa ggagtgcgcc gagagcgtta ccgcttgggg caggcagtac   1560

atcgagacta cgataaggga aatagaggag aaatttggct ttaaagtcct ctacgcggac   1620

acagatggat tttcgcaac aatacctgga gcggacgccg aaaccgtcaa aaagaaggca   1680

aaggagttcc tggactacat caacgccaaa ctgcccggcc tgctcgaact cgaatacgag   1740

ggcttctaca agcgcggctt cttcgtgacg aagaagaagt acgcggttat agacgaggag   1800

gacaagataa cgacgcgcgg gcttgaaata gttaggcgtg actggagcga gatagcgaag   1860

gagacgcagg cgagggttct tgaggcgata ctaaagcacg gtgacgttga agaagcggta   1920

aggattgtca aagaggttac ggagaagctg agcaagtacc aggttccacc gaaggagctg   1980

gtcatctacg cggagataac cagacccctg caggactaca aggccagggg gccgcatgtg   2040

gctgttgcaa aacgcctcgc cgcaaggggg ataaaaatcc ggcccggaac ggtcataagc   2100
```

```
tacatcgtgc tcaaaggctc gggaagggtt ggggacaggg ctataccctt tgacgaattt   2160

gacccggcaa agcacaagta cgatgcagaa tactacatcg agaaccaggt tcttccagct   2220

gtggagagga ttctgagggc ctttggttac cgtaaagaag atttaaggta tcagaaaacg   2280

cggcaggttg gcttgggggc gtggctaaaa cctaagacat aa                      2322
```

```
<210> SEQ ID NO 22
<211> LENGTH: 2322
<212> TYPE: DNA
<213> ORGANISM: Artificial Sequence
<220> FEATURE:
<223> OTHER INFORMATION: DNA Sequence to SEQ ID NO: 5

<400> SEQUENCE: 22

atgatcctcg atacagacta cataactgag gatggaaagc ccgtcatcag gatcttcaag     60

aaggagaacg gcgagttcaa aatagactac gacagaaact ttgagccata catctacgcg    120

ctcttgaagg acgactctgc gattgaggac gtcaagaaga taactgccga gaggcacggc    180

actaccgtta gggttgtcag ggccgagaaa gtgaagaaga agttcctagg caggccgata    240

gaggtctgga agctctactt cactcacccc caggaccagc ccgcaatcag ggacaagata    300

aaggagcatc ctgccgttgt ggacatctac gagtacgaca tccccttcgc gaagcgctac    360

ctcatagaca aaggcttaat cccgatggag ggcgacgagg aacttaagat gctcgccttc    420

gcgatcgcga cgctctatca cgagggcgag gagttcgccg aagggcctat cctgatgata    480

agctacgccg acgaggaagg ggcgcgcgtt attacctgga agaatatcga ccttccctat    540

gttgacgtcg tttccaccga gaaggagatg ataaagcgct tcctcaaggt cgtcaaggaa    600

aaggatcccg acgtcctcat aacctacaac ggcgacaact tcgacttcgc ctacctcaag    660

aagcgctccg agaagctcgg agtcaagttc atcctcggaa gggaagggag cgagccgaaa    720

atccagcgca tgggcgatcg ctttgcggtg gaggtcaagg gaaggattca cttcgacctc    780

taccccgtca ttaggagaac gattaacctc cccacttaca cccttgaggc agtatatgaa    840

gccatctttg gacagccgaa ggagaaggtc tacgctgagg agatagcgca ggcctgggaa    900

acgggcgagg gattagaaag ggtggcccgc tactcgatgg aggacgcaaa ggtaacctat    960

gaactcggaa aagaattctt ccctatggaa gcccagctct cgcgcctcgt aggccagagc   1020

ctctgggatg tatctcgctc gagtaccgga aacctcgtcg agtggttttt gctgaggaag   1080

gcctacgaga ggaatgaact tgcaccaaac aagccggacg agagggagct ggcaagaaga   1140

agggagagct acgcgggtgg atacgtcaag gagcccgaaa ggggactgtg ggagaacatc   1200

gtgtatctgg acttccgctc cctgtatcct tcgataataa tcacccataa cgtctcccct   1260

gatacactca acagggaggg ttgtgaggag tacgacgtgg ctcctcaggt aggccataag   1320

ttctgcaagg acttccccgg cttcatccca agcctcctcg gtgacctctt ggaggagaga   1380

cagaaggtaa agaagaagat gaaggccact atagacccaa tcgagaagaa actcctcgat   1440

tacaggcaac gactgatcaa aatccttgct aatagcttct acggttacta cggctatgca   1500

aaggcccgct ggtactgcaa ggagtgcgcc gagagcgtta ccgcttgggg caggcagtac   1560

atcgagacta cgataaggga aatagaggag aaatttggct ttaaagtcct ctacgcggac   1620

acagatggat tttcgcaac aatacctgga gcggacgccg aaaccgtcaa aaagaaggca    1680

aaggagttcc tggactacat caacgccaaa ctgcccggcc tgctcgaact cgaatacgag   1740

ggcttctaca agcgcggctt cttcgtgacg aagaagaagt acgcggttat agacgaggag   1800

gacaagataa cgacgcgcgg gcttgaaata gttaggcgtg actggagcga gatagcgaag   1860
```

```
gagacgcagg cgagggttct tgaggcgata ctaaagcacg gtgacgttga agaagcggta   1920

aggattgtca aagaggttac ggagaagctg agcaagtacc aggttccacc gcagcaactg   1980

gccatctacc agccgataac cagagccctg caggactaca aggccaaggg gccgcatgtg   2040

gctgttgcaa aacgcctcgc cgcaaggggg ataaaaatcc ggcccggaac ggtcataagc   2100

tacatcgtgc tcaaaggctc gggaaagatt ggggacaggg ctataccctt tgacgaattt   2160

gacccggcaa agcacaagta cgatgcagaa tactacatcg agaaccaggt tcttccagct   2220

gtggagagga ttctgagggc ctttggttac cgtaaagaag atttaaggta tcagaaaacg   2280

cggcaggttg gcttgggggc gtggctaaaa cctaagacgt aa                      2322
```

```
<210> SEQ ID NO 23
<211> LENGTH: 2322
<212> TYPE: DNA
<213> ORGANISM: Artificial Sequence
<220> FEATURE:
<223> OTHER INFORMATION: DNA sequence to SEQ ID NO: 6

<400> SEQUENCE: 23

atgatcctcg atacagacta cataactgag gatggaaagc ccgtcatcag gatcttcaag     60

aaggagaacg gcgagttcaa aatagactac gacagaaact ttgagccata catctacgcg    120

ctcttgaagg acgactctgc gattgaggac gtcaagaaga taactgccga gaggcacggc    180

actaccgtta gggttgtcag ggccgagaaa gtgaagaaga agttcctagg caggccgata    240

gaggtctgga agctctactt cactcacccc caggaccagc ccgcaatcag ggacaagata    300

aaggagcatc ctgccgttgt ggacatctac gagtacgaca tccccttcgc gaagcgctac    360

ctcatagaca aaggcttaat cccgatggag ggcgacgagg aacttaagat gctcgccttc    420

gcgatcgcga cgctctatca cgagggcgag gagttcgccg aagggcctat cctgatgata    480

agctacgccg acgaggaagg ggcgcgcgtt attacctgga agaatatcga ccttccctat    540

gttgacgtcg tttccaccga gaaggagatg ataaagcgct tcctcaaggt cgtcaaggaa    600

aaggatcccg acgtcctcat aacctacaac ggcgacaact tcgacttcgc ctacctcaag    660

aagcgctccg agaagctcgg agtcaagttc atcctcggaa gggaagggag cgagccgaaa    720

atccagcgca tgggcgatcg ctttgcggtg gaggtcaagg gaaggattca cttcgacctc    780

taccccgtca ttaggagaac gattaacctc cccacttaca cccttgaggc agtatatgaa    840

gccatctttg gacagccgaa ggagaaggtc tacgctgagg agatagcgca ggcctgggaa    900

acgggcgagg gattagaaag ggtggcccgc tactcgatgg aggacgcaaa ggtaacctat    960

gaactcggaa aagaattctt ccctatggaa gcccagctct cgcgcctcgt aggccagagc   1020

ctctgggatg tatctcgctc gagtaccgga aacctcgtcg agtggttttt gctgaggaag   1080

gcctacgaga ggaatgaact tgcaccaaac aagccggacg agagggagct ggcaagaaga   1140

agggagagct acgcgggtgg atacgtcaag gagcccgaaa ggggactgtg ggagaacatc   1200

gtgtatctgg acttccgctc cctgtatcct tcgataataa tcacccataa cgtctcccct   1260

gatacactca acagggaggg ttgtgaggag tacgacgtgg ctcctcaggt aggccataag   1320

ttctgcaagg acttccccgg cttcatccca agcctcctcg gtgacctctt ggaggagaga   1380

cagaaggtaa agaagaagat gaaggccact atagacccaa tcgagaagaa actcctcgat   1440

tacaggcaac gactgatcaa aatccttgct aatagcttct acggttacta cggctatgca   1500

aaggcccgct ggtactgcaa ggagtgcgcc gagagcgtta ccgcttgggg caggcagtac   1560
```

```
atcgagacta cgataaggga aatagaggag aaatttggct ttaaagtcct ctacgcggac   1620

acagatggat ttttcgcaac aatacctgga gcggacgccg aaaccgtcaa aaagaaggca   1680

aaggagttcc tggactacat caacgccaaa ctgcccggcc tgctcgaact cgaatacgag   1740

ggcttctaca agcgcggctt cttcgtgacg aagaagaagt acgcggttat agacgaggag   1800

gacaagataa cgacgcgcgg gcttgaaata gttaggcgtg actggagcga gatagcgaag   1860

gagacgcagg cgagggttct tgaggcgata ctaaagcacg gtgacgttga agaagcggta   1920

aggattgtca aagaggttac ggagaagctg agcaagtacg aggttccaac gcagcacctg   1980

gtcatccacc agcagataac cagagccctg aacgactaca aggccatcgg gccgcatgtg   2040

gctgttgcaa aacgcctcgc cgcaaggggg ataaaaatcc ggcccggaac ggtcataagc   2100

tacatcgtgc tcaaaggctc gggaaggatt ggggacaggg ctataccctt tgacgaattt   2160

gacccggcaa agcacaagta cgatgcagaa tactacatcg agaaccaggt tcttccagct   2220

gtggagagga ttctgagggc ctttggttac cgtaaagaag atttaaggta tcagaaaacg   2280

cggcaggttg gcttgggggc gtggctaaaa cctaagacat aa                       2322
```

<210> SEQ ID NO 24
<211> LENGTH: 2322
<212> TYPE: DNA
<213> ORGANISM: Artificial Sequence
<220> FEATURE:
<223> OTHER INFORMATION: DNA sequence to SEQ ID NO: 7

<400> SEQUENCE: 24

```
atgatcctcg atacagacta cataactgag gatggaaagc ccgtcatcag gatcttcaag     60

aaggagaacg gcgagttcaa aatagactac gacagaaact ttgagccata catctacgcg    120

ctcttgaagg acgactctgc gattgaggac gtcaagaaga taactgccga gaggcacggc    180

actaccgtta gggttgtcag ggccgagaaa gtgaagaaga agttcctagg caggccgata    240

gaggtctgga agctctactt cactcacccc caggaccagc ccgcaatcag ggacaagata    300

aaggagcatc ctgccgttgt ggacatctac gagtacgaca tccccttcgc gaagcgctac    360

ctcatagaca aaggcttaat cccgatggag ggcgacgagg aacttaagat gctcgccttc    420

gcgatcgcga cgctctatca cgagggcgag gagttcgccg aagggcctat cctgatgata    480

agctacgccg acgaggaagg ggcgcgcgtt attacctgga agaatatcga ccttccctat    540

gttgacgtcg tttccaccga gaaggagatg ataaagcgct tcctcaaggt cgtcaaggaa    600

aaggatcccg acgtcctcat aacctacaac ggcgacaact tcgacttcgc ctacctcaag    660

aagcgctccg agaagctcgg agtcaagttc atcctcggaa gggaagggag cgagccgaaa    720

atccagcgca tgggcgatcg ctttgcggtg gaggtcaagg gaaggattca cttcgacctc    780

taccccgtca ttaggagaac gattaacctc cccacttaca cccttgaggc agtatatgaa    840

gccatctttg gacagccgaa ggagaaggtc tacgctgagg agatagcgca ggcctgggaa    900

acgggcgagg gattagaaag ggtggcccgc tactcgatgg aggacgcaaa ggtaacctat    960

gaactcggaa aagaattctt ccctatggaa gcccagctct cgcgcctcgt aggccagagc   1020

ctctgggatg tatctcgctc gagtaccgga aacctcgtcg agtggttttt gctgaggaag   1080

gcctacgaga ggaatgaact tgcaccaaac aagccggacg agagggagct ggcaagaaga   1140

agggagagct acgcgggtgg atacgtcaag gagcccgaaa ggggactgtg ggagaacatc   1200

gtgtatctgg acttccgctc cctgtatcct tcgataataa tcacccataa cgtctcccct   1260

gatacactca acagggaggg ttgtgaggag tacgacgtgg ctcctcaggt aggccataag   1320
```

```
ttctgcaagg acttccccgg cttcatccca agcctcctcg gtgacctctt ggaggagaga   1380

cagaaggtaa agaagaagat gaaggccact atagacccaa tcgagaagaa actcctcgat   1440

tacaggcaac gactgatcaa aatccttgct aatagcttct acggttacta cggctatgca   1500

aaggcccgct ggtactgcaa ggagtgcgcc gagagcgtta ccgcttgggg caggcagtac   1560

atcgagacta cgataaggga aatagaggag aaatttggct ttaaagtcct ctacgcggac   1620

acagatggat ttttcgcaac aatacctgga gcggacgccg aaaccgtcaa aaagaaggca   1680

aaggagttcc tggactacat caacgccaaa ctgcccggcc tgctcgaact cgaatacgag   1740

ggcttctaca agcgcggctt cttcgtgacg aagaagaagt acgcggttat agacgaggag   1800

gacaagataa cgacgcgcgg gcttgaaata gttaggcgtg actggagcga gatagcgaag   1860

gagacgcagg cgagggttct tgaggcgata ctaaagcacg gtgacgttga agaagcggta   1920

aggattgtca aagaggttac ggagaagctg agcaagtacc aggttccacc gcagcagctg   1980

gtcatctacc aaaagataac caaacagctg cacgagtaca aggccagggg gccgcatgtg   2040

gctgttgcaa aacgcctcgc cgcaaggggg ataaaaatcc ggcccggaac ggtcataagc   2100

tacatcgtgc tcaaaggctc gggaaggatt ggggacaggg ctataccctt tgacgaattt   2160

gacccggcaa ggcacaagta cgatgcagaa tactacatcg agaaccaggt tcttccagct   2220

gtggagagga ttctgagggc ctttggttac cgtaaagaag atttaaggta tcagaaaacg   2280

cggcaggttg gcttgggggc gtggctaaaa cctaagacat aa                      2322
```

<210> SEQ ID NO 25
<211> LENGTH: 2322
<212> TYPE: DNA
<213> ORGANISM: Artificial Sequence
<220> FEATURE:
<223> OTHER INFORMATION: DNA sequence to SEQ ID NO: 8

<400> SEQUENCE: 25

```
atgatcctcg atacagacta cataactgag gatggaaagc ccgtcatcag gatcttcaag     60

aaggagaacg gcgagttcaa aatagactac gacagaaact ttgagccata catctacgcg    120

ctcttgaagg acgactctgc gattgaggac gtcaagaaga taactgccga gaggcacggc    180

actaccgtta gggttgtcag ggccgagaaa gtgaagaaga agttcctagg caggccgata    240

gaggtctgga agctctactt cactcacccc caggaccagc ccgcaatcag ggacaagata    300

aaggagcatc ctgccgttgt ggacatctac gagtacgaca tccccttcgc gaagcgctac    360

ctcatagaca aaggcttaat cccgatggag ggcgacgagg aacttaagat gctcgccttc    420

gcgatcgcga cgctctatca cgagggcgag gagttcgccg aagggcctat cctgatgata    480

agctacgccg acgaggaagg ggcgcgcgtt attacctgga agaatatcga ccttccctat    540

gttgacgtcg tttccaccga gaaggagatg ataaagcgct tcctcaaggt cgtcaaggaa    600

aaggatcccg acgtcctcat aacctacaac ggcgacaact tcgacttcgc ctacctcaag    660

aagcgctccg agaagctcgg agtcaagttc atcctcggaa gggaagggag cgagccgaaa    720

atccagcgca tgggcgatcg ctttgcggtg gaggtcaagg gaaggattca cttcgacctc    780

taccccgtca ttaggagaac gattaacctc cccacttaca cccttgaggc agtatatgaa    840

gccatctttg gacagccgaa ggagaaggtc tacgctgagg agatagcgca ggcctgggaa    900

acgggcgagg gattagaaag ggtggcccgc tactcgatgg aggacgcaaa ggtaacctat    960

gaactcggaa aagaattctt ccctatggaa gcccagctct cgcgcctcgt aggccagagc   1020
```

```
ctctgggatg tatctcgctc gagtaccgga aacctcgtcg agtggttttt gctgaggaag   1080
gcctacgaga ggaatgaact tgcaccaaac aagccggacg agagggagct ggcaagaaga   1140
agggagagct acgcgggtgg atacgtcaag gagcccgaaa ggggactgtg ggagaacatc   1200
gtgtatctgg acttccgctc cctgtatcct tcgataataa tcacccataa cgtctcccct   1260
gatacactca acagggaggg ttgtgaggag tacgacgtgg ctcctcaggt aggccataag   1320
ttctgcaagg acttccccgg cttcatccca agcctcctcg gtgacctctt ggaggagaga   1380
cagaaggtaa agaagaagat gaaggccact atagacccaa tcgagaagaa actcctcgat   1440
tacaggcaac gactgatcaa aatccttgct aatagcttct acggttacta cggctatgca   1500
aaggcccgct ggtactgcaa ggagtgcgcc gagagcgtta ccgcttgggg caggcagtac   1560
atcgagacta cgataaggga aatagaggag aaatttggct ttaaagtcct ctacgcggac   1620
acagatggat tttcgcaac aatacctgga gcggacgccg aaaccgtcaa aaagaaggca    1680
aaggagttcc tggactacat caacgccaaa ctgcccggcc tgctcgaact cgaatacgag   1740
ggcttctaca agcgcggctt cttcgtgacg aagaagaagt acgcggttat agacgaggag   1800
gacaagataa cgacgcgcgg gcttgaaata gttaggcgtg actggagcga gatagcgaag   1860
gagacgcagg cgagggttct tgaggcgata ctaaagcacg gtgacgttga agaagcggta   1920
aggattgtca aagaggttac ggagaagctg agcaagtacc aggttccatc ggagcagctg   1980
gtcatctacc atcagataac cagacccctg aaggagtaca gggccatggg gccgcatgtg   2040
gctgttgcaa aacgcctcgc cgcaaggggg ataaaaatcc ggcccggaac ggtcataagc   2100
tacatcgtgc tcaaaggctc gggaaggatt ggggacaggg ctataccctt tgacgaattt   2160
gacccggcaa agcacaagta cgatgcagaa tactacatcg agaaccaggt tcttccagct   2220
gtggagagga ttctgagggc ctttggttac cgtaaagaag atttaaggta tcagaaaacg   2280
cggcaggttg gcttgggggc gtggctaaaa cctaagacat aa                       2322
```

<210> SEQ ID NO 26
<211> LENGTH: 2319
<212> TYPE: DNA
<213> ORGANISM: Artificial Sequence
<220> FEATURE:
<223> OTHER INFORMATION: DNA sequence to SEQ ID NO: 9

<400> SEQUENCE: 26

```
atgatcctcg atacagacta cataactgag gatggaaagc ccgtcatcag gatcttcaag     60
aaggagaacg gcgagttcaa aatagactac gacagaaact ttgagccata catctacgcg    120
ctcttgaagg acgactctgc gattgaggac gtcaagaaga taactgccga gaggcacggc    180
actaccgtta gggttgtcag ggccgagaaa gtgaagaaga agttcctagg caggccgata    240
gaggtctgga agctctactt cactcacccc caggaccagc ccgcaatcag ggacaagata    300
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gcgatcgcga cgctctatca cgagggcgag gagttcgccg aagggcctat cctgatgata    480
agctacgccg acgaggaagg ggcgcgcgtt attacctgga agaatatcga ccttccctat    540
gttgacgtcg tttccaccga gaaggagatg ataaagcgct tcctcaaggt cgtcaaggaa    600
aaggatcccg acgtcctcat aacctacaac ggcgacaact tcgacttcgc ctacctcaag    660
aagcgctccg agaagctcgg agtcaagttc atcctcggaa gggaagggag cgagccgaaa    720
atccagcgca tgggcgatcg ctttgcggtg gaggtcaagg gaaggattca cttcgacctc    780
```

-continued

```
taccccgtca ttaggagaac gattaacctc cccacttaca cccttgaggc agtatatgaa    840
gccatctttg gacagccgaa ggagaaggtc tacgctgagg agatagcgca ggcctgggaa    900
acgggcgagg gattagaaag ggtggcccgc tactcgatgg aggacgcaaa ggtaacctat    960
gaactcggaa aagaattctt ccctatggaa gcccagctct cgcgcctcgt aggccagagc   1020
ctctgggatg tatctcgctc gagtaccgga aacctcgtcg agtggttttt gctgaggaag   1080
gcctacgaga ggaatgaact tgcaccaaac aagccggacg agagggagct ggcaagaaga   1140
agggagagct acgcgggtgg atacgtcaag gagcccgaaa ggggactgtg ggagaacatc   1200
gtgtatctgg acttccgctc cctgtatcct tcgataataa tcacccataa cgtctcccct   1260
gatacactca acagggaggg ttgtgaggag tacgacgtgg ctcctcaggt aggccataag   1320
ttctgcaagg acttccccgg cttcatccca agcctcctcg gtgacctctt ggaggagaga   1380
cagaaggtaa agaagaagat gaaggccact atagacccaa tcgagaagaa actcctcgat   1440
tacaggcaac gactgatcaa aatccttgct aatagcttct acggttacta cggctatgca   1500
aaggcccgct ggtactgcaa ggagtgcgcc gagagcgtta ccgcttgggg caggcagtac   1560
atcgagacta cgataaggga aatagaggag aaatttggct ttaaagtcct ctacgcggac   1620
acagatggat tttcgcaac aatacctgga gcggacgccg aaaccgtcaa aaagaaggca   1680
aaggagttcc tggactacat caacgccaaa ctgcccggcc tgctcgaact cgaatacgag   1740
ggcttctaca agcgcggctt cttcgtgacg aagaagaagt acgcggttat agacgaggag   1800
gacaagataa cgacgcgcgg gcttgaaata gttaggcgtg actggagcga gatagcgaag   1860
gagacgcagg cgagggttct tgaggcgata ctaaagcacg gtgacgttga agaagcggta   1920
aggattgtca aagaggttac ggagaagctg agcaagtacg aggtttcaca gcagcagctg   1980
gtcatctacc agcagataac caaagagctg agcgagtaca aggccaccgg gccgcatgtg   2040
gctgttgcaa aacgcctcgc cgcaaggggg gtaaaaatcc ggcccggaac ggtcataagc   2100
tacatcgtgc tcaaaggctc gggaaggatt ggggacaggg ctataccctt tgacgaattt   2160
gacccggcaa agcacaagta cgatgcagaa tactacatcg agaaccaggt tcttccagct   2220
gtggagagga ttctgagggc ctttggttac cgtaaagaag atttaaggta tcagaaaacg   2280
cggcaggttg gcttgggggc gtggctaaaa cctaagaca                          2319

<210> SEQ ID NO 27
<211> LENGTH: 2322
<212> TYPE: DNA
<213> ORGANISM: Artificial Sequence
<220> FEATURE:
<223> OTHER INFORMATION: DNA sequence to SEQ ID NO: 10

<400> SEQUENCE: 27

atgatcctcg atacagacta cataactgag gatggaaagc ccgtcatcag gatcttcaag     60
aaggagaacg gcgagttcaa aatagactac gacagaaact ttgagccata catctacgcg    120
ctcttgaagg acgactctgc gattgaggac gtcaagaaga taactgccga gaggcacggc    180
actaccgtta gggttgtcag ggccgagaaa gtgaagaaga agttcctagg caggccgata    240
gaggtctgga agctctactt cactcacccc caggaccagc ccgcaatcag ggacaagata    300
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gcgatcgcga cgctctatca cgagggcgag gagttcgccg aagggcctat cctgatgata    480
```

-continued

```
agctacgccg acgaggaagg ggcgcgcgtt attacctgga agaatatcga ccttccctat    540
gttgacgtcg tttccaccga gaaggagatg ataaagcgct tcctcaaggt cgtcaaggaa    600
aaggatcccg acgtcctcat aacctacaac ggcgacaact tcgacttcgc ctacctcaag    660
aagcgctccg agaagctcgg agtcaagttc atcctcggaa gggaagggag cgagccgaaa    720
atccagcgca tgggcgatcg ctttgcggtg gaggtcaagg gaaggattca cttcgacctc    780
taccccgtca ttaggagaac gattaacctc cccacttaca cccttgaggc agtatatgaa    840
gccatctttg gacagccgaa ggagaaggtc tacgctgagg agatagcgca ggcctgggaa    900
acgggcgagg gattagaaag ggtggcccgc tactcgatgg aggacgcaaa ggtaacctat    960
gaactcggaa aagaattctt ccctatggaa gcccagctct cgcgcctcgt aggccagagc   1020
ctctgggatg tatctcgctc gagtaccgga aacctcgtcg agtggttttt gctgaggaag   1080
gcctacgaga ggaatgaact tgcaccaaac aagccggacg agagggagct ggcaagaaga   1140
agggagagct acgcgggtgg atacgtcaag gagcccgaaa ggggactgtg ggagaacatc   1200
gtgtatctgg acttccgctc cctgtatcct tcgataataa tcacccataa cgtctcccct   1260
gatacactca acagggaggg ttgtgaggag tacgacgtgg ctcctcaggt aggccataag   1320
ttctgcaagg acttccccgg cttcatccca agcctcctcg gtgacctctt ggaggagaga   1380
cagaaggtaa agaagaagat gaaggccact atagacccaa tcgagaagaa actcctcgat   1440
tacaggcaac gactgatcaa gatccttgct aatagcttct acggttacta cggctatgca   1500
aaggcccgct ggtactgcaa ggagtgcgcc gagagcgtta ccgcttgggg caggcagtac   1560
atcgagacta cgataaggga aatagaggag aaatttggct ttaaagtcct ctacgcggac   1620
acagatggat tttcgcaac aatacctgga gcggacgccg aaaccgtcaa aaagaaggca   1680
aaggagttcc tggactgcat caacgccaaa ctgcccggcc tgctcgaact cgaatacgag   1740
ggcttctaca agcgcggctt cttcgtgacg aagaagaagt acgcggttat agacgaggag   1800
gacaagataa cgacgcgcgg gcttgaaata gttaggcgtg actggagcga gatagcgaag   1860
gagacgcagg cgagggttct tgaggcgata ctaaagcacg gtgacgttga agaagcggta   1920
aggattgtca aagaggttac ggagaagctg agcaagtacc aggttccacc gcagccgctg   1980
gtcatctacc agaagataac caaagagctg aacgactaca gggccatcgg gccgcatgtg   2040
gctgttgcaa aacgcctcgc cgcaaggggg ataaaaatcc ggcccggaac ggtcataagc   2100
tacatcgtgc tcaaaggctc gggaaggatt ggggacaggg ctataccctt tgacgaattt   2160
gacccggcaa agcacaagta cgatgcagaa tactacatcg agaaccaggt tcttccagct   2220
gtggagagga ttctgagggc ctttggttac cgtaaagaag atttaaggta tcagaaaacg   2280
cggcaggttg gcttgggggc gtggctaaaa cctaagacat aa                      2322
```

<210> SEQ ID NO 28
<211> LENGTH: 2322
<212> TYPE: DNA
<213> ORGANISM: Artificial Sequence
<220> FEATURE:
<223> OTHER INFORMATION: DNA sequence to SEQ ID NO: 11

<400> SEQUENCE: 28

```
atgatcctcg atacagacta cataactgag gatggaaagc ccgtcatcag gatcttcaag     60
aaggagaacg gcgagttcaa aatagactac gacagaaact ttgagccata catctacgcg    120
ctcttgaagg acgactctgc gattgaggac gtcaagaaga taactgccga gaggcacggc    180
actaccgtta gggttgtcag ggccgagaaa gtgaagaaga agttcctagg caggccgata    240
```

-continued

```
gaggtctgga agctctactt cactcacccc caggaccagc ccgcaatcag ggacaagata    300
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gcgatcgcga cgctctatca cgagggcgag gagttcgccg aagggcctat cctgatgata    480
agctacgccg acgaggaagg ggcgcgcgtt attacctgga agaatatcga ccttccctat    540
gttgacgtcg tttccaccga gaaggagatg ataaagcgct tcctcaaggt cgtcaaggaa    600
aaggatcccg acgtcctcat aacctacaac ggcgacaact tcgacttcgc ctacctcaag    660
aagcgctccg agaagctcgg agtcaagttc atcctcggaa gggaagggag cgagccgaaa    720
atccagcgca tgggcgatcg ctttgcggtg gaggtcaagg gaaggattca cttcgacctc    780
taccccgtca ttaggagaac gattaacctc cccacttaca cccttgaggc agtatatgaa    840
gccatctttg gacagccgaa ggagaaggtc tacgctgagg agatagcgca ggcctgggaa    900
acgggcgagg gattagaaag ggtggcccgc tactcgatgg aggacgcaaa ggtaacctat    960
gaactcggaa aagaattctt ccctatggaa gcccagctct cgcgcctcgt aggccagagc   1020
ctctgggatg tatctcgctc gagtaccgga aacctcgtcg agtggttttt gctgaggaag   1080
gcctacgaga ggaatgaact tgcaccaaac aagccggacg agagggagct ggcaagaaga   1140
agggagagct acgcgggtgg atacgtcaag gagcccgaaa ggggactgtg ggagaacatc   1200
gtgtatctgg acttccgctc cctgtatcct tcgataataa tcacccataa cgtctcccct   1260
gatacactca acagggaggg ttgtgaggag tacgacgtgg ctcctcaggt aggccataag   1320
ttctgcaagg acttccccgg cttcatccca agcctcctcg gtgacctctt ggaggagaga   1380
cagaaggtaa agaagaagat gaaggccact atagacccaa tcgagaagaa actcctcgat   1440
tacaggcaac gactgatcaa aatccttgct aatagcttct acggttacta cggctatgca   1500
aaggcccgct ggtactgcaa ggagtgcgcc gagagcgtta ccgcttgggg caggcagtac   1560
atcgagacta cgataaggga aatagaggag aaatttggct ttaaagtcct ctacgcggac   1620
acagatggat tttcgcaac aatacctgga gcggacgccg aaaccgtcaa aaagaaggca   1680
aaggagttcc tggactacat caacgccaaa ctgcccggcc tgctcgaact cgaatacgag   1740
ggcttctaca agcgcggctt cttcgtgacg aagaagaagt acgcggttat agacgaggag   1800
gacaagataa cgacgcgcgg gcttgaaata gttaggcgtg actggagcga gatagcgaag   1860
gagacgcagg cgagggttct tgaggcgata ctaaagcacg gtgacgttga agaagcggta   1920
aggattgtca aagaggttac ggagaagctg agcaagtacg aggttccacc ggagaagctg   1980
gtcatctacg agcagataac ccgcgacctg aaggactaca aggccaccgg gccgcatgtg   2040
gctgttgcaa aacgcctcgc cgcaaggggg ataaaaatcc ggcccggaac ggtcataagc   2100
tacatcgtgc tcaaaggctc aggaaggatt ggggacaggg ctataccctc tgacgaattt   2160
gacccggcaa agcacaagta cgatgcagaa tactacatcg agaaccaggt tcttccagct   2220
gtgcagagca ttctgggggc ctttggttac catagaggtg atttaaagta ccagaagagc   2280
caacagatgg gcttgggggc gtggctaaaa cctaagacat aa                      2322
```

<210> SEQ ID NO 29
<211> LENGTH: 2319
<212> TYPE: DNA
<213> ORGANISM: Artificial Sequence
<220> FEATURE:
<223> OTHER INFORMATION: DNA sequence to SEQ ID NO: 12

<400> SEQUENCE: 29

```
atgatcctcg atacagacta cataactgag gatggaaagc ccgtcatcag gatcttcaag     60
aaggagaacg gcgagttcaa aatagactac gacagaaact ttgagccata catctacgcg    120
ctcttgaagg acgactctgc gattgaggac gtcaagaaga taactgccga gaggcacggc    180
actaccgtta gggttgtcag ggccgagaaa gtgaagaaga agttcctagg caggccgata    240
gaggtctgga agctctactt cactcacccc caggaccagc ccgcaatcag ggacaagata    300
aaggagcatc ctgccgttgt ggacatctac gagtacgaca tccccttcgc gaagcgctac    360
ctcatagaca aaggcttaat cccgatggag ggcgacgagg aacttaagat gctcgccttc    420
gcgatcgcga cgctctatca cgagggcgag gagttcgccg aagggcctat cctgatgata    480
agctacgccg acgaggaagg ggcgcgcgtt attacctgga agaatatcga ccttccctat    540
gttgacgtcg tttccaccga gaaggagatg ataaagcgct tcctcaaggt cgtcaaggaa    600
aaggatcccg acgtcctcat aacctacaac ggcgacaact tcgacttcgc ctacctcaag    660
aagcgctccg agaagctcgg agtcaagttc atcctcggaa gggaagggag cgagccgaaa    720
atccagcgca tgggcgatcg ctttgcggtg gaggtcaagg gaaggattca cttcgacctc    780
taccccgtca ttaggagaac gattaacctc cccacttaca cccttgaggc agtatatgaa    840
gccatctttg gacagccgaa ggagaaggtc tacgctgagg agatagcgca ggcctgggaa    900
acgggcgagg gattagaaag ggtggcccgc tactcgatgg aggacgcaaa ggtaacctat    960
gaactcggaa aagaattctt ccctatggaa gcccagctct cgcgcctcgt aggccagagc   1020
ctctgggatg tatctcgctc gagtaccgga aacctcgtcg agtggttttt gctgaggaag   1080
gcctacgaga ggaatgaact tgcaccaaac aagccggacg agagggagct ggcaagaaga   1140
agggagagct acgcgggtgg atacgtcaag gagcccgaaa ggggactgtg ggagaacatc   1200
gtgtatctgg acttccgctc cctgtatcct tcgataataa tcacccataa cgtctcccct   1260
gatacactca acagggaggg ttgtgaggag tacgacgtgg ctcctcaggt aggccataag   1320
ttctgcaagg acttccccgg cttcatccca agcctcctcg gtgacctctt ggaggagaga   1380
cagaaggtaa agaagaagat gaaggccact atagacccaa tcgagaagaa actcctcgat   1440
tacaggcaac gactgatcaa aatccttgct aatagcttct acggttacta cggctatgca   1500
aaggcccgct ggtactgcaa ggagtgcgcc gagagcgtta ccgcttgggg caggcagtac   1560
atcgagacta cgataaggga aatagaggag aaatttggct ttaaagtcct ctacgcggac   1620
acagatggat tttcgcaac aatacctgga gcggacgccg aaaccgtcaa aaagaaggca   1680
aaggagttcc tggactacat caacgccaaa ctgcccggcc tgctcgaact cgaatacgag   1740
ggcttctaca agcgcggctt cttcgcgacg aagaagaagt acgcggttat agacgaggag   1800
gacaagataa cgacgcgcgg gcttaaaatg gttaggcgtg actggagcga gatagcgaag   1860
gagacgcagg cgagggttct tgaggcgata ctaaagcacg gtgacgttga agaagcggta   1920
aggattgtca aagaggttac ggagaagctg agcaagtacg aggttccacc ggagcagctg   1980
gtcatctacc agccgataac caaacagttg cacgactaca gggccagggg gccgcatgtg   2040
tctgttgcaa aacgcctcgc cgcaaggggg ataaaaatcc ggcccggaac ggtcataagc   2100
tacatcgtgc ccaaaggctc gggaaggatt ggggacaggg ctatacccttt tgacgaattt   2160
gacccggcaa agcacaagta cgatgcagga tactacatcg agaaccaggt tcttccagct   2220
gtggagagga ttctgagggc ctttggttac cgtaaagaag atttaaggta tcagaaaacg   2280
cggcaggttg gcttgggggc gtggctaaaa cctaagaca                          2319
```

<210> SEQ ID NO 30
<211> LENGTH: 2319
<212> TYPE: DNA
<213> ORGANISM: Artificial Sequence
<220> FEATURE:
<223> OTHER INFORMATION: DNA sequence to SEQ ID NO: 13

<400> SEQUENCE: 30
atgatcctcg atacagacta cataactgag gatggaaagc ccgtcatcag gatcttcaag 60
aaggagaacg gcgagttcaa aatagactac gacagaaact ttgagccata catctacgcg 120
ctcttgaagg acgactctgc gattgaggac gtcaagaaga taactgccga gaggcacggc 180
actaccgtta gggttgtcag ggccgagaaa gtgaagaaga agttcctagg caggccgata 240
gaggtctgga agctctactt cactcacccc caggaccagc ccgcaatcag ggacaagata 300
aaggagcatc ctgccgttgt ggacatctac gagtacgaca tccccttcgc gaagcgctac 360
ctcatagaca aaggcttaat cccgatggag ggcgacgagg aacttaagat gctcgccttc 420
gcgatcgcga cgctctatca cgagggcgag gagttcgccg aagggcctat cctgatgata 480
agctacgccg acgaggaagg ggcgcgcgtt attacctgga agaatatcga ccttccctat 540
gttgacgtcg tttccaccga gaaggagatg ataaagcgct tcctcaaggt cgtcaaggaa 600
aaggatcccg acgtcctcat aacctacaac ggcgacaact tcgacttcgc ctacctcaag 660
aagcgctccg agaagctcgg agtcaagttc atcctcggaa gggaagggag cgagccgaaa 720
atccagcgca tgggcgatcg ctttgcggtg gaggtcaagg gaaggattca cttcgacctc 780
taccccgtca ttaggagaac gattaacctc cccacttaca cccttgaggc agtatatgaa 840
gccatctttg gacagccgaa ggagaaggtc tacgctgagg agatagcgca ggcctgggaa 900
acgggcgagg gattagaaag ggtggcccgc tactcgatgg aggacgcaaa ggtaacctat 960
gaactcggaa aagaattctt ccctatggaa gcccagctct cgcgcctcgt aggccagagc 1020
ctctgggatg tatctcgctc gagtaccgga aacctcgtcg agtggttttt gctgaggaag 1080
gcctacgaga ggaatgaact tgcaccaaac aagccggacg agagggagct ggcaagaaga 1140
agggagagct acgcgggtgg atacgtcaag gagcccgaaa ggggactgtg ggagaacatc 1200
gtgtatctgg acttccgctc cctgtatcct tcgataataa tcacccataa cgtctcccct 1260
gatacactca acagggaggg ttgtgaggag tacgacgtgg ctcctcaggt aggccataag 1320
ttctgcaagg acttccccgg cttcatccca agcctcctcg gtgacctctt ggaggagaga 1380
cagaaggtaa agaagaagat gaaggccact atagacccaa tcgagaagaa actcctcgat 1440
tacaggcaac gactgatcaa gatccttgct aatagcttct acggttacta cggctatgca 1500
aaggcccgct ggtactgcaa ggagtgcgcc gagagcgtta ccgcttgggg caggcagtac 1560
atcgagacta cgataaggga aatagaggag aaatttggct ttaaagtcct ctacgcggac 1620
acagatggat ttttcgcaac aatacctgga gcggacgccg aaaccgtcaa aaagaaggca 1680
aaggagttcc tggactacat caacgccaaa ctgcccggcc tgctcgaact cgaatacgag 1740
ggcttctaca agcgcggctt cttcgtgacg aagaaggagt acgcggttat agacgaggag 1800
gacaagataa cgacgcgcgg gcttgaaata gttaggcgtg actggagcga gatagcgaag 1860
gagacgcagg cgagggttct tgaggcgata ctaaagcacg gtgacgttga agaagcggta 1920
aggattgtca aagaggttac ggagaagctg agcaagtacc aggttccaac gaagcagctg 1980
gtcatctacc aggagataac caaagagctg cgggactaca aggccagggg gccgcatgtg 2040
gctgttgcaa aacgcctcgc cgcaaggggg ataaaaatcc ggcccggaac ggtcataagc 2100
tacatcgtgc tcaaaggctc gggaaggatt ggggacaggg ctataccctt tgacgaattt 2160
gacccggcaa agcacaagta cgatgcagaa tactacatcg agaaccaggt tcttccagct 2220
gtggagagga ttctgagggc ctttggttac cgtaaagagg atttaaggta tcagaaaacg 2280
cggcaggttg gcttgggggc gtggctaaaa cctaagaca 2319

<210> SEQ ID NO 31
<211> LENGTH: 2322
<212> TYPE: DNA
<213> ORGANISM: Artificial Sequence
<220> FEATURE:
<223> OTHER INFORMATION: DNA sequence to SEQ ID NO: 14

<400> SEQUENCE: 31
atgatcctcg atacagacta cataactgag gatggaaagc ccgtcatcag gatcttcaag 60
aaggagaacg gcgagttcaa aatagactac gacagaaact ttgagccata catctacgcg 120
ctcttgaagg acgactctgc gattgaggac gtcaagaaga taactgccga gaggcacggc 180
actaccgtta gggttgtcag ggccgagaaa gtgaagaaga agttcctagg caggccgata 240
gaggtctgga agctctactt cactcacccc caggaccagc ccgcaatcag ggacaagata 300
aaggagcatc ctgccgttgt ggacatctac gagtacgaca tccccttcgc gaagcgctac 360
ctcatagaca aaggcttaat cccgatggag ggcgacgagg aacttaagat gctcgccttc 420
gcgatcgcga cgctctatca cgagggcgag gagttcgccg aagggcctat cctgatgata 480
agctacgccg acgaggaagg ggcgcgcgtt attacctgga agaatatcga ccttccctat 540
gttgacgtcg tttccaccga gaaggagatg ataaagcgct tcctcaaggt cgtcaaggaa 600
aaggatcccg acgtcctcat aacctacaac ggcgacaact tcgacttcgc ctacctcaag 660
aagcgctccg agaagctcgg agtcaagttc atcctcggaa gggaagggag cgagccgaaa 720
atccagcgca tgggcgatcg ctttgcggtg gaggtcaagg gaaggattca cttcgacctc 780
taccccgtca ttaggagaac gattaacctc cccacttaca cccttgaggc agtatatgaa 840
gccatctttg gacagccgaa ggagaaggtc tacgctgagg agatagcgca ggcctgggaa 900
acgggcgagg gattagaaag ggtggcccgc tactcgatgg aggacgcaaa ggtaacctat 960
gaactcggaa aagaattctt ccctatggaa gcccagctct cgcgcctcgt aggccagagc 1020
ctctgggatg tatctcgctc gagtaccgga aacctcgtcg agtggttttt gctgaggaag 1080
gcctacgaga ggaatgaact tgcaccaaac aagccggacg agagggagct ggcaagaaga 1140
agggagagct acgcgggtgg atacgtcaag gagcccgaaa ggggactgtg ggagaacatc 1200
gtgtatctgg acttccgctc cctgtatcct tcgataataa tcacccataa cgtctcccct 1260
gatacactca acagggaggg ttgtgaggag tacgacgtgg ctcctcaggt aggccataag 1320
ttctgcaagg acttccccgg cttcatccca agcctcctcg gtgacctctt ggaggagaga 1380
cagaaggtaa agaagaagat gaaggccact atagacccaa tcgagaagaa actcctcgat 1440
tacaggcaac gactgatcaa gatccttgct aatagcttct acggttacta cggctatgca 1500
aaggcccgct ggtactgcaa ggagtgcgcc gagagcgtta ccgcttgggg caggcagtac 1560
atcgagacta cgataaggga aatagaggag aaatttggct ttaaagtcct ctacgcggac 1620
acagatggat ttttcgcaac aatacctgga gcggacgccg aaaccgtcaa aaagaaggca 1680
aaggagttcc tggactacat caacgccaaa ctgcccggcc tgctcgaact cgaatacgag 1740
ggcttctaca agcgcggctt cttcgtgacg aagaagaagt acgcggttat agacgaggag 1800

```
gacaagataa cgacgcgcgg gcttgaaata gttaggcgtg accggagcga gatagcgaag   1860

gagacgcagg cgagggttct tgaggcgata ctaaagcacg gtgacgttga agaagcggta   1920

aggattgtca aagaggttac ggagaagctg agcaagtacg aggttccacc ggagaagctg   1980

gtcatctacg agcagataac ccgcgacctg aaggactaca aggccaccgg gccgcatgtg   2040

gctgttgcaa aacgcctcgc cgcaaggggg ataaaaatcc ggcccggaac ggtcataagc   2100

tacatcgtgc tcaaaggctc gggaaggatt ggggacaggg ctataccctt tgacgaattt   2160

gacccggcaa agcacaagta cgatgcagaa tactacatcg agaaccaggt tcttccagct   2220

gtggagagga ttctgagggc ctttggttac cgtaaagaag atttaaggta tcagaaaacg   2280

cggcaggttg gcttgggggc gtggctaaaa cctaagacat aa                       2322
```

<210> SEQ ID NO 32
<211> LENGTH: 2322
<212> TYPE: DNA
<213> ORGANISM: Artificial Sequence
<220> FEATURE:
<223> OTHER INFORMATION: DNA sequence to SEQ ID NO: 15

<400> SEQUENCE: 32

```
atgatcctcg atacagacta cataactgag gatggaaagc ccgtcatcag gatcttcaag     60

aaggagaacg gcgagttcaa aatagactac gacagaaact ttgagccata catctacgcg    120

ctcttgaagg acgactctgc gattgaggac gtcaagaaga taactgccga gaggcacggc    180

actaccgtta gggttgtcag ggccgagaaa gtgaagaaga agttcctagg caggccgata    240

gaggtctgga agctctactt cactcacccc caggaccagc ccgcaatcag ggacaagata    300

aaggagcatc ctgccgttgt ggacatctac gagtacgaca tccccttcgc gaagcgctac    360

ctcatagaca aaggcttaat cccgatggag ggcgacgagg aacttaagat gctcgccttc    420

gcgatcgcga cgctctatca cgagggcgag gagttcgccg aagggcctat cctgatgata    480

agctacgccg acgaggaagg ggcgcgcgtt attacctgga agaatatcga ccttccctat    540

gttgacgtcg tttccaccga gaaggagatg ataaagcgct tcctcaaggt cgtcaaggaa    600

aaggatcccg acgtcctcat aacctacaac ggcgacaact tcgacttcgc ctacctcaag    660

aagcgctccg agaagctcgg agtcaagttc atcctcggaa gggaagggag cgagccgaaa    720

atccagcgca tgggcgatcg ctttgcggtg gaggtcaagg gaaggattca cttcgacctc    780

taccccgtca ttaggagaac gattaacctc cccacttaca cccttgaggc agtatatgaa    840

gccatctttg gacagccgaa ggagaaggtc tacgctgagg agatagcgca ggcctgggaa    900

acgggcgagg gattagaaag ggtggcccgc tactcgatgg aggacgcaaa ggtaacctat    960

gaactcggaa aagaattctt ccctatggaa gcccagctct cgcgcctcgt aggccagagc   1020

ctctgggatg tatctcgctc gagtaccgga aacctcgtcg agtggttttt gctgaggaag   1080

gcctacgaga ggaatgaact tgcaccaaac aagccggacg agagggagct ggcaagaaga   1140

agggagagct acgcgggtgg atacgtcaag gagcccgaaa ggggactgtg ggagaacatc   1200

gtgtatctgg acttccgctc cctgtatcct tcgataataa tcacccataa cgtctcccct   1260

gatacactca acagggaggg ttgtgaggag tacgacgtgg ctcctcaggt aggccataag   1320

ttctgcaagg acttccccgg cttcatccca agcctcctcg gtgacctctt ggaggagaga   1380

cagaaggtaa agaagaagat gaaggccact atagacccaa tcgagaagaa actcctcgat   1440

tacaggcaac gactgatcaa gatccttgct aatagcttct acggttacta cggctatgca   1500
```

-continued

```
aaggcccgct ggtactgcaa ggagtgcgcc gagagcgtta ccgcttgggg caggcagtac   1560

atcgagacta cgataaggga aatagaggag aaatttggct ttaaagtcct ctacgcggac   1620

acagatggat ttttcgcaac aatacctgga gcggacgccg aaaccgtcaa aaagaaggca   1680

aaggagttcc tggactacat caacgccaaa ctgcccggcc tgctcgaact cgaatacgag   1740

ggcttctaca agcgcggctt cttcgtgacg aagaagaagt acgcggttat agacgaggag   1800

gacaagataa cgacgcgcgg gcttgaaata gttaggcgtg actggagcga gatagcgaag   1860

gagacgcagg cgagggttct tgaggcgata ctaaagcacg gtgacgttga agaagcggta   1920

aggattgtca aagaggttac ggagaagctg agcaagtacc aggttccacc gcagcagctg   1980

gtcatctacc agccgataac caaacacctg agggactaca aggccaaggg gccgcatgtg   2040

gctgttgcaa aacgcctcgc cgcaaggggg ataaaaatcc ggcccggaac ggtcataagc   2100

tacatcgtgc tcaaaggctc gggaaggatt ggggacaggg ctataccctt tgacgaattt   2160

gacccggcaa agcacaagta cgatgcagaa tactacatcg agaaccaggt tcttccagct   2220

gtggagagga ttctgagggc ctttggttac cgtaaagaag atttaaggta tcagaaaacg   2280

cggcaggttg gcttgggggc gtggctaaaa cctaagacat aa                      2322
```

<210> SEQ ID NO 33
<211> LENGTH: 2307
<212> TYPE: DNA
<213> ORGANISM: Artificial Sequence
<220> FEATURE:
<223> OTHER INFORMATION: DNA sequence to SEQ ID NO: 16

<400> SEQUENCE: 33

```
atgatcctcg atacagacta cataactgag gatggaaagc ccgtcatcag gatcttcaag     60

aaggagaacg gcgagttcaa aatagactac gacagaaact ttgagccata catctacgcg    120

ctcttgaagg acgactctgc gattgaggac gtcaagaaga taactgccga gaggcacggc    180

actaccgtta gggttgtcag ggccgagaaa gtgaagaaga agttcctagg caggccgata    240

gaggtctgga agctctactt cactcacccc caggaccagc ccgcaatcag ggacaagata    300

aaggagcatc ctgccgttgt ggacatctac gagtacgaca tccccttcgc gaagcgctac    360

ctcatagaca aaggcttaat cccgatggag ggcgacgagg aacttaagat gctcgccttc    420

gcgatcgcga cgctctatca cgagggcgag gagttcgccg aagggcctat cctgatgata    480

agctacgccg acgaggaagg ggcgcgcgtt attacctgga agaatatcga ccttccctat    540

gttgacgtcg tttccaccga gaaggagatg ataaagcgct tcctcaaggt cgtcaaggaa    600

aaggatcccg acgtcctcat aacctacaac ggcgacaact tcgacttcgc ctacctcaag    660

aagcgctccg agaagctcgg agtcaagttc atcctcggaa gggaagggag cgagccgaaa    720

atccagcgca tgggcgatcg ctttgcggtg gaggtcaagg gaaggattca cttcgacctc    780

taccccgtca ttaggagaac gattaacctc cccacttaca cccttgaggc agtatatgaa    840

gccatctttg gacagccgaa ggagaaggtc tacgctgagg agatagcgca ggcctgggaa    900

acgggcgagg gattagaaag ggtggcccgc tactcgatgg aggacgcaaa ggtaacctat    960

gaactcggaa aagaattctt ccctatggaa gcccagctct cgcgcctcgt aggccagagc   1020

ctctgggatg tatctcgctc gagtaccgga aacctcgtcg agtggttttt gctgaggaag   1080

gcctacgaga ggaatgaact tgcaccaaac aagccggacg agagggagct ggcaagaaga   1140

agggagagct acgcgggtgg atacgtcaag gagcccgaaa ggggactgtg ggagaacatc   1200

gtgtatctgg acttccgctc cctgtatcct tcgataataa tcacccataa cgtctcccct   1260
```

gatacactca acagggaggg ttgtgaggag tacgacgtgg ctcctcaggt aggccataag 1320
ttctgcaagg acttccccgg cttcatccca agcctcctcg gtgacctctt ggaggagaga 1380
cagaaggtaa agaagaagat gaaggccact atagacccaa tcgagaagaa actcctcgat 1440
tacaggcaac gactgatcaa gatccttgct aatagcttct acggttacta cggctatgca 1500
aaggcccgct ggtactgcaa ggagtgcgcc gagagcgtta ccgcttgggg caggcagtac 1560
atcgagacta cgataaggga aatagaggag aaatttggct ttaaagtcct ctacgcggac 1620
acagatggat ttttcgcaac aatacctgga gcggacgccg aaaccgtcaa aaagaaggca 1680
aaggagttcc tggactacat caacgccaaa ctgcccggcc tgctcgaact cgaatacgag 1740
ggcttctaca agcgcggctt cttcgtgacg aagaagaagt acgcggttat agacgaggag 1800
gacaagataa cgacgcgcgg gcttgaaata gttaggcgtg actggagcga gatagcgaag 1860
gagacgctgg cgagggttct tgaggcgata ctaaagcacg gtgacgttga agaagcggta 1920
aggattgtca aagaggttac ggagaagctg agcaagtacg aggttccacc ggagaagctg 1980
gtcatctacg agcagataac ccgcgccctg aaggactaca aggccaccgg gccgcatgtg 2040
gctgttgcaa aacgcctcgc cgcaaggggg ataaaaatcc ggcccggaac ggtcataagc 2100
tacatcgtgc tcaaaggctc gggaaggatt ggggacaggg ctataccctt tgacgaattt 2160
gacccggcaa agcacaagta cgatgcagaa tactacatcg agaaccaggt tcttcaagat 2220
gtgcagagga ttctgagggc ctttggttac aaaaatggag atttaaggtg ccagaagaca 2280
atcagacggg cttgggggcg tggctaa 2307

<210> SEQ ID NO 34
<211> LENGTH: 2256
<212> TYPE: DNA
<213> ORGANISM: Artificial Sequence
<220> FEATURE:
<223> OTHER INFORMATION: DNA sequence to SEQ ID NO: 17

<400> SEQUENCE: 34
atgatcctcg atacagacta cataactgag gatggaaagc ccgtcatcag gatcttcaag 60
aaggagaacg gcgagttcaa aatagactac gacagaaact ttgagccata catctacgcg 120
ctcttgaagg acgactctgc gattgaggac gtcaagaaga taactgccga gaggcacggc 180
actaccgtta gggttgtcag ggccgagaaa gtgaagaaga agttcctagg caggccgata 240
gaggtctgga agctctactt cactcacccc caggaccagc ccgcaatcag ggacaagata 300
aaggagcatc ctgccgttgt ggacatctac gagtacgaca tccccttcgc gaagcgctac 360
ctcatagaca aaggcttaat cccgatggag ggcgacgagg aacttaagat gctcgccttc 420
gcgatcgcga cgctctatca cgagggcgag gagttcgccg aagggcctat cctgatgata 480
agctacgccg acgaggaagg ggcgcgcgtt attacctgga agaatatcga ccttccctat 540
gttgacgtcg tttccaccga gaaggagatg ataaagcgct tcctcaaggt cgtcaaggaa 600
aaggatcccg acgtcctcat aacctacaac ggcgacaact tcgacttcgc ctacctcaag 660
aagcgctccg agaagctcgg agtcaagttc atcctcggaa gggaagggag cgagccgaaa 720
atccagcgca tgggcgatcg ctttgcggtg gaggtcaagg gaaggattca cttcgacctc 780
taccccgtca ttaggagaac gattaacctc cccacttaca cccttgaggc agtatatgaa 840
gccatctttg gacagccgaa ggagaaggtc tacgctgagg agatagcgca ggcctgggaa 900
acgggcgagg gattagaaag ggtggcccgc tactcgatgg aggacgcaaa ggtaacctat 960

```
gaactcggaa aagaattctt ccctatggaa gcccagctct cgcgcctcgt aggccagagc   1020

ctctgggatg tatctcgctc gagtaccgga aacctcgtcg agtggttttt gctgaggaag   1080

gcctacgaga ggaatgaact tgcaccaaac aagccggacg agagggagct ggcaagaaga   1140

agggagagct acgcgggtgg atacgtcaag gagcccgaaa ggggactgtg ggagaacatc   1200

gtgtatctgg acttccgctc cctgtatcct tcgataataa tcacccataa cgtctcccct   1260

gatacactca acagggaggg ttgtgaggag tacgacgtgg ctcctcaggt aggccataag   1320

ttctgcaagg acttccccgg cttcatccca agcctcctcg gtgacctctt ggaggagaga   1380

cagaaggtaa agaagaagat gaaggccact atagacccaa tcgagaagaa actcctcgat   1440

tacaggcaac gactgatcaa gatccttgct aatagcttct acggttacta cggctatgca   1500

aaggcccgct ggtactgcaa ggagtgcgcc gagagcgtta ccgcttgggg caggcagtac   1560

atcgagacta cgataaggga aatagaggag aaatttggct ttaaagtcct ctacgcggac   1620

acagatggat ttttcgcaac aatacctgga gcggacgccg aaaccgtcaa aaagaaggca   1680

aaggagttcc tggactacat caacgccaaa ctgcccggcc tgctcgaact cgaatacgag   1740

ggcttctaca agcgcggctt cttcgtgacg aagaagaagt acgcggttat agacgaggag   1800

gacaagataa cgacgcgcgg gcttgaaata gttaggcgtg actggagcga gatagcgaag   1860

gagacgcagg cgagggttct tgaggcgata ctaaagcacg gtgacgttga agaagcggta   1920

aggattgtca aagaggttac ggagaagctg agcaagtacg aggttccacc ggagaagctg   1980

gtcatctacg agcagataac ccgcgacctg aaggactaca aggccaccgg gccgcatgtg   2040

gctgttgcaa aacgcctcgc cgcaaggggg ataaaaatcc ggcccggaac ggtcataagc   2100

tacatcgtgc tcaaaggctc gggaaggatt ggggacaggg ctataccctt tgacgaattt   2160

gacccggcaa agcacaagta cgatgcagaa tactacatcg agaaccaggt tcttccatat   2220

gtgctagatg attctgaggg cctttggtta caataa                             2256


<210> SEQ ID NO 35
<211> LENGTH: 2271
<212> TYPE: DNA
<213> ORGANISM: Artificial Sequence
<220> FEATURE:
<223> OTHER INFORMATION: DNA sequence to SEQ ID NO: 18

<400> SEQUENCE: 35

atgatcctcg atacagacta cataactgag gatggaaagc ccgtcatcag gatcttcaag     60

aaggagaacg gcgagttcaa aatagactac gacagaaact ttgagccata catctacgcg    120

ctcttgaagg acgactctgc gattgaggac gtcaagaaga taactgccga gaggcacggc    180

actaccgtta gggttgtcag ggccgagaaa gtgaagaaga agttcctagg caggccgata    240

gaggtctgga agctctactt cactcacccc caggaccagc ccgcaatcag ggacaagata    300

aaggagcatc ctgccgttgt ggacatctac gagtacgaca tccccttcgc gaagcgctac    360

ctcatagaca aaggcttaat cccgatggag ggcgacgagg aacttaagat gctcgccttc    420

gcgatcgcga cgctctatca cgagggcgag gagttcgccg aagggcctat cctgatgata    480

agctacgccg acgaggaagg ggcgcgcgtt attacctgga agaatatcga ccttccctat    540

gttgacgtcg tttccaccga gaaggagatg ataaagcgct tcctcaaggt cgtcaaggaa    600

aaggatcccg acgtcctcat aacctacaac ggcgacaact tcgacttcgc ctacctcaag    660

aagcgctccg agaagctcgg agtcaagttc atcctcggaa gggaagggag cgagccgaaa    720

atccagcgca tgggcgatcg ctttgcggtg gaggtcaagg gaaggattca cttcgacctc    780
```

```
taccccgtca ttaggagaac gattaacctc cccacttaca cccttgaggc agtatatgaa    840

gccatctttg gacagccgaa ggagaaggtc tacgctgagg agatagcgca ggcctgggaa    900

acgggcgagg gattagaaag ggtggcccgc tactcgatgg aggacgcaaa ggtaacctat    960

gaactcggaa aagaattctt ccctatggaa gcccagctct cgcgcctcgt aggccagagc   1020

ctctgggatg tatctcgctc gagtaccgga aacctcgtcg agtggttttt gctgaggaag   1080

gcctacgaga ggaatgaact tgcaccaaac aagccggacg agagggagct ggcaagaaga   1140

agggagagct acgcgggtgg atacgtcaag gagcccgaaa ggggactgtg ggagaacatc   1200

gtgtatctgg acttccgctc cctgtatcct tcgataataa tcacccataa cgtctcccct   1260

gatacactca acagggaggg ttgtgaggag tacgacgtgg ctcctcaggt aggccataag   1320

ttctgcaagg acttccccgg cttcatccca agcctcctcg gtgacctctt ggaggagaga   1380

cagaaggtaa agaagaagat gaaggccact atagacccaa tcgagaagaa actcctcgat   1440

tacaggcaac gactgatcaa aatccttgct aatagcttct acggttacta cggctatgca   1500

aaggcccgct ggtactgcaa ggagtgcgcc gagagcgtta ccgcttgggg caggcagtac   1560

atcgagacta cgataaggga aatagaggag aaatttggct ttaaagtcct ctacgcggac   1620

acagatggat ttttcgcaac aatacctgga gcggacgccg aaaccgtcaa aaagaaggca   1680

aaggagttcc tggactacat caacgccaaa ctgcccggcc tgctcgaact cgaatacgag   1740

ggcttctaca agcgcggctt cttcgtgacg aagaagaagt acgcggttat agacgaggag   1800

gacaagataa cgacgcgcgg gcttgaaata gttaggcgtg actggagcga gatagcgaag   1860

gagacgcagg cgagggttct tgaggcgata ctaaagcacg gtgacgttga agaagcggta   1920

aggattgtca aagaggttac ggagaagctg agcaagtacg aggttccacc ggagaagctg   1980

gtcatctacg agcagataac ccgcgacctg aaggactaca aggccaccgg gccgcatgtg   2040

gctgttgcaa aacgcctcgc cgcaaggggg ataaaaatcc ggcccggaac ggtcataagc   2100

tacatcgtgc tcaaaggctc gggaaggatt ggggacaggg ctataccctt tgacgaattt   2160

gacccggcaa agcacaagta cgatgcagaa tactacatcg agaaccaggt tcttccagct   2220

gtgcagatga ttttgagggc ctttggttac caaaaagatg atttaaggta g             2271
```

```
<210> SEQ ID NO 36
<211> LENGTH: 2319
<212> TYPE: DNA
<213> ORGANISM: Artificial Sequence
<220> FEATURE:
<223> OTHER INFORMATION: DNA sequence to SEQ ID NO: 37

<400> SEQUENCE: 36

atgatcctcg atacagacta cataactgag gatggaaagc ccgtcatcag gatcttcaag     60

aaggagaacg gcgagttcaa aatagactac gacagaaact ttgagccata catctacgcg    120

ctcttgaagg acgactctgc gattgaggac gtcaagaaga taactgccga gaggcacggc    180

actaccgtta gggttgtcag ggccgagaaa gtgaagaaga agttcctagg caggccgata    240

gaggtctgga agctctactt cactcacccc caggaccagc ccgcaatcag ggacaagata    300

aaggagcatc ctgccgttgt ggacatctac gagtacgaca tccccttcgc gaagcgctac    360

ctcatagaca aaggcttaat cccgatggag ggcgacgagg aacttaagat gctcgccttc    420

gcgatcgcga cgctctatca cgagggcgag gagttcgccg aagggcctat cctgatgata    480

agctacgccg acgaggaagg ggcgcgcgtt attacctgga agaatatcga ccttccctat    540
```

```
gttgacgtcg tttccaccga gaaggagatg ataaagcgct tcctcaaggt cgtcaaggaa    600

aaggatcccg acgtcctcat aacctacaac ggcgacaact tcgacttcgc ctacctcaag    660

aagcgctccg agaagctcgg agtcaagttc atcctcggaa gggaagggag cgagccgaaa    720

atccagcgca tgggcgatcg ctttgcggtg gaggtcaagg gaaggattca cttcgacctc    780

taccccgtca ttaggagaac gattaacctc cccacttaca cccttgaggc agtatatgaa    840

gccatctttg gacagccgaa ggagaaggtc tacgctgagg agatagcgca ggcctgggaa    900

acgggcgagg gattagaaag ggtggcccgc tactcgatgg aggacgcaaa ggtaacctat    960

gaactcggaa aagaattctt ccctatggaa gcccagctct cgcgcctcgt aggccagagc   1020

ctctgggatg tatctcgctc gagtaccgga aacctcgtcg agtggttttt gctgaggaag   1080

gcctacgaga ggaatgaact tgcaccaaac aagccggacg agagggagct ggcaagaaga   1140

agggagagct acgcgggtgg atacgtcaag gagcccgaaa ggggactgtg ggagaacatc   1200

gtgtatccgg acttccgctc cctgaaccct tcgataataa tcacccataa cgtctcccct   1260

gatacactca acagggaggg ttgtgaggag tacgacgtgg ctcctcaggt aggccataag   1320

ttctgcaagg acttccccgg cttcatccca agcctcctcg gtgacctctt ggaggagaga   1380

cagaaggtaa agaagaagat gaaggccact atagacccaa tcgagaagaa actcctcgat   1440

tacaggcaac gactgatcaa gatccttgct aatagcttct acggttacta cggctatgca   1500

aaggcccgct ggtactgcaa ggagtgcgcc gagagcgtta ccgcttgggg caggcagtac   1560

atcgagacta cgataaggga aatagaggag aaatttggct ttaaagtcct ctacgcggac   1620

acagatggat tttcgcaac aatacctgga gcggacgccg aaaccgtcaa aaagaaggca    1680

aaggagttcc tggactacat caacgccaaa ctgcccggcc tgctcgaact cgaatacgag   1740

ggcttctaca agcgcggctt cttcgtgacg aagaagaagt acgcggttat agacgaggag   1800

gacaagataa cgacgcgcgg gcttgaaata gttaggcgtg actggagcga gatagcgaag   1860

gagacgcagg cgagggttct tgaggcgata ctaaagcacg gtgacgttga agaagcggta   1920

aggattgtca aagaggttac ggagaagctg agcaagtacg aggttccaac gcagcacctg   1980

gtcatccacc agcagataac cagagccctg aacgactaca aggccatcgg gccgcatgtg   2040

gctgttgcaa aacgcctcgc cgcaaggggg ataaaaatcc ggcccggaac ggtcataagc   2100

tacatcgtgc tcaaaggctc gggaaggatt ggggacaggg ctatacccttt tgacgaattt  2160

gacccggcaa agcacaagta cgatgcagaa tactacatcg agaaccaggt tcttccagct   2220

gtggagagga ttctgagggc ctttggttac cgtaaagaag atttaaggta tcagaaaacg   2280

cggcaggttg gcttgggggc gtggctaaaa cctaagaca                          2319
```

<210> SEQ ID NO 37
<211> LENGTH: 773
<212> TYPE: PRT
<213> ORGANISM: Artificial Sequence
<220> FEATURE:
<223> OTHER INFORMATION: Mutated protein according to specification

<400> SEQUENCE: 37

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45
```

-continued

```
Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Pro Asp Phe Arg Ser Leu Asn Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
```

```
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Thr Gln His Leu Val Ile His Gln Gln Ile Thr Arg Ala Leu Asn Asp
            660                 665                 670

Tyr Lys Ala Ile Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 38
<211> LENGTH: 2319
<212> TYPE: PRT
<213> ORGANISM: Artificial Sequence
<220> FEATURE:
<223> OTHER INFORMATION: DNA sequence to protein SEQ ID NO: 39

<400> SEQUENCE: 38

Ala Thr Gly Ala Thr Cys Cys Thr Cys Gly Ala Thr Ala Cys Ala Gly
1               5                   10                  15

Ala Cys Thr Ala Cys Ala Thr Ala Ala Cys Thr Gly Ala Gly Gly Ala
            20                  25                  30

Thr Gly Gly Ala Ala Ala Gly Cys Cys Cys Gly Thr Cys Ala Thr Cys
        35                  40                  45

Ala Gly Gly Ala Thr Cys Thr Thr Cys Ala Ala Gly Ala Ala Gly Gly
```

50 55 60

Ala Gly Ala Ala Cys Gly Gly Cys Gly Ala Gly Thr Thr Cys Ala Ala
65 70 75 80

Ala Ala Thr Ala Gly Ala Cys Thr Ala Cys Gly Ala Cys Ala Gly Ala
85 90 95

Ala Ala Cys Thr Thr Thr Gly Ala Gly Cys Cys Ala Thr Ala Cys Ala
100 105 110

Thr Cys Thr Ala Cys Gly Cys Gly Cys Thr Cys Thr Thr Gly Ala Ala
115 120 125

Gly Gly Ala Cys Gly Ala Cys Thr Cys Thr Gly Cys Gly Ala Thr Thr
130 135 140

Gly Ala Gly Gly Ala Cys Gly Thr Cys Ala Ala Gly Ala Ala Gly Ala
145 150 155 160

Thr Ala Ala Cys Thr Gly Cys Cys Gly Ala Gly Ala Gly Gly Cys Ala
165 170 175

Cys Gly Gly Cys Ala Cys Thr Ala Cys Cys Gly Thr Thr Ala Gly Gly
180 185 190

Gly Thr Thr Gly Thr Cys Ala Gly Gly Gly Cys Cys Gly Ala Gly Ala
195 200 205

Ala Ala Gly Thr Gly Ala Ala Gly Ala Ala Gly Ala Ala Gly Thr Thr
210 215 220

Cys Cys Thr Ala Gly Gly Cys Ala Gly Gly Cys Cys Gly Ala Thr Ala
225 230 235 240

Gly Ala Gly Gly Thr Cys Thr Gly Gly Ala Ala Gly Cys Thr Cys Thr
245 250 255

Ala Cys Thr Thr Cys Ala Cys Thr Cys Ala Cys Cys Cys Cys Cys Ala
260 265 270

Gly Gly Ala Cys Cys Ala Gly Cys Cys Cys Gly Cys Ala Ala Thr Cys
275 280 285

Ala Gly Gly Gly Ala Cys Ala Ala Gly Ala Thr Ala Ala Ala Gly Gly
290 295 300

Ala Gly Cys Ala Thr Cys Cys Thr Gly Cys Cys Gly Thr Thr Gly Thr
305 310 315 320

Gly Gly Ala Cys Ala Thr Cys Thr Ala Cys Gly Ala Gly Thr Ala Cys
325 330 335

Gly Ala Cys Ala Thr Cys Cys Cys Cys Thr Thr Cys Gly Cys Gly Ala
340 345 350

Ala Gly Cys Gly Cys Thr Ala Cys Cys Thr Cys Ala Thr Ala Gly Ala
355 360 365

Cys Ala Ala Ala Gly Gly Cys Thr Thr Ala Ala Thr Cys Cys Cys Gly
370 375 380

Ala Thr Gly Gly Ala Gly Gly Gly Cys Gly Ala Cys Gly Ala Gly Gly
385 390 395 400

Ala Ala Cys Thr Thr Ala Ala Gly Ala Thr Gly Cys Thr Cys Gly Cys
405 410 415

Cys Thr Thr Cys Gly Cys Gly Ala Thr Cys Gly Cys Gly Ala Cys Gly
420 425 430

Cys Thr Cys Thr Ala Thr Cys Ala Cys Gly Ala Gly Gly Gly Cys Gly
435 440 445

Ala Gly Gly Ala Gly Thr Thr Cys Gly Cys Cys Gly Ala Ala Gly Gly
450 455 460

Gly Cys Cys Thr Ala Thr Cys Cys Thr Gly Ala Thr Gly Ala Thr Ala
465 470 475 480

```
Ala Gly Cys Thr Ala Cys Gly Cys Cys Gly Ala Cys Gly Ala Gly Gly
                485                 490                 495

Ala Ala Gly Gly Gly Gly Cys Gly Cys Gly Cys Gly Thr Thr Ala Thr
            500                 505                 510

Thr Ala Cys Cys Thr Gly Gly Ala Ala Gly Ala Ala Thr Ala Thr Cys
        515                 520                 525

Gly Ala Cys Cys Thr Thr Cys Cys Cys Thr Ala Thr Gly Thr Thr Gly
    530                 535                 540

Ala Cys Gly Thr Cys Gly Thr Thr Thr Cys Cys Ala Cys Cys Gly Ala
545                 550                 555                 560

Gly Ala Ala Gly Gly Ala Gly Ala Thr Gly Ala Thr Ala Ala Ala Gly
                565                 570                 575

Cys Gly Cys Thr Thr Cys Cys Thr Cys Ala Ala Gly Gly Thr Cys Gly
            580                 585                 590

Thr Cys Ala Ala Gly Gly Ala Ala Ala Ala Gly Gly Ala Thr Cys Cys
        595                 600                 605

Cys Gly Ala Cys Gly Thr Cys Cys Thr Cys Ala Thr Ala Ala Cys Cys
    610                 615                 620

Thr Ala Cys Ala Ala Cys Gly Gly Cys Gly Ala Cys Ala Ala Cys Thr
625                 630                 635                 640

Thr Cys Gly Ala Cys Thr Thr Cys Gly Cys Cys Thr Ala Cys Cys Thr
                645                 650                 655

Cys Ala Ala Gly Ala Ala Gly Cys Gly Cys Thr Cys Cys Gly Ala Gly
            660                 665                 670

Ala Ala Gly Cys Thr Cys Gly Gly Ala Gly Thr Cys Ala Ala Gly Thr
        675                 680                 685

Thr Cys Ala Thr Cys Cys Thr Cys Gly Gly Ala Ala Gly Gly Gly Ala
    690                 695                 700

Ala Gly Gly Gly Ala Gly Cys Gly Ala Gly Cys Cys Gly Ala Ala Ala
705                 710                 715                 720

Ala Thr Cys Cys Ala Gly Cys Gly Cys Ala Thr Gly Gly Gly Cys Gly
                725                 730                 735

Ala Thr Cys Gly Cys Thr Thr Thr Gly Cys Gly Gly Thr Gly Gly Ala
            740                 745                 750

Gly Gly Thr Cys Ala Ala Gly Gly Gly Ala Ala Gly Gly Ala Thr Thr
        755                 760                 765

Cys Ala Cys Thr Thr Cys Gly Ala Cys Cys Thr Cys Thr Ala Cys Cys
    770                 775                 780

Cys Cys Gly Thr Cys Ala Thr Thr Ala Gly Gly Ala Gly Ala Ala Cys
785                 790                 795                 800

Gly Ala Thr Thr Ala Ala Cys Cys Thr Cys Cys Cys Cys Ala Cys Thr
                805                 810                 815

Thr Ala Cys Ala Cys Cys Cys Thr Thr Gly Ala Gly Gly Cys Ala Gly
            820                 825                 830

Thr Ala Thr Ala Thr Gly Ala Ala Gly Cys Cys Ala Thr Cys Thr Thr
        835                 840                 845

Thr Gly Gly Ala Cys Ala Gly Cys Cys Gly Ala Ala Gly Gly Ala Gly
    850                 855                 860

Ala Ala Gly Gly Thr Cys Thr Ala Cys Gly Cys Thr Gly Ala Gly Gly
865                 870                 875                 880

Ala Gly Ala Thr Ala Gly Cys Gly Cys Ala Gly Gly Cys Cys Thr Gly
                885                 890                 895
```

```
Gly Gly Ala Ala Ala Cys Gly Gly Gly Cys Gly Ala Gly Gly Gly Ala
            900                 905                 910

Thr Thr Ala Gly Ala Ala Ala Gly Gly Gly Thr Gly Gly Cys Cys Cys
        915                 920                 925

Gly Cys Thr Ala Cys Thr Cys Gly Ala Thr Gly Gly Ala Gly Gly Ala
    930                 935                 940

Cys Gly Cys Ala Ala Ala Gly Gly Thr Ala Ala Cys Cys Thr Ala Thr
945                 950                 955                 960

Gly Ala Ala Cys Thr Cys Gly Gly Ala Ala Ala Ala Gly Ala Ala Thr
                965                 970                 975

Thr Cys Thr Thr Cys Cys Cys Thr Ala Thr Gly Gly Ala Ala Gly Cys
            980                 985                 990

Cys Cys Ala Gly Cys Thr Cys Thr  Cys Gly Cys Gly Cys  Cys Thr Cys
        995                 1000                1005

Gly Thr  Ala Gly Gly Cys Cys  Ala Gly Ala Gly Cys  Cys Thr Cys
    1010                1015                1020

Thr Gly  Gly Gly Ala Thr Gly  Thr Ala Thr Cys Thr  Cys Gly Cys
    1025                1030                1035

Thr Cys  Gly Ala Gly Thr Ala  Cys Cys Gly Gly Ala  Ala Ala Cys
    1040                1045                1050

Cys Thr  Cys Gly Thr Cys Gly  Ala Gly Thr Gly Gly  Thr Thr Thr
    1055                1060                1065

Thr Thr  Gly Cys Thr Gly Ala  Gly Gly Ala Ala Gly  Gly Cys Cys
    1070                1075                1080

Thr Ala  Cys Gly Ala Gly Ala  Gly Gly Ala Ala Thr  Gly Ala Ala
    1085                1090                1095

Cys Thr  Thr Gly Cys Ala Cys  Cys Ala Ala Ala Cys  Ala Ala Gly
    1100                1105                1110

Cys Cys  Gly Gly Ala Cys Gly  Ala Gly Ala Gly Gly  Gly Ala Gly
    1115                1120                1125

Cys Thr  Gly Gly Cys Ala Ala  Gly Ala Ala Gly Ala  Ala Gly Gly
    1130                1135                1140

Gly Ala  Gly Ala Gly Cys Thr  Ala Cys Gly Cys Gly  Gly Gly Thr
    1145                1150                1155

Gly Gly  Ala Thr Ala Cys Gly  Thr Cys Ala Ala Gly  Gly Ala Gly
    1160                1165                1170

Cys Cys  Cys Gly Ala Ala Ala  Gly Gly Gly Gly Ala  Cys Thr Gly
    1175                1180                1185

Thr Gly  Gly Gly Ala Gly Ala  Ala Cys Ala Thr Cys  Gly Thr Gly
    1190                1195                1200

Thr Ala  Thr Cys Cys Gly Gly  Ala Cys Thr Thr Cys  Cys Gly Cys
    1205                1210                1215

Thr Cys  Cys Cys Thr Gly Ala  Gly Cys Cys Cys Thr  Thr Cys Gly
    1220                1225                1230

Ala Thr  Ala Ala Thr Ala Ala  Thr Cys Ala Cys Cys  Cys Ala Thr
    1235                1240                1245

Ala Ala  Cys Gly Thr Cys Thr  Cys Cys Cys Cys Thr  Gly Ala Thr
    1250                1255                1260

Ala Cys  Ala Cys Thr Cys Ala  Ala Cys Ala Gly Gly  Gly Ala Gly
    1265                1270                1275

Gly Gly  Thr Thr Gly Thr Gly  Ala Gly Gly Ala Gly  Thr Ala Cys
    1280                1285                1290

Gly Ala  Cys Gly Thr Gly Gly  Cys Thr Cys Cys Thr  Cys Ala Gly
```

```
    1295                1300                1305

Gly Thr  Ala Gly Gly Cys Cys  Ala Thr Ala Ala Gly  Thr Thr Cys
    1310                1315                1320

Thr Gly  Cys Ala Ala Gly Gly  Ala Cys Thr Thr Cys  Cys Cys Cys
    1325                1330                1335

Gly Gly  Cys Thr Thr Cys Ala  Thr Cys Cys Cys Ala  Ala Gly Cys
    1340                1345                1350

Cys Thr  Cys Cys Thr Cys Gly  Gly Thr Gly Ala Cys  Cys Thr Cys
    1355                1360                1365

Thr Thr  Gly Gly Ala Gly Gly  Ala Gly Ala Gly Ala  Cys Ala Gly
    1370                1375                1380

Ala Ala  Gly Gly Thr Ala Ala  Ala Gly Ala Ala Gly  Ala Ala Gly
    1385                1390                1395

Ala Thr  Gly Ala Ala Gly Gly  Cys Cys Ala Cys Thr  Ala Thr Ala
    1400                1405                1410

Gly Ala  Cys Cys Cys Ala Ala  Thr Cys Gly Ala Gly  Ala Ala Gly
    1415                1420                1425

Ala Ala  Ala Cys Thr Cys Cys  Thr Cys Gly Ala Thr  Thr Ala Cys
    1430                1435                1440

Ala Gly  Gly Cys Ala Ala Cys  Gly Ala Cys Thr Gly  Ala Thr Cys
    1445                1450                1455

Ala Ala  Gly Ala Thr Cys Cys  Thr Thr Gly Cys Thr  Ala Ala Thr
    1460                1465                1470

Ala Gly  Cys Thr Thr Cys Thr  Ala Cys Gly Gly Thr  Thr Ala Cys
    1475                1480                1485

Thr Ala  Cys Gly Gly Cys Thr  Ala Thr Gly Cys Ala  Ala Ala Gly
    1490                1495                1500

Gly Cys  Cys Cys Gly Cys Thr  Gly Gly Thr Ala Cys  Thr Gly Cys
    1505                1510                1515

Ala Ala  Gly Gly Ala Gly Thr  Gly Cys Gly Cys Cys  Gly Ala Gly
    1520                1525                1530

Ala Gly  Cys Gly Thr Thr Ala  Cys Cys Gly Cys Thr  Thr Gly Gly
    1535                1540                1545

Gly Gly  Cys Ala Gly Gly Cys  Ala Gly Thr Ala Cys  Ala Thr Cys
    1550                1555                1560

Gly Ala  Gly Ala Cys Thr Ala  Cys Gly Ala Thr Ala  Ala Gly Gly
    1565                1570                1575

Gly Ala  Ala Ala Thr Ala Gly  Ala Gly Gly Ala Gly  Ala Ala Ala
    1580                1585                1590

Thr Thr  Thr Gly Gly Cys Thr  Thr Thr Ala Ala Ala  Gly Thr Cys
    1595                1600                1605

Cys Thr  Cys Thr Ala Cys Gly  Cys Gly Gly Ala Cys  Ala Cys Ala
    1610                1615                1620

Gly Ala  Thr Gly Gly Ala Thr  Thr Thr Thr Thr Cys  Gly Cys Ala
    1625                1630                1635

Ala Cys  Ala Ala Thr Ala Cys  Cys Thr Gly Gly Ala  Gly Cys Gly
    1640                1645                1650

Gly Ala  Cys Gly Cys Cys Gly  Ala Ala Ala Cys Cys  Gly Thr Cys
    1655                1660                1665

Ala Ala  Ala Ala Ala Gly Ala  Ala Gly Gly Cys Ala  Ala Ala Gly
    1670                1675                1680

Gly Ala  Gly Thr Thr Cys Cys  Thr Gly Gly Ala Cys  Thr Ala Cys
    1685                1690                1695
```

-continued

```
Ala Thr  Cys Ala Ala Cys Gly  Cys Cys Ala Ala Ala  Cys Thr Gly
    1700                 1705                 1710

Cys Cys  Cys Gly Gly Cys Cys  Thr Gly Cys Thr Cys  Gly Ala Ala
    1715                 1720                 1725

Cys Thr  Cys Gly Ala Ala Thr  Ala Cys Gly Ala Gly  Gly Gly Cys
    1730                 1735                 1740

Thr Thr  Cys Thr Ala Cys Ala  Ala Gly Cys Gly Cys  Gly Gly Cys
    1745                 1750                 1755

Thr Thr  Cys Thr Thr Cys Gly  Thr Gly Ala Cys Gly  Ala Ala Gly
    1760                 1765                 1770

Ala Ala  Gly Ala Ala Gly Thr  Ala Cys Gly Cys Gly  Gly Thr Thr
    1775                 1780                 1785

Ala Thr  Ala Gly Ala Cys Gly  Ala Gly Gly Ala Gly  Gly Ala Cys
    1790                 1795                 1800

Ala Ala  Gly Ala Thr Ala Ala  Cys Gly Ala Cys Gly  Cys Gly Cys
    1805                 1810                 1815

Gly Gly  Gly Cys Thr Thr Gly  Ala Ala Ala Thr Ala  Gly Thr Thr
    1820                 1825                 1830

Ala Gly  Gly Cys Gly Thr Gly  Ala Cys Thr Gly Gly  Ala Gly Cys
    1835                 1840                 1845

Gly Ala  Gly Ala Thr Ala Gly  Cys Gly Ala Ala Gly  Gly Ala Gly
    1850                 1855                 1860

Ala Cys  Gly Cys Ala Gly Gly  Cys Gly Ala Gly Gly  Gly Thr Thr
    1865                 1870                 1875

Cys Thr  Thr Gly Ala Gly Gly  Cys Gly Ala Thr Ala  Cys Thr Ala
    1880                 1885                 1890

Ala Ala  Gly Cys Ala Cys Gly  Gly Thr Gly Ala Cys  Gly Thr Thr
    1895                 1900                 1905

Gly Ala  Ala Gly Ala Ala Gly  Cys Gly Gly Thr Ala  Ala Gly Gly
    1910                 1915                 1920

Ala Thr  Thr Gly Thr Cys Ala  Ala Ala Gly Ala Gly  Gly Thr Thr
    1925                 1930                 1935

Ala Cys  Gly Gly Ala Gly Ala  Ala Gly Cys Thr Gly  Ala Gly Cys
    1940                 1945                 1950

Ala Ala  Gly Thr Ala Cys Gly  Ala Gly Gly Thr Thr  Cys Cys Ala
    1955                 1960                 1965

Ala Cys  Gly Cys Ala Gly Cys  Ala Cys Cys Thr Gly  Gly Thr Cys
    1970                 1975                 1980

Ala Thr  Cys Cys Ala Cys Cys  Ala Gly Cys Ala Gly  Ala Thr Ala
    1985                 1990                 1995

Ala Cys  Cys Ala Gly Ala Gly  Cys Cys Cys Thr Gly  Ala Ala Cys
    2000                 2005                 2010

Gly Ala  Cys Thr Ala Cys Ala  Ala Gly Gly Cys Cys  Ala Thr Cys
    2015                 2020                 2025

Gly Gly  Gly Cys Cys Gly Cys  Ala Thr Gly Thr Gly  Gly Cys Thr
    2030                 2035                 2040

Gly Thr  Thr Gly Cys Ala Ala  Ala Ala Cys Gly Cys  Cys Thr Cys
    2045                 2050                 2055

Gly Cys  Cys Gly Cys Ala Ala  Gly Gly Gly Gly Gly  Ala Thr Ala
    2060                 2065                 2070

Ala Ala  Ala Ala Thr Cys Cys  Gly Gly Cys Cys Cys  Gly Gly Ala
    2075                 2080                 2085
```

```
Ala Cys  Gly Gly Thr Cys Ala  Thr Ala Ala Gly Cys  Thr Ala Cys
    2090                 2095                 2100

Ala Thr  Cys Gly Thr Gly Cys  Thr Cys Ala Ala Ala  Gly Gly Cys
    2105                 2110                 2115

Thr Cys  Gly Gly Gly Ala Ala  Gly Gly Ala Thr Thr  Gly Gly Gly
    2120                 2125                 2130

Gly Ala  Cys Ala Gly Gly Gly  Cys Thr Ala Thr Ala  Cys Cys Cys
    2135                 2140                 2145

Thr Thr  Thr Gly Ala Cys Gly  Ala Ala Thr Thr Thr  Gly Ala Cys
    2150                 2155                 2160

Cys Cys  Gly Gly Cys Ala Ala  Ala Gly Cys Ala Cys  Ala Ala Gly
    2165                 2170                 2175

Thr Ala  Cys Gly Ala Thr Gly  Cys Ala Gly Ala Ala  Thr Ala Cys
    2180                 2185                 2190

Thr Ala  Cys Ala Thr Cys Gly  Ala Gly Ala Ala Cys  Cys Ala Gly
    2195                 2200                 2205

Gly Thr  Thr Cys Thr Thr Cys  Cys Ala Gly Cys Thr  Gly Thr Gly
    2210                 2215                 2220

Gly Ala  Gly Ala Gly Gly Ala  Thr Thr Cys Thr Gly  Ala Gly Gly
    2225                 2230                 2235

Gly Cys  Cys Thr Thr Thr Gly  Gly Thr Thr Ala Cys  Cys Gly Thr
    2240                 2245                 2250

Ala Ala  Ala Gly Ala Ala Gly  Ala Thr Thr Thr Ala  Ala Gly Gly
    2255                 2260                 2265

Thr Ala  Thr Cys Ala Gly Ala  Ala Ala Ala Cys Gly  Cys Gly Gly
    2270                 2275                 2280

Cys Ala  Gly Gly Thr Thr Gly  Gly Cys Thr Thr Gly  Gly Gly Gly
    2285                 2290                 2295

Gly Cys  Gly Thr Gly Gly Cys  Thr Ala Ala Ala Ala  Cys Cys Thr
    2300                 2305                 2310

Ala Ala  Gly Ala Cys Ala
    2315


<210> SEQ ID NO 39
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 39

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110
```

```
Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Pro Asp Phe Arg Ser Leu Ser Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
```

```
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Thr Gln His Leu Val Ile His Gln Gln Ile Thr Arg Ala Leu Asn Asp
            660                 665                 670

Tyr Lys Ala Ile Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770
```

<210> SEQ ID NO 40
<211> LENGTH: 2319
<212> TYPE: DNA
<213> ORGANISM: Artificial Sequence
<220> FEATURE:
<223> OTHER INFORMATION: DNA sequence to SEQ ID NO: 41

<400> SEQUENCE: 40

```
atgatcctcg atacagacta cataactgag gatggaaagc ccgtcatcag gatcttcaag     60

aaggagaacg gcgagttcaa aatagactac gacagaaact ttgagccata catctacgcg    120

ctcttgaagg acgactctgc gattgaggac gtcaagaaga taactgccga gaggcacggc    180

actaccgtta gggttgtcag ggccgagaaa gtgaagaaga agttcctagg caggccgata    240

gaggtctgga agctctactt cactcacccc caggaccagc ccgcaatcag ggacaagata    300

aaggagcatc ctgccgttgt ggacatctac gagtacgaca tcccccttcgc gaagcgctac    360

ctcatagaca aaggcttaat cccgatggag ggcgacgagg aacttaagat gctcgccttc    420

gcgatcgcga cgctctatca cgagggcgag gagttcgccg aagggcctat cctgatgata    480

agctacgccg acgaggaagg ggcgcgcgtt attacctgga agaatatcga ccttccctat    540

gttgacgtcg tttccaccga gaaggagatg ataaagcgct tcctcaaggt cgtcaaggaa    600

aaggatcccg acgtcctcat aacctacaac ggcgacaact tcgacttcgc ctacctcaag    660
```

```
aagcgctccg agaagctcgg agtcaagttc atcctcggaa gggaagggag cgagccgaaa    720

atccagcgca tgggcgatcg ctttgcggtg gaggtcaagg gaaggattca cttcgacctc    780

taccccgtca ttaggagaac gattaacctc cccacttaca cccttgaggc agtatatgaa    840

gccatctttg gacagccgaa ggagaaggtc tacgctgagg agatagcgca ggcctgggaa    900

acgggcgagg gattagaaag ggtggcccgc tactcgatgg aggacgcaaa ggtaacctat    960

gaactcggaa aagaattctt ccctatggaa gcccagctct cgcgcctcgt aggccagagc   1020

ctctgggatg tatctcgctc gagtaccgga aacctcgtcg agtggttttt gctgaggaag   1080

gcctacgaga ggaatgaact tgcaccaaac aagccggacg agagggagct ggcaagaaga   1140

agggagagct acgcgggtgg atacgtcaag gagcccgaaa ggggactgtg ggagaacatc   1200

gtgtatctgg acttccgctc cctgtatcct tcgataataa tcacccataa cgtctcccct   1260

gatacactca acagggaggg ttgtgaggag tacgacgtgg ctcctcaggt aggccataag   1320

ttctgcaagg acttccccgg cttcatccca agcctcctcg gtgacctctt ggaggagaga   1380

cagaaggtaa agaagaagat gaaggccact atagacccaa tcgagaagaa actcctcgat   1440

tacaggcaac gactgatcaa aatccttgct aatagcttct acggttacta cggctatgca   1500

aaggcccgct ggtactgcaa ggagtgcgcc gagagcgtta ccgcttgggg caggcagtac   1560

atcgagacta cgataaggga aatagaggag aaatttggct ttaaagtcct ctacgcggac   1620

acagatggat tttcgcaac aatacctgga gcggacgccg aaaccgtcaa aaagaaggca   1680

aaggagttcc tggactacat caacgccaaa ctgcccggcc tgctcgaact cgaatacgag   1740

ggcttctaca agcgcggctt cttcgtgacg aagaagaagt acgcggttat agacgaggag   1800

gacaagataa cgacgcgcgg gcttgaaata gttaggcgtg actggagcga gatagcgaag   1860

gagacgcagg cgagggttct tgaggcgata ctaaagcacg gtgacgttga agaagcggta   1920

aggattgtca aagaggttac ggagaagctg agcaagtacg aggttccacc ggagaagctg   1980

gtcatctacc agcagataac ccgcgacctg aaggactaca aggccaccgg gccgcatgtg   2040

gctgttgcaa aacgcctcgc cgcaaggggg ataaaaatcc ggcccggaac ggtcataagc   2100

tacatcgtgc tcaaaggctc gggaaggatt ggggacaggg ctataccctt tgacgaattt   2160

gacccggcaa agcacaagta cgatgcagaa tactacatcg agaaccaggt tcttccagct   2220

gtggagagga ttctgagggc ctttggttac cgtaaagaag atttaaggta tcagaaaacg   2280

cggcaggttg gcttgggggc gtggctaaaa cctaagaca                          2319
```

<210> SEQ ID NO 41
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 41

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
```

-continued

```
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495
```

```
Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Gln Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770
```

<210> SEQ ID NO 42
<211> LENGTH: 2319
<212> TYPE: DNA
<213> ORGANISM: Artificial Sequence
<220> FEATURE:
<223> OTHER INFORMATION: DNA sequence to SEQ ID NO: 43

<400> SEQUENCE: 42

```
atgatcctcg atacagacta cataactgag gatggaaagc ccgtcatcag gatcttcaag      60

aaggagaacg gcgagttcaa aatagactac gacagaaact ttgagccata catctacgcg     120

ctcttgaagg acgactctgc gattgaggac gtcaagaaga taactgccga gaggcacggc     180

actaccgtta gggttgtcag ggccgagaaa gtgaagaaga agttcctagg caggccgata     240

gaggtctgga agctctactt cactcacccc caggaccagc ccgcaatcag ggacaagata     300

aaggagcatc ctgccgttgt ggacatctac gagtacgaca tcccctttcgc gaagcgctac    360

ctcatagaca aaggcttaat cccgatggag ggcgacgagg aacttaagat gctcgccttc     420
```

-continued gcgatcgcga cgctctatca cgagggcgag gagttcgccg aagggcctat cctgatgata 480
agctacgccg acgaggaagg ggcgcgcgtt attacctgga agaatatcga ccttccctat 540
gttgacgtcg tttccaccga gaaggagatg ataaagcgct tcctcaaggt cgtcaaggaa 600
aaggatcccg acgtcctcat aacctacaac ggcgacaact tcgacttcgc ctacctcaag 660
aagcgctccg agaagctcgg agtcaagttc atcctcggaa gggaagggag cgagccgaaa 720
atccagcgca tgggcgatcg ctttgcggtg gaggtcaagg gaaggattca cttcgacctc 780
taccccgtca ttaggagaac gattaacctc cccacttaca cccttgaggc agtatatgaa 840
gccatctttg gacagccgaa ggagaaggtc tacgctgagg agatagcgca ggcctgggaa 900
acgggcgagg gattagaaag ggtggcccgc tactcgatgg aggacgcaaa ggtaacctat 960
gaactcggaa aagaattctt ccctatggaa gcccagctct cgcgcctcgt aggccagagc 1020
ctctgggatg tatctcgctc gagtaccgga aacctcgtcg agtggttttt gctgaggaag 1080
gcctacgaga ggaatgaact tgcaccaaac aagccggacg agagggagct ggcaagaaga 1140
agggagagct acgcgggtgg atacgtcaag gagcccgaaa ggggactgtg ggagaacatc 1200
gtgtatctgg acttccgctc cctgtatcct tcgataataa tcacccataa cgtctcccct 1260
gatacactca acagggaggg ttgtgaggag tacgacgtgg ctcctcaggt aggccataag 1320
ttctgcaagg acttccccgg cttcatccca agcctcctcg gtgacctctt ggaggagaga 1380
cagaaggtaa agaagaagat gaaggccact atagacccaa tcgagaagaa actcctcgat 1440
tacaggcaac gactgatcaa aatccttgct aatagcttct acggttacta cggctatgca 1500
aaggcccgct ggtactgcaa ggagtgcgcc gagagcgtta ccgcttgggg caggcagtac 1560
atcgagacta cgataaggga aatagaggag aaatttggct ttaaagtcct ctacgcggac 1620
acagatggat tttcgcaac aatacctgga gcggacgccg aaaccgtcaa aaagaaggca 1680
aaggagttcc tggactacat caacgccaaa ctgcccggcc tgctcgaact cgaatacgag 1740
ggcttctaca agcgcggctt cttcgtgacg aagaagaagt acgcggttat agacgaggag 1800
gacaagataa cgacgcgcgg gcttgaaata gttaggcgtg actggagcga gatagcgaag 1860
gagacgcagg cgagggttct tgaggcgata ctaaagcacg gtgacgttga agaagcggta 1920
aggattgtca aagaggttac ggagaagctg agcaagtacg aggttccacc ggagaagctg 1980
gtcatctaca agcagataac ccgcgacctg aaggactaca aggccaccgg gccgcatgtg 2040
gctgttgcaa aacgcctcgc cgcaaggggg ataaaaatcc ggcccggaac ggtcataagc 2100
tacatcgtgc tcaaaggctc gggaaggatt ggggacaggg ctatacccttt tgacgaattt 2160 gacccggcaa agcacaagta cgatgcagaa tactacatcg agaaccaggt tcttccagct 2220
gtggagagga ttctgagggc ctttggttac cgtaaagaag atttaaggta tcagaaaacg 2280
cggcaggttg gcttgggggc gtggctaaaa cctaagaca 2319

<210> SEQ ID NO 43
<211> LENGTH: 773
<212> TYPE: PRT
<213> ORGANISM: Artificial Sequence
<220> FEATURE:
<223> OTHER INFORMATION: Mutated SEQ ID NO:1 according to the invention

<400> SEQUENCE: 43

Met Ile Leu Asp Thr Asp Tyr Ile Thr Glu Asp Gly Lys Pro Val Ile
1 5 10 15

Arg Ile Phe Lys Lys Glu Asn Gly Glu Phe Lys Ile Asp Tyr Asp Arg
20 25 30

```
Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Gln Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445
```

```
Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Lys Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770
```

<210> SEQ ID NO 44
<211> LENGTH: 146
<212> TYPE: PRT
<213> ORGANISM: Artificial Sequence
<220> FEATURE:
<223> OTHER INFORMATION: Section of SEQ ID NO: 1 at position 587 - 732
mutated according to invention

<400> SEQUENCE: 44

```
Phe Phe Ala Thr Lys Lys Lys Tyr Ala Val Ile Asp Glu Glu Asp Lys
1               5                   10                  15

Ile Thr Thr Arg Gly Leu Lys Met Val Arg Arg Asp Trp Ser Glu Ile
            20                  25                  30
```

Ala Lys Glu Thr Gln Ala Arg Val Leu Glu Ala Ile Leu Lys His Gly
35 40 45

Asp Val Glu Glu Ala Val Arg Ile Val Lys Glu Val Thr Glu Lys Leu
50 55 60

Ser Lys Tyr Glu Val Pro Pro Glu Gln Leu Val Ile Tyr Gln Pro Ile
65 70 75 80

Thr Lys Gln Leu His Asp Tyr Arg Ala Arg Gly Pro His Val Ser Val
85 90 95

Ala Lys Arg Leu Ala Ala Arg Gly Ile Lys Ile Arg Pro Gly Thr Val
100 105 110

Ile Ser Tyr Ile Val Pro Lys Gly Ser Gly Arg Ile Gly Asp Arg Ala
115 120 125

Ile Pro Phe Asp Glu Phe Asp Pro Ala Lys His Lys Tyr Asp Ala Gly
130 135 140

Tyr Tyr
145

<210> SEQ ID NO 45
<211> LENGTH: 146
<212> TYPE: PRT
<213> ORGANISM: Thermococcus gorgonarius

<400> SEQUENCE: 45

Phe Phe Val Thr Lys Lys Lys Tyr Ala Val Ile Asp Glu Glu Asp Lys
1 5 10 15

Ile Thr Thr Arg Gly Leu Glu Ile Val Arg Arg Asp Trp Ser Glu Ile
20 25 30

Ala Lys Glu Thr Gln Ala Arg Val Leu Glu Ala Ile Leu Lys His Gly
35 40 45

Asp Val Glu Glu Ala Val Arg Ile Val Lys Glu Val Thr Glu Lys Leu
50 55 60

Ser Lys Tyr Glu Val Pro Pro Glu Lys Leu Val Ile Tyr Glu Gln Ile
65 70 75 80

Thr Arg Asp Leu Lys Asp Tyr Lys Ala Thr Gly Pro His Val Ala Val
85 90 95

Ala Lys Arg Leu Ala Ala Arg Gly Ile Lys Ile Arg Pro Gly Thr Val
100 105 110

Ile Ser Tyr Ile Val Leu Lys Gly Ser Gly Arg Ile Gly Asp Arg Ala
115 120 125

Ile Pro Phe Asp Glu Phe Asp Pro Ala Lys His Lys Tyr Asp Ala Glu
130 135 140

Tyr Tyr
145

<210> SEQ ID NO 46
<211> LENGTH: 42
<212> TYPE: DNA
<213> ORGANISM: Artificial Sequence
<220> FEATURE:
<223> OTHER INFORMATION: TempT template

<400> SEQUENCE: 46
tttttttttt tttttttttt ctccctatag tgagtcgtat ta 42

<210> SEQ ID NO 47
<211> LENGTH: 67
<212> TYPE: DNA

<213> ORGANISM: Artificial Sequence
<220> FEATURE:
<223> OTHER INFORMATION: DNA template Testbind 3

<400> SEQUENCE: 47
gatccgtttc ctcctcccta gttcttcctc ttccctctct tcccttctgg caaacgctaa 60
taagggg 67

<210> SEQ ID NO 48
<211> LENGTH: 16
<212> TYPE: DNA
<213> ORGANISM: Artificial Sequence
<220> FEATURE:
<223> OTHER INFORMATION: DNA test primer 6 for binding to HNA molecules

<400> SEQUENCE: 48
tccctctctt cccttc 16

<210> SEQ ID NO 49
<211> LENGTH: 20
<212> TYPE: DNA
<213> ORGANISM: Artificial Sequence
<220> FEATURE:
<223> OTHER INFORMATION: DNA test primer 7 for binding to HNA molecules

<400> SEQUENCE: 49
ccctagttct tcctcttccc 20

<210> SEQ ID NO 50
<211> LENGTH: 18
<212> TYPE: DNA
<213> ORGANISM: Artificial Sequence
<220> FEATURE:
<223> OTHER INFORMATION: DNA test primer 8 for binding to HNA molecules

<400> SEQUENCE: 50
gatccgtttc ctcctccc 18

<210> SEQ ID NO 51
<211> LENGTH: 89
<212> TYPE: DNA
<213> ORGANISM: Artificial Sequence
<220> FEATURE:
<223> OTHER INFORMATION: TempNpurine

<400> SEQUENCE: 51
cctagttctt cctcttcccg atgctggacc agataagcac ttagccacgt agtgctgttc 60
ggtaatcgat ctggcaaacg ctaataagg 89

<210> SEQ ID NO 52
<211> LENGTH: 110
<212> TYPE: DNA
<213> ORGANISM: Artificial Sequence
<220> FEATURE:
<223> OTHER INFORMATION: Template ApLib5
<220> FEATURE:
<221> NAME/KEY: misc_feature
<222> LOCATION: (21)..(60)
<223> OTHER INFORMATION: n is a, c, g, or t

<400> SEQUENCE: 52
ccctagttct tcctcttccc nnnnnnnnnn nnnnnnnnnn nnnnnnnnnn nnnnnnnnnn 60
cgaacagcac taccttttgg caaacgctaa taaggggtcc taaaaaaaaa 110

<210> SEQ ID NO 53
<211> LENGTH: 20
<212> TYPE: DNA
<213> ORGANISM: Artificial Sequence
<220> FEATURE:
<223> OTHER INFORMATION: Primer FD

<400> SEQUENCE: 53
ccccttatta gcgtttgcca 20

<210> SEQ ID NO 54
<211> LENGTH: 77
<212> TYPE: DNA
<213> ORGANISM: Artificial Sequence
<220> FEATURE:
<223> OTHER INFORMATION: TempN

<400> SEQUENCE: 54
ctcacgatgc tggaccagat aagcacttag ccacgtagtg ctgttcggta atcgatctgg 60
caaacgctaa taagggg 77

<210> SEQ ID NO 55
<211> LENGTH: 31
<212> TYPE: DNA
<213> ORGANISM: Artificial Sequence
<220> FEATURE:
<223> OTHER INFORMATION: Primer YtRHNA2HNA2

<400> SEQUENCE: 55
caggaaacag ctatgacaaa tggtggtggg g 31

<210> SEQ ID NO 56
<211> LENGTH: 85
<212> TYPE: DNA
<213> ORGANISM: Artificial Sequence
<220> FEATURE:
<223> OTHER INFORMATION: Template tRNAtemp1

<400> SEQUENCE: 56
ggtggggttc ccgagcggcc aaagggagca gactctaaat ctgccgtcat cgacttcgaa 60
ggttcgaatc cttcccccac cacca 85

<210> SEQ ID NO 57
<211> LENGTH: 41
<212> TYPE: DNA
<213> ORGANISM: Artificial Sequence
<220> FEATURE:
<223> OTHER INFORMATION: RNA primer L3T32

<400> SEQUENCE: 57
aggaaacagc tatgacaaac aaggtagtgc tgttcgtggg g 41

<210> SEQ ID NO 58
<211> LENGTH: 40
<212> TYPE: DNA
<213> ORGANISM: Artificial Sequence
<220> FEATURE:
<223> OTHER INFORMATION: primer GB1lucfo

<400> SEQUENCE: 58
gaaatggtaa ggcaaatacg gttacaattt ggactttccg 40

<210> SEQ ID NO 59
<211> LENGTH: 48
<212> TYPE: DNA

<213> ORGANISM: Artificial Sequence
<220> FEATURE:
<223> OTHER INFORMATION: Primer GB1GFPfo

<400> SEQUENCE: 59
gaaatggtaa ggcaaatacg gctatttgta tagttcatcc atgccatg 48

<210> SEQ ID NO 60
<211> LENGTH: 20
<212> TYPE: DNA
<213> ORGANISM: Artificial Sequence
<220> FEATURE:
<223> OTHER INFORMATION: primers LMB3+

<400> SEQUENCE: 60
caggaaacag ctatgacaaa 20

<210> SEQ ID NO 61
<211> LENGTH: 17
<212> TYPE: DNA
<213> ORGANISM: Artificial Sequence
<220> FEATURE:
<223> OTHER INFORMATION: Primer NAP

<400> SEQUENCE: 61
cagtatcgac aaaggac 17

<210> SEQ ID NO 62
<211> LENGTH: 53
<212> TYPE: DNA
<213> ORGANISM: Artificial Sequence
<220> FEATURE:
<223> OTHER INFORMATION: primer L3SDGFPba

<400> SEQUENCE: 62
caggaaacag ctatgacagg aggagcgaga tgagtaaagg agaagaactt ttc 53

<210> SEQ ID NO 63
<211> LENGTH: 20
<212> TYPE: DNA
<213> ORGANISM: Artificial Sequence
<220> FEATURE:
<223> OTHER INFORMATION: Primer L3AGG

<400> SEQUENCE: 63
caggaaacag ctatgacagg 20

<210> SEQ ID NO 64
<211> LENGTH: 15
<212> TYPE: DNA
<213> ORGANISM: Artificial Sequence
<220> FEATURE:
<223> OTHER INFORMATION: primer K0

<400> SEQUENCE: 64
gcacggcagc acgtg 15

<210> SEQ ID NO 65
<211> LENGTH: 47
<212> TYPE: DNA
<213> ORGANISM: Artificial Sequence
<220> FEATURE:
<223> OTHER INFORMATION: Template TempK4

<400> SEQUENCE: 65
actgcgatga ctgtactcgt ctagtagcac tgcacgtgct gccgtgc 47

<210> SEQ ID NO 66
<211> LENGTH: 48
<212> TYPE: DNA
<213> ORGANISM: Artificial Sequence
<220> FEATURE:
<223> OTHER INFORMATION: DNA template
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (30)..(31)
<223> OTHER INFORMATION: nucleotide positions can be tt or tt-cpd(cis-syn cyclobutane pyrimidine dimer) or TAb (Ab-abasic site)

<400> SEQUENCE: 66
tcgatactgg tactaatgat taacgaayna agcacgtccg taccatcg 48

<210> SEQ ID NO 67
<211> LENGTH: 16
<212> TYPE: DNA
<213> ORGANISM: Artificial Sequence
<220> FEATURE:
<223> OTHER INFORMATION: Primer

<400> SEQUENCE: 67
tggtacggac gtgctt 16

<210> SEQ ID NO 68
<211> LENGTH: 124
<212> TYPE: DNA
<213> ORGANISM: Artificial Sequence
<220> FEATURE:
<223> OTHER INFORMATION: HNA
<220> FEATURE:
<221> NAME/KEY: misc_feature
<222> LOCATION: (20)..(20)
<223> OTHER INFORMATION: n is c or t
<220> FEATURE:
<221> NAME/KEY: misc_feature
<222> LOCATION: (39)..(39)
<223> OTHER INFORMATION: n is g or a
<220> FEATURE:
<221> NAME/KEY: misc_feature
<222> LOCATION: (47)..(47)
<223> OTHER INFORMATION: n is a or g
<220> FEATURE:
<221> NAME/KEY: misc_feature
<222> LOCATION: (55)..(55)
<223> OTHER INFORMATION: n is g or a
<220> FEATURE:
<221> NAME/KEY: misc_feature
<222> LOCATION: (58)..(58)
<223> OTHER INFORMATION: n is c or a
<220> FEATURE:
<221> NAME/KEY: misc_feature
<222> LOCATION: (62)..(62)
<223> OTHER INFORMATION: n is c or a
<220> FEATURE:
<221> NAME/KEY: misc_feature
<222> LOCATION: (64)..(64)
<223> OTHER INFORMATION: n is a or t
<220> FEATURE:
<221> NAME/KEY: misc_feature
<222> LOCATION: (81)..(81)
<223> OTHER INFORMATION: n is t or c
<220> FEATURE:
<221> NAME/KEY: misc_feature
<222> LOCATION: (85)..(85)
<223> OTHER INFORMATION: n is g or a
<220> FEATURE:

<221> NAME/KEY: misc_feature
<222> LOCATION: (97)..(97)
<223> OTHER INFORMATION: n is t or c
<220> FEATURE:
<221> NAME/KEY: misc_feature
<222> LOCATION: (102)..(102)
<223> OTHER INFORMATION: n is c or a
<220> FEATURE:
<221> NAME/KEY: misc_feature
<222> LOCATION: (103)..(103)
<223> OTHER INFORMATION: n is c or a
<220> FEATURE:
<221> NAME/KEY: misc_feature
<222> LOCATION: (121)..(121)
<223> OTHER INFORMATION: n is t or c

<400> SEQUENCE: 68
ccctattagc gtttgccacn ttcggtaatc gatctggtng tgggggnagg attcnaanct 60
tngnagtcga tgacggcaga nttanagtct gctcccnttg gnngctcggg aaccccacga 120 nttg 124

<210> SEQ ID NO 69
<211> LENGTH: 125
<212> TYPE: DNA
<213> ORGANISM: Artificial Sequence
<220> FEATURE:
<223> OTHER INFORMATION: HNA
<220> FEATURE:
<221> NAME/KEY: misc_feature
<222> LOCATION: (21)..(21)
<223> OTHER INFORMATION: n is c or t
<220> FEATURE:
<221> NAME/KEY: misc_feature
<222> LOCATION: (40)..(40)
<223> OTHER INFORMATION: n is g or a
<220> FEATURE:
<221> NAME/KEY: misc_feature
<222> LOCATION: (48)..(48)
<223> OTHER INFORMATION: n is a or g
<220> FEATURE:
<221> NAME/KEY: misc_feature
<222> LOCATION: (56)..(56)
<223> OTHER INFORMATION: n is g or a
<220> FEATURE:
<221> NAME/KEY: misc_feature
<222> LOCATION: (59)..(59)
<223> OTHER INFORMATION: n is c or a
<220> FEATURE:
<221> NAME/KEY: misc_feature
<222> LOCATION: (63)..(63)
<223> OTHER INFORMATION: n is c or a
<220> FEATURE:
<221> NAME/KEY: misc_feature
<222> LOCATION: (65)..(65)
<223> OTHER INFORMATION: n is a or t
<220> FEATURE:
<221> NAME/KEY: misc_feature
<222> LOCATION: (82)..(82)
<223> OTHER INFORMATION: n is t or c
<220> FEATURE:
<221> NAME/KEY: misc_feature
<222> LOCATION: (86)..(86)
<223> OTHER INFORMATION: n is g or a
<220> FEATURE:
<221> NAME/KEY: misc_feature
<222> LOCATION: (98)..(98)
<223> OTHER INFORMATION: n is t or c
<220> FEATURE:
<221> NAME/KEY: misc_feature
<222> LOCATION: (103)..(103)
<223> OTHER INFORMATION: n is c or a
<220> FEATURE:
<221> NAME/KEY: misc_feature
<222> LOCATION: (104)..(104)
<223> OTHER INFORMATION: n is c or a -continued

```
<220> FEATURE:
<221> NAME/KEY: misc_feature
<222> LOCATION: (122)..(122)
<223> OTHER INFORMATION: n is t or c

<400> SEQUENCE: 69

cccttattag cgtttgccac nttcggtaat cgatctggtn gtgggggnag gattcnaanc     60

ttngnagtcg atgacggcag anttanagtc tgctcccntt ggnngctcgg gaaccccacg    120

anttg                                                                125


<210> SEQ ID NO 70
<211> LENGTH: 16
<212> TYPE: RNA
<213> ORGANISM: Artificial Sequence
<220> FEATURE:
<223> OTHER INFORMATION: Primer

<400> SEQUENCE: 70

ugguacggac gugcuu                                                     16
```

ENZYMES

CROSS-REFERENCE TO RELATED APPLICATIONS

The present application is a national stage entry of PCT/GB2011/000583, filed Apr. 14, 2011, which claims the benefit of British application serial no. 1007384.9, filed Apr. 30, 2010, and U.S. provisional No. 61/396,008 filed May 20, 2010.

BACKGROUND TO THE INVENTION

Life's diversity is largely based on the versatility of two polymers: polypeptides (i.e. proteins) and polynucleotides (nucleic acids). Information storage and propagation in biological systems is commonly based on just two types of nucleic acids, DNA and RNA. Nucleic acids in particular display unique properties beyond their ability to encode genetic information, which make them important tools in chemistry, biotechnology, nanotechnology and medicine. Nucleic acids also have enormous potential as therapeutics but suffer from systemic constraints inherent in DNA and RNA chemistry such as poor serum/nuclease stability.

Systematic chemical studies have begun to uncover the critical chemical and physico-chemical parameters that have enabled DNA and RNA to serve as the molecular basis for life's genetic systems. Changes to the chemical structure of nucleic acids, including unnatural nucleobases[1-3] have been used to investigate the molecular determinants for information storage. Synthetic exploration of alternative backbone linkages[4] and ribofuranose congeners[5,6] have been explored and have revealed the profound influence of the chemical makeup of backbone and/or sugar (or equivalent) chemistry on nucleic acid properties, structure and conformation. Crucially, only a small subset of chemistries allows cross-polymer information transfer through efficient pairing with DNA or RNA: a prerequisite for the formation of a synthetic genetic system capable of crosstalk with extant biology. However, cross-hybridization experiments alone cannot conclusively determine the capacity of a given chemistry to serve as a genetic system as hybridization does not necessarily preserve information content.

A more thorough examination of the potential of a potential genetic polymer for information storage, propagation and evolution requires a system of replication. In principle, artificial polymers might be synthesized and replicated chemically but non-enzymatic polymerization is usually inefficient and error-prone[7] and consequently unattractive as a generic approach despite significant advances in the polymerization of mononucleotide[8] or short oligomer (pentamer) units[9] using specialized chemistries. Enzymatic polymerization using DNA or RNA polymerases is potentially powerful but is restricted but the tight substrate specificity of natural polymerases. Despite significant progress in understanding determinants of polymerase substrate specificity[10] and the engineering of polymerases with expanded substrate spectra[11,12], most unnatural nucleotide analogues have remained inadequate polymerase substrates at full substitution for either synthesis and/or as templates for reverse transcription.

DNA and RNA are not only a repository of genetic information for life. They are also unique polymers with remarkable properties: they associate according to well-defined rules, can be assembled into diverse nanostructures of defined geometry, can be evolved to bind ligands and catalyze chemical reactions and can serve as a supramolecular scaffold to arrange chemical groups in space.

Aptamers are a promising class of biomolecular therapeutics based on structured single-stranded nucleic acids with the potential to rival antibodies in some clinical settings. A broad spectrum of both RNA- and DNA-based aptamers have been described directed against a wide-range of targets and several are currently undergoing in clinical trails underlining their potential. However, reagents based on natural nucleic acids such as RNA or DNA have drawbacks with respect to a number of desirable properties for clinical reagents and therapeutics, such as in vivo stability and/or bioavailability. In principle, aptamers may be stabilized (post-selection) by medicinal chemistry approaches and this approach has been validated by Macugen, the 1st aptamers based drug, which has been approved for the treatment of macular degeneration. However, post-selection modifications can alter and/or weaken aptamer structure and target interactions and may modify aptamer specificity, which is a problem.

A wide range of modified nucleotides has been used in SELEX to create aptamers comprising unnatural chemistries. Some of these modifications confer desirable characteristics on the selected aptamers such as increased nuclease resistance and stability but also have drawbacks such as toxicity and increased non-specific interaction with proteins.

Orthogonality (i.e. a lack of interaction/interference with the cellular machinery) and the resulting lack of toxicity, increased nuclease resistance as well as other potentially desirable properties may in principle arise from the use of more radically engineered nucleic acids. However, their application to the aptamer field requires both the design and synthesis of such nucleic acids as well as the generation of custom-made polymerases for their synthesis, replication and evolution. It is a problem that such reagents and polymerases do not exist in the art.

Many novel nucleic acid structures have been built with a view towards increased orthogonality. The challenge here is to design scaffolds that lead to minimal interaction/interference with the cellular genetic machinery while simultaneously maintaining an ability to communicate with it. Notable achievements include attempts at expanding the genetic alphabet (informational orthogonality) and altering the structure or size of nucleobases (steric orthogonality). However, in each of these cases issues of cellular toxicity and/or informational specificity remain.

A different approach towards chemically orthogonal nucleic acids involves the modification of the backbone but leaves the informational nucleobases intact. Replacement of the canonical ribofuranose with other pentoses (or hexoses and tetroses) can indeed have dramatic effects on helical conformation and duplex stability and formation.

SUMMARY OF THE INVENTION

Certain orthogonal nucleic acids are known in the art. These are based on orthogonal nucleic acid chemistry so as to be structurally different from naturally occurring DNA or RNA. One example of an orthogonal nucleic acid is that based on hexitol (HNA). Another example is one based on cyclohexenyl (CeNA) nucleotides. However, to date such orthogonal nucleic acids have only been able to be produced chemically. This has meant that production of a polymer of biologically useful length has been extremely demanding, and expensive.

The present invention provides nucleic acid polymerases which are able to be polymerise orthogonal nucleotides into orthogonal nucleic acid polymers. The inventors have created and selected individual polymerase enzymes possessing orthogonal polymerase activities. As a result of their studies, the inventors have defined specific regions and patches in the polymerases which determine and allow the manipulation of the polymerase activity towards the orthogonal nucleotides. The invention is based upon these surprising findings.

Thus in one aspect the invention provides nucleic acid polymerase capable of producing a non-DNA nucleotide polymer from a DNA nucleotide polymer template, said polymerase comprising amino acid sequence having at least 36% identity to the amino acid sequence of SEQ ID NO:1, wherein said amino acid sequence is mutated relative to the amino acid sequence of SEQ ID NO:1 at one or more residues of the thumb region, said residues selected from: amino acids 651 to 679 (patch 10A);

wherein said amino acid sequence is mutated relative to the amino acid sequence of SEQ ID NO:1 at residue E664.

Suitably said non-DNA nucleotide polymer is a RNA polymer; and said amino acid sequence is mutated relative to the amino acid sequence of SEQ ID NO:1 at residue Y409. Suitably when the non-DNA nucleotide polymer is a RNA polymer then the polymerase comprises the mutation Y409N or Y409G. Suitably when the non-DNA nucleotide polymer is a RNA polymer then the polymerase comprises the mutation E664K or E664Q. Suitably when the non-DNA nucleotide polymer is a RNA polymer then the polymerase comprises the mutations Y409N and E664Q (TgoT Y409N E664Q; TNQ). Suitably when the non-DNA nucleotide polymer is a RNA polymer then the polymerase comprises the mutations Y409G and E664K (TgoT Y409G E664K; TGK). Suitably said polymerase comprises the mutations Y409G and E664K. In another aspect, the invention relates to a method for making a RNA nucleotide polymer, said method comprising contacting a DNA template with a nucleic acid polymerase as described above and incubating to allow polymerisation.

In another aspect, the invention relates to a nucleic acid polymerase as described above wherein said polymerase is capable of producing a HNA nucleotide polymer from a DNA nucleotide polymer template and said polymerase comprises amino acid sequence corresponding to amino acids 651 to 679 (patch 10A) of SEQ ID NO: 12. Suitably said polymerase is capable of producing a HNA nucleotide polymer from a DNA nucleotide polymer template and said polymerase comprises amino acid sequence corresponding to SEQ ID NO:12. In another aspect, the invention relates to a method for making a HNA nucleotide polymer, said method comprising contacting a DNA template with a nucleic acid polymerase as described above and incubating to allow polymerisation.

In another aspect, the invention relates to a nucleic acid polymerase capable of reverse transcribing a HNA nucleotide polymer into a DNA nucleotide polymer, said polymerase comprising amino acid sequence having at least 36% identity to the amino acid sequence of SEQ ID NO:1, wherein said amino acid sequence is mutated relative to the amino acid sequence of SEQ ID NO:1 at residue I521. Suitably said polymerase comprises a mutation selected from the group consisting of: I521L, I521P and I521H. Suitably said polymerase comprises the mutation I521L.

Suitably said polymerase further comprises the mutation A485L.

Suitably said polymerase further comprises the mutation V93Q.

Suitably said polymerase further comprises the mutations E141A and E143A.

In another aspect, the invention relates to a nucleic acid polymerase as described above wherein said non-DNA polymer is a HNA polymer and wherein said polymerase comprises the mutation I521L and said polymerase further comprises the mutation A485L and said polymerase further comprises the mutation V93Q and said polymerase further comprises the mutations E141A and E143A.

In another aspect, the invention relates to a method for making a DNA nucleotide polymer, said method comprising contacting a HNA template with a nucleic acid polymerase as described above and incubating to allow polymerisation.

In another aspect, the invention relates to a nucleic acid encoding a polymerase as described above.

In another aspect, the invention relates to a host cell comprising a nucleic acid as described above.

In another aspect, the invention relates to a system comprising:

(i) a nucleic acid polymerase capable of producing a HNA nucleotide polymer from a DNA nucleotide polymer template according to any of claim 1, 5 or 6; and (ii) a nucleic acid polymerase capable of reverse transcribing a HNA nucleotide polymer into a DNA nucleotide polymer according to any of claims 8 to 14.

In another aspect the invention provides a nucleic acid polymerase capable of producing a non-DNA nucleotide polymer from a DNA nucleotide polymer template, said polymerase comprising amino acid sequence having at least 36% identity to the amino acid sequence of SEQ ID NO:1, wherein said amino acid sequence is mutated relative to the amino acid sequence of SEQ ID NO:1 at one or more residues of the thumb region, said residues selected from:

(i) amino acids 651 to 679 (patch 10A); or (ii) amino acids 734 to 765 (patch 12).

Suitably said amino acid sequence is mutated relative to the amino acid sequence of SEQ ID NO:1 at one or more residues selected from:

(i) amino acids 651 to 679 (patch 10A).

Suitably said polymerase is capable of producing a HNA nucleotide polymer from a DNA nucleotide polymer template and said polymerase comprises amino acid sequence corresponding to amino acids 651 to 679 (patch 10A) of any of SEQ ID NO:s 12, 13, 14 or 15; and/or said polymerase comprises amino acid sequence corresponding to amino acids 734 to 765 (patch 12) of any of SEQ ID NO:s 16, 17 or 18.

Suitably said polymerase is capable of producing a HNA nucleotide polymer from a DNA nucleotide polymer template and said polymerase comprises amino acid sequence corresponding to SEQ ID NO:12.

Suitably said polymerase is capable of producing a CeNA nucleotide polymer from a DNA nucleotide polymer template and said polymerase comprises amino acid sequence corresponding to amino acids 651 to 679 (patch 10A) of any of SEQ ID NO:s 3, 4, 5, 6, 7, 8, 9 or 10; and/or said polymerase comprises amino acid sequence corresponding to amino acids 734 to 765 (patch 12) of any of SEQ ID NO: 11.

Suitably said polymerase is capable of producing a CeNA nucleotide polymer from a DNA nucleotide polymer template and said polymerase comprises amino acid sequence corresponding to SEQ ID NO:5 or SEQ ID NO:6.

Suitably said polymerase comprises the mutation E664Q.

Suitably said polymerase is capable of producing a RNA nucleotide polymer from a DNA nucleotide polymer template and said polymerase comprises the mutation E664Q.

Suitably said polymerase further comprises the mutation A485L.

Suitably said polymerase further comprises the mutation V93Q.

Suitably said polymerase further comprises the mutations E141A and E143A.

In another aspect, the invention relates to a method for making a non-DNA nucleotide polymer, said method comprising contacting a DNA template with a nucleic acid polymerase as described above and incubating to allow polymerisation. Suitably synthesis may be followed by suitable step(s) to either dissociate said polymer from the DNA template or remove the DNA template to free the polymer.

In another aspect, the invention relates to a non-DNA nucleotide polymer which comprises at least 50 nucleotides. Suitably said non-DNA nucleotide polymer comprises HNA or CeNA.

In another aspect, the invention relates to a non-DNA nucleotide polymer obtained by the method as described above.

In another aspect, the invention relates to a nucleic acid polymerase capable of reverse transcribing a non-DNA nucleotide polymer into a DNA nucleotide polymer, said polymerase comprising amino acid sequence having at least 36% identity to the amino acid sequence of SEQ ID NO:1, wherein said amino acid sequence is mutated relative to the amino acid sequence of SEQ ID NO:1 at one or more residues selected from: I521 and Y388.

Suitably said non-DNA polymer is an HNA polymer or a CeNA polymer or a RNA polymer.

Suitably said polymerase capable of reverse transcription comprises a mutation selected from the group consisting of: I521L, I521P and I521H. Suitably said polymerase comprises the mutation I521L.

Suitably said polymerase capable of reverse transcription comprises a mutation selected from the group consisting of: Y388V, Y388R, Y388H, Y388N and Y388T.

Suitably said polymerase capable of reverse transcription further comprises the mutation A485L.

Suitably said polymerase capable of reverse transcription further comprises the mutation V93Q.

Suitably said polymerase capable of reverse transcription further comprises the mutations E141A and E143A.

Suitably said non-DNA polymer is a HNA polymer and said polymerase capable of reverse transcription comprises the mutation I521L and said polymerase further comprises the mutation A485L and said polymerase further comprises the mutation V93Q and said polymerase further comprises the mutations E141A and E143A.

In another aspect, the invention relates to a nucleic acid encoding a polymerase as described above.

In another aspect, the invention relates to a host cell comprising a nucleic acid as described above.

In another aspect, the invention relates to a method of screening for a non-DNA nucleotide polymer having a particular predetermined characteristic, said method comprising preparing a candidate non-DNA nucleotide polymer as described above, and assaying said non-DNA nucleotide polymer for said characteristic.

In another aspect, the invention relates to a method for making a DNA polymer from a non-DNA nucleotide polymer template, said method comprising contacting said template with a nucleic acid polymerase as described above and incubating to allow polymerisation.

In another aspect, the invention relates to a method of making a medicament, said method comprising preparing a non-DNA nucleotide polymer as described above.

In another aspect, the invention relates to a system comprising (i) a nucleic acid polymerase capable of producing a non-DNA nucleotide polymer from a DNA nucleotide polymer template as described above and (ii) a nucleic acid polymerase capable of reverse transcribing a non-DNA nucleotide polymer into a DNA nucleotide polymer as described above.

In another aspect, the invention relates to a system comprising (i) a nucleic acid polymerase capable of producing a repertoire of diverse non-DNA nucleotide polymers from a repertoire of diverse DNA nucleotide polymer templates as described above (ii) the selection or screening of above repertoire of diverse non-DNA nucleotide polymers for a desired function such as 1) binding to a specified target or 2) the catalysis of a specified chemical reaction (iii) a nucleic acid polymerase capable of reverse transcribing the selected non-DNA nucleotide polymer with the desired phenotype (binding or catalysis) into a DNA nucleotide polymer as described above.

BRIEF DESCRIPTION OF THE DRAWINGS

FIG. 3 shows a graph and a photograph of typical results from the two-step polymerase activity ELISA.

FIG. 5 shows an illustrated rendering of Rb69 (A), Tgo (B), and phi29 (C) polymerases; and an accompanying amino acid seauence of wild-type polymerase (SEQ ID NO:1).

FIG. 8 shows results of isolated mutants tested for rNTP incorporation. The presence of the Y409 steric gate reduced rNTP incorporation; but D4 showed considerable incorporation of rNTPs, FIG. 9 shows 6G12 mutations mapped to Tgo (A) and RB69 (B) structures.

FIG. 12 shows results of HNA synthesis by 6G12 when lacking one of the four hNTPs.

FIG. 13 shows the structure of site specific steric modification and affects on polymerase activity. Panel (a) shows a steric gate design; panel (b) shows the extension of a yeast tRNA requesting 87 incorporations to make a 105mer product; panel (c) compares DNA with RNA primer extension by D4N3; panel (d) shows the primer extension activity of D4N3 mutant polymerases contemplated in panel (a).

FIG. 29 presents a illustrations of directed evolution of polymerases for synthesis of artificial biopolymers. Panel (a) shows structure of deoxyribose (DNA), 1,5-anhydrohexitol (HNA) and cyclohexenyl (CeNA) nucleic acids; panel (b) shows compartmentalised self-tagging (CST); panel (c) shows heat maps indicating ranked library polyclonal activity mapped to the wild-type (1TGO) and to the ternary complex of the related *E. coli* pol II (3MAQ).

FIG. 33 shows a region of HNA (SEQ ID NO:68 and SEQ ID NO:69) flanked by primers NAPfd (SEQ ID NO:61) and LMB3+ (SEQ ID NO:60), and depicts the error spectrum and error rates of the HNA genetic system. Panel (a) shows misincorporations, deletions (closed triangles) and insertions (open triangles) collated from 1974 sequenced bases after a round of HNA synthesis and reverse transcription using an *E. coli* tRNA gene as the original template; panel (b) illustrates aggregate and individual error rates determined for Pol6G12 and RT521 for HNA and DNA syntheses.

FIG. 36 is a cheamitc of a polymerase activity ELISA (PAE). Panel (a) illustrates the principles of PAE; panel (b) shows how individual isolates from small, single-residue, partial coverage libraries (encoded as NWC) were screened with PAE for DNA synthesis against a chemically synthesized HNA template.

FIG. 37 shows mutagenesis libraries. Residues targeted for diversity are shown (surface representation) on the Tgo (panel (a)) and *E. coli* Pol II (panel (b)) backbones. Individual libraries are shown against the TgoT seauence (panel (c) SEQ ID NO:1).

FIG. 43 demonstrates the contributions of different mutations to RNA polymerase activity, particularly the enhanced RNA polymerase activity with thumb domain mutations. Panel (a) illustrates the structure of D4N, mapped onto the homologous *E. coli* DNA pol II (PDB: 3MAQ[42]). The nine mutations in D4, the steric gate mutation (added to make D4 Y409N) and the existing mutations in TgoT (D141A, E143A, A485L) are shown; panel (b) shows the helical parameters of B-DNA, A-RNA and HNA-RNA heteroduplex; panel (C) shows RNA extensions from DNA; and panel (d) shows RNA primers by D4N and its parent polymerases.

FIG. 44 shows the relative activity of RNA polymerase mutants. Panel (a) is reversion analysis of thumb mutations in D4. Each mutation was reverted to wild type individually and the effect on processive RNA polymerase activity assayed with lysates normalised according to dNTP activity; panel (b) is a time-course of *E. coli* $tRNA^{Tyr}$ synthesis by purified polymerases D4N, TNQ and TGK from RNA primers.

FIG. 52 shows a table of steric gate residues in DNA polymerase families A, B, C, X, Y, and the RT family.

DETAILED DESCRIPTION OF THE INVENTION

Figure 1:
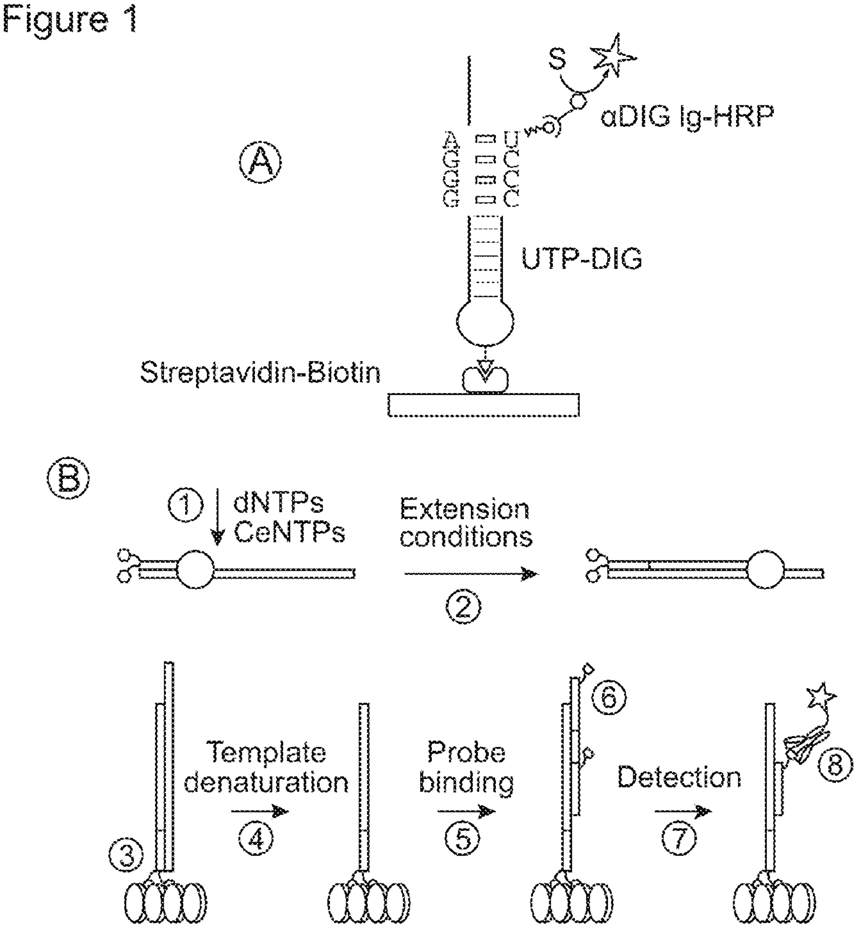
FIG. 1 shows a schematic depiction of a polymerase end-point ELISA assay, denoted (A); and a two-step polymerase activity ELISA, denoted (B), developed to monitor incorporation of unnatural nucleic acids.

Information storage and propagation in biology is based on just two types of nucleic acids, DNA and RNA. However, it is not known whether their prevalence was the result of circumstance ("historic accident"), reflecting constraints imposed at the origin of life, or if chemical alternatives to ribofuranose-based nucleic acids are limited. Here we describe the development of an artificial genetic system based on 1,5 anhydrohexitol nucleic acids (HNA), a chemically simple nucleic acid architecture not found in nature, and demonstrate this system's capacity for heredity and evolution. Using polymerase evolution and design, we have engineered both a DNA-templated HNA polymerase and an HNA reverse transcriptase. Together these allow efficient transfer of genetic information from DNA into HNA and back into DNA, establishing HNA-based heredity with an aggregate fidelity of $1.4\times10^{-2}$—comparable to RNA virus replication. We furthermore demonstrate evolution of this new synthetic genetic material by the de novo selection of specific all-HNA aptamers against an RNA target (HIV-TAR). Our results show that both heredity and evolution can be provided by an entirely unnatural system, suggesting that there is no fundamental functional imperative for life to be built on ribofuranose-based nucleic acids.

The present invention relates to the design and construction of an artificial genetic system based on a third type of genetic material using orthogonal nucleic acid chemistry and in particular evolved polymerases for the templated synthesis, replication and evolution of novel, sequence-defined nucleic acid polymers.

Such a system is a key enabling technology for the synthesis, replication and evolution of novel nucleic acid polymers with potential applications as diagnostics, prognostics and therapeutics. It also promises to address some of the systemic constraints inherent in DNA and RNA chemistry with regards to therapeutic application.

We have selected two unnatural nucleic acid architectures, Hexitol nucleic acid (HNA) and Cyclohexenyl nucleic acids (CeNA) as exemplary backbone structures to illustrate the invention. HNA and CeNA nucleotides are very poor substrates for naturally occurring kinases and are thus non-toxic to cells. HNA and CeNA polymers are not substrates for naturally occurring nucleases and are therefore not degraded by either DNases nor RNAses. Both HNA and CeNA are completely resistant to nuclease degradation and appear not to be substrates for DNA or RNA modifying enzymes. Significantly, they are non-toxic to cells as nucleotides and appear to be not recognized as substrates by the cellular replication, transcription and translation machinery. At the same time, they crucially retain the ability to form sequence specific duplexes with DNA and RNA, an essential property for the transfer of genetic information. HNA is known (and CeNA is predicted) to form duplex structures that are different from canonical A- or B-form helices, which may allow formation of novel aptamer conformational and structural motifs with potential for novel functions. HNA monomers (such as might arise from the eventual degradation of long-lived therapeutics) have been shown to be non-toxic to cells. HNA and CeNA therefore unite an ideal spectrum of properties for the assembly of an orthogonal genetic system and its application to the isolation of nucleic acid therapeutics such as aptamers.

Suitably for HNA polymerase applications, the polymerase of the invention comprises mutations as shown for '6G12'.

Suitably for RNA polymerase applications, the polymerase of the invention comprises mutations as shown for 'D4' such as 'D4N3'. In particular this comprises a Y409 mutation which in 'D4N3' is Y409N.

Suitably for CeNA polymerase applications of the invention, the polymerase comprises mutations as shown for 'C7' or 6G12.

It will be appreciated that numerous polymerases of the invention show activity for multiple orthogonal nucleic acids. For example, one enzyme can display both RNA reverse transcriptase and HNA reverse transcriptase activity. If that enzyme has the proof reading function intact then it is unlikely to be suitable as an HNA reverse transcriptase, but remains suitable as an RNA reverse transcriptase.

To be considered a useful enzyme according to the invention (i.e. to be considered capable of having the specified functions, the polymerase or reverse transcriptase of the invention should be able to produce a polymer of at least 14 nucleotides in length, suitably at least 15 nucleotides in length; more suitably 40 nucleotides in length, most suitably at least 50 nucleotides in length.

According to the most stringent criterion of synthesis of a polymer at least 50 nucleotides in length, polymerases C7 and 6G12 may not be regarded as acting on RNA; polymerases D4 and C7 may not be regarded as acting on HNA. Thus, if polymerases of the invention are discussed as being for or specific for a particular type of orthogonal nucleic acid, it should be understood that they are expected to be able to consistently produce a polymer or at least 40 nucleotides, suitably at least 50 nucleotides in length.

Typically the smallest aptamers or ribozymes need approximately 40 nucleotides of sequence in order to fold. More suitably, small aptamers or ribozymes also comprise a few extra nucleotides for polymerase binding, therefore suitably being at least about 50 nucleotides in length. For aptamer screening applications, a typical preferred minimum length is therefore 50 nucleotides.

DEFINITIONS

The term 'comprises' (comprise, comprising) should be understood to have its normal meaning in the art, i.e. that the stated feature or group of features is included, but that the term does not exclude any other stated feature or group of features from also being present.

As used herein, the term reverse transcriptase or "reverse transcriptase activity" refers to the manufacture of a DNA polymer from a non DNA polymer template. Thus, when the non DNA template comprises RNA, then the term has its normal meaning in the art. As will be apparent from the context, in numerous aspects and embodiments the invention relates to reverse transcriptase activity in the sense of manufacturing a DNA polymer from a non DNA polymer template which may be, for example, RNA, HNA, CeNA, or other such non DNA template. Thus, reverse transcriptase may be classically regarded as an RNA dependant DNA polymerase. For other non DNA nucleotide polymers the term "reverse transcriptase" has the same overall meaning, except that the template nucleic acid may of course vary. For example, a reverse transcriptase for HNA means an HNA dependant DNA polymerase; a reverse transcriptase for CeNA means a CeNA dependant DNA polymerase.

A non DNA nucleotide means a nucleotide other than a deoxy ribonucleotide. For example, it may mean a conventional ribonucleotide which may be used to make an RNA polymer. Alternatively, it may mean any other kind of non DNA nucleotide, such as a hexitol (HNA) nucleotide or a cyclohexenyl (CeNA) nucleotide or other such nucleotide polymer. Most suitable non DNA nucleotide or polymer is also a non RNA nucleotide or polymer i.e. most suitably a non DNA polymer may be XNA or 3NA (such as HNA or CeNA).

Suitably the invention relates to the production of a complete new polymer i.e. orthogonal nucleic acid. The aim is to keep the information which is encoded in that polymer the same as the information encoded in a conventional DNA polymer. For example, it is not an aim of the invention to include a fifth base or to expand the genetic alphabet beyond the four conventional bases, although the invention could be applied in this manner by the skilled operator if desired. Suitably, the polymers of the invention reflect the same four bases as conventional DNA polymers in terms of their information content.

Orthogonal nucleic acids are non DNA nucleic acids. Examples include HNA or CeNA as described herein. These non DNA nucleic acids are sometimes referred to as "3NA" or as "XNA" as will be apparent from the context. Suitably the orthogonal nucleic acid is HNA or CeNA. Most suitably, the orthogonal nucleic acid is HNA. HNA is particularly advantageous since it is the most experimentally tractable of the orthogonal nucleic acids discussed herein.

Polymerase

In principle, polymerases of the invention may be made by introducing the specific mutations described herein into the corresponding site of a starting polymerase or 'polymerase backbone' of the operator's choice. In this way, the activity of that starting polymerase may be modified to provide the orthogonal activities as described herein.

The polymerase backbone may be any member of the well known polB enzyme family (including the pol delta variant which shows only 36% identity with the exemplary true wild type TgoT sequence of SEQ ID NO:1). More suitably the polymerase backbone may be any member of the well known polB enzyme family excluding viral polymerases. More suitably the polymerase backbone may be any member of the well known polB enzyme family having at least 36% identity to SEQ ID NO:1; suitably at least 50%; suitably at least 60%; suitably at least 70%; suitably at least 80%. At the 80% identity level, the invention suitably embraces polB enzymes from the Archaeal *Thermococcus* and/or *Pyrococcus* genera. In a preferred embodiment suitably the polymerase backbone has at least 90% identity to SEQ ID NO:1.

When using other polymerase backbones, mutations are transferred to the equivalent position as is well known in the art and as noted above. For example, with reference to the exemplary polymerase 6G12, the following table illustrates how the transfer of mutations to alternate backbones may be carried out. The table shows Pol6G12 mutations and structural equivalent positions in other PolBs. The mutations found in Pol6G12 are shown against the underlying sequence of the wild-type Tgo. The structurally equivalent residue in other well-studied B-family polymerases is given. Residues that were not mapped to equivalent positions are shown as N.D.

| Tgo (1TGO) | | Pol6G12 | RB69 (1IG9) | *E. coli* (3MAQ) |
|---|---|---|---|---|
| V | 589 | A | 703 | 604 |
| E | 609 | K | 732 | N.D. |
| I | 610 | M | 733 | N.D. |
| K | 659 | Q | 778 | 681 |
| E | 664 | Q | 783 | 686 |
| Q | 665 | P | 784 | 687 |
| R | 668 | K | 788 | 690 |
| D | 669 | Q | 789 | 691 |
| K | 671 | H | N.D. | 693 |
| K | 674 | R | 792 | N.D. |
| T | 676 | R | 801 | 700 |
| A | 681 | S | 806 | 705 |

-continued

| Tgo (1TGO) | | Pol6G12 | RB69 (1IG9) | *E. coli* (3MAQ) |
|---|---|---|---|---|
| L | 704 | P | 835 | 733 |
| E | 730 | G | 869 | 750 |

Most suitably, the polymerase backbone is Archaeal *thermococcus* TgoT polB; the true wild type sequence is as shown in SEQ ID NO:1. This will serve as the reference sequence, and preferred embodiments of the invention are described with reference to this sequence.

Reference Sequence

When particular amino acid residues of polymerase are referred to using numeric addresses, the numbering is taken with reference to the true wild type TgoT polB amino acid sequence of SEQ ID NO:1 (or to the nucleic acid sequence encoding same).

This is to be used as is well understood in the art to locate the residue of interest. This is not always a strict counting exercise—attention must be paid to the context. For example, if the protein of interest is of a slightly different length, then location of the correct residue in that sequence corresponding to (for example) E664 may require the sequences to be aligned and the equivalent or corresponding residue picked, rather than simply taking the 664th residue of the sequence of interest. This is well within the ambit of the skilled reader.

Mutating may refer to the substitution or truncation or deletion of the residue, motif or domain referred to. Preferably mutation means substitution. Thus, unless otherwise indicated expressly or by context, 'mutation' may be taken to refer to substitution of the amino acid referred to herein.

Mutation may be effected at the polypeptide level e.g. by synthesis of a polypeptide having the mutated sequence, or may be effected at the nucleotide level e.g. by making a nucleic acid encoding the mutated sequence, which nucleic acid may be subsequently translated to produce the mutated polypeptide. Where no amino acid is specified as the replacement amino acid for a given mutation site, as a default alanine (A) may be used. Suitably the mutations used at particular site(s) are as set out herein.

A fragment is suitably at least 10 amino acids in length, suitably at least 25 amino acids, suitably at least 50 amino acids, suitably at least 100 amino acids, or suitably the majority of the polymerase polypeptide of interest i.e. 387 amino acids or more, suitably at least 500 amino acids, suitably at least 600 amino acids, suitably at least 700 amino acids, suitably the entire 773 amino acids of the TgoT polB sequence.

Sequence Variation

The polymerase of the invention may comprise sequence changes relative to the wild type sequence in addition to the key mutations described in more detail herein. Specifically the polymerase of the invention may comprise sequence changes at sites which do not significantly compromise the function or operation of the polymerase as described herein.

Polymerase function may be easily tested by operating the polymerase as described, such as in the examples section, in order to verify that function has not been abrogated or significantly altered.

Thus, provided that the polymerase retains its function which can be easily tested as set out herein, sequence variations may be made in the polymerase molecule relative to the wild type reference sequence.

Conservative substitutions may be made, for example according to the table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In considering what mutations, substitutions or other such changes might be made relative to the wild type sequence, retention of the function of the polymerase is paramount. Typically conservative amino acid substitutions would be less likely to adversely affect the function. Suitably the polymerase of the invention varies from the wild type sequence only by conservative amino acid substitutions except as discussed.

Sequence Homology/Identity

Although sequence homology can also be considered in terms of functional similarity (i.e., amino acid residues having similar chemical properties/functions), in the context of the present document it is preferred to express homology in terms of sequence identity.

Sequence comparisons can be conducted by eye or, more usually, with the aid of readily available sequence comparison programs. These publicly and commercially available computer programs can calculate percent homology (such as percent identity) between two or more sequences.

Percent identity may be calculated over contiguous sequences, i.e., one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example in an otherwise identical pair of sequences, one insertion or deletion will cause the following amino acid residues to be put out of alignment, thus potentially resulting in a large reduction in percent homology (percent identity) when a global alignment (an alignment across the whole sequence) is performed. Consequently, most sequence comparison methods are designed to produce optimal alignments that take into consideration possible insertions and deletions without penalising unduly the overall homology (identity) score. This is achieved by inserting "gaps" in the sequence alignment to try to maximise local homology/identity.

These more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum percent homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package, FASTA (Altschul et al., 1990, J. Mol. Biol. 215:403-410) and the GENEWORKS suite of comparison tools.

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62. Once the software has produced an optimal alignment, it is possible to calculate percent homology, preferably percent sequence identity. The software typically does this as part of the sequence comparison and generates a numerical result.

Suitably identity is assessed at the amino acid level over at least 400 or 500, preferably 600, 700, or even more amino acids with the relevant polypeptide sequence(s) disclosed herein, most suitably with the full length progenitor "true wild type" TgoT polB sequence of SEQ ID NO:1.

Suitably, homology should be considered with respect to one or more of those regions of the sequence known to be essential for protein function rather than non-essential neighbouring sequences. This is especially important when considering homologous sequences from distantly related organisms.

When considering conserved regions, suitably the 36% of residues common to both SEQ ID NO:1 and to the pol delta member of the polB enzyme family should be taken to be potentially important residues which are suitably not mutated in the polypeptide of the invention unless otherwise discussed. Thus suitably the polypeptide of the invention has at least 36% identity to SEQ ID NO:1 and suitably the amino acid residues making up said at least 36% identity comprise the amino acid residues corresponding to those which are identical between SEQ 1N NO:1 and the pol delta member of the polB enzyme family. Suitably the polypeptide of the invention has at least 36% identity to SEQ ID NO:1 and has at least 36% identity to the pol delta member of the polB enzyme family.

The same considerations apply to nucleic acid nucleotide sequences.

Polynucleotides of the Invention

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli.*

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Vectors of the invention may be transformed or transfected into a suitable host cell as described to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

Protein Expression and Purification

Proteins of the invention are typically made by recombinant means, for example as described below and in the examples. However they may also be made by synthetic means using techniques well known to skilled persons such as solid phase synthesis. Proteins of the invention may also be produced as fusion proteins, for example to aid in extraction and purification. Examples of fusion protein partners include glutathione-S-transferase (GST), 6xHis, GAL4 (DNA binding and/or transcriptional activation domains) and β-galactosidase. It may also be convenient to include a proteolytic cleavage site between the fusion protein partner and the protein sequence of interest to allow removal of fusion protein sequences. Clearly the fusion protein selected must not hinder the function of the polymerase of the invention.

Suitably the polymerase of the invention is not fused to any sequence for purification since the polymerase of the invention may be advantageously purified based on its thermostable properties and/or using simple well known purification schemes as noted herein.

Host cells comprising polynucleotides of the invention may be used to express proteins of the invention. Host cells may be cultured under suitable conditions which allow expression of the proteins of the invention. Expression of the proteins of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Proteins of the invention can be extracted from host cells by a variety of techniques known in the art, including enzymatic, chemical and/or osmotic lysis and physical disruption.

Polymerase Mutants

We have identified a novel region of the polymerase enzyme which may be varied in order to provide orthogonal polymerase functions. Referring to the conventional structural model of the polymerase enzyme, the patch which has been identified is located in the "thumb" part of the enzyme. In the accepted model, the polymerase is thought of as a right "hand" extending around a DNA "rod" which passes through a central space defined by the structure of the enzyme. The region of the enzyme which we teach may be varied in order to provide the orthogonal polymerase functions described is the "thumb" part of the enzyme. In more detail, it is that part of the thumb at the exit point where the DNA "rod" leaves the enzymatic "hand".

The region of the enzyme which we teach should be varied is the "thumb" region. The thumb region represents a single three dimensional part of the enzyme. However, this single three dimensional thumb structure is represented by separate linear parts of the amino acid sequence. Within this linear parts two patches are identified that specify orthogonal polymerase function. These two patches are designated patch 10A and patch 12 and are discussed in more detail below.

Patch 10A

Patch 10A corresponds to amino acids 651 to 679 of SEQ ID NO: 1. Mutations in this patch can provide orthogonal polymerase activity for at least RNA, CeNA, or HNA. Patch 10A is considered the most important patch described herein.

Within patch 10A is a motif of special importance, which is the small beta-sheet region from aa 662 to 666. This region occupies a space near the nucleic acid backbone and is especially suitably mutated for polymerase(s) acting to produce RNA. In particular, residue E664 is especially suitable to mutate, for example E664Q or E664K; most preferred is E664K. This mutant is especially suitable for RNA production.

Although the 662-666 region (and E664 in particular) is especially important for RNA polymerase, the effect is not confined to RNA polymerase. For example the E664 position is mutated in both C7 (SEQ ID NO:5; excellent CeNA pol activity) and 6G12 (SEQ ID NO:12; excellent HNA pol activity). Thus suitably the orthogonal polymerase of the invention comprises an E664 mutation such as E664Q.

For RNA polymerase suitably a Y409 mutation is included such as Y409N, which is located outside the patch10A. This has the advantage of increasing RNA pol activity.

Patch 12

Patch 12 comprises amino acids 734 to 765 of SEQ ID NO: 1. Mutation of patch 12 can provide orthogonal polymerase activity to at least HNA or CeNA. Patch 12 is important, but may be considered less important than Patch 10A.

Suitably mutations may be made to one or other or both Patches 12 and 10A. If only one patch is to be mutated, suitably that is patch 10A.

Without wishing to be bound by theory, it is thought that the best mutations in these patches are those which alter the "thumb" structure of this region so that it no longer performs its gate keeping function at the exit of the nucleotide polymer from the enzyme. It is thought that by making these types of mutation, the natural "filtering" function of the enzyme is altered or disabled, thereby advantageously making the enzyme more promiscuous and more capable of producing orthogonal nucleic acid polymers.

Further polymerase mutations are found in the specific exemplary sequences provided but which lie outside of the key thumb domain patches 10A and 12. These may be defined by comparing exemplary sequence(s) for the polymerase(s) of the invention given in the sequence listing with the preferred backbone polypeptide given in SEQ ID NO:2, and by ignoring the mutations occurring in patch 10A (aa 651 to 679) and patch 12 (aa 734-765). The resulting mutations, which are identified by this process are each possible further optimising mutations which may be included in the polymerase(s) of the invention.

Important to HNA synthesis by the exemplary Pol6G12 are mutations in a flexible region of the polymerase thumb subdomain (Tgo: G586-T773), typically not visible in many PolB apo structures (e.g. 2JGU[27], 1Q8I, 1QHT[28], 1WNS[29]) but resolved in the *E. coli* Pol II ternary complex (3MAQ)[30]. Structurally, this region transverses the thumb along the face proximal to the exonuclease domain and makes close contacts with the nascent strand from +3 to +7. We posit that this structural region serves as an extension checkpoint and has been remodeled by mutation in Pol 6G12 to allow processive HNA synthesis. Indeed, other mutations in the same motif enable processive synthesis of other non-cognate nucleic acid polymers (CC, VBP, PH manuscript in preparation), pointing to a general specificity function for this polymerase region. Several of Pol6G12's other mutations (V589A, 1610M, E664Q, Q665P, R668K, T676R and A681S), cluster around the internal surface of the polymerase in proximity to the nascent strand. These mutations are likely to further reshape the duplex binding 'funnel' of the polymerase to allow accommodation of the non-canonical HNA•DNA hybrid.

Reverse Transcriptase Mutants

The polymerase of the invention maybe mutated in order to endow it with reverse transcriptase activity. In other words, the polymerase of the invention may be mutated such as to allow the manufacture of a DNA polymer from an orthogonal nucleic acid template.

Suitably, in order to produce orthogonal reverse transcriptase activity the polymerase of the invention is mutated at I521 and/or Y388.

A shorter adaptive path led us to an HNA-RT. While, L408 the residue previously identified to be associated with RNA-RT activity in the related polB family polymerase Pfu did not score highly, SCA identified four proximal residues with clear involvement in covariation networks, mutation of just one of which (I521L) yielded a polymerase with significant HNA reverse transcriptase activity. Surprisingly, I521 is not located in proximity to the HNA template strand, but rather packs onto residues 540-542 (DTD motif) in the conserved C-motif in the polymerase active site, proximal to the primer strand 3' terminus. The I521L mutation may therefore not directly alter interactions of the polymerase with the HNA template strand but rather promote RT activity on a HNA template by repositioning of the nascent strand 3' end to allow productive extension.

It is a specific advantage of the mutations described above that they permit the mutated polymerase to be used in the production of a DNA nucleic acid from an RNA template with the proof reading function of the polymerase preserved. In other words, the reverse transcriptase mutants of the invention may be used with RNA as the template whilst the exonuclease of the polymerase is intact (e.g. leaving at least D141 and E143 as functional residues such as wild type residues.) This provides excellent results, for example one or even two orders of magnitude greater fidelity than conventional reverse transcriptase enzymes.

It should be noted that optimum activity on other orthogonal nucleic acid templates such as HNA or CeNA may require the proof reading/exonuclease function of the polymerase to be inhibited or ablated, for example by further mutation. Specifically, when the template is HNA then the proof reading/exonuclease function of the polymerase should be in activated.

The reverse transcriptase activity of the enzyme may be further optimised. For example, there are a number of known mutations which may be made in combination with the mutations of the invention in order to enhance activity when RNA is the template. For example, the asparagine mutation of the preferred D4N3 polymerase may be made in order to enhance the activity when used on RNA as the template.

Backbone Mutations

Whether the enzyme of the invention is a non-DNA polymerase or a reverse transcriptase, there are a number of mutations which may advantageously be made to the backbone polypeptide.

One such mutation is the 'therminator' mutant (New England Bio Labs) at position A485 of SEQ ID NO:1. Suitably the backbone has an A485 mutation such as A485L. This has the advantage of enhancing incorporation of unnatural substrates.

Another such mutation is at position V93 of SEQ ID NO:1. Suitably the backbone has a V93 mutation such as V93Q. This has the advantage of disabling read-ahead stalling which can occur for example when the template comprises uracil.

Another such mutation is at positions D141 and E143 of SEQ ID NO:1. Suitably the backbone has a D141 mutation such as D141A; suitably the backbone has an E143 mutation such as E143A; most suitably the backbone has both D141 and E143 mutations such as D141A and E143A. This has the advantage of disabling the exonuclease function of the enzyme. This further enhances incorporation of unnatural substrates.

The mutations mentioned are mutually compatible; in other words the polypeptide of the invention may have each of the backbone mutations in the same polypeptide. An example of this is in SEQ ID NO:2. This is sometimes referred to as the 'wild type' sequence and may be regarded as an excellent example of a starting polymerase backbone into which the mutations of the invention may be introduced. Thus suitably all four of the preferred backbone mutations V93Q, A485L, D141A and E143A are present in the polypeptides of the invention.

In a strict sense of course it will be noted that the sequence of SEQ ID NO:2 is not the true 'wild type' because it has these four mutations in the backbone already. For ease of reference the true wild type sequence is given as SEQ ID NO:1; this sequence is referred to as the "true wild type" herein for clarity.

Other conventional mutations may be applied to the polymerase/reverse transcriptase. Moreover, other optimising mutations may be made as appropriate.

Truncations

Truncations of the overall full length polymerase enzyme of the invention may be made if desired. Suitably full length polymerase polypeptide is used as the backbone polypeptide, such as full length TgoT polymerase 1-773 as shown in the attached sequence listing. Any truncations used should be carefully checked for activity. This may be easily done by assaying the enzyme(s) as described herein.

Purification

Polymerases of the invention are advantageously thermostable. By expressing these polymerases in a conventional (non thermo-stable) host strain, purification is advantageously simplified. For example, when the polymerases of the invention are expressed in a conventional non thermo-stable host cell, approximately 90% purity may be obtained simply by heating the host cells to 99° C. followed by centrifugal removal of cellular debris. Higher purity levels may easily be obtained for example by subjecting the heat treated soluble fraction of the host cell to ion exchange and/or heparin column purifications.

Suitably the polymerase of the invention is not fused to any other polypeptide.

Suitably the polymerase of the invention is not tagged with any further polypeptides or fusions.

It is an advantage of the invention that mutations directed to the particular patches discussed may be substitutions to any of a wide range of amino acids without loss of function of the polymerase. The patches defined are extremely tolerant of amino acid changes.

Fidelity

It is clearly important that sufficient fidelity is maintained for accurate production (or reproduction) of the orthogonal nucleic acid polymers. Suitably polymerases of the invention retain at least 95% fidelity. Fidelity (error threshold) may be taken as the number of errors introduced divided by the number of nucleotides polymerised. In other words, an error rate of 1% equates to the introduction of one error for every 100 nucleotides polymerised. In fact, the polymerases of the invention attain a much better fidelity than this. An error rate of 5% or less is considered as the minimum useful fidelity level for the polymerases of the invention; suitably the polymerases of the invention have an error rate of 4% or less; suitably 3% or less; suitably 2% or less; suitably 1% or less.

Unless otherwise stated, fidelity may be assessed as aggregate fidelity (e.g. DNA-3NA-DNA) which thus encompasses two conversion events (DNA-3NA and 3NA-DNA); the figures should be adjusted or interpreted accordingly.

Compartmentalised Self-Replication Technology

The techniques of directed evolution and compartmentalised self replication are detailed in GB 97143002 and GB 98063936 and GB 01275643. These documents are herein incorporated by reference.

The inventors modified the methods of compartmentalised self tagging and surprisingly generated DNA polymerases which exhibited an expanded substrate range as herein defined.

Further details of the method of compartmentalised self tagging in general are given below. Of particular importance in the selection of polymerases which exhibit an enhanced ability to synthesize orthogonal nucleic acid polymers such as exemplified for HNA or CeNA herein (as compared with the polymerase from which they are derived) is that the compartmentalised self tagging method was modified. These modifications are detailed below.

(i) Microcapsules

The microcapsules used in some applications of the invention require appropriate physical properties to allow the working of the invention.

First, to ensure that the nucleic acids and gene products may not diffuse between microcapsules, the contents of each microcapsule must be isolated from the contents of the surrounding microcapsules, so that there is no or little exchange of the nucleic acids and gene products between the microcapsules over the timescale of the experiment.

Second, microcapsule methods of the present invention requires that there are only a limited number of nucleic acids per microcapsule. This ensures that the gene product of an individual nucleic acid will be isolated from other nucleic acids. Thus, coupling between nucleic acid and gene product will be highly specific. The enrichment factor is greatest with on average one or fewer nucleic acids per microcapsule, the linkage between nucleic acid and the activity of the encoded gene product being as tight as is possible, since the gene product of an individual nucleic acid will be isolated from the products of all other nucleic acids. However, even if the theoretically optimal situation of, on average, a single nucleic acid or less per microcapsule is not used, a ratio of 5, 10, 50, 100 or 1000 or more nucleic acids per microcapsule may prove beneficial in sorting a large library. Subsequent rounds of sorting, including renewed encapsulation with differing nucleic acid distribution, will permit more stringent sorting of the nucleic acids. Preferably, there is a single nucleic acid, or fewer, per microcapsule.

Third, the formation and the composition of the microcapsules must not abolish the function of the machinery the expression of the nucleic acids and the activity of the gene products.

Consequently, any microencapsulation system used must fulfil these three requirements. The appropriate system(s) may vary depending on the precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

These include membrane enveloped aqueous vesicles such as lipid vesicles (liposomes) (New, 1990) and non-ionic surfactant vesicles (van Hal et al., 1996). These are closed-membranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

With a membrane-enveloped vesicle system much of the aqueous phase is outside the vesicles and is therefore non-compartmentalised. This continuous, aqueous phase should be removed or the biological systems in it inhibited or destroyed (for example, by digestion of nucleic acids with DNase or RNase) in order that the reactions are limited to the microcapsules (Luisi et al., 1987).

Enzyme-catalysed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Microcapsules can also be generated by interfacial polymerisation and interfacial complexation (Whateley, 1996). Microcapsules of this sort can have rigid, nonpermeable membranes, or semipermeable membranes. Semipermeable microcapsules bordered by cellulose nitrate membranes, polyamide membranes and lipid-polyamide membranes can all support biochemical reactions, including multienzyme systems (Chang, 1987; Chang, 1992; Lim, 1984). Alginate/polylysine microcapsules (Lim & Sun, 1980), which can be formed under very mild conditions, have also proven to be very biocompatible, providing, for example, an effective method of encapsulating living cells and tissues (Chang, 1992; Sun et al., 1992).

Non-membranous microencapsulation systems based on phase partitioning of an aqueous environment in a colloidal system, such as an emulsion, may also be used.

Preferably, the microcapsules of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

(ii) Emulsions

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and non-ionic surfactants (Schick, 1966) such as sorbitan monooleate (Span™ 80; ICI) and polyoxyethylenesorbitan monooleate (Tween™ 80; ICI) and Triton-X-100.

The use of anionic surfactants may also be beneficial. Suitable surfactants include sodium cholate and sodium taurocholate. Particularly preferred is sodium deoxycholate, preferably at a concentration of 0.5% w/v, or below. Inclusion of such surfactants can in some cases increase the expression of the nucleic acids and/or the activity of the gene products. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalisation.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994).

Aqueous microcapsules formed in water-in-oil emulsions are generally stable with little if any exchange of nucleic acids or gene products between microcapsules. Additionally, we have demonstrated that several biochemical reactions proceed in emulsion microcapsules. Moreover, complicated biochemical processes, notably gene transcription and translation are also active in emulsion microcapsules. The technology exists to create emulsions with volumes all the way up to industrial scales of thousands of liters (Becher, 1957; Sherman, 1968; Lissant, 1974; Lissant, 1984).

The preferred microcapsule size will vary depending upon the precise requirements of any individual selection process that is to be performed according to the present invention. In all cases, there will be an optimal balance between gene library size, the required enrichment and the required concentration of components in the individual microcapsules to achieve efficient expression and reactivity of the gene products.

Details of emulsion/s used when performing the method of the present invention are provided in the Examples.

(iii) Expression within Microcapsules

The processes of expression usually occur within each individual microcapsule provided by the present invention. Both in vitro transcription and coupled transcription-translation become less efficient at sub-nanomolar DNA concentrations. Because of the requirement for only a limited number of DNA molecules to be present in each microcapsule, this therefore sets a practical upper limit on the possible microcapsule size. Preferably, the mean volume of the microcapsules is less that $5.2\times10^{-16}$ $m^3$, (corresponding to a spherical microcapsule of diameter less than 10 m, more preferably less than $6.5\times10^{-17}$ $m^3$ (5 m), more preferably about $4.2\times10^{-18}$ $m^3$ (2 m) and ideally about $9\times10^{-18}$ $m^3$ (2.6 m).

The effective DNA or RNA concentration in the microcapsules may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969; Blattner and Dahlberg, 1972; Roberts et al., 1975; Rosenberg et al., 1975), eukaryotes e.g. (Weil et al., 1979; Manley et al., 1983) and bacteriophage such as T7, T3 and SP6 (Melton et al., 1984); the polymerase chain reaction (PCR) (Saiki et al., 1988); Q replicase amplification (Miele et al., 1983; Cahill et al., 1991; Chetverin and Spirin, 1995; Katanaev et al., 1995); the ligase chain reaction (LCR) (Landegren et al., 1988; Barany, 1991); and self-sustained sequence replication system (Fahy et al., 1991) and strand displacement amplification (Walker et al., 1992). Even gene amplification techniques requiring thermal cycling such as PCR and LCR could be used if the emulsions and the in vitro transcription or coupled transcription-translation systems are thermostable (for example, the coupled transcription-translation systems could be made from a thermostable organism such as *Thermus aquaticus*).

Increasing the effective local nucleic acid concentration enables larger microcapsules to be used effectively. This allows a preferred practical upper limit to the microcapsule volume of about $5.2\times10^{16}$ $m^3$ (corresponding to a sphere of diameter 10 um).

The microcapsule size must be sufficiently large to accommodate all of the required components of the biochemical reactions that are needed to occur within the microcapsule. For example, in vitro, both transcription reactions and coupled transcription-translation reactions require a total nucleoside triphosphate concentration of about 2 mM.

For example, in order to transcribe a gene to a single short RNA molecule of 500 bases in length, this would require a minimum of 500 molecules of nucleoside triphosphate per microcapsule ($8.33\times10^{-22}$ moles). In order to constitute a 2 mM solution, this number of molecules must be contained within a microcapsule of volume $4.17\times10^{-19}$ liters ($4.17\times10^{-22}$ $m^3$ which if spherical would have a diameter of 93 nm.

Furthermore, particularly in the case of reactions involving translation, it is to be noted that the ribosomes necessary for the translation to occur are themselves approximately 20 nm in diameter. Hence, the preferred lower limit for microcapsules is a diameter of approximately 100 nm.

Therefore, the microcapsule volume is preferably of the order of between $5.2\times10^{-22}$ $m^3$ and $5.2\times10^{-16}$ $m^3$ corresponding to a sphere of diameter between 0.1 um and 10 um, more preferably of between about $5.2\times10^{-19}$ $m^3$ and $6.5\times10^{-17}$ $m^3$ (1 um and 5 um). Sphere diameters of about 2.6 um are most advantageous.

It is no coincidence that the preferred dimensions of the compartments (droplets of 2.6 um mean diameter) closely resemble those of bacteria, for example, *Escherichia* are 1.1-1.5×2.0-6.0 um rods and *Azotobacter* are 1.5-2.0 um diameter ovoid cells. In its simplest form, Darwinian evolution is based on a 'one genotype one phenotype' mechanism. The concentration of a single compartmentalised gene, or genome, drops from 0.4 nM in a compartment of 2 um diameter, to 25 μM in a compartment of 5 um diameter. The prokaryotic transcription/translation machinery has evolved to operate in compartments of ~1-2 um diameter, where single genes are at approximately nanomolar concentrations. A single gene, in a compartment of 2.6 um diameter is at a concentration of 0.2 nM. This gene concentration is high enough for efficient translation. Compartmentalisation in such a volume also ensures that even if only a single molecule of the gene product is formed it is present at about 0.2 nM, which is important if the gene product is to have a modifying activity of the nucleic acid itself. The volume of the microcapsule should thus be selected bearing in mind not only the requirements for transcription and translation of the nucleic acid/nucleic acid, but also the modifying activity required of the gene product in the method of the invention.

The size of emulsion microcapsules may be varied simply by tailoring the emulsion conditions used to form the emulsion according to requirements of the selection system. The larger the microcapsule size, the larger is the volume that will be required to encapsulate a given nucleic acid/nucleic acid library, since the ultimately limiting factor will be the size of the microcapsule and thus the number of microcapsules possible per unit volume.

The size of the microcapsules is selected not only having regard to the requirements of the transcription/translation system, but also those of the selection system employed for the nucleic acid/nucleic acid construct. Thus, the components of the selection system, such as a chemical modification system, may require reaction volumes and/or reagent concentrations which are not optimal for transcription/translation. As set forth herein, such requirements may be accommodated by a secondary re-encapsulation step; moreover, they may be accommodated by selecting the microcapsule size in order to maximise transcription/translation and selection as a whole. Empirical determination of optimal microcapsule volume and reagent concentration, for example as set forth herein, is preferred.

A "nucleic acid" in accordance with the present invention is, preferably, a molecule or construct selected from the group consisting of a DNA molecule, an RNA molecule, a partially or wholly artificial nucleic acid molecule consisting of exclusively synthetic or a mixture of naturally-occurring and synthetic bases. Any one of the foregoing may be linked to a polypeptide.

The nucleic acid portion of the nucleic acid may comprise suitable regulatory sequences, such as those required for efficient expression of the gene product, for example promoters, enhancers, translational initiation sequences, polyadenylation sequences, splice sites and the like.

(iv) Product Selection.

Details of a preferred method of performing the method of the invention are provided in the Examples. However, those skilled in the art will appreciate that the examples given are non-limiting and methods for product selection are discussed in more general terms below.

A ligand or substrate can be connected to the nucleic acid by a variety of means that will be apparent to those skilled in the art (see, for example, Hermanson, 1996). According to the method of the present invention, the ligand or substrate is a 'detection agent label', preferably a dye-labelled nucleotide analogue, in particular Cy3CTP and/or Cy5CTP.

Sorting can be by any method which allows the preferential separation, amplification or survival of the detection agent labelled nucleic acid. Examples include selection by binding (including techniques based on magnetic separation, for example using Dynabeads™), and by resistance to degradation (for example by nucleases, including restriction endonucleases).

When all reactions are stopped and the microcapsules are combined, the nucleic acids encoding the active engineered polymerases selected can be enriched using an antibody or other molecule which binds, or reacts specifically with the "detection agent label". Although both substrates and product have the detection agent label, only the nucleic acids encoding active gene product will co-purify.

The terms "isolating", "sorting" and "selecting", as well as variations thereof, are used herein. Isolation, according to the present invention, refers to the process of separating an entity from a heterogeneous population, for example a mixture, such that it is substantially, preferably totally, free of at least one substance with which it was associated before the isolation process. In a preferred embodiment, isolation refers to purification of an entity essentially to homogeneity. Sorting of an entity refers to the process of preferentially isolating desired entities over undesired entities. In as far as this relates to isolation of the desired entities, the terms "isolating" and "sorting" are equivalent. The method of the present invention permits the sorting of desired nucleic acids from pools (libraries or repertoires) of nucleic acids which contain the desired nucleic acid. Selecting is used to refer to the process (including the sorting process) of isolating an entity according to a particular property thereof.

Initial selection of a nucleic acid from a nucleic acid library (for example a mutant Pfu library) using the present invention will in most cases require the screening of a large number of variant nucleic acids. Libraries of nucleic acids can be created in a variety of different ways, including the following.

Pools of naturally occurring nucleic acids can be cloned from genomic DNA or cDNA (Sambrook et al., 1989); for example, mutant Tgo libraries or other DNA polymerase libraries, made by PCR amplification repertoires of Tgo or other DNA polymerase genes have proved very effective sources of DNA polymerase fragments. Further details are given in the examples.

Libraries of genes can also be made by encoding all (see for example Smith, 1985; Parmley and Smith, 1988) or part of genes (see for example Lowman et al., 1991) or pools of genes (see for example Nissim et al., 1994) by a randomised or doped synthetic oligonucleotide. Libraries can also be made by introducing mutations into a nucleic acid or pool of nucleic acids 'randomly' by a variety of techniques in vivo, including; using 'mutator strains', of bacteria such as *E. coli* mutD5 (Liao et al., 1986; Yamagishi et al., 1990; Low et al., 1996). Random mutations can also be introduced both in vivo and in vitro by chemical mutagens, and ionising or UV irradiation (see Friedberg et al., 1995), or incorporation of mutagenic base analogues (Freese, 1959; Zaccolo et al., 1996). 'Random' mutations can also be introduced into genes in vitro during polymerisation for example by using error-prone polymerases (Leung et al., 1989). Further diversification can be introduced by using homologous recombination either in vivo (see Kowalczykowski et al., 1994 or in vitro (Stemmer, 1994a; Stemmer, 1994b)).

(V) Microcapsules/Sorting

In addition to the nucleic acids described above, the microcapsules according to the invention will comprise further components required for the sorting process to take place. Other components of the system will for example comprise those necessary for transcription and/or translation of the nucleic acid. These are selected for the requirements of a specific system from the following; a suitable buffer, an in vitro transcription/replication system and/or an in vitro translation system containing all the necessary ingredients, enzymes and cofactors, RNA polymerase, nucleotides, nucleic acids (natural or synthetic), transfer RNAs, ribosomes and amino acids, and the substrates of the reaction of interest in order to allow selection of the modified gene product.

A suitable buffer will be one in which all of the desired components of the biological system are active and will therefore depend upon the requirements of each specific reaction system. Buffers suitable for biological and/or chemical reactions are known in the art and recipes provided in various laboratory texts, such as Sambrook et al., 1989.

The in vitro translation system will usually comprise a cell extract, typically from bacteria (Zubay, 1973; Zubay, 1980; Lesley et al., 1991; Lesley, 1995), rabbit reticulocytes (Pelham and Jackson, 1976), or wheat germ (Anderson et al., 1983). Many suitable systems are commercially available (for example from Promega) including some which will allow coupled transcription/translation (all the bacterial systems and the reticulocyte and wheat germ TNT™ extract systems from Promega). The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected (Ellman et al., 1991; Benner, 1994; Mendel et al., 1995).

After each round of selection the enrichment of the pool of nucleic acids for those encoding the molecules of interest can be assayed by non-compartmentalised in vitro transcription/replication or coupled transcription-translation reactions. The selected pool is cloned into a suitable plasmid vector and RNA or recombinant protein is produced from the individual clones for further purification and assay.

(Vi) Microcapsule Identification

Microcapsules may be identified by virtue of a change induced by the desired gene product which either occurs or manifests itself at the surface of the microcapsule or is detectable from the outside as described in section iii (Microcapsule Sorting). This change, when identified, is used to trigger the modification of the gene within the compartment. In a preferred aspect of the invention, microcapsule identification relies on a change in the optical properties of the microcapsule resulting from a reaction leading to luminescence, phosphorescence or fluorescence within the microcapsule. Modification of the gene within the microcapsules would be triggered by identification of luminescence, phosphorescence or fluorescence. For example, identification of luminescence, phosphorescence or fluorescence can trigger bombardment of the compartment with photons (or other particles or waves) which leads to modification of the nucleic acid. A similar procedure has been described previously for the rapid sorting of cells (Keij et al., 1994). Modification of the nucleic acid may result, for example, from coupling a molecular "fluorescent detection agent label", caged by a photolabile protecting group to the nucleic acids: bombardment with photons of an appropriate wavelength leads to the removal of the cage. Afterwards, all microcapsules are combined and the nucleic acids pooled together in one environment. Nucleic acids encoding gene products exhibiting the desired activity can be selected by affinity purification using a molecule that specifically binds to, or reacts specifically with, the "fluorescent label".

(Vi) Multi Step Procedure

It will also be appreciated that according to the present invention, it is not necessary for all the processes of transcription/replication and/or translation, and selection to proceed in one single step, with all reactions taking place in one microcapsule. The selection procedure may comprise two or more steps. First, transcription/replication and/or translation of each nucleic acid of a nucleic acid library may take place in a first microcapsule. Each gene product is then linked to the nucleic acid which encoded it (which resides in the same microcapsule). The microcapsules are then broken, and the nucleic acids attached to their respective gene products optionally purified. Alternatively, nucleic acids can be attached to their respective gene products using methods which do not rely on encapsulation. For example phage display (Smith, G. P., 1985), polysome display (Mattheakkis et al., 1994), RNA-peptide fusion (Roberts and Szostak, 1997) or lac repressor peptide fusion (Cull, et al., 1992).

In the second step of the procedure, each purified nucleic acid attached to its gene product is put into a second microcapsule containing components of the reaction to be selected. This reaction is then initiated. After completion of the reactions, the microcapsules are again broken and the modified nucleic acids are selected. In the case of complicated multistep reactions in which many individual components and reaction steps are involved, one or more intervening steps may be performed between the initial step of creation and linking of gene product to nucleic acid, and the final step of generating the selectable change in the nucleic acid.

(Vii) Amplification

In all the above configurations, genetic material comprised in the nucleic acids may be amplified and the process repeated in iterative steps. Amplification may be by the polymerase chain reaction (Saiki et al., 1988) or by using one of a variety of other gene amplification techniques including; Q replicase amplification (Cahill, Foster and Mahan, 1991; Chetverin and Spirin, 1995; Katanaev, Kurnasov and Spirin, 1995); the ligase chain reaction (LCR) (Landegren et al., 1988; Barany, 1991); the self-sustained sequence replication system (Fahy, Kwoh and Gingeras, 1991) and strand displacement amplification (Walker et al., 1992).

BRIEF DESCRIPTION OF THE FIGURES

The figures are individually described in the following examples section.

The invention is now described by way of example. These examples are intended to be illustrative, and are not intended to limit the appended claims.

EXAMPLES

Example 1

Development of a Novel High-Throughput Screening System for XNA Synthesis

An effective scalable screen is an essential step to test individual clones and to select clones with improved activity from a population. The polymerase ELISA endpoint assay, developed by Ong and colleagues (1), is summarised in FIG. 1A. Basically, extension of a biotinylated primer-template hairpin leads to incorporation of labelled-nucleotides (e.g. digoxigenin-labelled UTP) that can be detected through an ELISA. Hairpin sequence can be altered to modulate the minimal polymerase activity required for a detectable signal (incorporations prior to the labelled nucleotide) and incorporation of labelled nucleotides are linked to polymerase activity. The key limitation of the assay is that activity is correlated to labelled-nucleotide incorporation, which may not correlate to polymerase activity, e.g. in the case of low-fidelity polymerases or template-independent extension.

FIG. 1 shows a diagram of Polymerase ELISA endpoint assay (A) and the two-step polymerase activity ELISA (B) developed to monitor incorporation of unnatural nucleic acids.

The polymerase ELISA endpoint assay was used to screen A-motif TgoT mutants selected in the second round of CSR (both single nucleotide and dinucleotide substitution selections) with mixed results. A number of mutants were identified by the assay, which used a hairpin that required ten CeRTP incorporations prior to the first dUTP-DIG one. However, further screening with primer extension reactions showed that few of the isolated mutants had comparable activity to wild-type TgoT and of the 40 isolated mutants, only three showed improvement in activity.

A possible explanation is that the labelled-nucleotide incorporation does not correlate as well to activity in PolB-type polymerases (e.g. TgoT) as it does to activity in PolA-type ones (e.g. Taq). The more accommodating catalytic site of PolB enzymes or the unnatural nucleotides being used may favour labelled-nucleotide incorporation leading to a higher signal in the ELISA that does not represent the desired polymerase activity.

One alternative further explored was to separate the extension from the detection steps. As described in FIG. 1B, polymerase extension against a known template allows the extension product to be assessed through binding of a sequence-specific probe that can be detected. The two-step assay has a number of advantages over the endpoint assay: First, low-fidelity enzymes are penalised as sequence mismatches reduce probe binding affinity and thus signal. Second, selection pressure can be modulated by the choice of probe in a single template (e.g. the blue probe shown in FIG. 1B requires longer extension for binding than the red one) thus increasing the range of usefulness of a single primer-template combination. Third, the two-step assay is compatible with the primer-extension assay which can be carried out jointly to further validate ELISA-identified candidates.

A number of steps (shown in FIG. 1B as 1 through 8) were standardised or optimised to obtain an assay that is stable and can be reliably reproduced. Nucleotide concentration (particularly for unnatural nucleotides), primer/template ratio, polymerase concentration and extension conditions were all investigated to determine the optimal range for the assay (steps 1 and 2). Template denaturation (step 4) was successfully obtained chemically both with dilute sodium hydroxide and with urea solutions after binding of the extended molecules to a streptavidin-coated matrix (step 3). Denaturation with sodium hydroxide was substantially more efficient than other methods tried and it did not lead to increased background. Probe binding and subsequent ELISA steps were standardised. The sensitivity of the assay was assessed and is shown in FIG. 2; as little as 0.1% of extended product could be detected.

Figure 2:
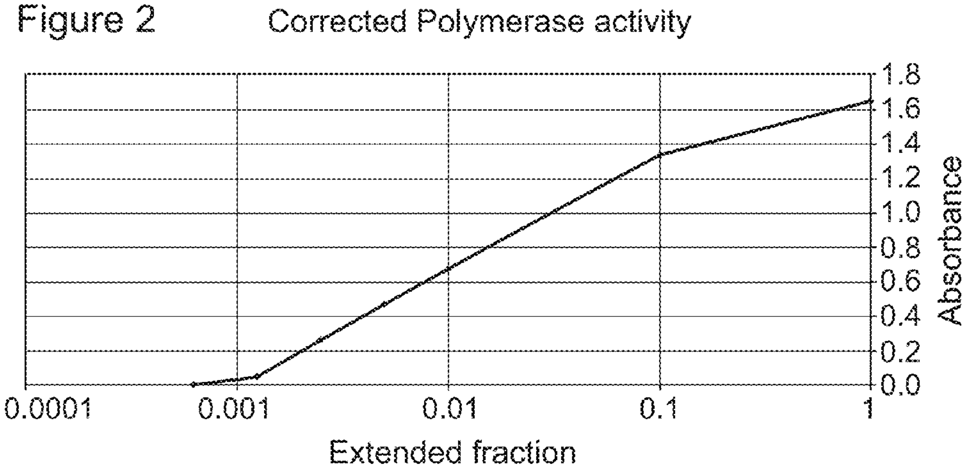
FIG. 2 presents a graph of sensitivity of a two-step polymerase activity ELISA.

FIG. 2 shows a graph of Sensitivity of the two-step polymerase activity ELISA. Fully extended templates were diluted in unextended primer to determine the minimum fraction of extended primer required to obtain an ELISA signal. Background was subtracted from the signals, suggesting that the minimum fraction of extended primers that can be detected is around 0.12%.

Similar experiments carried out with dilutions from pre-extended primers also suggest that extensions that allow high levels of probe binding are sensitive enough to detect down to 1 fmol of extension product (data not shown). Short extensions, which result in lower levels of probe binding, did not have the same detection range as expected.

The results of a successful screen carried out with the two-step polymerase activity ELISA are shown in FIG. 3. They refer to A- and B-motif CST selections and served to validate the assay as a powerful screening tool.

FIG. 3 shows a graph and a photograph of typical results from the two-step polymerase activity ELISA. The values obtained from the ELISA screen clearly correlate with the primer extension assay (logarithmic trendline; R2=0.94). Wild-type is shown in red.

A typical reaction is carried out as follows: An annealing master reaction containing biotinylated primer (and fluorescently labelled primer is direct detection is required), excess template (usually 4:1), nucleotides (optimum results above 100 μM final concentration) and polymerase buffer is made, heated and cooled to allow primer annealing. Remaining reaction components (enzyme, extra buffer or additional supplements) are added and reaction carried out (either as a single extension cycle or with thermocycling akin to PCR). Reaction time is adjusted according to the enzyme's level of activity and desired screening stringency. Each 10 μl reaction is transferred to a streptavidin-coated well (100 μl PBST+10 μl reaction+90 μl PBST) and incubated at room temperature for 30 min. The supernatant is discarded and each well washed thrice with PBST (Phosphate-buffered saline supplemented with 0.1% Tween20). The buffer is removed and the plate incubated in 100 mM NaOH for 30 sec. Wells are washed once with 100 μl mM NaOH and a second time with PBST. PBST is removed and 200 μl of probe solution (diluted in PBST to 0.2 μM final concentration) is added to each well and incubated at room temperature for 30 minutes. Wells are washed thrice with PBST and the antibody against the probe added. Reaction then proceeds as a standard ELISA.

Example 2

Development of a Selection System for XNA Synthesis

Development of a selection system suitable for isolating a CeNA or an HNA synthetase was carried out in parallel with selection itself. Thus, this section focuses on the development of the system and on the unsuccessful attempts for selecting a synthetase. The successful selection of the HNA synthetase will be described in the subsequent sections.

Initially, selection was attempted by short-patch compartmentalised self-replication (spCSR) (1); a technique previously developed in our lab. But this approach proved unproductive.

Consequently, a second selection methodology was developed: compartmentalised self-tagging (CST). As replication is decoupled from incorporation, CST is more likely to isolate successful synthetases due to the lowered selection barrier. In addition, the genetic information being selected remains as DNA throughout and is more likely to be successfully recovered.

The basic principles of CST have been described. Further optimisation of selection conditions and of the methodology itself led to the development of a new version of the CST strategy (CST2.0), summarised in FIG. 4. As in its predecessor, a short biotinylated primer is used to target plasmids encoding the mutant polymerases. In emulsion, polymerases extend the primers incorporating the modified nucleotides supplied in the reaction—polymerases better at CeNTP (or hNTP) incorporation extend the primer further than poorer mutants. Plasmids are recovered through the biotinylated primer and washed to remove unspecific or poorly bound plasmids. The resultant plasmid population should be enriched for plasmids coding polymerases that can more efficiently extend the primer under the reaction conditions. Those can be amplified, cloned and used as the starting population for subsequent selection rounds.

Figure 4:
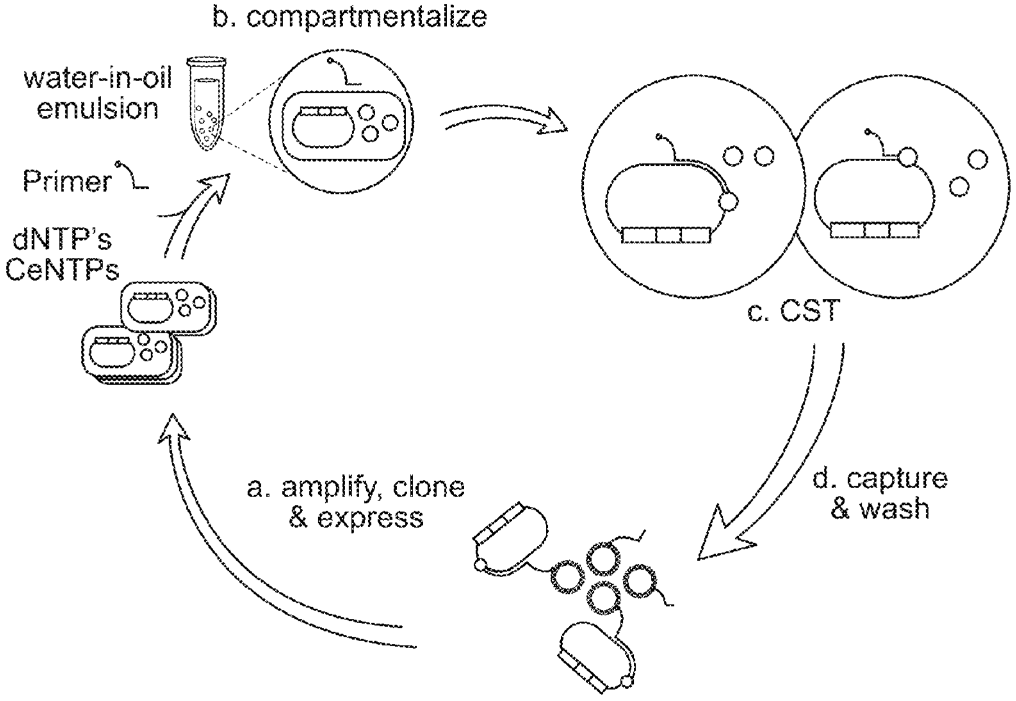
FIG. 4 demonstrates hNTP incorporation against tRNA templates by part-purified mutant polymerases.

FIG. 4 shows a diagram of compartmentalised self-transcription (CST). As described in the text, a DNA biotinylated primer was used to isolate polymerases better at incorporating CeNTPs and hNTPs.

The key differences between the two variations lie on the primer of choice (random rather than specific, poor binder rather than stable binder) and on the downstream sample processing (formamide wash rather than 37° C. incubation). These changes in the methodology were key to the improvements observed.

A simple in silico model of the CST experiment suggested that amplification of total recovered DNA did not need to correlate with activity for libraries in which improved clones were rare. Once all modifications were incorporated, a model selection comparing wild-type and an inactive frame-shift mutant, yielded a 3-fold poorer enrichment than pre-modification (10-fold wt enrichment rather than the previous 30-fold observed), for instance. But that would then be expected if efficient selection required higher than wild-type activity levels.

Figure 6:
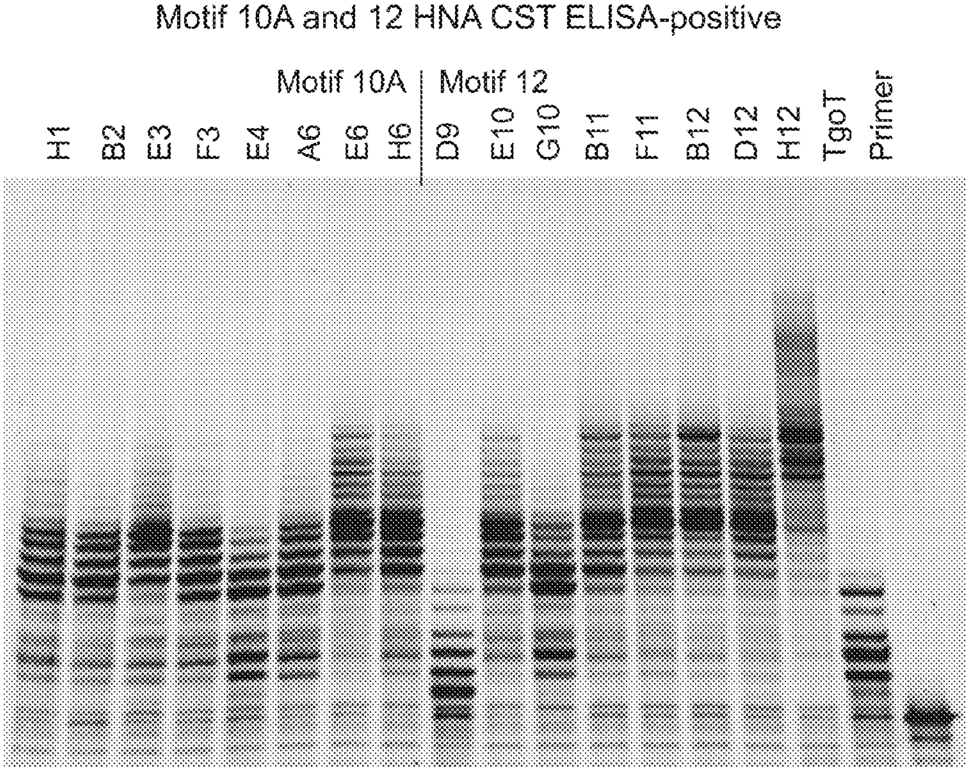
FIG. 6 shows an example of improved polymerases isolated after a single CST round on motif 10A and motif 12 libraries.

A single round of selection on a 10A motif library (hNTP selection using an N6 primer) was carried out and a number of individual clones assessed for hNTP activity. The results, summarised in Table 2, confirmed that selection was indeed taking place and a number of improved polymerases were isolated, as shown in FIG. 6.

TABLE 1

Effect of one round of CST selection on motif 10A naive library. Polymerase activity for each mutant was determined with the polymerase ELISA previously developed. In the case of TgoT (wild-type) under the reaction conditions used, ELISA signal was around 0.05 (hNTP) and 3.0 (dNTP). Polymerases with dNTP activity below 0.2 were deemed inactive. Polymerases with hNTP signal between 0.1 and 0.9 were deemed wild-type like. Enzymes above the 0.9 threshold were deemed improved. Improved enzymes were selected for downstream screening and analysis. The two populations were compared using a $\chi 2$ test ($\chi 2$ = 0.019, 2 d.f.)

| Unselected motif 10A library | | 1st round selected from motif 10A library | |
|---|---|---|---|
| Mutants screened | 72 | Mutants screened | 56 |
| No dNTP or hNTP activity | 9 | No dNTP or hNTP activity | 3 |
| Wt-like activity | 19 | Wt-like activity | 10 |
| Substantially improved | 6 | Substantially improved | 8 |

Example 3

DNA Polymerase Library Design

Initially, three libraries in both TgoT and 9° NT polymerases were made targeted against the 3 conserved motifs that make the polymerase active site: A, B and C motifs. The libraries tried to encompass any phylogenetic diversity available in the region as well as low levels of mutations in all but the functionally important residues (e.g. catalytic aspartate). Similar libraries in Pfu had successfully been used to isolate a polymerase capable of incorporation and replication of Cy-labelled nucleotides (2).

While the three motifs line the active site of the polymerase and the incoming nucleotide pocket, it was clear that their optimisation could not be sufficient to obtain a processive polymerase. As a result, further libraries were designed using a similar approach to introduce mutations (as detailed in attached ppt file).

As only two polymerases of the PolB family have been crystallised with DNA to date (in a processive conformation)—Rb69 (3) and more recently phi29 (4) polymerases, shown in FIGS. 5A and 5C—and sequence alignments alone were not sufficient to identify other candidate regions for diversification, a structural alignment of the three polymerases (phi29, Rb69 and Tgo) was used to identify other possible regions for diversification.

Initial primer extension reactions identified that TgoT would efficiently incorporate a natural nucleotide after a cyclohexenyl nucleotide prior to stalling. Hence, further residues to be explored were identified by locating all residues within 10 Å of the +1 incorporation in the primer strand of the Rb69 polymerase structure. Water molecules identified in that search were then used to search a further 5 Å sphere. Residues identified on Rb69 structure were mapped to the available Tgo structure. Nine patches were identified in the Tgo sequence that would be expected to lie in the vicinity of the nascent helix. Two more patches were identified by structural comparison of the thumb structures of Rb69 and Tgo. The motifs identified were then mapped to phi29 to confirm their location; all but the thumb motifs (phi29 has a structurally divergent thumb) were successfully mapped.

The resultant eleven patches were used as the basis to design a further 18 libraries, shown in FIGS. 5D and 5E.

FIG. 5 lists SEQ ID NO: 1 and_shows Rb69 (A), Tgo (B) and phi29 (C) polymerase structures. N-terminal domains, exonuclease domains and other domains are all shown in light yellow. Palm subdomains are shown in pink, finger subdomains in grey and thumb domains in light blue. The three conserved polymerase motifs target in the original libraries are shown in red and are highlighted in the Tgo sequence (D). The new libraries are shown in the Tgo structure and are underlined in the Tgo sequence (D). The three initially available libraries are underlined in red. Libraries 10A and 12 are shown in blue.

Diversity was introduced through oligonucleotide synthesis of the primers used to generate the library (see attached ppt file). A typical amplification reaction (100 μl) would be carried out with Roche's Expand High Fidelity using the conditions recommended by the manufacturer and our wild-type plasmid DNA. The PCR would be carried out as a "touch-down" reaction (annealing temperature decreased after each extension cycle). As the primers have a small overlap downstream of Bsal sites, it allows the whole plasmid to be amplified and cloned seamlessly following Bsal (NEB) and Dpnl (NEB) restriction reactions, and subsequent ligation with T4 DNA polymerase (NEB). All reactions were carried out according to the manufacturer's recommendations. For first round libraries, a further amplification step using phi29 (NEB) was carried out using N6 oligos as primers and reaction conditions as recommended by the manufacturer.

It is important to notice that the polymerase we have termed "wild-type", and that makes the basis of all synthesised libraries, has a number of mutations present which are not present in the polymerase gene as isolated from *Thermococcus gorgonarius*. Our "wild-type" harbours 4 mutations: V93Q (introduced to reduce the polymerase read-ahead function that causes stalls if uracil is detected on the template)(5), D141A and E143A (introduced to inactivate the 3'→5' exonuclease domain) (6-8), and A485L (commercially available as Therminator, but shown to improve incorporation of unnatural substrates in B-family polymerases)(9).

Once synthesised by PCR, the ligated plasmids were transformed and a small sample of clones (between 10 and 30 clones per library) sequenced to confirm identity and estimate library diversity. Once gene integrity (dNTP incorporation activity and sequencing results) and library diversity were estimated to be high, large scale transformations were carried out to generate the libraries used for the remainder of the project.

Example 4

Selected Clones with Enhanced HNA/CeNA/RNA Polymerase Activity

FIG. 6 shows an example of improved polymerases isolated after a single CST round on motif 10A and motif 12 libraries.

Crude lysates of all available libraries normalised for their dNTP incorporation activity were used to identify which ones had the highest potential to house possible synthetases. Selection was carried out in those libraries.

Single round selections were carried out in motif libraries B−, 8, 9, 10A, 10B, 10C, 11 and 12 for both CeNTP and hNTP incorporations. Small-scale screens were carried out on motifs 8, 10A and 12. Although CeNTP incorporation improvement was detected, hNTP improvements were substantially higher. Those results, confirmed that CST was suitable for synthetase selection.

Mutants with improved incorporation parameters for both HNA and CeNA were isolated (see attached file containing sequences) validating the CST2.0 approach and a further round of CST selection was carried out on the resulting 10A library. CST selections were also carried out on the 10A motif library (made in the context of a steric gate mutant Y409N) to isolate enzymes that could outperform the wild-type TgoT in synthesising RNA (see Examples 7-12).

Example 5

Design and Evolution of Polymerase for Processive Synthesis of CeNA and/or HNA As improved mutants were isolated from different motif libraries, we investigated whether the mutations being identified could be additive. For that, we crossed two motif 12 mutants and four motif 10A ones to obtain the eight possible chimeras.

While mutant activity always exceeded wild-type activity no significant gain was attained by any of the chimeras. This suggests that mutations in motif 10A and motif 12 target a similar function in the polymerase hence 10N12 chimeras do not lead to any gain in activity.

Figure 7:
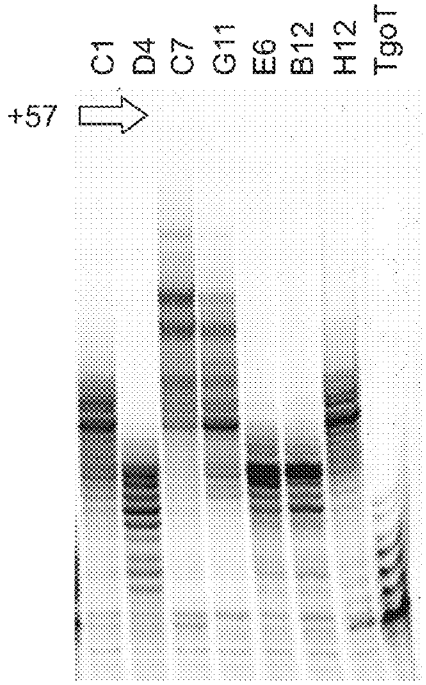
FIG. 7 shows a photograph illustrating hNTP incorporation by CeNTP-selected (C1, D4, C7, and G11) and hNTP-selected (E6, B12, H12) mutant polymerases using cleared bacterial lysates.

Another possibility investigated was the cross-substrate activity. Selection for CeNTP or hNTP incorporation may alter the enzyme's ability to recognise a modified nucleic acid structure, which may be similar for hNTP and CeNTP. While no gain in activity was observed for hNTP-selected mutants on CeNTP incorporation, the complementary experiment (hNTP incorporation by CeNTP-selected enzymes) identified a number of clones with even higher hNTP activity, as shown in FIG. 7. Thus, selection using CeNTPs provided a stronger selective pressure for the evolution of polymerases capable of synthesizing orthogonal polymers.

FIG. 7 shows a photograph illustrating hNTP incorporation by CeNTP-selected (C1, D4, C7 and G11) and hNTP-selected (E6, B12, H12) mutant polymerases using cleared bacterial lysates. Total extension time of one hour. The length of the DNA template allows 57 incorporations.

Similarly, the isolated mutants were also tested for rNTP (ribonucleotide) incorporation. Despite the presence of the Y409 steric gate (9) in all the selected polymerases which greatly reduces rNTP incorporation, D4 showed considerable incorporation of rNTPs, as shown in FIG. 8. Because of its activity, D4 was isolated for further characterisation and to serve as the starting point for further diversification with an aim to isolate a DNA-dependent processive RNA polymerase (see Examples 7).

Sequence analysis of the 18 isolated motif 10A mutants have identified two clusters of mutations within the introduced diversity, targeting residues likely to be involved in maintaining local protein structure as well as residues likely to be in close proximity to the extending primer phosphate backbone (based on a structural alignment with RB69 polB) and thus of potential functional importance.

Example 6

A Processive HNA Polymerase: 6G12

A second round of CST (CeNTP selection) was carried out on a 10A motif library (initially selected with CeNTP) to investigate the effect of further selection rounds on the library activity. One screen identified a mutant with improved CeNTP incorporation potential (marginally better than all the mutants identified in the first round) that also showed significant cross-substrate (hNTP) activity: 6G12.

TABLE 2

TgoT and 6G12 protein sequence highlighting the mutations isolated in 6G12.

| Polymerase | Sequence (587-732) |
|---|---|
| 6G12 | FFATKKKYAVIDEEDKITTRGLKMVRRDWSEIAKETQAR<br>VLEAILKHGDVEEAVRIVKEVTEKLSKYEVPPEQLVIYQ<br>PITKQLHDYRARGPHVSVAKRLAARGIKIRPGTVISYIV<br>PKGSGRIGDRAIPFDEFDPAKHKYDAGYY<br>(SEQ ID NO: 44) |
| TgoT | FFVTKKKYAVIDEEDKITTRGLEIVRRDWSEIAKETQAR<br>VLEAILKHGDVEEAVRIVKEVTEKLSKYEVPPEKLVIYE<br>QITRDLKDYKATGPHVAVAKRLAARGIKIRPGTVISYIV<br>LKGSGRIGDRAIPFDEFDPAKHKYDAEYY<br>(SEQ ID NO: 45) |

A total of 14 mutations have accumulated in 6G12, including 6 which lie outside of the selected motif. All mutations, when mapped to a RB69 structure, line the inner surface of the polymerase in close contact with the nascent primer strand, as shown in FIG. 9.

FIG. 9 shows 6G12 mutations mapped to Tgo (A) and RB69 (B) structures. All mutations identified in 6G12 were mapped onto the Tgo structure (red spheres) and a structural alignment was used to identify the equivalent residues in RB69. All the mutations identified lie within the thumb domain (blue) and most map to the internal protein surface in contact with the nascent primer strand.

Each 6G12 mutation has been reverted back to TgoT to determine the contribution of each mutation to its HNA synthetase activity. Two of the tested back mutations showed improved HNA incorporation activity, the remaining 11 mutations tested yielded small decreases in activity but retained activity above TgoT levels.

Figure 10:
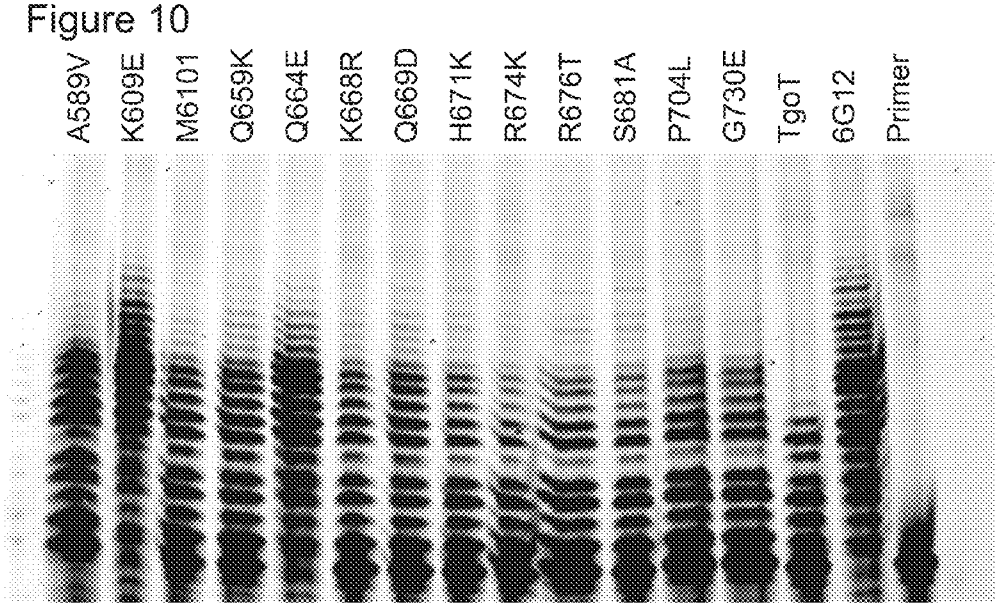
FIG. 10 shows hNTP incorporation activity of 6G12 reversion point mutant polymerases against a mixed template.

FIG. 10 shows 6G12 reversion point mutant hNTP incorporation activity against a mixed template. Polymerase activity was normalised against dNTP and all mutants so far obtained were assessed for their hNTP incorporation activity. Mutations K609 and Q664E seem not to contribute to the polymerase activity while all other mutations seem additive to the improved HNA synthetase phenotype.

Figure 11:
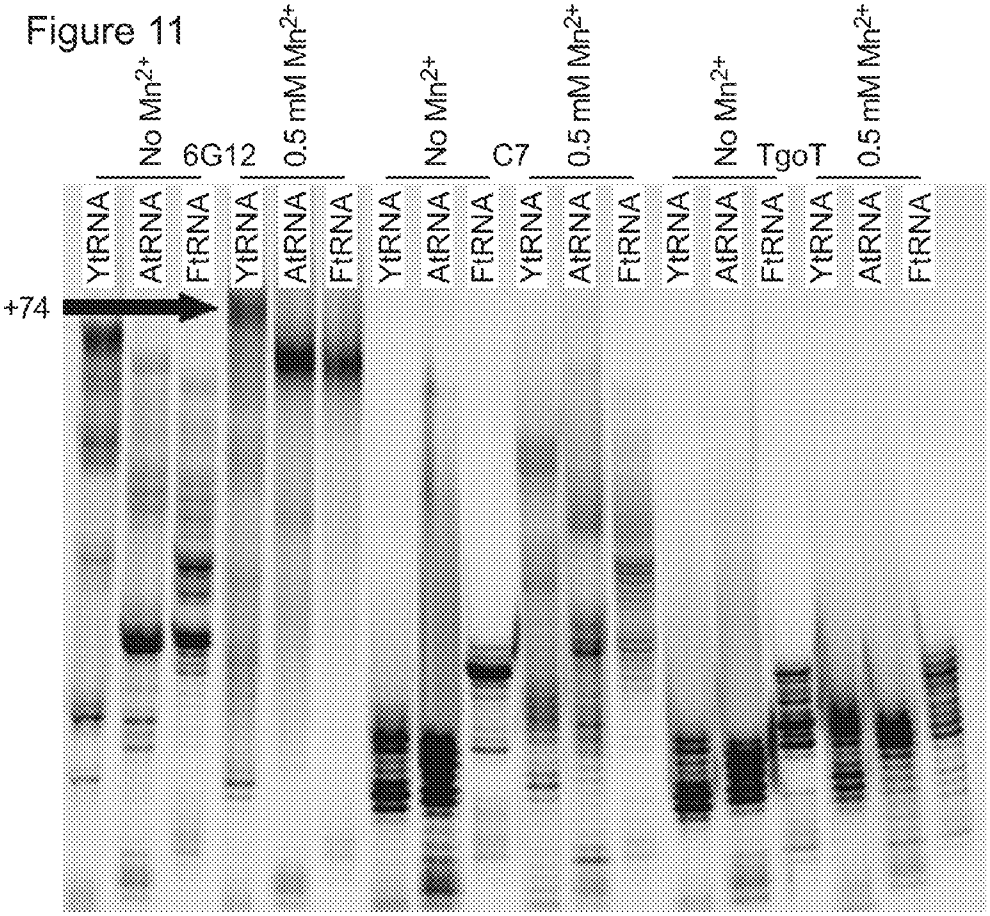
FIG. 11 shows hNTP incorporation activity of polymerases 6G12, C7, and TgoT against yeast tRNA templates. 6G12 outperformed other polymerases isolated and synthesized longer tRNA templates, even in the absence of $Mn^{+2}$ ions.

In terms of activity, 6G12 also outperforms all other polymerases isolated to date and has allowed synthesis of a longer tRNA template, even in the absence of Mn+2 ions, which is known to increase polymerase activity (at some fidelity cost). The difference in activity is shown in FIG. 11.

FIG. 4 shows hNTP incorporation against tRNA templates by part-purified mutant polymerases. Two mutants (6G12 and C7) were used to test whether a tRNA gene could be synthesised in hNTP. As observed with the shorter template, 6G12 greatly outperformed C7 (isolated from single round of CST selection) particularly in the absence of Mn+2. Nearly 100% of the primer was extended to completion in 2 hours.

HNA was typically synthesised with purified 6G12 in 100 μl reactions containing 100 pmol labelled primer, excess template (2:1), modified nucleotides and 0.5 mM manganese in reaction buffer (ThermoPol buffer—NEB). Reactions without polymerase were heated and cooled to allow primer annealing, polymerase was added and reactions were then carried out as a 3-cycle PCR (90 min@50° C., 90 min@65° C., 1 min@94° C.).

Example 6a

Fidelity of 6G12 HNA Synthesis

We probed the fidelity of HNA synthesis by 6G12 by performing extension reactions lacking each one of the hNTPs. No full-length product was obtained unless all 4 hNTPs were present, as shown in FIG. 12. FIG. 12 shows HNA synthesis with 3 of the 4 available hNTPs by 6G12. In the absence of any one of the nucleotides, 6G12 is not capable of processive HNA synthesis. This indicates that 6G12 is a template-dependent polymerase with good fidelity unable to synthesize HNA polymers in the absence of all four hNTPs.

Further indications of 6G12 fidelity derive from the ELISA screen (example 1) by which 6G12 was ultimately isolated. It involves synthesis of an HNA polymer and detection thereof by hybridization of a complementary oligonucleotide probe. Detection in ELISA is thus dependent on the accurate synthesis of the desired polymer.

A more stringent and quantitative measure of 6G12 fidelity has been obtained in conjunction with 521L (the HNA RT) (see Example) suggesting that the aggregate error rate (i.e. HNA synthesis with 6G12, followed by 521L DNA synthesis from HNA, followed by amplification of the recovered DNA with Taq) to be <7×103 errors per base pair (see Example)

REFERENCES TO EXAMPLES 1-6

1. J. L. Ong, D. Loakes, S. Jaroslawski, K. Too, P. Holliger, Journal of Molecular Biology 361, 537 (August, 2006).
2. N. Ramsay et al., J Am Chem Soc 132, 5096 (Apr. 14, 2010).

3. M. C. Franklin, J. Wang, T. A. Steitz, Cell 105, 657 (Jun. 1, 2001).
4. A. J. Berman et al., EMBO J. 26, 3494 (Jul. 25, 2007).
5. M. J. Fogg, L. H. Pearl, B. A. Connolly, Nat Struct Biol 9, 922 (December, 2002).
6. C. M. Joyce, V. Derbyshire, Methods Enzymol 262, 3 (1995).
7. L. Blanco, A. Bernad, M. Salas, Gene 112, 139 (Marl, 1992).
8. A. Bernad, L. Blanco, J. M. Lazaro, G. Martin, M. Salas, Cell 59, 219 (Oct. 6, 1989).
9. A. F. Gardner, W. E. Jack, Nucleic Acids Research 27, 2545 (Jun. 15, 1999).

The following examples pertain to the isolation of a processive RNA polymerase from the CST selection experiments aimed at isolating (a) processive HNA and/or CeNA polymerase(s).

Example 7

Mutation of the Steric Gate Residue Y409 in D4 Yields a Processive, High-Fidelity RNA Polymerase D4 is derived from Tgo, the replicative DNA polymerase from the hyperthermophillic archaeon *Thermococcus gorgonarius*. The starting gene (TgoT) bore mutations to disable read-ahead stalling (V93Q) and the exonuclease domain (D141A, E143A) and the Therminator mutation (A485L) to enhance incorporation of unnatural substrates. Critically, it also comprises a cluster of 8 mutations in a region of the thumb domain (residues 586-773) (motif 10A) and which appears critical for processivity with unnatural substrates.

However, the steric gate residue in D4 is still intact and greatly hinders the incorporation of rNTPs. In order to improve RNA polymerase activity, the steric gate (Y409 in Tgo), was mutated and various mutants investigated (FIGS. 13*a, d*).

FIG. 13 (*a*) Steric gate design. The 2'OH of the incoming rNTP can clearly be seen clashing with the tyrosine steric gate. This is alleviated by mutation to leucine, asparagine or serine. (b) Extension of a yeast YtRNA requiring 87 incorporations to make a 105 mer product. Reaction conditions: 1× Thermopol buffer, 1.8 pmol primer, 3.6 pmol template, 2 mM rNTPs, 3 mM $MgCl_2$, 0.5 mM $MnCl_2$, 0.15 μl purified D4N3 in 3 μl final volume. Thermocycling: 1 minute 94° C., 5 minutes 50° C., 5 minutes 65° C., 10 seconds 94° C., 5 minutes 50° C., 5 minutes 65° C. making 20 minutes extension time. (c) Comparison of DNA and RNA primer extension by D4N3. Reaction carried out as indicated in methods. (d) Primer extensions with complete rNTP substitution demonstrating the effect of modifying the steric gate in D4. Mutation of the steric gate residue to asparagine (Y409N) yielded D4N3, a mutant polymerase with a striking ability to processively synthesize RNAs up to 87 nt, including e.g. yeast Y-tRNA (FIG. 13*b*). Furthermore, D4N3 can extend both DNA and RNA primers (FIG. 13*c*).

Following the observation that RNA polymerases often require higher $Mg^{2+}$ and NTP concentrations than DNA polymerases for optimal activity, I systematically varied both rNTP and $Mg^{2+}$ concentrations. The optimized conditions significantly improved processivity and speed of RNA synthesis by D4N3 as well as product yields, with D4N3 now capable of synthesising an 87 mer tRNA<20 minutes (FIG. 13*b*).

A critical parameter of polymerase function is fidelity. To investigate if D4N3 had accurately copied the DNA template strand into RNA, I cloned D4N3 transcripts by polyA-tailing and RT-PCR (Superscript II) using standard methods. Sequencing revealed a aggregate fidelity (comprising RNA synthesis by D4N3, reverse transcription by Superscript II and 30 cycles of PCR by Platinum Taq polymerase) with only 4 point mutations and 7 deletions across 19 reads of >69 bases, making a total of 13 errors in >1300 incorporations or an aggregate error rate of approximately $10^{-2}$.

Example 8

Different Mutations of the D4 Steric Gate Enable Incorporation of Other 2'-Modified NTPs 2' modified nucleotides occur widely in natural RNAs and are essential for some functions (e.g. ribosome function, thermostability of thermophile rRNA). They also have a number of interesting biotechnological applications including in nucleic acid therapeutics such as RNAi and aptamers, where they enhance potency and serum stability. However, many are poor substrates for naturally occurring RNA polymerases.

Figure 14:
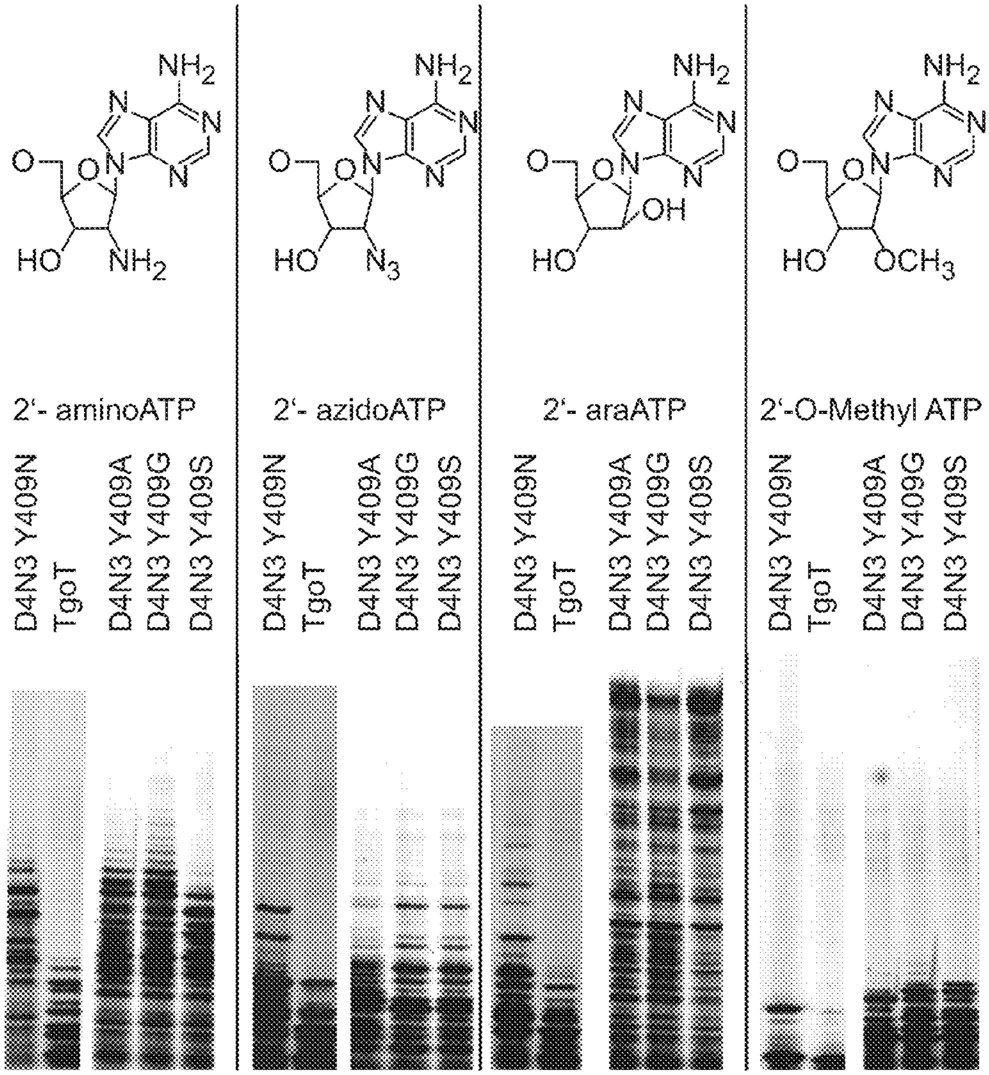
FIG. 14 demonstrates that further modification of the steric gate (Y409) of D4 allows better-than-wild-type incorporation of various substrates.

We performed a second round of modelling of the D4N3 active site, which suggested alanine, glycine or serine as optimal to accommodate bulkier 2' modifications (e.g. O-Methyl), The smaller alanine and glycine mutations indeed allowed improved incorporation of 2' amino-ATP, 2' ara-ATP, 2' azido-ATP and 2-O-Methyl-ATP (FIG. 14). FIG. 14—Primer extensions with 2' modified ATP. Further modification of the steric gate (Y409) of D4 allows better-than-wild-type incorporation of various substrates. This suggests steric gates can be optimised according to substrate, as opposed to simply removed by mutation to small, neutral residues. Structures from Trilink Biotechnologies (www.trilinkbiotech.com)

The complete CeTempN template (57 incorporations, including 13As) was synthesised with 2'Ara-ATP and GTP, CTP, TTP.

This suggests D4N3 and its derivatives may have improved ability to incorporate 2' modified NTPs (notably arabino-derivatives) into RNA (or DNA).

Example 9

Only a Single Point Mutation in Motif 10A is Necessary for D4N3 Processivity As only modifying the steric gate does not yield a processive RNA polymerase, we concluded that mutations in the 10A motif must be critical for processive RNA synthesis.

Figure 15:
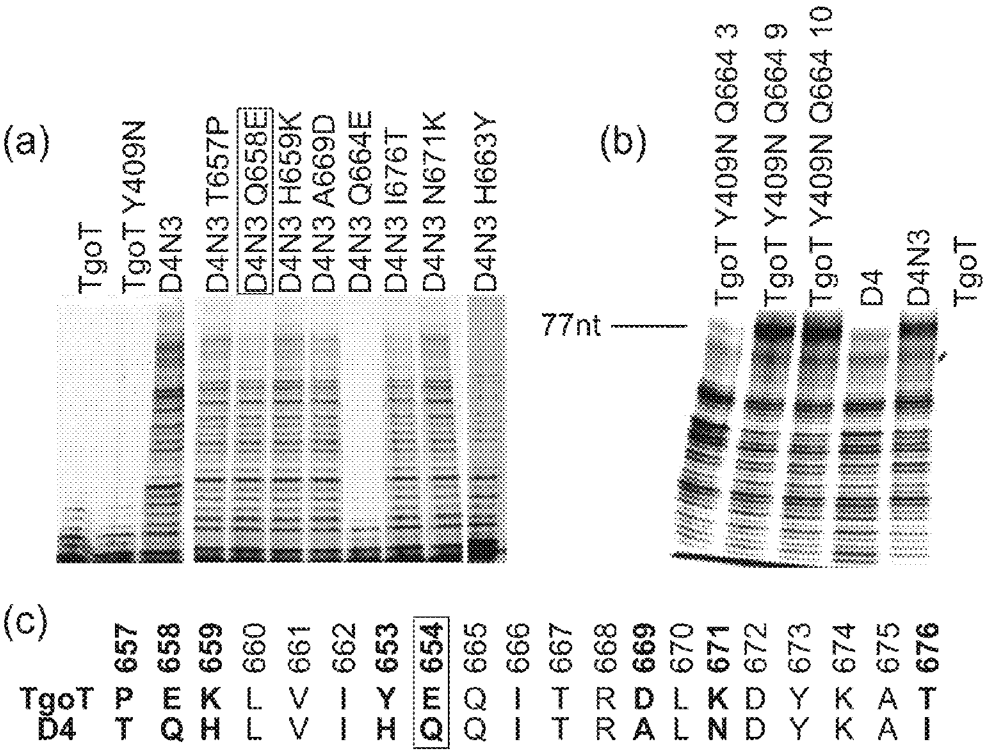
FIG. 15 shows the effect of various point mutation reversions on primer extension. Panel (a): 10A back mutations; panel (b): Q664 forward mutations; panel (c) shows 10A mutations of Tgo and D4.

D4 has 8 mutations compared to wild-type Tgo in motif 10A and a sporadic L to P mutation in the A motif. Individual point mutations to revert each of the 8 mutated positions in the 10A region to wild type had little effect on RNA synthesis with the exception of position 664, reversion of which resulted in a dramatic drop in activity (FIG. 15*a*). This suggested that a single mutation Q664E was mainly responsible for enabling processive RNA synthesis. To test this hypothesis, I introduced this mutation into TgoT Y409N bearing a mutated steric gate yielding a new polymerase (TNQ). Indeed, this single mutation Q664E proved sufficient to confer RNA polymerisation ability superior to D4N3 to polymerase TNQ (FIG. 15*b*). FIG. 15—Primer extension reactions with complete rNTP substitution. (a) 10A back mutations: TgoT, TgoT with steric gate mutated to asparagine (TgoT Y409N), D4 with asparagine steric gate (D4N3), D4 with wild type steric gate (D4) and point mutations to revert mutation in the D4 10A region back to wild type. (b) Q664 forward mutations. From left to right TgoT with wild type steric gate and Q664E mutation (TgoT Y409 Q664E), 2 lanes with TgoT with asparagine steric gate and Q664E mutation (TgoT Y490N, Q664E 9 and 10), D4 with wild type steric gate (D4) and with asparagine steric gate (D4N3) and TgoT. Reactions were carried out indicated in Methods. (c) 10A sequence in Tgo and D4. Numbering is according to Tgo.

Example 10

RNA Primer Dependent tRNA Synthesis by the Thermostable RNA Polymerase (TNQ

YtRNA was synthesised using purified TNQ (TgoT/Y409N/E664Q) in the presence of NEB ThermoPol buffer supplemented with an extra 2 mM MgSO4 (4 mM total) and 0.625 mM of each dNTP. 20 ml reactions contained 10 pmol FITC-labelled RNA primer, 20 pmol DNA template and 1.5 ml purified enzyme at 1:10 dilution. Cycling conditions:

| | Cycle 1 | Cycle 2 |
|---|---|---|
| 94° C. | 20 seconds | 10 seconds |
| 50° C. | 1 minute | 1 minute |
| 65° C. | 1 min/5 min/20 min* | 1 min/5 min/20 min* |

*NB: Incubation time at 65° C. was 1 minute or 5 minutes or 20 minutes for each of 2 cycles, depending on the stringency of the extension. A control containing no rNTPs was also run to demonstrate any product is dependent on their presence.

Figure 16:
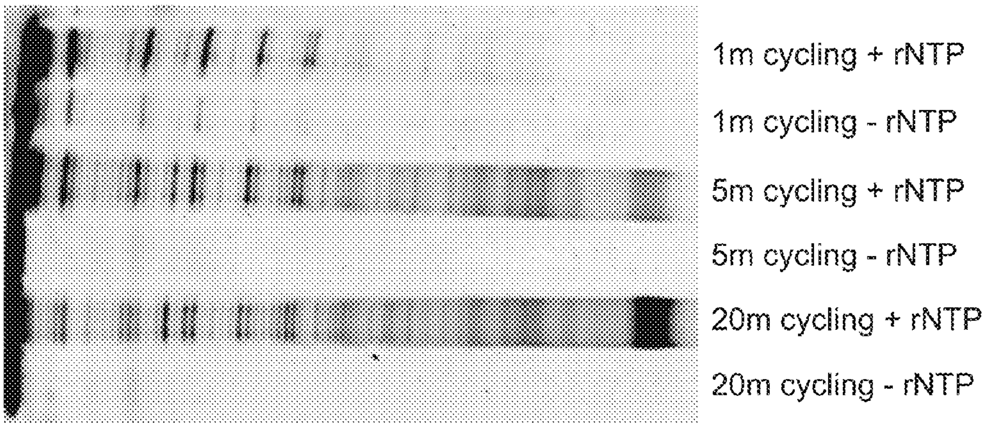
FIG. 16 shows the synthesis of yeast tRNA by purified TNQ (TgoT/Y409N/E664Q).

5 ul of neat extensions (theoretically containing 2.5 pmol primer) were run on 13% acrylamide/8M urea/1×TBE gel (see FIG. 16; FIG. 16 shows a photograph)

This demonstrates that 2×5 minute extension cycles is sufficient to synthesise the full-length tRNA, requiring 117 rNTP incorporations, and that no product is generated in the absence of rNTPs.

The remainder of the reaction was isopropanol precipitated, pelleted and resuspended in 100 ml 1× Turbo DNase buffer containing 3 ml Turbo DNase and incubated for 90 minutes at 37° C. before acid phenol:chloroform extraction and a second isopropanol precipitation. This time the pellet was suspended in 100 ml dH2O, 100 ml isopropanol and 100 ml buffer RLT from a QIAGEN RNeasy kit and the RNA purified according to the manufacturer's instructions. The pure RNA was eluted in 30 ml of the provided nuclease-free water and 2 ml used for RT-PCR with both SuperScript OneStep RT-PCR System (Invitrogen) and Transcriptor One-Step RT-PCR kit (Roche):

The expected product size of 150 bp confirms the PAGE result that 2×5 minute extension cycles is sufficient to synthesise the tRNA, requiring 117 rNTP incorporations.

Example 11

Synthesis of the mRNA of Protein Encoding Gene (GFP) by the Thermostable RNA Polymerase (TNQ)

Figure 17:
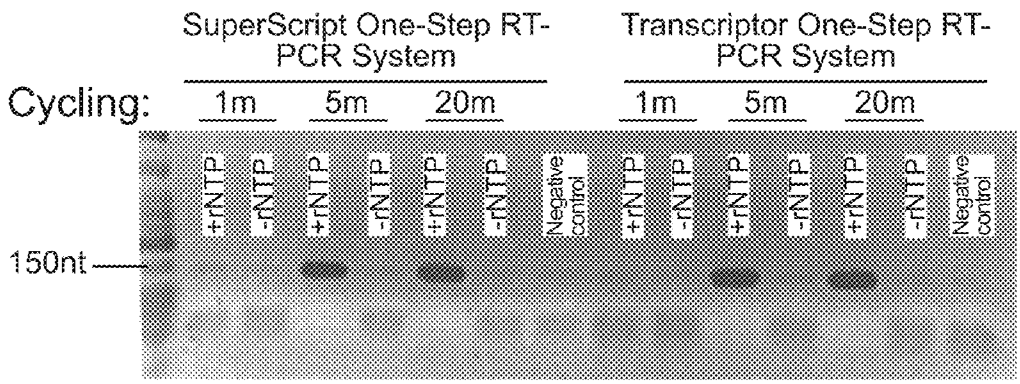
FIG. 17 shows the RT-PRC of TNQ-synthesized RNA as template.

A GFP gene requiring 748 rNTP incorporations was synthesised using TNQ (TgoT/Y409N/E664Q) from a single-stranded DNA template made from an m6GFP-encoding plasmid. The template was prepared using one biotinylated primer and one non-biotinylated primer, such that both strands could be captured and the desired strand washed off using 0.1M NaOH. See FIG. 17. FIG. 17 shows a photograph.

Synthesis was carried out in a 10 ml reaction containing 0.625 mM each rNTP, 5 pmol FITC-labelled RNA primer, 9.9 pmol ssDNA template and 0.75 ml enzyme at 1:10 dilution NEB ThermoPol buffer supplemented with 2 mM MgSO4, giving a final concentration of 4 mM Mg2+. Cycling conditions:

| | Cycle 1 | Cycle 2 |
|---|---|---|
| 94° C. | 1 minute | 10 seconds |
| 50° C. | 12 minutes | 12 minutes |
| 65° C. | 48 minutes | 48 minutes |

Figure 18:
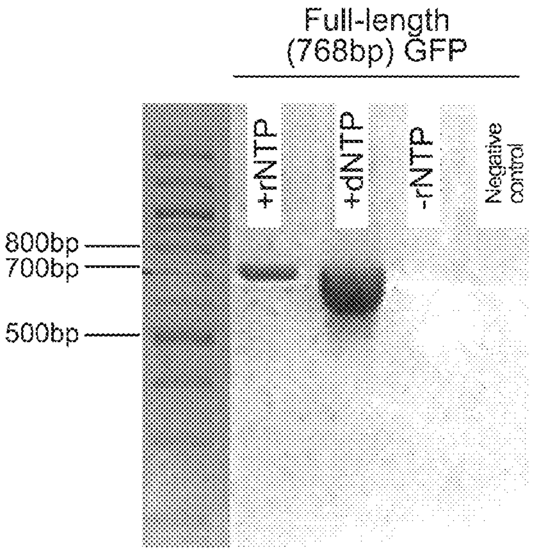
FIG. 18 shows synthesis of a GFP gene requiring 748 rNTP incorporations by TNQ (TgoT/Y409N/E664Q), from a single-stranded DNA template made from a m6GFP-encoding plasmid.

Following synthesis, the reactions were isopropanol precipitated and the pellet suspended in 48 ml 1× Turbo DNase buffer containing 2 ml Turbe DNase. Following a 60 minute incubation at 37° C., the RNA was acid phenol:chloroform extracted and isoproponal precipitated again. The pellet was suspended in 100 ml dH2O, 100 ml isopropanol and 100 ml buffer RLT from a QIAGEN RNeasy kit and the RNA purified according to the manufacturer's instructions. The pure RNA was eluted in 30 ml of the provided nuclease-free water. A positive control reaction was run with dNTPs which was neither DNase treated nor RNeasy purified; it was purified only using a QIAGEN QIAquick PCR purification column and eluted in the same volume (30 ml) of the same water. 2.5 ml of the purified RNA was used as a template for RT-PCR using SuperScript OneStep RT-PCR System (Invitrogen) using an internal RT primer to generate a 500 bp fragment and a second primer set to generate the full-length GFP gene (see FIG. 18). FIG. 18 shows a photograph.

A critical parameter of polymerase function is fidelity. To investigate if TNQ had accurately copied the DNA template strand into RNA and to compare its fidelity of RNA synthesis with that of D4N3 (and other RNA polymerases we cloned the full-length +rNTP and +dNTP lanes using a TOPO cloning kit (Invitrogen). A majority of the resulting colonies were visibly green, and sequencing of 9 random colonies deriving from the RNA synthesis and RT-PCR confirmed an excellent aggregate fidelity (comprising RNA synthesis by D4N3, reverse transcription by Superscript II and 30 cycles of PCR by Platinum Taq polymerase) of ca. $10^{-3}$ (5 single base misincorporations and 1 insertion in 6732 sequenced bases) superior to D4N3.

Example 12

An Improved Second Gate Mutation for RNA Polymerisation

Following the finding that only a single point mutation in the 10A region (E664Q) was necessary for processive RNA synthesis, both that position and its adjacent residues (E662, Y663, E664, Q665) were diversified individually using an NNS codon. 2×96 well plates were screened by ELISA, and limiting diversity to a single residue per experiment meant there was a low chance of missing any of the 20 possible amino acids. A typical ELISA result is shown in FIG. 18.

Positive hits were sequenced and the following mutations were found to allow processive RNA synthesis:

| Wild Type amino acid | Mutations allowing RNA synthesis (not in order) |
|---|---|
| I662 | Leu, Lys, Phe, Arg, Thr, Val, Trp, His |
| Y663 | Gly, His, Leu, Phe, Ser |
| E664 | Gly, Leu, Lys, Pro, Gln, Arg, Ser |
| Q665 | Ala, Met, Ser, Thr |

Figures 19, 20:
FIG. 19 is an illustration of a typical ELISA result confirming mutations.
FIG. 20 compares RNA polymerization by TNQ and TNK mutant polymerases.
Figure 21:
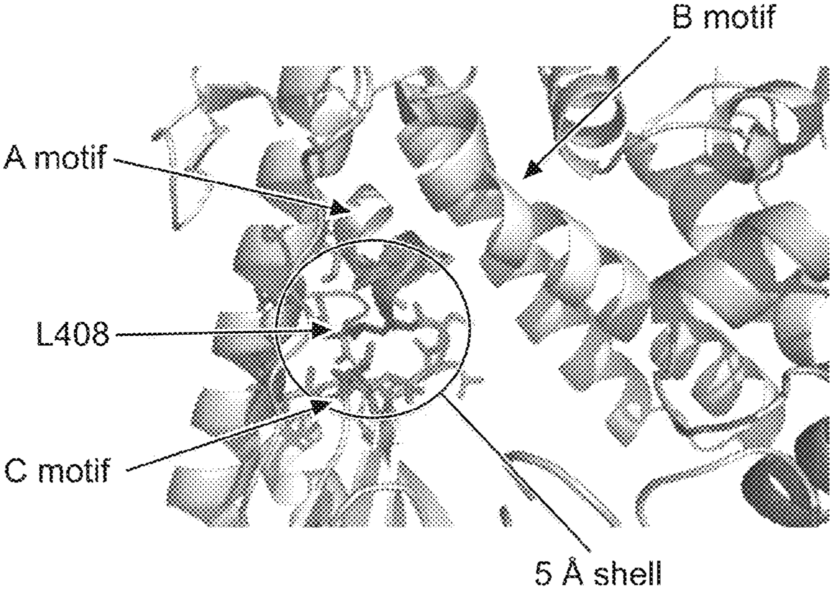
FIG. 21 is an illustration of polymerase motifs, identifying residue L408, conserved polymerase motifs and a 5 Å shell used to identify potential "informational" residues.
Figure 22:
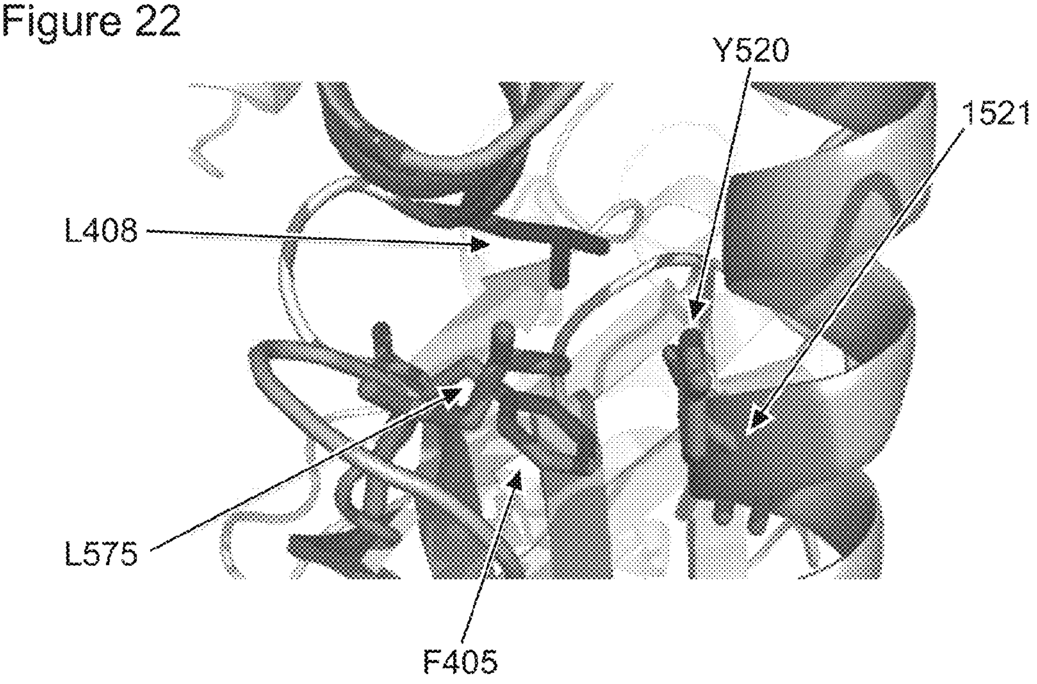
FIG. 22 is an illustration of residues identified by SCA within the Å shell around 408.
Figure 23:
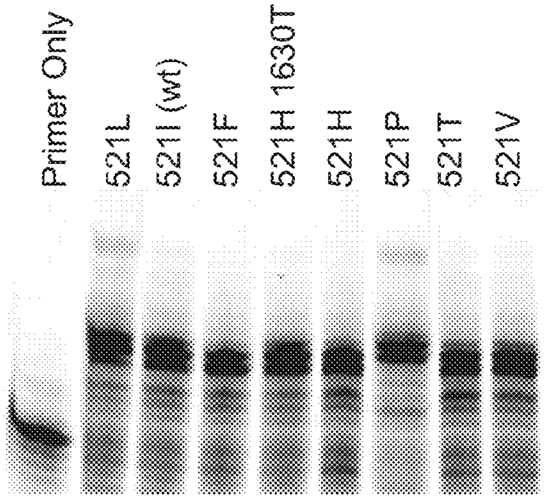
FIG. 23 shows synthesis activity of several polymerases mutated at position 521.

In depth investigation has not yet been carried out, but mutations at E664 have the greatest effect on RNA polymerisation, with E664K appearing the most effective by a fair margin (FIG. 20).

Example 13

CST 2.0 Approach

The compartmentalised self-transcription (CST) approach: as in CSR, compartmentalisation isolates different genotypes. A biotinylated DNA primer is used in an in vitro primer extension reaction, thus linking genotype to phenotype. Plasmid-bound primers are recovered and isolated using streptavidin-coated paramagnetic beads. Ideally, primers are too short for effective plasmid capture unless extended. Extension and processing conditions can be tailored to modulate selective pressure. Recovered plasmids are amplified and used as the starting population of subsequent rounds.

Compartimentalised self-transcription. A short biotinylated DNA primer (A) is used to select for enzymes capable of extending it in emulsion (B).

The biggest advantage of CST over CSR for selecting a CeNA synthetase is that the genetic information selected remains as DNA throughout the reaction, thus sidestepping one of the large limitations of the CSR methodology, the pull-through. Selective pressure in CST is substantially lower than in CSR and that has enabled us to carry out CST selections with full CeNTP and HNTP substitution. Enrichment estimates obtained from model experiments (w.t. vs. frameshift mutant) suggest that it is possible to obtain a 30-fold improvement per round of selection. Some of the system's selection parameters may be optimised to further increase selection.

Protocol:

| Aqueous phase (150 ul): | |
|---|---|
| Thermopol buffer (10x) | 15 ul |
| 50% glycerol | 30 ul |
| MnCl2 (30 mM) | 5 ul |
| MgCl2 (25 mM) | 3 ul |
| Primer (BC36N6-50 uM) | 1 ul |
| formamide | 3 ul |
| DTT (100 mM) | 1.5 ul |
| BSA (10 mg ml-1) | 1.5 ul |
| Nucleotides (2.5 mM each) | 8 ul |
| Cells + Water | 82 ul |
| | 150 ul |
| Vogelstein oil phase | 600 ul |

All in a 2 ml tube with a 5 mm steel bearing.

Induced library cells are prepared as in CSR. Briefly, 1 ml of culture is harvested by low speed centrifugation and resuspended in 1 ml of 1× Pol buffer. The process is repeated lowering the resuspension volume first to 500 ul and finally to 200 ul. Cell number is estimated from A595 of a 1:50 dilution. 2E8 (2×108) cells are used per selection reaction.

Emulsion is prepared in the tissuelyser using standard conditions (10"@15 Hz, 7"@17 Hz) and transferred to PCR tubes as appropriate.

Successful extension conditions for BC36N8 on a synthetic Tgo library for a first round selection with full cyclohexenyl substitution:

| cycle: | 1 | 2 | 3 | 4 | 5 |
|---|---|---|---|---|---|
| 4' 15" @ | 94° C. | — | — | — | — |
| 1' @ | 94° C. | 94° C. | 94° C. | 94° C. | 94° C. |
| 15' @ | 37° C. | 37° C. | 50° C. | 60° C. | 65° C. |
| 15' @ | 50° C. | 65° C. | 65° C. | 65° C. | 65° C. |

Reactions are then kept at 4° C. (this step may be optional).

Emulsion is broken with EBS and saturated hexanol (approximately 100 ul TBT2 and 1000 ul hexanol). Centrifuge 10'@13,000 RPM to separate phases. Remove 1 ml of the hexanol/oil phase, add 700 ul of hexanol, resuspend interface and re-separate by centrifugation.

DNA is recovered by isopropanol precipitation (1:10 V 3 M NaOAc, 1 ul glycogen, 2V of isopropanol, overnight at −20° C.) and resuspended in 100 ul TBT2.

25 ul of the DNA solution are added to 475 ul of TBT2 and added to a Microcon YM100. Columns are spun at 2000 RPM for 40 minutes to filter the DNA solution. Approximately 25-50 ul are recovered, and are added to pre-blocked MyOne C1 beads (10 ul per sample) in BWBS.

*Beads Preparation and Washing Steps*

10 ul beads per reaction

Washes (500 ul): 1×BWBS

1×TBT2

1×BWBS

Incubate for 1 hour at room temperature under gentle agitation to block the beads in BWBS Resuspend in 20 ul BWBS Add 20 ul beads to approximately 25 ul YM100-purified plasmid and add a further 400 ul of BWBS. Allow capture overnight (at least 2 hours) in overhead rotator at room temperature.

Beads are purified using the Kingfisher mL robot and the CST program (detailed in the Kingfisher mL protocol).

1 ul beads can be used as template for pull-through (best done as dilution series of 20 ul reactions; around 25 cycles for a 1.8 kb product). Direct amplification of DNA from beads can also be achieved using 2 ul beads with phi29 (detailed in phi29 protocol)

Example 14

Design of Polymerase for Processive Reverse Transcription of HNA/RNA

There has been a single report to date on a B-family DNA polymerase capable of RNA reverse transcription (US2003/0228616). It reports that a mutation to the polymerase active site (A motif) on a highly conserved residue (L408) generates polymerase mutants capable of DNA synthesis from an RNA template. The mutants reported were tested (on our TgoT "wild-type" background) for HNA-RT activity unsuccessfully—no significant DNA synthesis against an HNA oligomer was detected by the polymerase activity ELISA after 2 hours extension at a range of temperatures (50° C. to 65° C.) compatible with TgoT activity.

A method has been reported to obtain information from large protein alignments based not only on sequence conservation but also on sequence co-variation: statistical coupling analysis (SCA) (1). It has been proposed that SCA can also be used to identify allosteric information transfer within proteins (2, 3).

Working on the assumption that there are allosteric networks in polymerases and that they can affect polymerase function, we hypothesized that if there is any "information"

available in the polymerase-template-primer complex regarding the nature of the template molecule, it should be possible to use SCA to indentify residues near and far from the active site that correlate to polymerase function. Starting from a manually curated structural alignment of over 600 B-family DNA polymerases, SCA was used to identify potential allosteric networks within the polymerase. Unfortunately, the high conservation of residue 408 meant that it could not be included in the SCA. However, as "information" must be transferred physically between a sender and receiver, we hypothesized that the residues identified by SCA in the physical vicinity of 408 could be part of an allosteric network involved in template recognition.

In that context, a shell of 5 Å around residue 408 in the 1TGO structure was selected and residues identified by SCA were selected for random mutagenesis. This approach identified residues 405, 408, 520, 521 and 575 as possible sites involved in "template information transfer".

Figure 25:
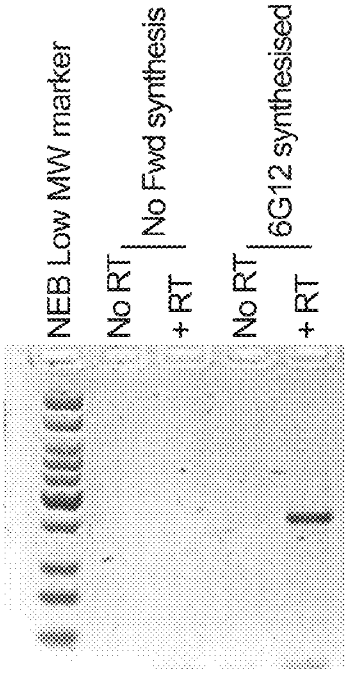
FIG. 25 shows reverse transcription by 521L from a HNA template synthesized by polymerase 6G12.

FIG. 25: Residue L408, conserved polymerase motifs and 5 Å shell used to identify potential "informational" residues FIG. 26: Residues identified by SCA within the A shell around 408.

Initially, a conservative approach was attempted introducing a limited set of possible mutations in each of these sites (primarily hydrophobics and aromatics). Mutations were introduced by iPCR using primers coding NWC at the targeted positions. Primers were designed to have a small overlap downstream of a Bsal site. Using Roche's Expand High Fidelity according to the manufacturer's recommendations, the whole plasmid was amplified, Bsal- and Dpnl-restricted and subsequently T4 DNA ligated prior to transformation.

A number of mutants were isolated and screened for HNA-RT activity using the polymerase activity ELISA screen established. Low level HNA-RT activity was detected on Y520F and L575V mutants as well as in a number of candidates mutated at position 521.

Given the results obtained, residue 521 was screened more thoroughly with mutants encoded by a primer containing NNS. Results of the subsequent screen are summarized in table 1.

TABLE 3

Summary of mutations at residue 521 identified by polymerase activity ELISA that have shown RT activity. Low HNA RT activity refers to mutants capable of incorporating at least 4 dNTP against an HNA template within the experimental time frame. High activity describes mutants that successfully synthesized a 15-mer DNA against an HNA template.

| | |
|---|---|
| Low level of HNA RT activity | F, N, D, T, V, M, C, Q and I(wt) |
| High level of HNA RT activity | L, P, H |

The I521L mutant was chosen for further characterisation and optimisation of reaction conditions as well as to investigate whether such mutant also had RNA-RT activity.

Figure 27:
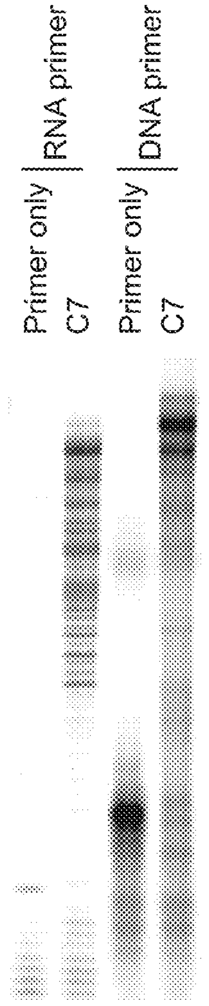
FIG. 27 shows CeNA synthesis by C7.

FIG. 27: Primer extension screen of 521 mutants for HNA RT activity. Activity normalized (dNTP) crude lysates were used to test HNA RT activity of a selection of 521 mutants. Under the experimental conditions, 521L and 521P were the only polymerases capable of synthesizing the HNA template to completion.

Purified 521L displayed considerable template-independent activity that could be suppressed by a number of additives, including Triton X-100 (0~5%), unrelated RNA (0.01~3 μg/μl).

Figure 28:
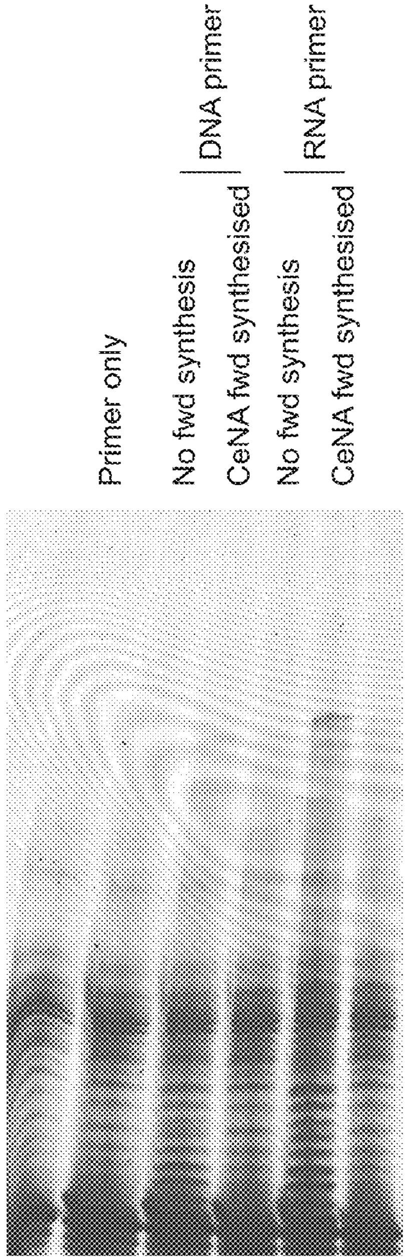
FIG. 28 shows DNA synthesis with 521L using a C7-synthesized CeNA template.

FIG. 28: HNA RT reactions to synthesiseDNA from an HNA template based on a tRNA gene (103 bases template, 76 dNTP incorporations against HNA). HIV RT (AB), *Sulfolobus islandicus* DNA polymerase IV (NEB)—a Y-family polymerase that has some HNA RT activity and the 521L mutant. Reactions were carried out as a single extension cycle @65° C. for 4 hours. As 521L shows some template-independent activity, a no template control was included in the reaction. "No extension" refers to the HNA synthesis reaction in which a reaction without 6G12 was used as a background control of template DNA carry over.

Example 15

Information Transfer from DNA to HNA and Back from HNA to DNA

While 6G12 allowed transfer of information from a DNA template into HNA, that step alone is of limited use. There have been reports on how unnatural DNA-analogue polymers (TNA and PNA) could be selected for function from forward synthesis alone (4, 5). However, there is little evidence that such systems would provide a strong genotype-phenotype linkage (as fidelity information is limited) or that those moieties would allow sizeable molecules to be synthesised.

Thus 521L is key to the process as it allows information retrieval from HNA back into DNA. As the cycle completes, it becomes possible to assess the aggregate fidelity of the two enzymes as well as begin selection for function by SELEX (6). To prove that this was possible with our system we synthesised a tRNA molecule into HNA, using 6G12, and recovered the encoded information back into DNA, using 521L.

A number of controls and processes were introduced to minimise the possibility that the HNA synthesis step could be bypassed by the system. The key steps are summarised below:

- Template/primer mismatches: As previously reported (7), mismatches were introduced in the template so that upon sequencing of the obtained DNA, the origin of the sequencing molecule could be determined, i.e. it should contain the primer sequences, not the original template sequence.
- Primer overhangs: Primers longer than the original template have been used to allow primer outnesting for the amplification of the recovered DNA. This increases the specificity regarding what molecules will be recovered.
- Strand-dependent reactions: Template-independent addition of DNA tails was also used to select the correct strand prior to further amplification.
- DNase and exonuclease treatments: A combination of these enzymes was used to ensure that as much as possible of the original template was degraded after 6G12 synthesis. Exonuclease was again used after 521L reaction to remove unextended RT primers that could give rise to false positive results.
- Negative controls: Reactions in which no forward synthesis (no 6G12) was carried out, reactions in which no RT (no 521L) was carried out and combinations thereof were used to ensure the recovered molecules' origins.

In addition, all reaction steps were monitored by denaturing gel electrophoresis.

FIG. 29: Information transfer from DNA to HNA and back to DNA. A DNA template encoding a tRNA gene and flanked by specific tags was used to synthesize an HNA molecule with 6G12. The reaction was treated with DNase and ExoSAP-IT prior to HNA purification. HNA was then used as template in an RT reaction with 521L. The reaction was again treated with ExoSAP-IT prior to amplification by PCR using one outnested tag (not present in the original template) and the primer used in the forward synthesis, as primers. Primer only controls as well as a no template control for the PCR were carried out and no visible amplification was observed (data not shown). Reactions were carried out for 20 cycles.

Figure 24:
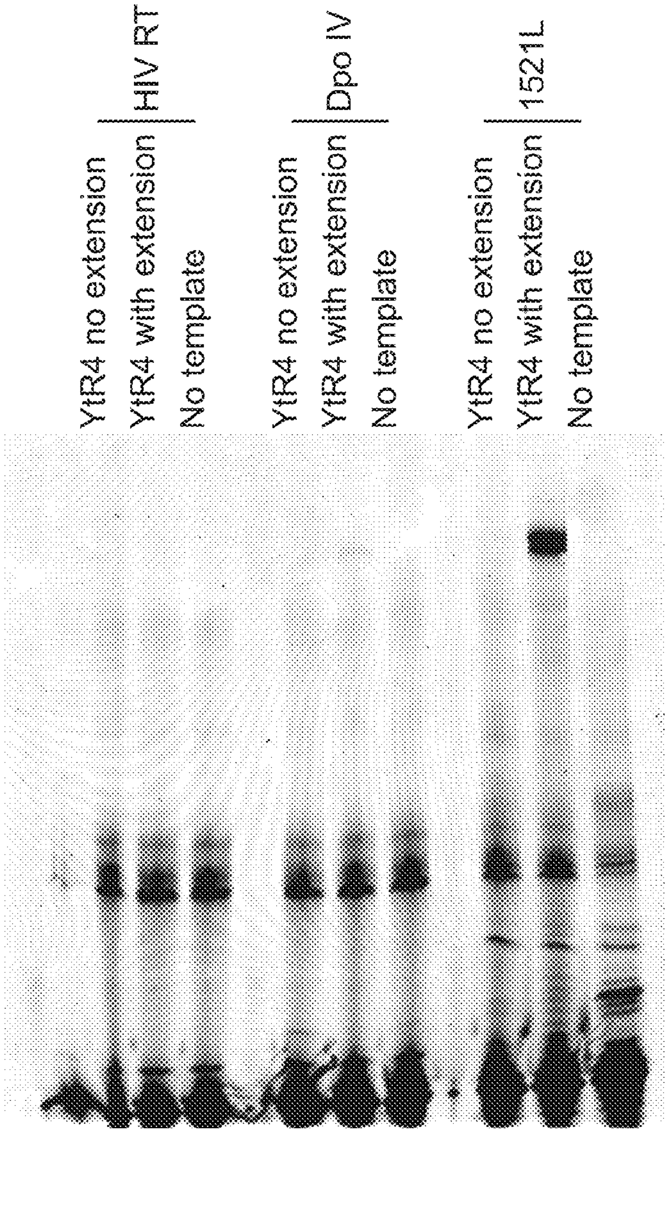
FIG. 24 shows yeast tRNA synthesis by HIV RT, DpolV, and mutant I521L polymerases.

A different information recovery strategy also yielded a result similar to FIG. 25. In that approach, the forward synthesis (6G12) was DNase treated and HNA purified, prior to the RT step (521L). DNA synthesis from the HNA template was carried out with 521L and is shown in FIG. 24; a typical 521L reaction (50 μl) was carried out using equal concentrations of labeled primer and HNA template in 1× ThermoPol buffer (NEB). After annealing the primer-template complex, 521L was added and the reaction carried out at 65° C. for 4 hours. RT reactions were purified and a terminal transferase (NEB) reaction was carried out following the manufacturer's recommendations to add a poly-dA tail to the synthesized DNA.

Tailed DNA molecules were gel purified using a denaturing gel and the DNA was successfully amplified using Superscript II RT-PCR (Invitrogen), a labeled poly-dT primer, and the same primer used to initiate RT. The Superscript (mesophilic reverse transcriptase) step was required to obtain an amplification product but, given that the enzyme does not have significant HNA-RT activity, it is believed that an enzyme capable of primer extension at low temperatures (due to the low melting temperature of the poly-dT primer) and with moderate strand displacing ability was required to generate enough DNA to be subsequently amplified by a thermostable polymerase.

The amplification product obtained was purified and TOPO-TA (Invitrogen) cloned. Isolated mutants were screened by PCR and sent for sequencing. Sequencing results showed that the (forward synthesis) primer/template mismatch was present and provided the first measure of aggregate fidelity of the two enzymes, as shown in Table 2.

TABLE 4

Aggregate fidelity of 6G12 DNA-dependent HNA synthesis and 521L HNA-dependent DNA synthesis. Of the 1260 bases sequenced, there were 4 deletions, 1 insertion and the substitutions described above. In all, it suggests an aggregate error rate of less than 7 x 10-3/bp.

| | Substitution | | | |
|---|---|---|---|---|
| Expected | A | C | G | T |
| A | — | | 1 | |
| C | | — | | 1 |
| G | 1 | | — | 1 |
| T | | | | — |

Example 16

Re-Introducing Proofreading to a Thermostable RT

As previously described, our "wild-type" enzyme has in fact four mutations over its true wild-type, including 2 mutations (D141A and E143A) which inactivate the 3'→5' exonuclease domain, important for the proofreading function of the polymerase.

The D141A and E143 mutations, which are also present in 521L, were reverted back to their wild-type as we investigated the effect on 521L RT function. 521L mutation to 521L (exo+) was carried out by iPCR as described previously.

Figure 26:
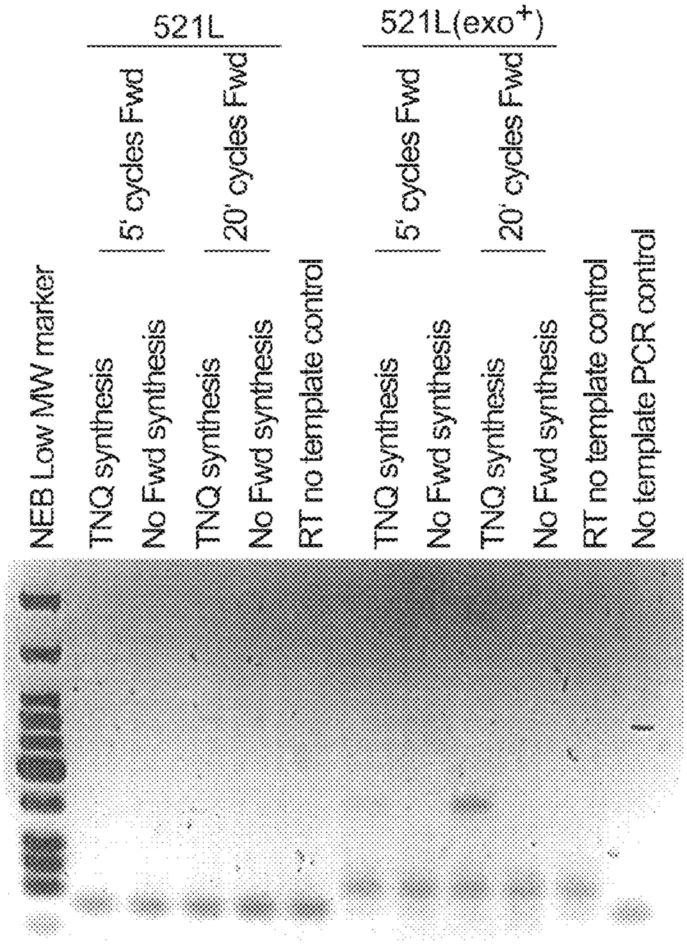
FIG. 26 shows PCR amplification of RT reactions carried out on a tRNA synthesized by TNQ.

As expected, reintroduction of exonuclease activity reduced the observed RT activity of the enzyme for HNA. However, it improved the enzyme's RT activity on RNA. In fact, 521L (exo+) outperformed 521L on DNA synthesis from an RNA template, as shown in FIG. 26.

FIG. 210: PCR amplification of RT reactions carried out on a tRNA gene synthesized as RNA by TNQ. Two RNA synthesis extension times were used (2 cycles of 5' or 20' each). RNA was purified as described in FIG. 25 with an additional purification step (RNeasy; Qiagen). RT reactions were carried out with 521L and 521L (exo+). The reaction was again treated with ExoSAP-IT prior to amplification by PCR using one outnested tag (not present in the original template) and the primer used in the forward synthesis, as primers. Reactions were carried out for 30 cycles.

Example 17

Further Design of Polymerases for Processive Reverse Transcription of HNA/RNA Inspection of other PolB structures available, particularly the ternary complex of RB69 (8) suggested that the equivalent residue to I521 (L594) would be further than 5 Å from the residue equivalent to L408 (L415) at the catalytic step, when template, primer and nucleotide are all present in the active site.

This raised 2 possibilities within the SCA "information transfer" paradigm: either the information transfer between 408 and 521 does not occur at this step in the polymerase cycle or information is transmitted by an unidentified intermediate residue. Another clear possibility is that the SCA framework is not valid.

To test those hypotheses, the same approach that identified I521 was taken; using the I521 residue as the centre of a 5 Å shell. A number of residues were identified within that distance from I521 that had also been identified through SCA. However, to test SCA we focused our search on those residues that had not been present in SCA: Y388, G517 and T541.

A scanning approach similar to 521 was taken with mutant libraries generated by iPCR with primers containing NNS at the target positions. Individual mutants were isolated and used to screen for RT activity.

Residues G517 and T541 are highly conserved residues (>96% identity), with T541 being flanked by two aspartate residues involved in the catalytic step. As expected, screening at those positions yielded no enzymes with HNA RT activity above wild-type.

Example 18

The remaining residue, Y388, is very poorly conserved which probably accounts for its absence in SCA. Interestingly, a number of different side-chains at residue 388 did display HNA RT activity: (V, R, H, N, T). These are now being further characterised to assess their potential as well as their potential in a 521L background. Residue 388 is immediately downstream of a motif reported to affect polymerase fidelity and processivity: YXGG/A (9, 10).

In view of those results, questions are raised regarding the use of SCA predictions to identify possible improvements in RT activity. While Y388 could be a false negative not identified by the method's current implementation, it may also suggest that a simpler hypothesis is at play: Residues within a certain distance from the catalytic site (particularly the C motif central triad DTD) can be mutated to subtly alter the polymerase function, in this case HNA RT activity.

REFERENCES TO EXAMPLES 14 TO 18

1. S. W. Lockless, R. Ranganathan, *Science* 286, 295 (Oct. 8, 1999).

2. G. M. Suel, S. W. Lockless, M. A. Wall, R. Ranganathan, *Nat Struct Biol* 10, 59 (January, 2003).
3. N. Halabi, O. Rivoire, S. Leibler, R. Ranganathan, *Cell* 138, 774 (Aug. 21, 2009).
4. J. K. Ichida et al., *J Am Chem Soc* 127, 2802 (Mar. 9, 2005).
5. Y. Brudno, M. E. Birnbaum, R. E. Kleiner, D. R. Liu, *Nat Chem Biol* 6, 148 (February, 2010).
6. C. Tuerk, L. Gold, *Science* 249, 505 (Aug. 3, 1990).
7. J. K. Ichida, A. Horhota, K. Zou, L. W. McLaughlin, J. W. Szostak, *Nucleic Acids Res* 33, 5219 (2005).
8. M. C. Franklin, J. Wang, T. A. Steitz, *Cell* 105, 657 (Jun. 1, 2001).
9. V. Truniger, J. M. Lazaro, M. Salas, L. Blanco, *EMBO J.* 15, 3430 (Jul. 1, 1996).
10. K. Bohlke et al., *Nucleic Acids Res* 28, 3910 (Oct. 15, 2000).

Example 19

Information Transfer from DNA to CeNA and Back from CeNA to DNA

Similar to earlier examples, genetic information from a DNA template can be transferred to a CeNA molecule and recovered using the isolated polymerases.

Forward synthesis (DNA→CeNA) was carried out with C7 in very similar conditions to previously described ones for 6G12. Typical reactions were carried out in ThermoPol buffer (NEB) with 1 μM primer and template and suitable CeNTP concentration (30~500 μM of each nucleotide). Reactions could be carried out in a range of temperatures compatible with B-family thermostable polymerases. Like 6G12, C7 can also start unnatural nucleic acid synthesis from both DNA and RNA primers (FIG. 27).

FIG. 27: CeNA synthesis by C7 (PAGE under denaturing conditions). Both RNA and DNA primers can be extended using C7 and CeNTPs to the end of a DNA template (57 incorporations).

Similar to reactions with 6G12 and HNA, a number of steps (described in the corresponding example above) were introduced to ensure that no original DNA template was carried forward and to be able to distinguish any potential carry over from primer synthesised molecules.

As 521L had already shown RT activity against RNA and HNA, it was the obvious candidate to be used against CeNA. As with HNA, a DNased and purified forward synthesis was used as template for the RT reaction, shown in FIG. 28.

FIG. 118: DNA synthesis with 521L using a C7-synthesised CeNA template. Extensions to the end of the templates can be observed for both C7-synthesized strands but the CeNA template generated from an RNA primer clearly outperformed the DNA-primed one.

DNA synthesis by 521L from a CeNA template was successful confirming 521L as an RNA, HNA and CeNA RT. A typical CeNA-RT 521L reaction (50 μl) was carried out using equal concentrations of labeled primer and CeNA template in 1× ThermoPol buffer (NEB). After annealing the primer-template complex, 521L was added and the reaction carried out as a 4 cycle PCR with extension steps of 4 hours at 65° C.

Example 20

Specific Exemplary Sequences

It should be noted that the designations in this example are clone names indexed in the sequence listing, and are not indications of amino acids (e.g. C7=clone C7 and does not indicate cysteine at position 7).

Polymerases selected for CeNTP incorporation:
Motif 10A: A1, C1, C7, D4, E8, G3, H2, NC11
Motif 12: G11
Polymerases selected for HNTP incorporation:
Motif 10A: 6G12, E3, E6, H6
Motif 12: B11, B12, H12
Our wild_type: TgoT
True wild-type: Tgo_wt

Example 21

HNA Based Genetic System

Figure 38:
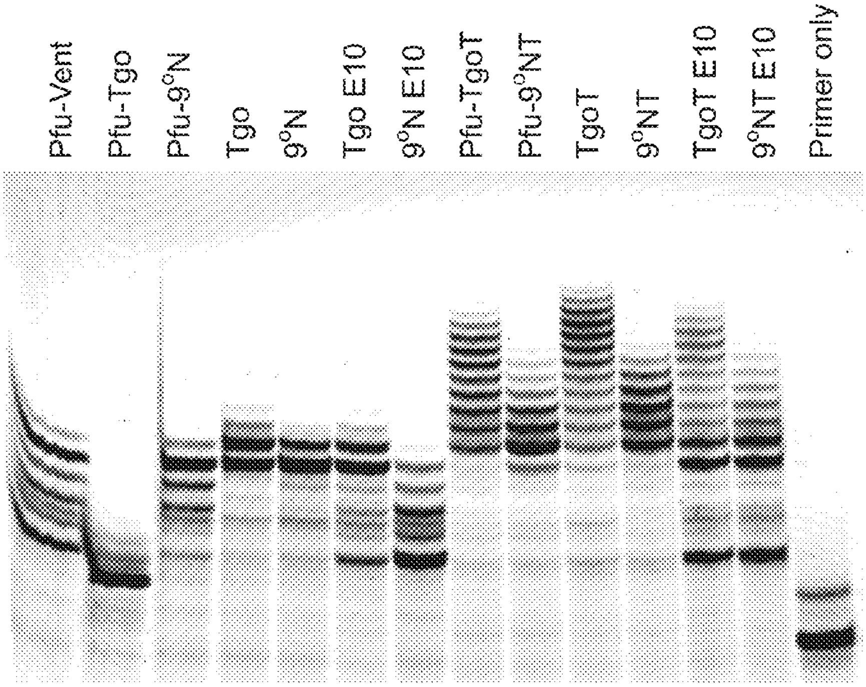
FIG. 38 shows activity of basal incorporation of unnatural nucleotides. Cleared polymerase lysates were used to test incorporation of CeATP against TempT template by available "wild-type", chimeras, and engineered polymerases. "Wild-type" polymerase included *Thermococcus gorgonarius Thermococcus* s.p. 9° N-7 (9° N), *T. litoralis* (Vent) and *Pyrococcus furiosus* (Pfu) devoid of uracyl stalling (V93Q or equivalent) and exonuclease (D141AE143A) activities. Variants harboring the "Therminator" mutations (A485L) are labeled T (e.g., TgoT); variants harboring mutations determined to improve incorporation of fluorescently labeled nucleotides are labeled E10. Chimeras are shows as exonuclease-polymerase (i.e., Pfu-Tgo is a chimera of Pfu's exonuclease domain to Tgo's polymerase domain).

We sought address genetic information en- and decoding. Broadly, we asked if an artificial genetic system supporting both heredity and evolution could be constructed from entirely unnatural components. Minimally such a system requires a chemical framework (XNA) capable of crosstalk with DNA or RNA, a means for XNA synthesis (i.e. a DNA-templated XNA polymerase, to transfer natural genetic information from DNA to XNA) and means for decoding XNA (i.e. a XNA reverse transcriptase). We identified HNA (1,5 anhydrohexitol nucleic acid) and CeNA (cyclohexenyl nucleic acids) as potential XNAs with desirable physico-chemical properties (FIG. 29*a*), because of their ability to cross-hybridize with both DNA and RNA, their helix forming properties, their chemical stability and their low toxicity as both nucleoside and oligomer[13]. However, the triphosphates of both HNA (hNTPs) and CeNA (ceNTPs) had proven to be poor substrates for both commercially available polymerases[14,15] as well as our own in-house repertoire of engineered polymerases (FIG. 38). Our screen identified a variant of the replicative polymerase from the hyperthermophilic archaeon *Thermococcus gorgonarius* (Tgo)(devoid of 3'-5' exonuclease activity (D141A, E143A), uracil-stalling function (V93Q) and comprising A485L ("Therminator" mutation)) as the most promising starting point for HNA/CeNA polymerase evolution. This polymerase, henceforth called TgoT, could polymerize up to 6 consecutive hNTPs (and ceNTPs) on a mixed template.

The poor activity of even TgoT in utilizing hNTPs or ceNTPs precluded the application of established methods of polymerase engineering[16-18]. We therefore developed a new highly sensitive selection strategy called compartmentalized self-tagging (CST) to enable the discovery of polymerases capable of processive HNA or CeNA synthesis. CST is based on a positive feedback loop, whereby a polymerase tags its own encoding gene by extension of a metastable biotinylated oligonucleotide. Extension stabilizes the oligonucleotide-plasmid complex and enables the selective capture of plasmids encoding active polymerases (FIG. 29*b*) with a sensitivity of 3-6 incorporation events per plasmid. Importantly, CST decouples selection from self-replication, thus recovery of a synthetase is not dependent of the availability of a reverse transcriptase for the synthesized polymer.

To expedite the discovery of HNA and/or CeNA polymerase activities diversified, we created 22 separate mutagenesis libraries of TgoT. Diversity comprised phylogenetic variability as well as 5 to 10% random mutations (at conserved positions) (FIG. 37 showing TgoT (SEQ ID NO: 1) and was focused on short sequence motifs (10 to 24 AA) located within 10 Å of the nascent DNA strand and its hydration shell as modeled in the tertiary complex structure of the related RB69 DNA polymerase[19,20].

Figure 30:
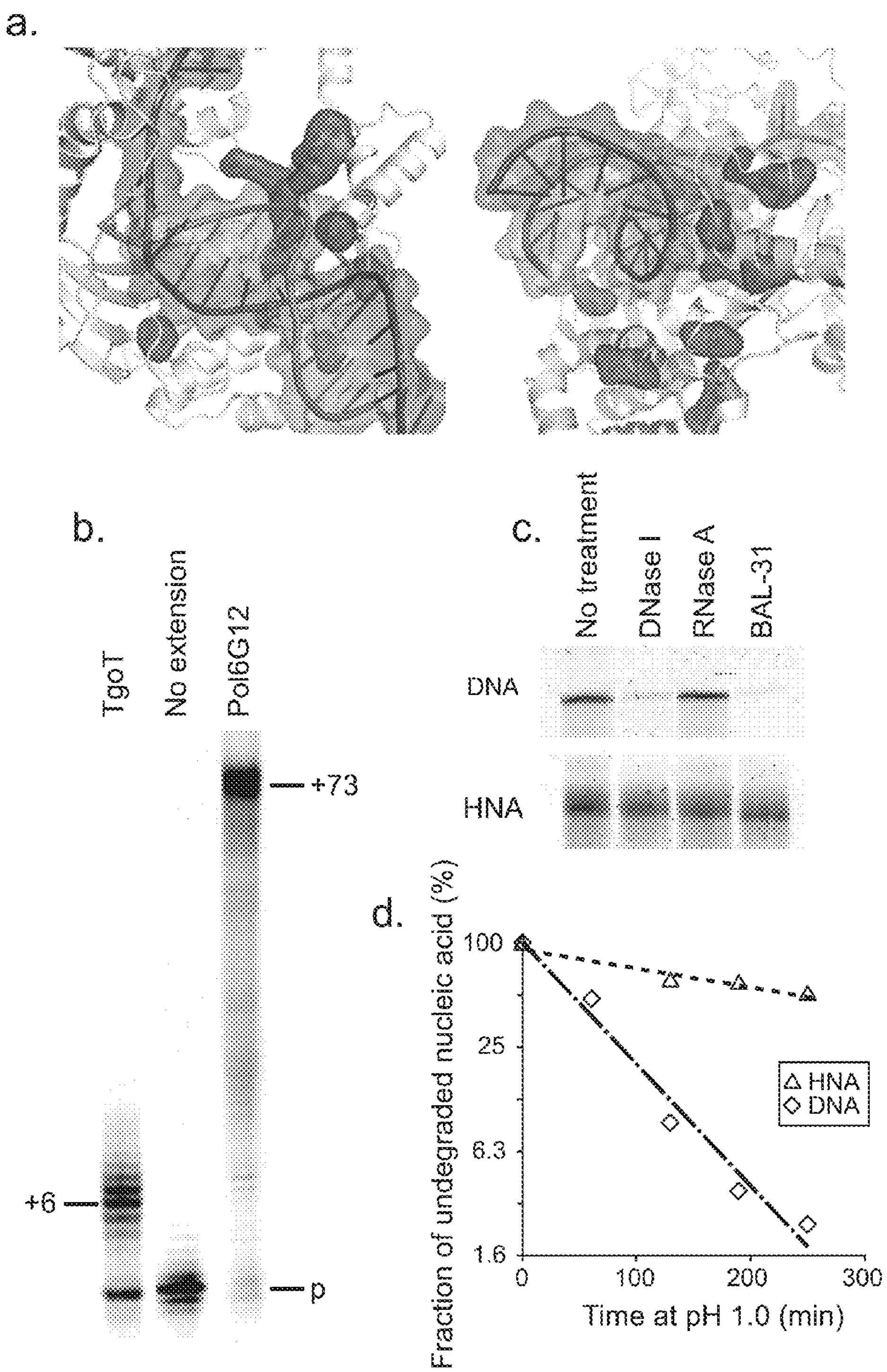
FIG. 30 shows HNA synthetase (Pol6G12) and single-stranded HNA properties. Panel (a) illustrates Pol6G12 mutations mapped to structurally eauivalent *E. coli* pol II (3MAQ) residues; panel (b) demonstrates that purified wild-type enzyme does not synthesise HNA much beyond six incorporations, but purified Pol6G12 can quantitatively synthesise HNA; panel (c) shows that single-stranded HNA is refractory to all nucleases tested and substantially more resistant than DNA in acidic environments; panel (d) shows the half-life of HNA under those conditions.

We first performed CST selection separately on each of the 22 TgoT libraries and scored their hNTP and ceNTP incorporation potential before and after selection by polyclonal primer extension (not shown). This screen, when mapped on the polymerase structure (FIG. 29*c*), revealed that the key structural motifs for HNA/CeNA polymerase activity were not located in the polymerase active site but rather at the periphery of the primer-template duplex interaction interface in the polymerase thumb domain >20 Å from the primer 3' end (in both Pol II (3MAQ) and RB69 (1IG9)). We therefore focused further CST selections on these regions. We performed two rounds of CST and screened selected polymerases using a novel high-throughput polymerase activity assay (PAA) based on solid-phase capture of extension products and their detection via hybridization to a specific, labeled probe (FIG. 33) with a sensitivity of <60 fmol of extended primer. PAA screening of round 2 clones revealed rapid adaptation of CST selected polymerase populations towards substantial HNA polymerase activity. One of those, Pol6G12 (TgoT: V589A, E609K, 1610M, K659Q, E664Q, Q665P, R668K, D669Q, K671H, K674R, T676R, A681S, L704P, E730G), displayed a striking general HNA polymerase activity enabling the processive and quantitative synthesis of HNAs long enough to encode meaningful genetic information such as e.g. tRNA genes. Using Pol6G12 we readily synthesized multiple such tHNAs of *S. cervisiae* $tRNA^{Ala}$ and $tRNA^{Phe}$ as well as *E. coli* tRNA supE (FIG. 30*a*), establishing Pol6G12 as a DNA-dependent HNA polymerase.

Natural nucleic acids can be decoded by the action of templated polymerases such as reverse transcriptases (RTs) in the case of RNA. Without a means of decoding HNA polymers, HNA synthesis (although potentially useful for the bulk production of ssHNA oligomers for applications in gene silencing), is a 'dead-end' because genetic information transferred from DNA remains locked in HNA, precluding both analysis and evolution. However, none of the available polymerases displayed HNA RT activity. We therefore decided to develop an HNA RT de novo in the parent polymerase TgoT. Reverse transcriptase activity (from an RNA template) had been described in the related Pfu DNA polymerase, upon mutation of L409[21]. We hypothesized that due the HNA's propensity for an RNA-like A-form conformation, HNA-RT activity might be found in the structural neighbourhood of an RNA RT. However, mutation of the equivalent L408 in TgoT only yielded variants with weak but detectable HNA-RT activity. We therefore chose to explore the structural and functional context of L408 (a highly conserved residue in the polB family) in more detail. We used Statistical Correlation analysis (SCA), a statistical approach to score pairwise positional correlations of sequence variation in phylogeny, to discover positional covariation in the vicinity of L408 as part of potential allosteric interaction network involved in template recognition. SCA has been suggested to allow inference of functional amino acid networks and had previously been applied to rationalize selected mutations[12,22] and aid protein design[23]. Sequence variation within the PolB family genes deposited in GenBank was found to be too high to provide sufficiently accurate alignments for SCA. We therefore compiled a hand-curated dataset of 671 non-redundant PolB sequences based on structural alignment as input for SCA. Random mutation of SCA hits (F405, Y520, I521, L575) and PAA screening of the four mini-repertoires identified TgoT: I521L (RT521), as a general and processive HNA RT as demonstrated by the reverse transcription of tHNA supE (see above) into DNA (FIG. 30*b*).

The ability to both synthesize and reverse transcribe HNA allowed us to determine the fidelity of information transfer between DNA and HNA. We determined aggregate error rates (the sum of error rates of both HNA synthesis and HNA reverse transcription) by cloning and sequencing of *E. coli* tRNA supE converted into HNA by Pol6G12 and back into DNA by RT521. Correcting for the contribution of 30 cycles of PCR we obtained an aggregate misincorporation rate of $8.3\times10^{-3}$ and aggregate indel (insertion/deletion) rates of $5.2\times10^{-3}$. Deconvolution of individual error rates (estimating RT521 fidelity from reverse transcription of an identical RNA template) yields a fidelity of $8\times10^{-3}$ for Pol6G12 (and $1.2\times10^{-3}$ for RT521) (SI FIG. 1) comparable to the error rates of viral RNA-dependent RNA polymerases (ref). Examination of mutation hotspots shows a striking clustering of mutations (>30% of total and >70% of indels) in the first five incorporation events. Mechanistic causes for this transition from an error prone initiation to a higher fidelity processive mode are currently unclear but may involve effects of the conformational transition from an RNA-DNA to an HNA-DNA hybrid upon RNA primer clearance. Future use of fully synthetic HNA primers might therefore significantly reduce error rates.

Inspection of the aggregate mutation spectrum reveals predominately A/G, C/T transition mutations commonly observed for all polymerases due to base tautomerism. However, we also observe an uncommon preponderance for T/G transversions indicative of hG misincorporation opposite template dT by Pol6G12 (or dA opposite template hC by RT521).

Together the HNA polymerase Pol6G12 and RT521 HNA RT establish a synthetic genetic system built on HNA-based heredity.

Example 22

Application of Invention to HNA Aptamers

Next we asked if such a HNA based synthetic genetic system might also support Darwinian evolution. We therefore initiated in vitro selection experiments for HNA aptamers. The aggregate fidelity of information transfer between DNA and HNA and back should be readily be compatible with selection of HNA sequences >100 nts in length[24] but the capacity of ssHNA oligomers to fold into stable three-dimensional structures capable of specific recognition of molecular targets was unknown.

Figure 32:
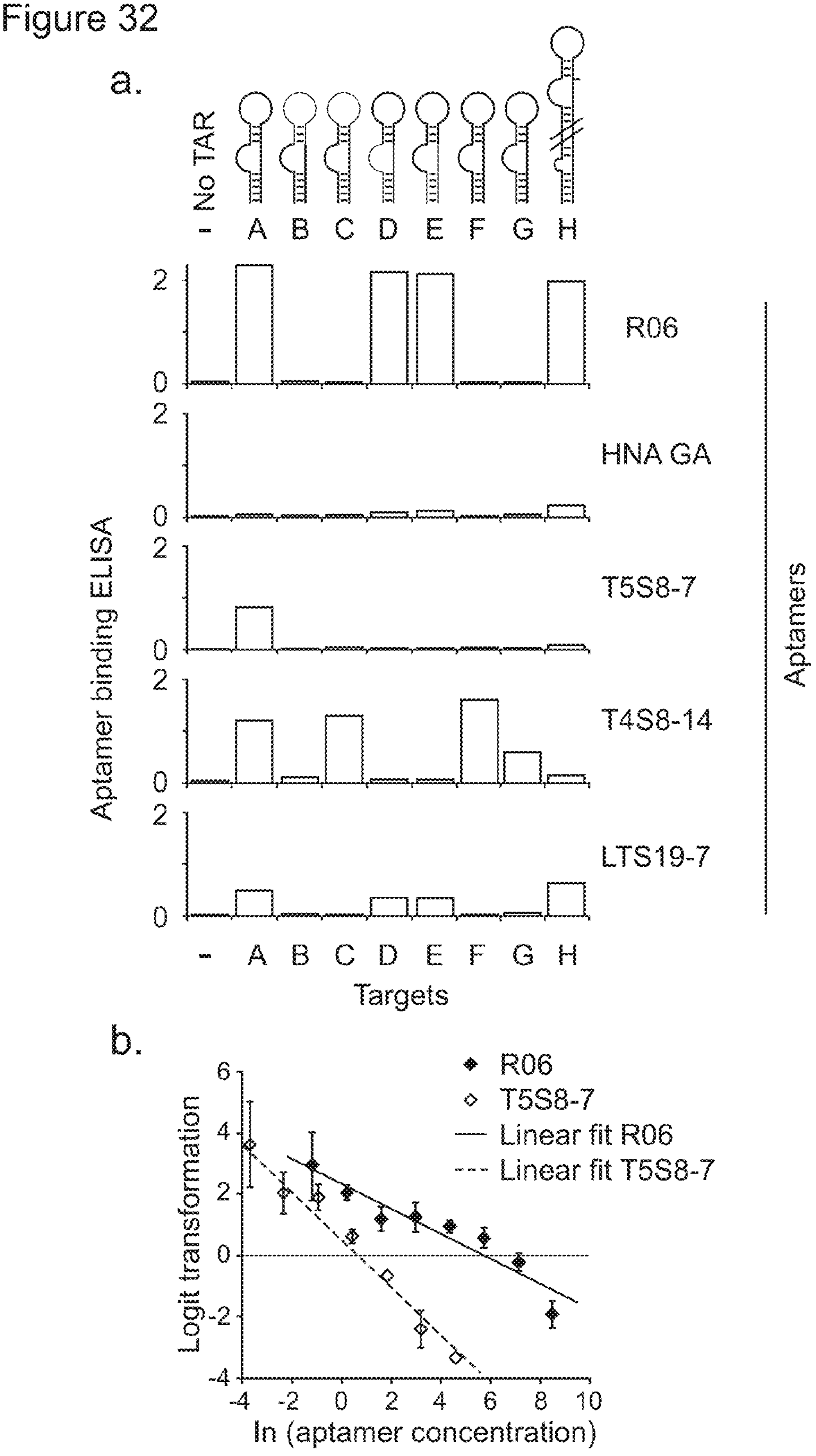
FIG. 32 shows HNA aptamer specificity and HIV-TAT binding inhibition. Panel (a) illustrates ELISA detection of aptamer binding to TAR and modified TAR RNA targets; panel (b) depicts results of a TAT-aptamer miniTAR binding competition assay.

We therefore first selected HNA aptamers against a well characterized nucleic acid target, the HIV TAR (trans-activating response) RNA for which both DNA and RNA aptamers had previously been isolated[25,26]. HNA TAR binders evolved readily but, unlike RNA or DNA aptamers, did not appear to bind TAR via a "kissing loop" interaction. Mapping the interaction of HNA anti-TAR aptamers revealed two clades targeting either the TAR-stem and asymmetric bulge or requiring both loop and bulge for binding (FIG. 32). Despite being of slightly lower affinity than the previously optimized RNA aptamers (mostly due to a slow $k_{on}$ rate), HNA anti-TAR aptamers proved more effective at inhibiting interaction of the HIV TAT (Trans-Activator of Transcription) protein with TAR RNA.

The synthetic genetic system described herein provides a synthetic route to a new sequence space not previously accessible for exploration. The invention may be used to investigate how this "HNA space" is populated with novel phenotypes; it appears that at least HNA aptamers displaying specific ligand binding are readily discovered. If selections are generalized to a wider range of targets, such HNA aptamers may have great biotechnological and therapeutic potential due to the non-cognate chemical makeup providing robust chemical stability and low toxicity as both nucleosides and oligomers.

Such synthetic genetic systems should provide a rich source of new receptors and catalysts with tailor-made chemistries for applications in diagnosis and therapy.

Description of Drawings for Examples 21-22

FIG. 29: Directed evolution of polymerases for synthesis of artificial biopolymers. (a) Structure of deoxyribose (DNA), 1,5-anhydrohexitol (HNA) and cyclohexenyl (CeNA) nucleic acids. (b) Compartmentalised self-tagging (CST). A water-in-oil emulsion allows polymerases and their genotypes to be isolated in a reaction containing labelled primers and the modified nucleotides. Extension of the primers by polymerases capable of incorporating the modified nucleotides, stabilize primer binding and tag their own encoding plasmid, allowing their genetic information to be recovered. (c) Heat map showing ranked library polyclonal activity mapped to the wild-type (1TGO) and to the ternary complex of the related *E. coli* pol II (3MAQ). Libraries targeted to the polymerase thumb showed the highest basal activity and best improvement after a single round of selection FIG. 30: HNA synthetase (Pol6G12) and single-stranded HNA properties. (a) Pol6G12 mutations mapped to structurally equivalent *E. coli* pol II (3MAQ) residues. Eleven of the 14 mutations identified in Pol6G12, shown in red, can be mapped to the pol II ternary complex, with nearly half of those clustering in the vicinity of the nascent HNA strand, shown in green. (b) Purified wild-type enzyme does not synthesise HNA much beyond six incorporations, but purified Pol6G12 can quantitatively synthesise HNA, such as the *E. coli* amber suppressor tRNA gene shown. (c) Single-stranded HNA is refractory to all nucleases tested and substantially more resistant than DNA in acidic environments (d). Half-life of HNA under those conditions (t1/2HNA=347 min, R2=0.899) is nearly eight times higher than DNA (t1/2DNA=43.3 min, R2=0.975). on.

Figure 31:
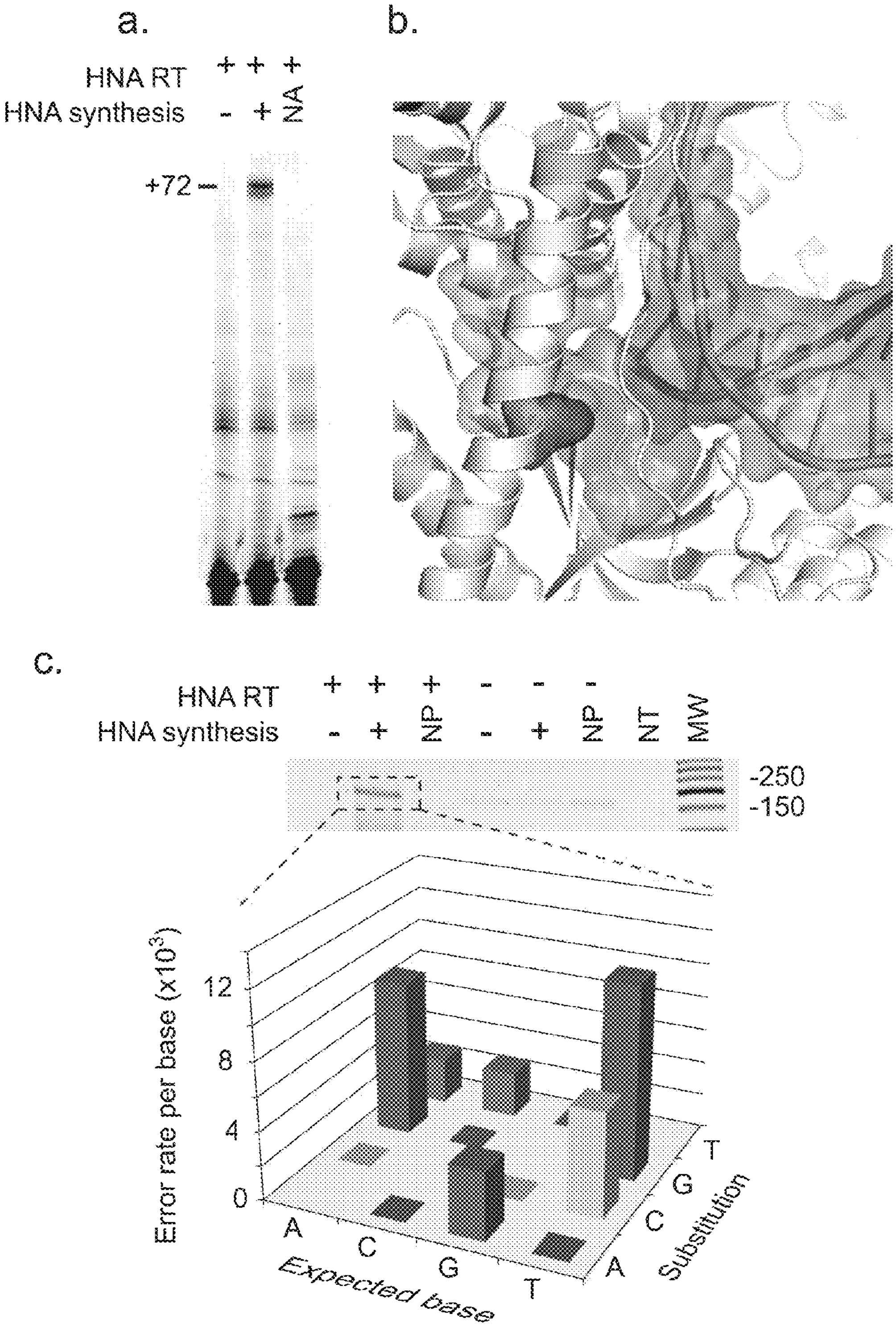
FIG. 31 shows HNA reverse transcriptase and the fidelity of the HNA genetic system. Panel (a) shows that RT521 can quantitatively synthesize DNA from an ssHNA template, such as an *E. coli* tRNA gene (with additional tags) synthesised by 6G12 (NA: RT only control); panel (b) illustrates how the structurally eauivalent residue to Tgo I521 is shown in *E. coli* pol II; panel (c) demonstrates how information transferred from DNA to HNA by 6G12 can be retrieved by RT521 back into DNA (NP: HNA synthesis carried out without primer; NT: PCR no template control).

FIG. 31 HNA reverse transcriptase and the fidelity of the HNA genetic system. (a) RT521 can quantitatively synthesise DNA from an ssHNA template, such as an *E. coli* tRNA gene (with additional tags) synthesised by 6G12 (NA: RT only control). (b) The structurally equivalent residue to Tgo I521 is shown in *E. coli* pol II (red). In the ternary complex, it is in close contact with the conserved active site motifs of the polymerase (A-motif in orange; C-motif in blue). The nascent DNA strand (purple) and HNA template (green) are shown. (c) Information transferred from DNA to HNA by 6G12 can be retrieved by RT521 back into DNA with an aggregate error rate of $12.2\times10^{-3}$ per base (NP: HNA synthesis carried out without primer; NT: PCR no template control). Error profile shown refers to the expected HNA strand. See supplementary information for more details.

FIG. 32: HNA aptamer specificity and HIV-TAT binding inhibition. (a) ELISA detection of aptamer binding to TAR and modified TAR RNA targets. R06 is the reported RNA aptamer against TAR and HNA-GA the previously reported HNA aptamer. T5S8-7 and T4S8-14 were selected for binding against the previously reported mini-TAR (target A)[31]. LTS19-7 was selected against a longer version of TAR (target H). Scrambling different regions of the target (orange) or removing them altogether (targets F and G) confirms that T5S8-7 is a true aptamer binding only the full, unmodified target. (b) TAT-aptamer miniTAR binding competition assay. Immunodetection of TAT binding to immobilized miniTAR was used to estimate the aptamer concentrations required to inhibit TAT binding ($IC_{50}$). The HNA aptamer T5S8-7 ($IC_{50}$=1.9 nM ($CI_{95\%}$ 1.3 to 2.8 nM)) could displace TAT at 100-fold lower concentrations that the original RNA R06 ($IC_{50}$=313 nM ($CI_{95\%}$ 166 to 675 nM).

FIG. 33 shows a region of HNA (SEQ ID NO: 68 and SEQ ID NO: 69) flanked by primers NAPfd (SEQ ID NO: 61) and LMB3+(SEQ ID NO: 60) and depicts the Error spectrum and error rates of the HNA genetic system. (a) Misincorporations, deletions (closed triangles) and insertions (open triangles) collated from 1974 sequenced bases after a round of HNA synthesis and reverse transcription using an *E. coli* tRNA gene as the original template. The RNA synthesis primer is shown in blue (outnesting tag is shown in bold superscript, synthesis mismatch is shown in red) and errors are mapped to the HNA synthesis strand. The number of hNTP incorporations is shown. Reverse transcription primer is shown in green (RT mismatch is shown in red, outnesting tag in bold). (b) Aggregate and individual error rates determined for Pol6G12 and RT521 for HNA and DNA syntheses. See supplementary materials and methods for mode details.

Figure 34:
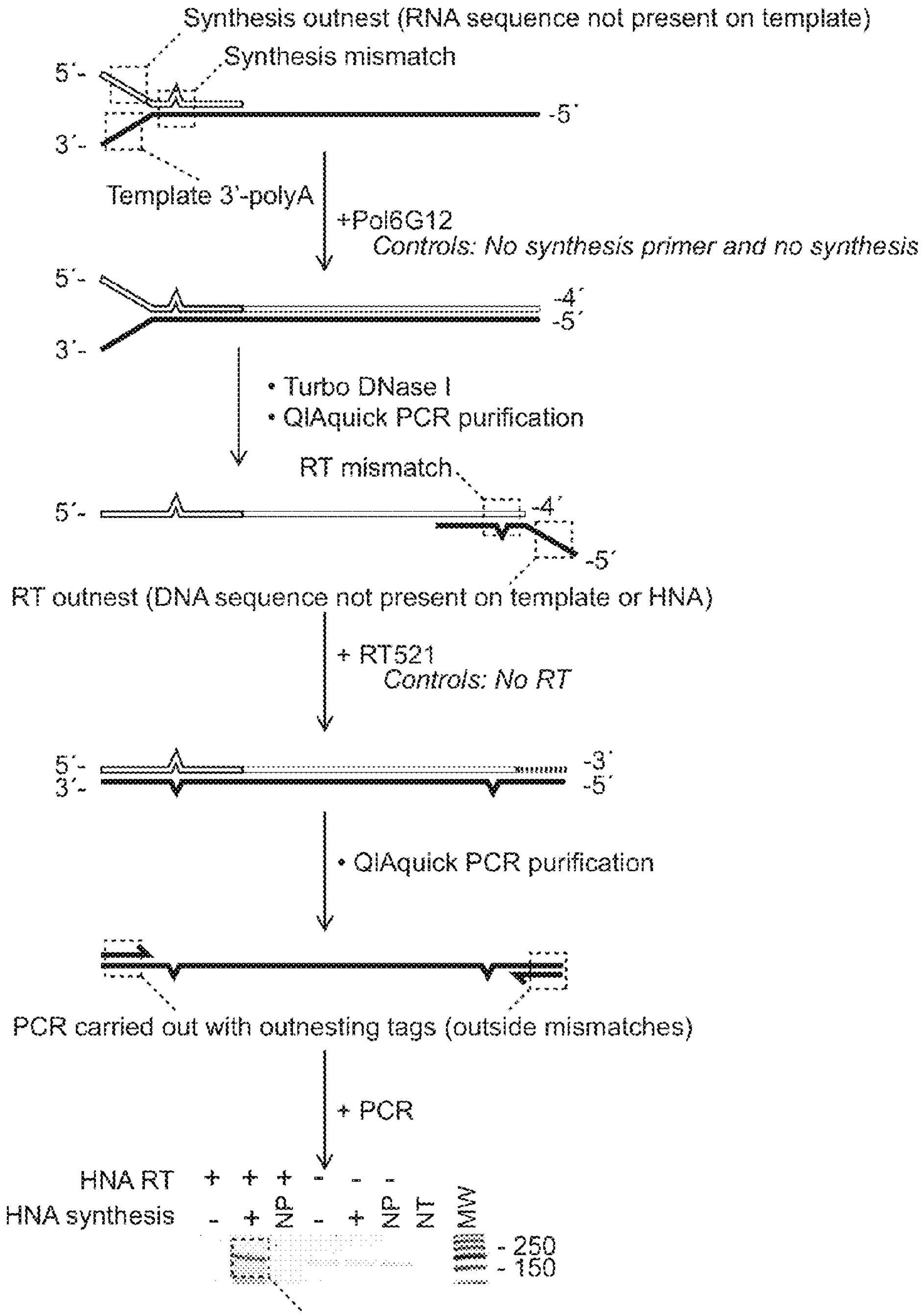
FIG. 34 shows a schematic of the method for the transcription of DNA to HNA to DNA.

FIG. 34: DNA to HNA to DNA: a schematic of the method used. The starting DNA template contained a short poly-dA tail to minimise primer independent synthesis of HNA, while the synthesis primer contained both an outnesting tag and a mismatch against the template to allow primer-dependent products to be identified. Forward syntheses were carried out with Pol6G12 as described in the materials and methods and included a no synthesis control (no nucleotides or enzyme) and a no primer control (allowing primer-independent HNA synthesis to proceed. After HNA synthesis, the template was removed with Turbo DNaseI and the reaction purified to remove DNA fragments and unextended primer. The RT reaction carried out with RT521 was then set up with a DNA primer containing a further mismatch and outnesting tag. Reactions were purified after RT and fragments amplified by PCR (using outnesting tags as primers). The outnesting tags ensure that only DNA fragments containing both forward and reverse synthesis outnests, i.e. fragments that were generated by successful primer-dependent synthesis followed by successful RT, are amplified. Cloned fragments are then checked for the two introduced mismatches to ensure that DNA obtained had to come from the original DNA template via the HNA intermediate (as shown in FIG. 31*c*).

Figure 35:
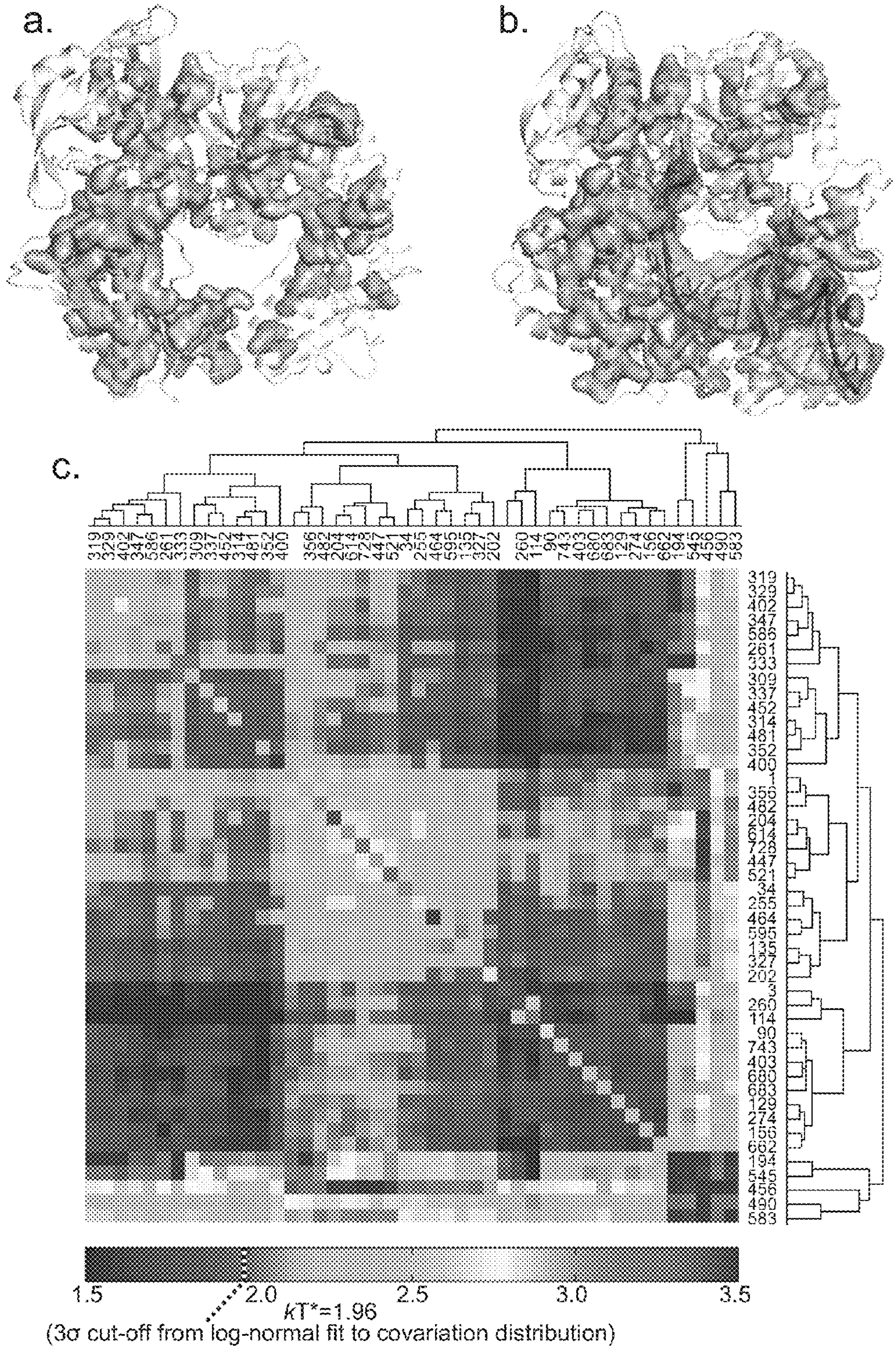
FIG. 35 presents a atatistical coupling analysis (SCA) of PolBs and 521 network. Panel (a) shows a hand-curated seauence alignment of 671 non-redundant B-family polymerases was used in SCA to identify pairs of co-varying residues to identify allosteric networks within the polymerase; panel (b) are SCA results shown in the related *E. coli* pol II (3MAQ); panel (c) is a hierarchical clustering of the residues identified to co-vary with I521 in the alignment used.

FIG. 35: Statistical coupling analysis (SCA) of PolBs and 521 network. (a) A hand-curated sequence alignment of 671 non-redundant B-family polymerases was used in SCA to identify pairs of co-varying residues to identify allosteric networks within the polymerase. The distribution of covariation values obtained fitted a log-normal distribution ($\mu=-1.749$, $\sigma=0.808$). Values above the $99^{th}$ percentile (kT*>1.964) were considered significant and used to establish a PolB allosteric network. Highly significant residues (kT*>2.4) are shown mapped onto the Tgo (1TGO) apo structure (orange) together with conserved residues that could not be included in SCA (cyan). (b) SCA results shown in the related *E. coli* pol II (3MAQ)—SCA and conserved residues are shown as in (a), primer strand in green and template in purple. (c) Hierarchical clustering of the residues identified to co-vary with I521 in the alignment used.

FIG. 36: Polymerase activity ELISA (PAE). (a) Principles of the PAE. A primer-extension reaction is carried out using a biotinylated primer that can be used to immobilise the extended product onto a solid surface coated in streptavidin. The original template is removed by heat or alkali treatment and a digoxigenin (DIG)-labelled probe bound to the extended product. The DIG label is then used in the immunodetection of extension. (b) Individual isolates from small, single-residue, partial coverage libraries (encoded as NWC)

were screened with PAE for DNA synthesis against a chemically synthesised HNA template. Residue 408 and significant SCA residues in its spatial vicinity (405, 520, 521 and 575) were initially investigated with significant activity identified in residues 521 and 575. Pre-extended controls are shown in magenta (+7) and green (+9) as well as the wild-type TgoT (red). Although some HNA RT activity is observed with TgoT as well as 521 and 575 mutants, only 521 could successfully synthesise DNA against longer stretches of HNA.

FIG. 37: Mutagenesis libraries. Residues targeted for diversity are shown in blue (surface representation) on the Tgo (a) and *E. coli* Pol II (b) backbones (white cartoon). Individual libraries in alternating colours are shown against the TgoT sequence (c). Libraries targeted parts of the exonuclease domain (Motifs 1 and 2) and the interhelical domain (Motifs 3 and 4) in addition to the polymerase palm (Motifs 4, A−, A, A+, 6−, 6+, C, C+ and 7), finger (Motifs 5, B−, B) and thumb (Motifs 8, 9, 10A, 10B, 11 and 12) subdomains.

FIG. 38: Basal incorporation of unnatural nucleotides. Cleared polymerase lysates were used to test incorporation of CeATP against TempT template (TTTTTTTTTTTTTTTTTTTTCTCCCTAT-AGTGAGTCGTATTA) (SEQ ID NO: 46) by available "wild-type", chimeras and engineered polymerases. "Wild-type" polymerase included *Thermococcus gorgonarius* (Tgo), *Thermococcus* sp. 9°N-7 (9°N), *Thermococcus litoralis* (Vent) and *Pyrococcus furiosus* (Pfu) devoid of uracyl stalling (V93Q or equivalent) and exonuclease (D141AE143A) activities. Variants harbouring the "Therminator" mutations (A485L)11 are labeled T (e.g. TgoT) and variants harboring mutations determined to improve incorporation of fluorescently labeled nucleotides32 are labeled E10. Chimeras are shows as exonuclease-polymerase (i.e. Pfu-Tgo is a chimera of Pfu's exonuclease domain to Tgo's polymerase domain).

REFERENCES FOR EXAMPLES 21-22

1 Benner, S. A. Understanding nucleic acids using synthetic chemistry. *Acc Chem Res* 37, 784-797, doi:10.1021/ar040004z (2004).

2 Leconte, A. M. et al. Discovery, characterization, and optimization of an unnatural base pair for expansion of the genetic alphabet. *J Am Chem Soc* 130, 2336-2343, doi:10.1021/ja078223d (2008).

3 Hirao, I. Unnatural base pair systems for DNA/RNA-based biotechnology. *Current Opinion in Chemical Biology* 10, 622-627, doi:10.1016/j.cbpa.2006.09.021 (2006).

4 Nielsen, P. E. DNA analogues with nonphosphodiester backbones. *Annu Rev Biophys Biomol Struct* 24, 167-183, doi:10.1146/annurev.bb.24.060195.001123 (1995).

5 Eschenmoser, A. Chemical etiology of nucleic acid structure. *Science* 284, 2118-2124, doi:7618 [pii] (1999).

6 Herdewijn, P. Nucleic acids with a six-membered 'carbohydrate' mimic in the backbone. *Chem Biodivers* 7, 1-59, doi:10.1002/cbdv.200900185 (2010).

7 Joyce, G. F., Inoue, T. & Orgel, L. E. Non-enzymatic template-directed synthesis on RNA random copolymers. Poly (C, U) templates. *J Mol Biol* 176, 279-306, doi:0022-2836(84)90425-X [pii] (1984).

8 Mansy, S. S. et al. Template-directed synthesis of a genetic polymer in a model protocell. *Nature* 454, 122-125, doi:nature07018 [pii] 10.1038/nature07018 (2008).

9 Rosenbaum, D. M. & Liu, D. R. Efficient and sequence-specific DNA-templated polymerization of peptide nucleic acid aldehydes. *J Am Chem Soc* 125, 13924-13925, doi:10.1021/ja038058b (2003).

10 Kool, E. T. Hydrogen bonding, base stacking, and steric effects in dna replication. *Annu Rev Biophys Biomol Struct* 30, 1-22, doi:10.1146/annurev.biophys.30.1.1 30/1/1 [pii] (2001).

11 Gardner, A. F. & Jack, W. E. Determinants of nucleotide sugar recognition in an archaeon DNA polymerase. *Nucleic Acids Research* 27, 2545-2553 (1999).

12 Loakes, D., Gallego, J., Pinheiro, V. B., Kool, E. T. & Holliger, P. Evolving a polymerase for hydrophobic base analogues. *J Am Chem Soc* 131, 14827-14837, doi:10.1021/ja9039696 (2009).

13 Vandermeeren, M. et al. Biological activity of hexitol nucleic acids targeted at Ha-ras and intracellular adhesion molecule-1 mRNA. Biochem Pharmacol 59, 655-663, doi:S0006-2952(99)00367-6 [pii] (2000).

14 Vastmans, K., Froeyen, M., Kerremans, L., Pochet, S. & Herdewijn, P. Reverse transcriptase incorporation of 1,5-anhydrohexitol nucleotides. *Nucleic Acids Res* 29, 3154-3163 (2001).

15 Kempeneers, V., Renders, M., Froeyen, M. & Herdewijn, P. Investigation of the DNA-dependent cyclohexenyl nucleic acid polymerization and the cyclohexenyl nucleic acid-dependent DNA polymerization. *Nucleic Acids Res* 33, 3828-3836, doi:33/12/3828 [pii] 10.1093/nar/gki695 (2005).

16 Sweasy, J. B. & Loeb, L. A. Detection and characterization of mammalian DNA polymerase beta mutants by functional complementation in *Escherichia coli. Proc Natl Acad Sci USA* 90, 4626-4630 (1993).

17 Ghadessy, F. J., Ong, J. L. & Holliger, P. Directed evolution of polymerase function by compartmentalized self-replication. *Proceedings of the National Academy of Sciences of the United States of America* 98, 4552-4557 (2001).

18 Xia, G. et al. Directed evolution of novel polymerase activities: mutation of a DNA polymerase into an efficient RNA polymerase. *Proc Natl Acad Sci USA* 99, 6597-6602, doi:10.1073/pnas.102577799 99/10/6597 [pii] (2002).

19 Franklin, M. C., Wang, J. & Steitz, T. A. Structure of the replicating complex of a pol alpha family DNA polymerase. *Cell* 105, 657-667, doi:S0092-8674(01)00367-1 [pii] (2001).

20 Wang, J. et al. Crystal structure of a pol alpha family replication DNA polymerase from bacteriophage RB69. *Cell* 89, 1087-1099, doi:S0092-8674(00)80296-2 [pii] (1997).

21 Arezi, B., Hogrefe, H., Sorge, J. A. & Hansen, C. J. DNA Polymerase mutants with reverse transcriptase activity. United States of America patent US 2003/0228616 A1 (2003).

22 Lockless, S. W. & Muir, T. W. Traceless protein splicing utilizing evolved split inteins. *Proc Natl Acad Sci USA* 106, 10999-11004, doi:0902964106 [pii] 10.1073/pnas.0902964106 (2009).

23 Russ, W. P., Lowery, D. M., Mishra, P., Yaffe, M. B. & Ranganathan, R. Natural-like function in artificial WW domains. *Nature* 437, 579-583, doi:nature03990 [pii] 10.1038/nature03990 (2005).

24 Ichida, J. K., Horhota, A., Zou, K., McLaughlin, L. W. & Szostak, J. W. High fidelity TNA synthesis by Therminator polymerase. *Nucleic Acids Res* 33, 5219-5225, doi:33/16/5219 [pii] 10.1093/nar/gki840 (2005).

25 Boiziau, C., Dausse, E., Yurchenko, L. & Toulme, J. J. DNA aptamers selected against the HIV-1 trans-activation-responsive RNA element form RNA-DNA kissing complexes. *J Biol Chem* 274, 12730-12737 (1999).

26 Duconge, F. & Toulme, J. J. In vitro selection identifies key determinants for loop-loop interactions: RNA aptamers selective for the TAR RNA element of HIV-1. *RNA* 5, 1605-1614 (1999).

27 Kim, S. W., Kim, D. U., Kim, J. K., Kang, L. W. & Cho, H. S. Crystal structure of Pfu, the high fidelity DNA polymerase from *Pyrococcus furiosus. Int J Biol Macromol* 42, 356-361, doi:S0141-8130(08)00025-1 [pii] 10.1016/j.ijbiomac.2008.01.010 (2008).

28 Rodriguez, A. C., Park, H. W., Mao, C. & Beese, L. S. Crystal structure of a pol alpha family DNA polymerase from the hyperthermophilic archaeon *Thermococcus* sp. 9 degrees N-7. *J Mol Biol* 299, 447-462, doi:10.1006/jmbi.2000.3728 S0022-2836(00)93728-8 [pii] (2000).

29 Hashimoto, H. et al. Crystal structure of DNA polymerase from hyperthermophilic archaeon *Pyrococcus* kodakaraensis KOD1. *J Mol Biol* 306, 469-477, doi: 10.1006/jmbi.2000.4403 S0022-2836(00)94403-6 [pii] (2001).

30 Wang, F. & Yang, W. Structural insight into translesion synthesis by DNA Pol II. *Cell* 139, 1279-1289, doi:S0092-8674(09)01501-3 [pii] 10.1016/j.cell.2009.11.043 (2009).

31 Kolb, G. et al. Hexitol nucleic acid-containing aptamers are efficient ligands of HIV-1 TAR RNA. *Biochemistry* 44, 2926-2933, doi:10.1021/bi048393s (2005).

32 Ramsay, N. et al. CyDNA: synthesis and replication of highly Cy-Dye substituted DNA by an evolved polymerase. *J Am Chem Soc* 132, 5096-5104, doi:10.1021/ja909180c (2010)

Example 23

Improving DNA Primer Binding to HNA Molecules

Base composition, particularly purine and pyrimidine bias, has a strong influence on HNA/DNA melting temperature (Boudou, V., et al., Base pairing of anhydrohexitol nucleosides with 2,6-diaminopurine, 5-methylcytosine and uracil asbase moiety. Nucleic Acids Res, 1999. 27(6): p. 1450-6). By making use of these biases, it is possible to design a DNA primer capable of binding HNA and to be successfully extended by 521-type polymerases (HNA RT).

Initially, 3 DNA primer sequences were tested against a known HNA molecule (to be synthesised from a DNA template (Testbind3):

| Primer | Sequence |
|---|---|
| Testbind3 | GATCCGTTTCCTCCTCCCTAGTTCTTCCTCTTCCCTCTCT TCCCTTC**TGGCAAACGCTAATAAGGGG** (SEQ ID NO: 47) |
| Test6 | TCCCTCTCTTCCCTTC (SEQ ID NO: 48) |
| Test7 | CCCTAGTTCTTCCTCTTCCC (SEQ ID NO: 49) |
| Test8 | GATCCGTTTCCTCCTCCC (SEQ ID NO: 50) |

An NAPfd (previously described; binding site shown above underlined) 2'OMe RNA primer is used to synthesise an HNA molecule that harbours the binding site for all three test probes. The synthesised HNA was isolated by PAGE-purifying a TURBO DNAsed synthesis reaction (as described) and primer binding experiments carried out in a variety of conditions, as shown in FIG. 39.

Figure 39:
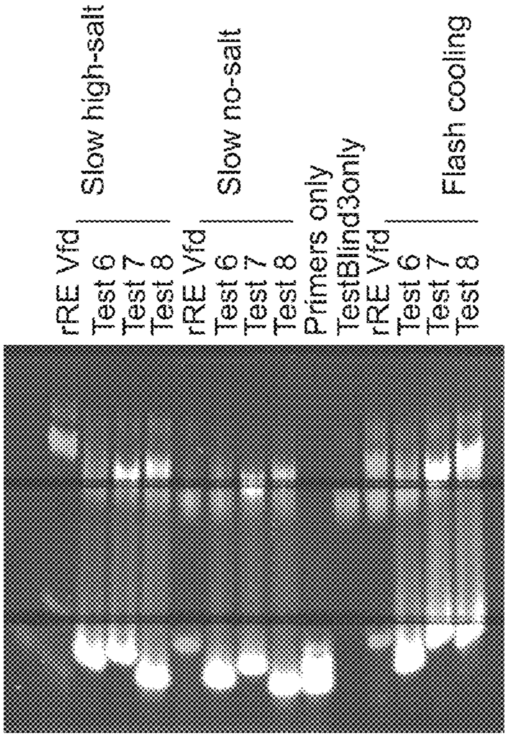
FIG. 39 shows DNA primer binding to purified HNA molecules. rREVfd is a RNA primer complementary to the fd tag used in HNA synthesis and was used as internal control for primer binding.

FIG. 39: DNA primer binding to purified HNA molecules. rREVfd is an RNA primer complementary to the fd tag used in HNA synthesis and was used as internal control for primer binding. 1 pmol of HNA was used to test 1 pmol of DNA primer binding. While inefficient, primers can clearly bind HNA, particularly Test7 and Test8. Further work focused on Test7.

Having proved that a DNA primer could bind a compositionally-biased HNA molecule, I repeated the experiment for test7 on an unbiased template (TempNpurine: CCTAGTTCTTCCTCTTCCCGATGCTGGACCAGATAAGCACTTAGCCACGTAGTGCTGT TCGGTAATCGATCTGGCAAACGCTAATAAGG) (SEQ ID NO: 51) with similar results. DNA primer binding to HNA was unaffected by a 5' overhang on the DNA.

Having obtained successful primer binding, we carried out a primer-dependent RT as a proof-of-principle.

Figure 40:
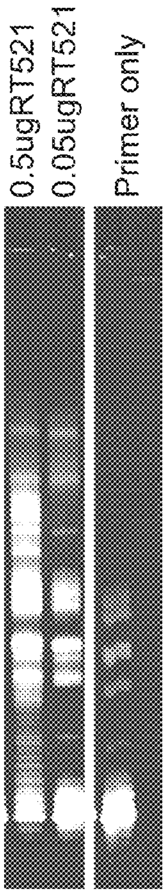
FIG. 40 shows primer-dependent HNA RT. FITC-labelled HNA was used as template for an RT carried out with RT521 using a Cy5-labelled Test7 primer.

FIG. 40: Primer-dependent HNA RT. FITC-labelled HNA (red) was used as template for an RT carried out with RT521 using a Cy5-labelled Test7 primer (green). Full-length product could be observed for both concentrations of RT521 used after a 4 h@65° C. extension. These results were corroborated by subsequent PCR from the RT reactions.

Having obtained an adequate RT product, we investigated the limit of detection of the system in a molecule of known sequence (TempNpurine). PCR detection of the RT product (using a double outnest approach) suggested RT521 could detect HNA RT products down to RTs carried out with 0.25 pmol HNA.

Further primer optimisation, including spiking of the DNA primer with other nucleotide chemistries (e.g. LNA, 2'OMe-RNA) is being carried out. However, an alternative was to further improve the RT enzyme itself

Example 24

Further Design of Polymerases for Processive Reverse Transcription of HNA/RNA The E664K mutation, described in the context of designing an RNA polymerase, was determined to increase the affinity of the polymerase for the primer-template complex. Since an HNA/DNA hybrid is expected to give rise to a substantially distorted helix, increasing the affinity of the RT521 for this template is likely to improve HNA reverse transcription.

iPCR was used to introduce the E664K mutation in the RT521 context and both enzymes were tested side-by-side for HNA RT-PCR using the TempNpurine system described above.

Figure 41:
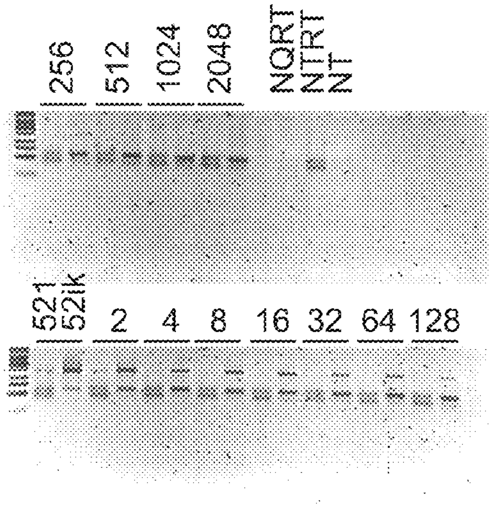
FIG. 41 shows results of HNA RT-PCR comparing RT521 with RT521K (RT521+E664K mutation).

FIG. 41: HNA RT-PCR comparing RT521 and RT521K (RT521+E664K mutation). The sensitivity of the RT-PCR was determined by titrating the input HNA template in the reaction from 1 pmol and following a 2-fold dilution series. For HNA, RT521K seems to yield at least a 60-fold improved detection limit. Controls included a no template for the PCR (NT), a no template for the RT (NTRT) and a reaction carried out without the RT step (NoRT).

Carrying out a similar experiment using an in-nested PCR to increase the sensitivity of detection yielded clear amplification of a single HNA sequence down to 9 attomoles of input HNA into the RT step carried out with 521K. This is not expected to be the limit of detection—further reaction optimisation would be expected to further improve sensitivity.

Figure 42:
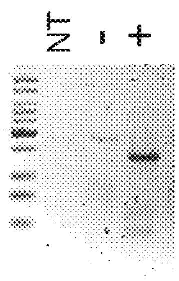
FIG. 42 shows HNA RT-PCR from a degenerate N40 library using the same double outnest approach described in herein.

Importantly, Test7 is portable and can be used against other templates, including degenerate libraries such as ApLib5 (CCCTAGTTCTTCCTCTTCCCNNNNNNNNNNNN NNNNNNNNNNNNNNNNNNNNNNNN CGAACAGCACTACCTtTTGGCAAACGCTAATAAGGGGTCCTA AAAAAAAA) (SEQ ID NO: 52) shown in FIG. 42.

FIG. 122: HNA RT-PCR from a degenerate N40 library using the same double outnest approach described in Example 2. Forward synthesis was carried out with NAPfd 2'OMe against AplibS template and RT carried out with LMB3+Test7 primer against 1 pmol HNA. Subsequent PCR was carried out with NAP and LMB3+ for 25 cycles. A no template control was included for the PCR (NT) and a no RT control was also carried out (−).

Example 25

RNA Polymerase

DNA polymerase substrate specificity is critical for genomic integrity; the current paradigm is that it is exclusively determined by the active site, as exemplified by steric gate mutations. Such mutations increase incorporation of NTPs by DNA polymerases from all families by several orders of magnitude but do not result in processive RNA polymerases. Indeed, most modified DNA polymerases stall after 6-7 NTP incorporations, despite impressive incorporation efficiency. Through a focus on the thumb domain of a B-family polymerase, Tgo, we have identified a point mutation in the immediate vicinity of the nascent strand which relieves this extension block: the "second gate". Mutation of the second gate of Tgo (E664K), combined with a classical steric gate mutation (Y409G) results in TGK: the first primer-dependent, thermostable RNA polymerase engineered from a DNA scaffold. TGK can synthesise a tRNA gene in less than a minute and can synthesise a 1.7 kb Luciferase gene in only 1 hour. Furthermore, the E664K mutation enables translesion synthesis even in the absence of the steric gate mutation. The "second gate" thus specifies the critical missing step in the evolutionary path from DNA to RNA polymerase, defines a new post-synthetic determinant of polymerase substrate specificity distal to the active site and establishes the thumb domain as region that merits further investigation in studies of both replication fidelity and polymerase substrate expansion.

DNA polymerase substrate specificity is of central importance for genome stability, as well as for applications in biotechnology and is generally assumed to be determined solely by the geometry and chemistry of the polymerase active site. Yet, highly efficient incorporation of nucleotide substrates does not necessarily beget processive synthesis of nucleic acid polymers, as is exemplified by mutation of the "steric gate" residue in the active site of the DNA polymerases. Such mutations increase the catalytic efficiency of NTP incorporation by several orders of magnitude, but the resulting polymerases still remain incapable of processive RNA synthesis. Here we describe the discovery of a critical secondary specificity determinant, a "second gate", located in the polymerase thumb domain, 25 Å from the primer 3' terminus. Mutation of this second gate residue (E664K) in Tgo, the replicative DNA polymerase from *T. gorgonarius*, together with a classic steric gate mutation (Y409G), yields a processive, thermostable, primer-dependent RNA polymerase, capable of synthesizing protein-coding mRNAs up to 1.7 kb in length with a fidelity comparable to T7 RNA polymerase. The "second gate" specifies the critical missing step in the evolutionary path from DNA to RNA polymerase and defines a new post-synthetic determinant of polymerase substrate specificity distal to the active site.

Despite significant progress in understanding polymerase substrate specificity, the engineering of a processive RNA polymerase from a DNA polymerase scaffold has proven elusive. Mutation of the "steric gate" residue in the active site of the DNA polymerases increases the catalytic efficiency of NTP incorporation, but the resulting polymerases remain incapable of processive RNA synthesis. Here we describe the discovery of a critical secondary determinant, a "second gate", located in the polymerase thumb domain, 25A from the primer 3' terminus. Mutation of this second gate residue (E664K) in Tgo, the replicative DNA polymerase from *T. gorgonarius*, together with a classic steric gate mutation (Y409G), yields the first processive, thermostable, primer-dependent RNA polymerase, capable of synthesizing protein-coding mRNAs up to 1.7 kb in length with fidelity comparable to T7 RNA polymerase. This "second gate" specifies the critical missing step in the evolutionary path from DNA to RNA polymerase and defines a new post-synthetic determinant of polymerase substrate specificity distal to the active site.

DNA polymerases enable the propagation of genetic information through faithful replication and maintenance of the genome and thus are of central importance to all life. Genome replication requires sophisticated substrate recognition mechanisms to ensure polymerase fidelity and to exclude non-cognate and/or damaged nucleotides from incorporation into the genome. Detailed structural investigations together with nucleotide chemistry have begun to reveal the molecular mechanisms of how the polymerase active site may distinguish cognate from non-cognate nucleotide chemistries and geometries. Of particular importance for the integrity of the DNA-based genomes is the exclusion of ribonucleotides from incorporation into the genome. Ribonucleotide triphosphates (NTPs) differ from the deoxyribonucleotide triphosphates (dNTPs) only by the presence of a 2'-hydroxyl (—OH) on the ribofuranose ring and are present in the cell at concentrations up to 100-fold in excess of the cognate dNTPs. Although DNA polymerases exclude NTPs from their active site and hence from the genome it has recently been shown that incorporation does occur to a detectable degree, with significant implications for genome stability and repair. This issue is even more acute for thermophillic organisms as high temperatures would further increase genome instability by accelerating the spontaneous degradation of RNA by nucleophilic attack of the vicinal 2' OH of ribose on the 3' phosphodiester bond.

Consequently, DNA polymerases use an exceptionally effective mechanism to prevent NTP incorporation into the nascent strand; a single residue, the "steric gate", exerts stringent steric control of the chemical nature of the 2' position of the incoming nucleotide. Steric gate residues have been identified in all replicative [6-9] (polB, polC) and repair [10-13] (polA, poly, polX—with the possible exception of Pol Mu [14]) polymerase families and the reverse transcriptases [15-18] (RTs, Table S1 FIG. 52). It thus is found in all polymerases from all three domains of life, attesting to its universal importance. Originally discovered by structural inspection of the Moloney murine leukemia virus RT [15], and more thoroughly explored in DNA polymerase I from *E. coli [*19] (a polA-family polymerase), this mechanism is so effective that mutating the steric gate to an amino acid residue with a smaller side chain can reduce discrimination against NTP incorporation by several orders of magnitude [7-13, 15-20].

However, while mutation of the steric gate residue commonly renders a DNA polymerase permissive for NTP incorporation, such mutations do not by themselves enable synthesis of extended RNA oligomers. The engineering of an RNA polymerase from a DNA polymerase has been attempted using rational design [8], in vitro or in vivo screening [21, 22] and directed evolution by phage display [23] or compartmentalized self-replication [24]. Although these efforts have yielded DNA polymerases that efficiently incorporate NTPs, most stall at n+6 and none are able to synthesize RNA oligomers longer than 58 nucleotide incorporations and even this typically requires long incubation times (several hours), high polymerase concentrations and mutagenic metal ions ($Mn^{2+}$) [21, 22, 25, 26]. Thus we [24] and others [10, 20] have reasoned that, apart from the steric gate residue in the active site, there must be at least one other critical determinant in the DNA polymerase structure that aborts processive RNA synthesis. Indeed, evolution of a processive RNA polymerase from a DNA polymerase framework must be possible, as there is a natural precedent. Structural and phylogenetic evidence suggest that the single subunit RNA polymerases (ssRNAP) of mitochondria and T-odd bacteriophages, to which the widely used T7 RNA polymerase belongs, derive from an ancestral A-family DNA polymerase [27-30]. Although the polymerases from the two families have diverged widely and there is no known extant "missing link", there must be an adaptive path linking RNA polymerases and DNA polymerases.

Here, we describe the discovery and characterisation of a critical determinant of polymerase substrate recognition located in the thumb domain of *T. gorgonarius* DNA polymerase (Tgo), 25 Å from the primer 3' terminus (FIG. 43). It comprises a single mutation that, when combined with a steric gate mutation, relieves the synthetic block for RNA polymerisation and enables the synthesis of mRNAs over 1.7 kb in length in only one hour, primed from either DNA or RNA oligonucleotide primers. The thumb mutation and steric gate mutation are both necessary and sufficient for RNA polymerase activity and thus define a minimal adaptive path from DNA polymerase to RNA polymerase. Finally, this mutation expands the polymerase substrate spectrum enabling the processive synthesis of chemically modified RNA as well as translesion synthesis (TLS), and thus pinpoints a new post-synthetic checkpoint of polymerase substrate specificity far from the active site.

Materials and Methods

All DNA oligonucleotides were from Sigma, IDT, Eurogentech or MWG Eurofins and all RNA oligonucleotides were from Dharmacon or IDT. All dNTPs used were from Roche (Roche Diagnostics GmbH, Germany), GE (GE Healthcare Life Sciences, UK) or Agilent (Agilent Technologies Inc, California, USA). All NTPs used were from Roche., 2' fluoro and 2' azido dNTPs were from (TriLink Biotechnologies Inc, California, USA) and 2' iodo-dATP was from Jena Bioscience (Jena Bioscience GmbH, Germany).

DNA Manipulation, Protein Expression and Purification

All DNA manipulation and small-scale expression was carried out in NEB cells (New England Biolabs Inc., Massachusetts, USA). TgoT and all mutants were maintained in pASK75. Large scale expression and purification was as described [69] except that either BL21 CodonPlus-RIL (Agilent Technologies) or NEB T7 Express LysY (NEB) were used; cultures were induced for 4 hours at 37° C. and cleared lysates were pre-cleaned on DE52 anion exchange resin (Whatman Inc, New Jersey, USA) prior to loading onto the 6/10 Hi-Prep Heparin FF column. All polymerases eluted at 0.7-0.8M NaCl, were filter dialyzed (Amicon Ultra Centrifugal Filters 50K; Millipore, Mass., USA) into 2× Vent storage buffer (NEB) and stored in 50% glycerol. Mutants were typically expressed from NEB cells (NEB), lysed by heat treatment and stored in 1× Thermopol buffer (NEB) and screened for activity as cleared 10× lysates.

Point mutations were introduced by iPCR using either Expand Hi-Fidelity PCR System (Roche) or Herculase II (Agilent Technologies), BsaI (NEB) digested, ligated with T4 DNA Ligase (NEB) and sequenced to confirm the presence of mutation prior to expression, except L403P which was introduced to TgoT by cutting TgoT and D4 with XbaI and Bsu36I, gel purifying the digests and ligating the appropriate fragments to generate TgoT L403P and D4 P403L.

Compartmentalised Self-Tagging (CST)

D4 was isolated from the first round of CST selection described in (VP, CC, PH, manuscript in preparation).

Primer Extension

Primer extension for screening (either for mutant polymerases or for activity with novel substrates) was carried in 3-5 μl reactions containing 1-10 pmol primer with template at 2-fold excess. Usually, primer FD (5'-CCCCTTATTAGCGTTTGCCA-3') (SEQ ID NO: 53) in either DNA or RNA with 5'biotin, 5'FITC, 5'Cy3, 5'Cy5 or dual-labelled with 5'FITC-dT-biotin was used to extend TempN (5'-CTCACGATGCTGGACCAGATAAGCACTTAGCCACGTAGTGCTGTTCGGTAATCGATC TGGCAAACGCTAATAAGGGG-3') (SEQ ID NO: 54) in 1× Thermopol buffer (NEB) with 0.25-0.75 mM each NTP and supplemented with MgSO4 in the case of certain steric gate mutants. A typical extension protocol was 2 cycles of 10 sec 94° C., 1 min 50° C., 10 min 65° C.

For timecourses, 2 pmol RNA primer YtRHNA2HNA2 (5'FITC-CAGGAAACAGCTATGACAAATGGTGGTGGGG-3'; (SEQ ID NO: 55)_underlined section is template binding site) was annealed to 4 pmol template tRNAtemp1 (5'-GGTGGGGTTCCCGAGCGGCCAAAGGGAGCAGACTCTAAATCTGCCGTCATCGACTT CGAAGGTTCGAATCCTTCCCCCACCACCA-3', based on GI:174470) (SEQ ID NO: 56)_per reaction in 1× Thermopol, +3 mM $MgSO_4$, 2.5 mM NTP (0.75 mM each NTP), by heating to 94° C. for 30 sec and cooling to 4° C. at 0.1 C/second. Enzyme was added on ice and the reactions incubated at 65° C. prior to quenching with 2V 98% formamide/10 mM EDTA and separating on 15% acrylamide/8M urea PAGE.

Polymerase Activity Assay (PAA) Screen

The polymerase activity assay (PAA) screen was carried out as described (VP, CC, PH, manuscript in preparation), except 10 μl 8M urea/10 mM EDTA containing the digoxygenin (DIG)-labelled probe oligonucleotide was added to the reaction mix (as for primer extension, typically 5 μl reactions containing 5 pmol 5'biotin-FD and 10 pmol TempN) following primer extension using biotinylated primer and incubated at 65° C. for 2 minutes. This hot mixture was added to 200 μl pre-chilled PBS-T (PBS+0.1% Tween-20) in a 96-well StreptaWell plate (Roche) and the probe allowed to hybridise to the extended primer while the biotin bound to the plate. The plate was washed 3 times by immersion in a PBS-T bath and the probe was detected using an anti-digoxygenin-POD Fab fragment (Roche) and Ultra-TMB ELISA substrate (Thermo Scientific, Massachusetts, USA).

Protein Concentration Assay

Purified protein concentration was assayed via separation on NuPAGE 4-12% Bis-Tris gels (Invitrogen Ltd, UK), staining with SYPRO orange (Sigma-Aldrich, Missouri, USA) and quantification by Typhoon TRIO and ImageQuant. A standard curve generated from BSA standards of known concentration (Thermo) was used to derive polymerase concentration.

GFP and Luciferase Template Preparation and Synthesis

Templates were prepared from mGFP6 [70] for GFP or Luciferase T7 Control DNA (Promega #L482A) by PCR using Herculase II (Agilent Technologies) with one biotinylated primer and one non-biotinylated primer. This method allowed the introduction of a unique forward priming site and allowed generation of single-strand DNA templates by binding the QIAquick (Qiagen NV, Netherlands)-purified PCR products to an appropriate volume of paramagnetic beads (DynaBeads MyONE Streptavidin C1, Invitrogen). The desired strand was eluted using 20 mM or 100 mM NaOH at 37° C., neutralised in an equal volume of 3M NaOAc pH5.5 and isopropanol precipitated.

Forward synthesis was from RNA primer L3T32 (5'TYE665-05'-AGGAAACAGCTATGACAAACAAGG-TAGTGCTGTTCGtgggg-3'; (SEQ ID NO: 57) underlined is template binding site, 5' of sequence introduces outnest for PCR) in a 50 μl reaction consisting 1× Thermopol (NEB), +3 mM $MgSO_4$, 2.5 mM NTP (0.75 mM each), 1:1 primer: template ratio varying from 10 pmol to 70 pmol of each and 150 nM TGK. Extension was 2 cycles of 10 s 94° C., 1 m 50° C., 1 h 65° C. to make 2 h total extension. The DNA template was digested by TURBO DNase (Applied Biosystems/Ambion, Texas, USA) treatment (8 U for 1 h at 37° C. in reaction mix supplemented with 1× TURBO DNase buffer) and RNA purified on an RNeasy column (Qiagen).

Reverse transcription of purified RNA was carried out using Transcriptor RT (Roche) with primer GB1lucfo (5'-GAAATGGTAAGGCAAATACGGTTA-CAATTTGGACTTTCCG-3'; (SEQ ID NO: 58)_underlined is template binding site, 5' of sequence introduces outnest for PCR) for luciferase or GB1GFPfo (5' GAAATGGTAAG-GCAAATACGGCTATTTGTATAGTTCATC-CATGCCATG-3'; (SEQ ID NO: 59) underlined is template binding site, 5' of sequence introduces outnest for PCR) and cDNA PCR-amplified using FastStart Taq (Roche) with primers LMB3+(5' CAGGAAACAGCTATGACAAA-3') (SEQ ID NO: 60) and NAP (5'-CAGTATCGACAAAGGA-3') (SEQ ID NO: 61). PCR products were TOPO TA-cloned into pCR4.1 using TOPO TA Cloning Kit For Sequencing (Invitrogen) and sequenced from colonies. Both forward synthesis and RT primers introduced mismatches so that sequences could be identified as having been both synthesized and reverse transcribed. Error rates were calculated using the Transcriptor error rate provided by Roche ($1.98 \times 10^{-5}$) and assuming Taq error rate as previously (VP, CC, PH, manuscript in preparation).

Synthesis and In Vitro Translation of TGK-Synthesised RNA ssDNA templates were described as above, except using primer L3SDGFPba (5'biotin-CAGGAAACAGCTATGA-CAGGAGGAGCGAGATGAGTAAAGGAGAA-GAACTTTTC-3') (SEQ ID NO: 62)_which encodes a Shine Dalgarno sequence (underlined). Primer RNA L3AGG (5'-CAGGAAACAGCTATGACAGG-3') (SEQ ID NO: 63)_was used for RNA synthesis as described above for 2 cycles of 10s 94° C., 1 m 50° C., 15 m 65° C. to make 30 m total extension and purified as previously described. IVT was carried out using 1.4 μg RNA added directly to PURExpress In Vitro Protein Synthesis Kit (NEB) supplemented with 3 μl FluoroText GreenLys in vitro Translation Labelling System (Promega) and incubated for 2 h at 37° C. prior to analysis on a NuPAGE Novex 10% Bis-Tris Gel (Invitrogen).

Electrophoretic Mobility Shift Assay (EMSA)

The affinity of mutant Tgo polymerases for DNA:DNA or DNA:RNA was assayed using 5'FITC-labelled primer K0 (5'-GCACGGCAGCACGTG-3') (SEQ ID NO: 64) in either DNA or RNA and template TempK4 (5'biotin-ACTGCGAT-GACTGTACTCGTCTAGTAGCACTG-CACGTGCTGCCGTGC-3') (SEQ ID NO: 65)_in a 5 ul reaction mixture containing 1× Thermpol buffer (NEB), 250 fmol primer K0, 2.5 nmol TempK4, 1 mM EDTA, 1 U RNasin (Promega) and 0.02-1.25 uM polymerase. The reactions were mixed, heated to 94° C. for 30 sec and cooled at 0.1° C./sec to 4° C. before loading onto precooled 6% TBE gel (Invitrogen) and run for 1 h at 100V in precooled 1× TBE. Bands were quantified using a Typhoon Trio and ImageQuant and the shift fitted to y=(Bmax*x)/(Kd+x) using MatLab (The MathWorks Ltd).

Polymerase Processivity and Lesion Bypass Assays

The 48-mer DNA templates, 5'-TCG-ATA-CTG-GTA-CTA-ATG-ATT-AAC-GAA-YXA-AGC-ACG-TCC-GTA-CCA-TCG-3', where YX=TT, TT-CPD (cis-syn cyclobutane pyrimidine dimer) or TAb (Ab-abasic site) (SEQ ID NO: 66), and 16-mer DNA primer (5'-TGG-TAC-GGA-CGT-GCT-T-3') (SEQ ID NO: 67), or RNA primer (5'-UGG-UAC-GGA-CGU-GCU-U-3') (SEQ ID NO: 70) were used in the primer extension experiments. Primers, undamaged and abasic site-containing templates were synthesized by Lofstrand Laboratories (Gaithersburg, Md.). The CPD-containing template was synthesized by Phoenix Biotechnologies (Huntsville, Ala.). All oligonucleotides were gel purified prior to use. Primers were 5'-end-labelled using T4 polynucleotide kinase and [y-32P]-ATP. DNA substrates were prepared by annealing DNA templates with 32P-labelled primers at a 1.5:1 molar ratio. Hybridization was achieved by heating the required mixture in an annealing buffer [50 mM Tris-HCl (pH 8), 5 mM $MgCl_2$, 50 μg ml-1 BSA, 1.42 mM 2-mercaptoethanol] for 10 min at 100° C. followed by slow cooling to room temperature over a period of about 2 h. Annealing efficiencies were >95%.

Standard reactions were performed for 4 min at 65° C. in 1× Thermopol buffer and contained 10 nM DNA templates (expressed as primer termini), 0.25 mM of dNTPs or NTPs mixtures and appropriate nM TgoT, TGE, TYK, or TGK. To analyze enzyme processivity, reactions were performed with a large molar excess of DNA template over the polymerase ensuring 'single-hit' conditions. The reactions were terminated by mixing with 1 vol. of formamide loading dye solution containing 50 mM EDTA, 0.1% xylene cyanol and 0.1% bromophenol blue in 90% formamide. Before loading onto the gel, the reactions were denatured by heating at 100° C. for 10 min and immediately transferred onto ice for 2 min. Products were resolved by denaturing polyacrylamide gel electrophoresis (8 M urea, 15% acrylamide, 3 h at 2000 V) and then visualized and quantified using a Fuji image analyser FLA-3000 and MultiGauge software. Termination probabilities (expressed as a percentage) for template positions 1-14 were calculated as the band intensity at the specific position divided by the intensity at that position plus all longer products [71].

Identification of a Polymerase Region Enabling Improved RNA Synthesis

Polymerases capable of synthesizing novel unnatural nucleic acid polymers are described. Some of these, in which the canonical ribofuranose ring is replaced by an alternative structure, for example a six-membered 1,5 anhydrohexitol ring (hexitol nucleic acids, HNA), display A-like (RNA-like) helical conformations [31, 32], (FIG. 43). Given this conformational analogy, we decided to test mutant polymerases that had been engineered for HNA synthesis (VP, CC, PH manuscript in preparation) for RNA polymerase activity. One of these polymerases (D4) displayed enhanced RNA polymerase activity and is the starting point of the work described herein.

D4 derives from a variant of the replicative DNA polymerase of the hyperthermophillic archaeon *Thermococcus gorgonarius* (Tgo), which bears additional mutations to disable uracil stalling (V93Q [33]) and 3'-5' exonuclease activity (D141A, E143A) as well as the "Therminator" [34] mutation (A485L) to enhance incorporation of unnatural substrates.

This mutant polymerase (henceforth termed TgoT) does not display RNA polymerase activity above background levels: RNA synthesis by TgoT stalls after 6-7 incorporations from a DNA primer and is absent from an RNA primer. In contrast, D4 extends both DNA and RNA primers by >20 nts, under the same conditions (FIG. 43). This gain of function in D4 is effected by an additional 9 mutations to the TgoT scaffold, comprising a cluster of 8 mutations (P657T, E658Q, K659H, Y663H, E664Q, D669A, N671K, 1676T) in the polymerase thumb domain and a single mutation in the polymerase A-motif (L403P).

Mutation of the Steric Gate Enables Processive RNA Polymerisation

We aimed to better understand the function of these mutations to the RNA polymerase phenotype, especially of the 8 mutations distal to the active site. In order to determine their contribution to RNA polymerase activity in the context of a more permissive active site we introduced a steric gate mutation into D4. Previous work on the B family (polB) polymerases had identified a conserved tyrosine (Tgo: Y409) as the steric gate residue. Replacing Y with a smaller residue is known to reduce NTP/dNTP discrimination by $>10^3$-fold, yet not to enable processive RNA synthesis [7-9]. However, Y409 is also thought to be involved in metal ion coordination and productive nucleotide positioning and we were concerned that a "null" mutation (e.g. to a small side-chain amino acid, such as A) might adversely affect overall polymerase function and fidelity [35-37]. Since no archaeal B-family polymerases have been crystallised as a ternary complex to date, we carried out in silico modelling using the homologous polB RB69 (PDB: 1Q9Y, [38]) to find an amino acid side chain that would relieve the steric clash with the incoming NTP while maintaining sufficient bulk to avoid relaxing the geometry of the active site. We found that replacement of Y with medium sized side-chains (e.g. S, L, N) improved RNA polymerase activity in a D4 background. Indeed, introduction of Y409N mutation into the D4 context (D4: Y409N, henceforth called D4N) yielded a highly proficient RNA polymerase capable of synthesizing a tRNA (*E. coli* supF $tRNA^{Tyr}$) gene consisting 65 nucleotide incorporations in 20 minutes, while the same mutation introduced into the "wild-type" polymerase TgoT (TgoT: Y409N, TN) only marginally improved RNA polymerase activity (FIG. 44). We therefore concluded that some (or all) of the mutations in the D4 polymerase were responsible for relieving the synthetic block in the simple steric gate mutant polymerases and enabling the synthesis of longer RNA oligomers.

Figure 49:
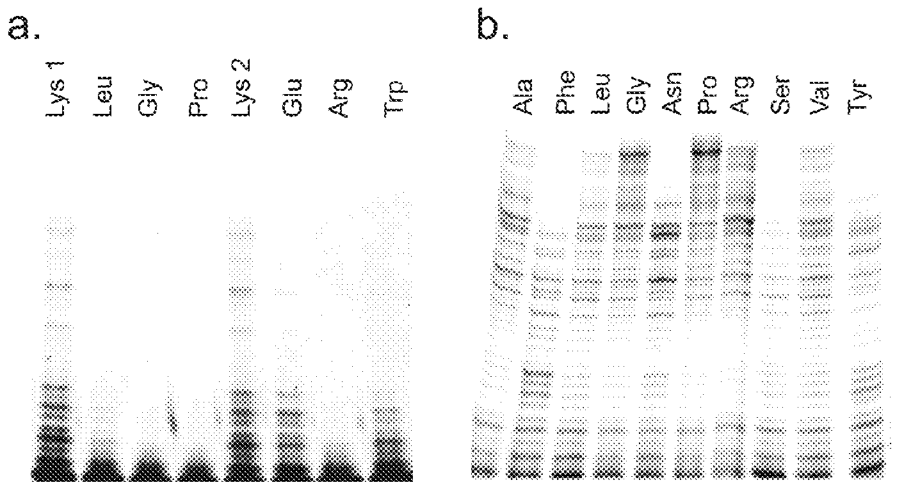
FIG. 49 shows RNA polymerase optimization. Panel (a) shows a RNA produced following a 664 position screen; panel (b) shows RNA produced following a steric gate screen.

A Single Point Mutation in the Thumb Domain is Critical for Processive RNA Synthesis Having established that the nine mutations in D4 in conjunction with the Y409N steric gate mutation enabled processive RNA synthesis, we sought to determine the contributions of the different mutations in D4N to RNA synthesis. To this end we reverted each individual D4N mutation to wild-type and determined the effect on RNA synthesis. Reversion of the thumb domain mutations revealed a striking pattern: seven of the eight back mutations (D4N: T657P, Q658E, H659K, H663Y, A669D, K671N, T676I) did not reduce RNA polymerase activity, whereas reversion of one specific residue to wild type (D4N: Q664E) had a dramatic negative effect on processive RNA synthesis (FIG. 44). Indeed, the reversion mutant D4N Q664E displayed essentially the same level of RNA polymerase activity as the parent polymerase TgoT, rendering the polymerase incapable of extending a primer beyond 6 NTP incorporations despite the presence of the other 8 mutations. This also suggested that the A-motif mutation, L403P, did not contribute to processive RNA polymerase activity; indeed it is detrimental to NTP incorporation in the presence of a mutated steric gate (FIG. 49).

To determine the effect of this key mutation free of the context of the other D4 mutations we introduced the E664Q forward mutation together with the steric gate mutation Y409N de novo into the TgoT framework. The resulting TgoT polymerase double mutant TNQ (TgoT: Y409N, E664Q) displayed superior RNA polymerase activity compared to both the steric gate mutant TN (TgoT Y409N) and the original D4N polymerase. These results indicate that the E664Q mutation is both necessary and sufficient for processive RNA synthesis. As DNA polymerases are incapable of processive RNA synthesis even when the steric gate is mutated (as shown previously [10, 21-24] and here in the example of TN), we conclude that E664 forms (or is a critical part of) a second checkpoint in the DNA polymerase structure that normally prevents the synthesis of RNA oligomers. Mutation of this "second gate" residue E664 disables the checkpoint and relieves the synthetic block and, together with mutation of the steric gate residue Y409, enables processive RNA synthesis in the double mutant polymerase TNQ, which is capable of synthesising the 65-nucleotide supF tRNA gene in <10 minutes (FIG. 44).

Polymerase Optimization for Processive RNA Synthesis

Having established that mutation of E664 plays a key role in enabling processive RNA synthesis, we randomized position 664 in TN and in order to identify an optimal "second gate" residue. We screened for enhanced RNA polymerase activity using a novel high-throughput polymerase activity assay (PAA), based on capture of primer extension products and their quantification via hybridization to a specific antisense probe. The PAA screen identified several mutations promoting RNA polymerase activity (E664 K, L, Q, R), with lysine (E664K) proving most effective (FIG. 49). Indeed, the new double mutant polymerase TNK (TgoT: Y409N E664K) displayed significantly improved RNA polymerase activity compared to the previous benchmark polymerase, TNQ.

Following the success of this strategy we randomized position 409 in the context of the E664K mutation and performed an analogous PAA screen. This identified several promising mutations (Y409 A, G, P) of which G and P proved most advantageous (FIG. 49). We chose the Y409G mutation and combined it with E664K to give the new TgoT double mutant polymerase TGK (TgoT: Y409G E664K). TGK proved an exceptionally active RNA polymerase, capable of quantitative synthesis of the supF tRNA gene in less than 30 seconds (FIG. 44). Reverting the Therminator mutation in TGK to wild-type (L485A) resulted in a less proficient RNA polymerase (FIG. 49), although the Therminator mutation alone does not result in a processive RNA polymerase phenotype [22, 25].

We conclude that there are two key positions in the B-family DNA polymerase structure that inhibit RNA synthesis in the wild-type polymerase, and that mutation of both is essential for the engineering of a processive RNA polymerase. One, the steric gate residue (Y409) lies in the active site and prevents incorporation of NTPs by steric exclusion and is thus best mutated to G to provide maximum steric flexibility in the active site. The other, the "second gate" residue (E664), blocks the synthesis of longer RNA oligomers and is best mutated to K, reversing the electrostatic charge at this position.

Figure 45:
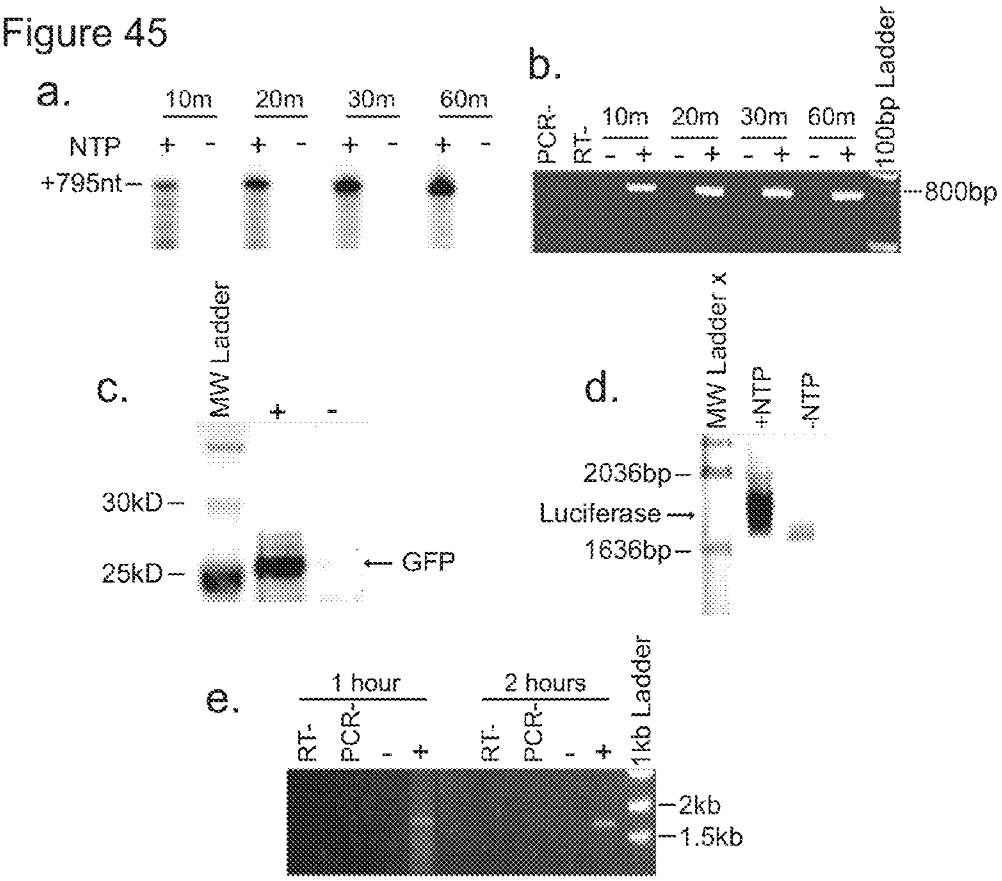
FIG. 45 demonstrates long-range RNA synthesis by TGK. Panel (a) reflects a denaturing agarose electrophoresis of Cy5-labelled GFP RNA synthesised by TGK from a labelled RNA primer; panel (b) is RT-PCR from the RNA shown in panel (a); panel (c) shows in vitro translation of GFP synthesised by TGK. GFP was visualised by excitation of fluorescent lysines incorporated into GFP without staining the gel; panel (d) is a native agarose electrophoresis of Luciferase synthesised by TGK. RNA is visualised directly by Cy5; the ladder has been stained with SYBR Gold; panel (e) shows RT-PCR from the RNA shown in panel (d).

Synthesis of Protein Coding and Functionalized mRNAs Using the Engineered RNA Polymerase TGK Encouraged by the striking activity of TGK in tRNA synthesis, we challenged TGK to generate substantially longer RNAs. We first tested synthesis of the 748 nucleotide mRNA encoding green fluorescent protein (GFP). Astonishingly, TGK generated a full length GFP RNA in less than 10 minutes as judged by agarose gel-electrophoresis, RT-PCR and sequencing (FIG. 45). The synthesized GFP mRNA directed the synthesis of a correct size 26.8 kDa protein product in an in vitro translation extract (FIG. 45) and yielded green fluorescent *E. coli* colonies when cloned (not shown). We also examined synthesis of a much longer 1,691 nucleotide mRNA encoding Firefly (*P. pyralis*) Luciferase. Again, TGK generated a full length Luciferase RNA, as judged by agarose gel-electrophoresis, RT-PCR and sequencing of full-length product, requiring 1 hour for the synthesis of this more challenging RNA (FIG. 45).

We determined the fidelity of RNA synthesis by TGK by a two-step RT-PCR protocol (below) using both forward synthesis and reverse transcription primers comprising a unique mismatch unambiguously identifying PCR products derived from RNA synthesis. Analysis of 8.2 kb of sequence data of Luciferase mRNA revealed a misincorporation rate of $5.5\times10^{-4}$, which is comparable to the error rate of T7 RNA polymerase ($2.1\times10^{-4}$) and to the fidelity of TgoT with dNTPs ($7.5\times10^{-3}$, FIG. 44).

Mechanistic Aspects of Second Gate Function

While the effect of mutating the steric gate residue on RNA synthesis has been investigated in some detail and its mechanism has been rationalized using structural and biochemical data [20], the basis for the striking effect of the "second gate" mutation on processive RNA synthesis is currently unclear. We sought to determine critical parameters of second gate function, in an attempt to better understand its mechanism. To this end we examined not just TGK and the parent polymerase TgoT, but also the intermediates TYK (TgoT E664K) and TGE (TgoT Y409G) for their RNA polymerase activity and processivity with RNA, DNA and chimeric primers.

Figure 51:
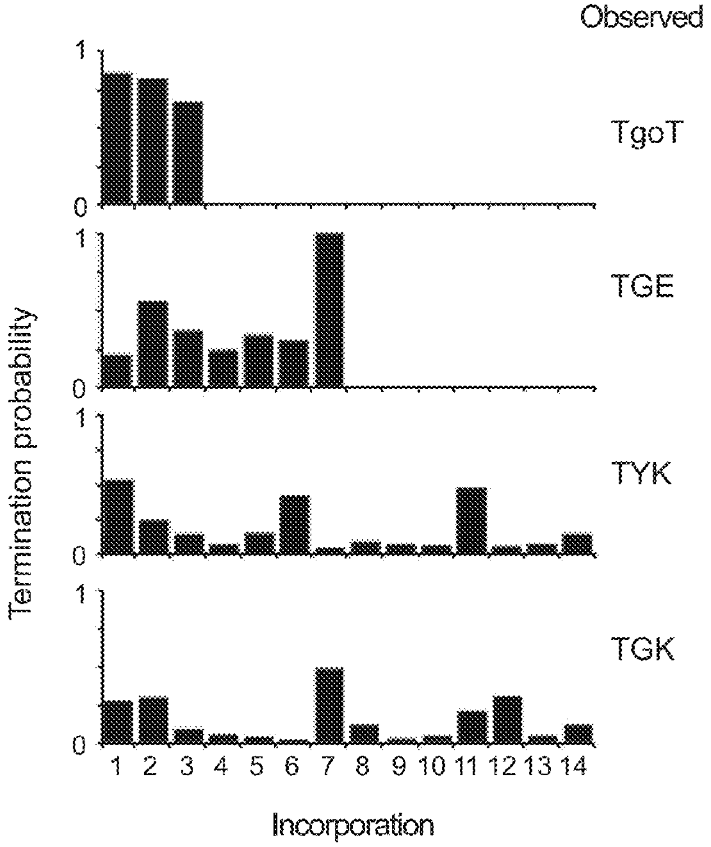
FIG. 51 is a chart showing termination probability. Analysis of the probability of termination at each NTP incorporation step demonstrates clearly the effect of the E664K mutation: TGE (TgoT Y409G) is able to incorporate 6 NTPs but 100% of primers chain terminate at +6. In contrast, TYK (TgoT E664K) and TGK (TgoT Y409G/E664K) can incorporate NTPs beyond +6 with little apparent change in termination probability.

As shown, TGK can efficiently and processively extend both DNA and RNA primers with NTPs. In contrast, TgoT cannot extend RNA primers (except under highly forcing conditions) and displays strong extension termination after the $6^{th}$ NTP incorporation from DNA primers. There appears to be a fundamental block to extension beyond a stretch of six ribonucleotides. When using DNA-RNA chimeric primers comprising one (or more) 3'-terminal NMPs, there is again a strong termination once a stretch of 6 NMPs is reached (i.e. extension of a primer with 1 terminal NMP is stalled after incorporation of a further 5 NMPs and a primer with 6 terminal NMPs is not extended, FIG. 46). Despite its modified active site, TGE also displays a strong termination at n+6 (FIG. 51). This implies that the second gate mutation is critical for overcoming this synthetic block and enabling processive RNA synthesis.

The second gate also appears to control other aspects of polymerase substrate specificity. Both TGK and TYK (but not TgoT and TGE) are capable of trans-lesion synthesis (TLS, FIG. 46), bypassing both template abasic sites and cyclopyrimidine dimers (CPD, FIG. 46). Thus, TLS appears to be controlled by a mutation located 25 Å from the template lesion.

Thus we demonstrate that the thumb subdomain of DNA polymerases makes many important interactions with the nascent DNA duplex [43, 44]. Mutations in this critical region for polymerase function can cause a loss in fidelity, processivity and DNA binding affinity and have been implicated in genomic instability and disease [45-49]. Here we have discovered an important post-synthetic substrate specificity checkpoint within the thumb domain of a replicative polymerase. Its inactivation by mutation releases a block on the synthesis of non-cognate nucleic acids and bypass of template lesions. Together with mutation of the steric gate residue, this "second gate" mutation converts a DNA polymerase into a primer-dependent RNA polymerase capable of the synthesis of 100-mer RNAs in seconds and of protein coding mRNAs of up to 1.7 kb in minutes to hours with fidelity comparable to the industry standard T7 RNA polymerase.

The existence of a synthetic checkpoint located in the polymerase thumb domain, was predicted by us and others [10, 20, 23, 24] on the basis of multiple lines of evidence including termination of extension after synthesis of short oligomers (typically n+6) and modelling of a nascent RNA-DNA heteroduplex [24]. Indeed, eight of the nine mutations in D4 (P657T, E658Q, K659H, Y663H, E664Q, D669A, N671K, 1676T) are located in a sequence segment (P657-T676) in the centre of the thumb domain and in close contact with the nascent strand around n+6. Using iterative cycles of screening and site-directed mutagenesis, we narrowed the critical functional determinant down to a single residue (E664), mutation of which proved both necessary and sufficient for processive RNA polymerase activity. This key residue, which we termed the "second gate", is most effectively mutated to the positively charged lysine (E664K) but mutation to an uncharged glutamine (E664Q) already provides significant RNA polymerase activity. This trend suggests that the negative charge of the parental E664 positioned in proximity to the nascent strand may be an important component of its function to arrest RNA synthesis.

Steric gate function is based on steric exclusion of the 2'OH on the incoming nucleotide [20, 37]. However, the mechanistic basis of second gate function is currently not clear and may involve mechanisms other than geometric control. Indeed, some of the improvement in RNA synthesis may be caused by a 3-10 fold increase in affinity for both DNA:DNA and DNA:RNA primer-template duplexes mediated by the second gate mutation, as determined by electrophoretic mobility shift assay (EMSA). Mutation of the second gate residue E664 removes a repulsive negative charge in the polymerase thumb domain close to the nascent strand phosphate backbone and this may increase affinity for the primer-template duplex. However, the striking termination at n+6 in polymerases lacking the E664 mutation (TgoT, TGE) strongly suggests a second, geometric component to the mechanism.

Formulation of a steric model is hindered by the fact that there are currently no structures of a tertiary complex of an archeal B-family polymerase. In the existing B-family polymerase structures the critical region in the polymerase thumb domain sequence is divergent from the archaeal sequence [43, 50-53], making comparisons by analogy problematic. We therefore used the structure of a secondary complex of a mutant of the closely related archaeal polB Pfu (S. Wynne, PH, A. Leslie, unpublished results) as well as the tertiary complex structure of more divergent RB69 DNA polymerase [44] to model a nascent RNA strand on a DNA template (based on the NMR structure of an RNA-DNA heteroduplex (PDB: 1EFS [54], FIG. 47). In both cases, we observed a clash around the n+6 position of the RNA strand with the polymerase thumb domain in proximity (7A) to the second gate residue E664 (RB69: S783).

The poor geometric complementarity of the RNA-DNA heteroduplex with the thumb domain contrasts with a much better fit in the polymerase active site. Indeed, the structures of tertiary complexes of A- and X-family DNA polymerases show that the preferred sugar pucker in and close to the active site is C3'-endo and the helical conformation of the primer-template duplex (up to n+3) is A-like but undergoes a conformational switch to cognate B-DNA as the primer-template duplex interacts with the thumb domain and exits the polymerase [55-57]. This conformational switch has previously been observed to play a role in polymerase specificity, whereby direct structural observation of the incorporation and extension of a G.T mismatch revealed a disruption of the A- to B-form transition by the mismatch that was "transmitted" back to the active site through the template strand and promoted stalling of the polymerase [58]. Such post-synthetic crosstalk between the second gate checkpoint in the thumb domain and the polymerase active site may similarly mediate the stalling at n+6 observed in RNA synthesis. The second gate checkpoint may therefore detect an emergent feature of the nascent nucleic acid duplex, possibly a non-cognate helical conformation.

The fact that the most effective second gate mutation (E664K) results in a charge reversal rather than removing side-chain bulk suggests that E664 does not function as a simple steric obstruction per se. Indeed, the steric clash at n+6 in our model does not occur directly with residue E664. Rather E664 but may act as an electrostatic "rudder", steering the nascent strand to allow readout of helical paramteres by the thumb domain. Alternatively, mutation of E664 may lead to structural rearrangements of the thumb domain, rendering it more permissive to non B-form nucleic acids. In either case, mutation of the second gate residue would allow the polymerase thumb domain to accommodate a range of helical conformations. Thus, the relaxed substrate specificity and lesion bypass ability of TGK would arise from relaxation of the geometric control of the positioning of the nascent and template strands in the active site, preventing stalling of polymerase extension upon encounter of a non-cognate duplex conformation.

While highly conserved among polB family members of the Thermococcales, the identity of the second gate residue 664 (or equivalent) varies among more distantly related members of the polB family. Yet structures of the tertiary complexes in both *S. cerevisiae* Pol delta and *E. coli* Pol II indicate at least a broad conservation of its structural neighbourhood in the thumb domain. It therefore seems possible that similar "second gate" checkpoints exist in the wider polB family (and indeed in other families) but in analogy to the steric gate residue, which varies among polymerase families (Table SI—FIG. 52) may be realized in different forms.

Exclusion of RNA from the genome is important for genome stability in mesophilic organisms like *S. cerevisiae* [4] and might be of even higher significance for thermophiles. However, the striking effect of the second gate mutation on TLS suggest that it may have biological functions that go beyond the prevention of RNA synthesis. These may include the post-synthetic recognition of misincorporation and/or read-through of DNA damage mirroring the read-ahead recognition of template uracil and hypoxanthin in the same class of archeal polymerases [62].

TGK differs in several potentially useful ways from the single-subunit RNAPs like T7 RNA polymerase, including thermostability and, most importantly, the ability to initiate RNA synthesis from an oligonucleotide primer. The engineered polymerase TGK is thus the first thermostable primer-dependent processive RNA polymerase. Primer-dependent RNA synthesis from a DNA template is a phenotype not commonly observed in nature, where RNA synthesis is typically initiated de novo from a specific promoter sequence (e.g. T7 RNA polymerase [63]) or a protein transcription factor complex, although there are examples where RNA synthesis is initiated from a short RNA primer derived by "Cap-snatching" from cellular mRNAs (e.g. viral RNA-dependent RNA polymerases [64, 65]). While T7 RNA polymerase is capable of primer dependent RNA synthesis [66, 67] it is weak and non-processive, presumably because binding to a pre-annealed DNA primer does not trigger the conformational change to the processive form of T7 RNA polymerase [68].

Primer-dependent RNA synthesis is potentially useful for a number of applications as it allows free choice of the RNA 5' end or RNA 5' UTR chemistry. TGK is capable of extending a wide variety of primers including those bearing 5' groups such as Biotin, Cy3 or FITC as well as both DNA and RNA primer oligonucleotides comprising internal alphaS, 2'OMe or LNA modifications. Indeed, we have yet to identify a primer modification which reduces extension by TGK to a significant degree. Furthermore, TGK frees enzymatic RNA synthesis from the T7 RNA polymerase need to initialise transcription with a G.

TGK also displays an expanded substrate spectrum with respect to the incorporation of modified NTPs. For example, TGK allowed the synthesis of the 1.7 kb Luciferase mRNA fully substituted with 5-methyl-C and pseudouridine (Ψ), with potential applications in gene therapy and stem cell reprogramming as shown recently [39, 40]. Furthermore, TGK efficiently synthesises fully 2'-azido (2'-$N_3$) or 2'-fluoro (2'-F) substituted DNA with applications in the evolution of nuclease resistant [41, 42] aptamers with expanded chemistries. While overnight synthesis of 2'F-RNA had previously been described [42], TGK is capable of synthesis of fully substituted 2'F-RNAs in minutes.

In conclusion, our results suggest that the adaptive path from DNA polymerase to RNA polymerase is surprisingly short. While our "wild-type" polymerase TgoT contained four mutations, disabling exonuclease (D141A, E143A) and uracil stalling (V93Q) functions as well as the Therminator mutation (A485L) to increase substrate promiscuity, these did not confer more than baseline RNA polymerase activity. Thus the "evolutionary jump" to RNA polymerase activity involved mutation of just two residues: the classic steric gate (Y409) in the active site and the newly described "second gate" (E664) in the thumb domain, which together enabled not only processive RNA polymerase activity but TLS and synthesis of highly modified RNA polymers. The identification of a "second gate", in the polymerase thumb subdomain, indicates that a key determinant of polymerase substrate specificity is located outside the active site and exerts its influence after the initial incorporation and extension steps.

Description of Drawings for Example 25

FIG. 43. Enhanced RNA polymerase activity with thumb domain mutations. a) Structure of D4N, mapped onto the homologous *E. coli* DNA pol II (PDB: 3MAQ [42]). The 9 mutations in D4 are shown in blue, the steric gate mutation (added to make D4 Y409N) in red and the existing mutations in TgoT (D141A, E143A, A485L) in yellow. b) Helical parameters of B-DNA, A-RNA and HNA-RNA heteroduplex [43]. c) RNA extensions from DNA and d) RNA primers by D4N and its parent polymerases FIG. 44. Effect of mutations to thumb domain on RNA polymerase activity. a) Reversion analysis of thumb mutations in D4. Each mutation was reverted to wild type individually and the effect on processive RNA polymerase activity assayed with lysates normalised according to dNTP activity. b) Timecourse of *E. coli* tRNATyr synthesis by purified polymerases D4N, TNQ and TGK from RNA primers FIG. 45. mRNA synthesis by TGK. a) Denaturing agarose electrophoresis of Cy5-labelled GFP RNA synthesised by TGK from a labelled RNA primer. b) RT-PCR from the RNA shown in a). c) In vitro translation of GFP synthesised by TGK. GFP was visualised by excitation of fluorescent lysines incorporated into GFP without staining the gel. d) Native agarose electrophoresis of Luciferase synthesised by TGK. RNA is visualised directly by Cy5; the ladder has been stained with SYBR Gold. e) RT-PCR from the RNA shown in d)

Figure 46:
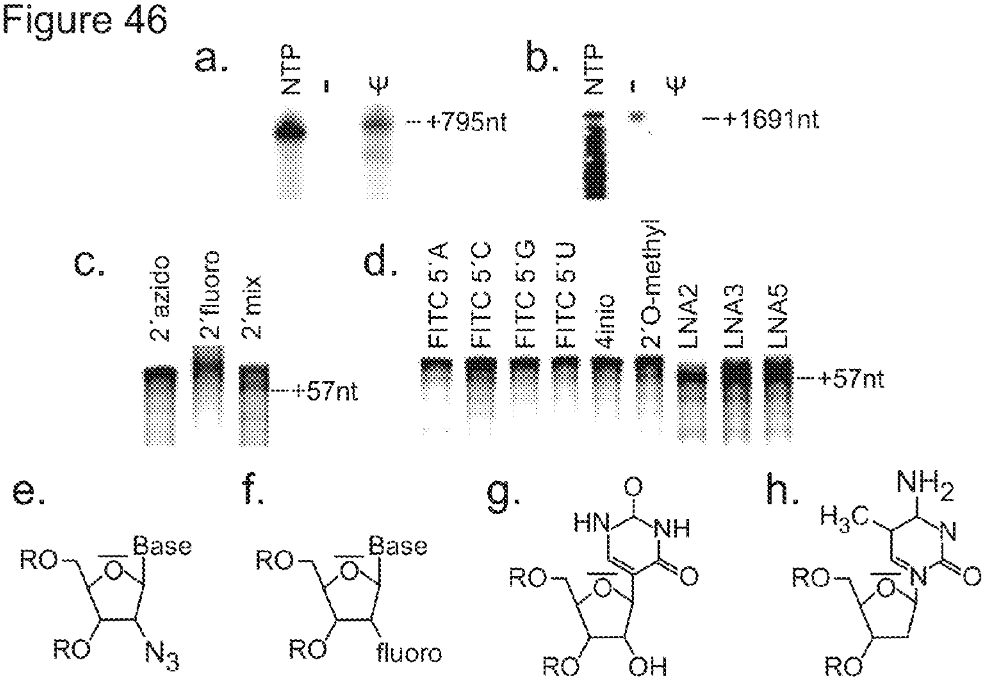
FIG. 46 shows synthesis of modified nucleic acids. Panels (a) and (b) show denaturing agarose electrophoresis of modified RNA using 2'OH purines, 5- methylCTP and pseudoUTP (ψ) showing full length of GFP (a) and Luciferase (b); panel (c) shows extension of RNA primers with fully substituted 2'fluoro-NTPs, 2'azido-NTPs and a mixture of 2'fluoro-ATP, 2'azido-GTP, CTP and dTTP; panel (d) shows RNA synthesis from modified primers by TGK. The structures of 2'azido ϵ (panel e), 2'fluoro (panel f), pseudouridine (panel g) and 5-methyldeoxycytidine (panel h) are also illustrated.

FIG. 46. Synthesis of modified nucleic acids. a) Denaturing agarose electrophoresis of modified RNA using 2'OH purines, 5-methylCTP and pseudoUTP (T) showing full length of GFP (a) and: b) Luciferase c) Extension of RNA primers with fully substituted 2'fluoro-NTPs, 2'azido-NTPs and a mixture of 2'fluoro-ATP, 2'azido-GTP, CTP and dTTP. d) RNA synthesis from modified primers by TGK. Primers FITC 5'A, FITC 5'C, FITC 5'G and FITC 5'U are RNA primers with the sequence 5'-CCCCTTATTAGCGTTTGCC-3' (SEQ ID NO: 53) with the 5' base modified as indicated. Primer 4thio is the same RNA sequence but with a phosphothiorate bond between bases 4 and 5. Primer 2'O-methyl is the same RNA sequence but with bases 4 and 5 replaced with 2'O-methyl bases. Primers LNA2, LNA3 and LNA5 are DNA primers with bases 19 and 20 (the two 3' bases) replaced by LNA (LNA2), bases 17 and 19 replaced by LNA (LNA3) or bases 17, 18 and 19 replaced by LNA (LNA5). e) Structures of 2'azido, 2'fluoro (f), pseudouridine (g) and 5-methyldeoxycytidine (h).

Figure 47:
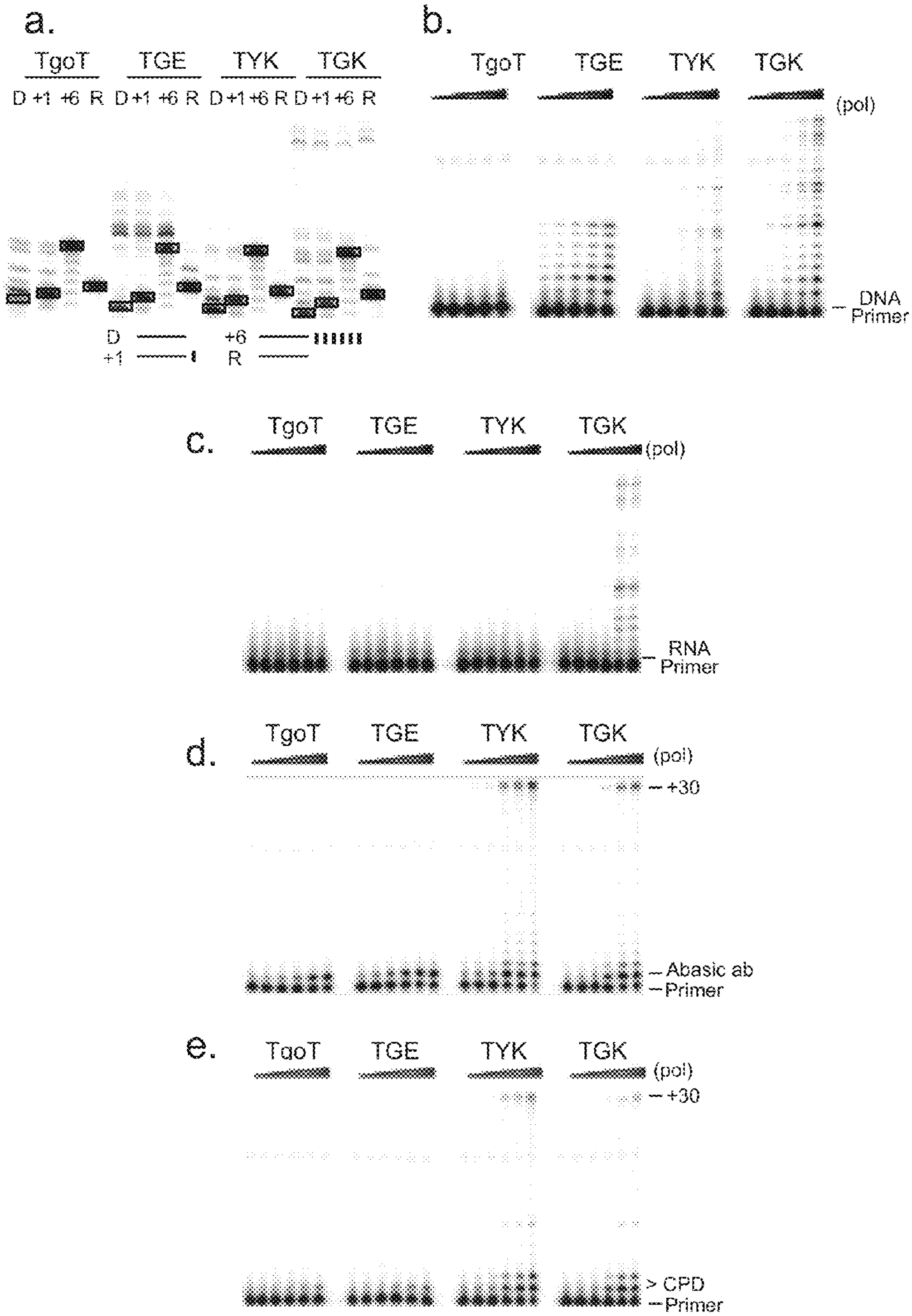
FIG. 47 demonstrates second-gate impact on processivity of RNA synthesis. Panel (a) shows primer extensions with NTPs showing the importance of the 664 mutation, boxes highlight the unextended primers; panel (b) processivity of TgoT, TGE (TgoT Y409G), TYK (TgoT E664K) and TGK (TgoT Y409G E664K) with NTPs was assayed under single hit conditions from a DNA primer; panel (c) is as in panel (b), except for a RNA primer: only TGK is capable of extending the primer with NTPs; panel (d) is as in panel (b), except for a DNA primer with an abasic site as indicated with dNTPs: in this case, both TYK and TGK (both of the polymerases with the E664K mutation) are capable of primer extension, whereas TgoT and TGE are not; panel (e) is as in (b), except the lesion is a cyclopyrimidine dimer (CPD).

FIG. 47. Mechanistic aspects of second gate function. a) Primer extensions with NTPs showing the importance of the 664 mutation. Primer D is all DNA, Primer +1 is an identical DNA primer +1 NMP, Primer +6 is the same DNA stretch +6 NMPs and Primer R is the equivalent of Primer D but as RNA. Red boxes highlight the 3' of the primers. Here TgoT and TYK incorporate NTPs poorly, TGE incorporates 6NTPs efficiently but then stalls and TGK is able to fully extend the primer b) Processivity of TgoT, TGE (TgoT Y409G), TYK (TgoT E664K) and TGK (TgoT Y409G E664K) with NTPs was assayed under single hit conditions from a DNA primer. c) As (b), except from an RNA primer. Only TGK is capable of extending the primer with NTPs. d) As (b), except from a DNA primer with an abasic site as indicated with dNTPs. In this case, both TYK and TGK (both of the polymerases with the E664K mutation) are capable of primer extension, whereas TgoT and TGE are not. e) As (e), except the lesion is a cyclopyrimidine dimer (CPD). Again, Only TYK and TGK are capable of lesion bypass.

Figure 48:
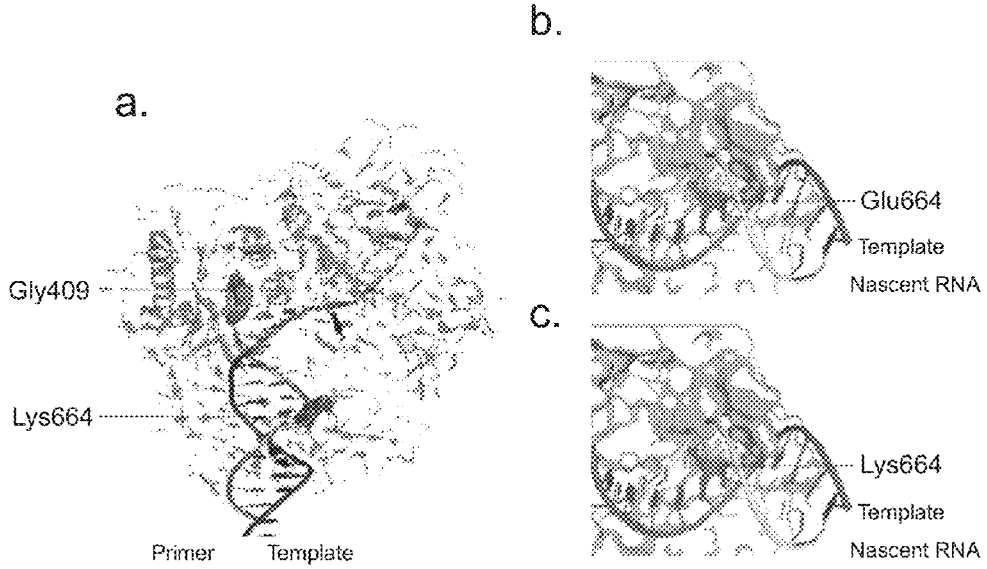
FIG. 48 presents structural models of a engineered processive RNA polymerase. Panel (a) shows structure of TGK, mapped onto the homologous *E. coli* DNA pol II (3MAQ); panel (b) is a RNA:DNA hybrid duplex (1EFS); panel (c) is as in (b), except with the E664K second-gate mutation that creates a continuous positively charged binding surface.

FIG. 48. Structural model of an engineered processive RNA polymerase a) Structure of TGK, mapped onto the homologous *E. coli* DNA pol II (3MAQ; [42]). The key mutations forming the 2-step adaptive path are shown in red. Other mutations from wild type (V93Q, D141A, E143A, A485L) are shown in yellow. The template strand is shown as a purple cartoon and the primer strand as an orange cartoon. The incoming dGTP is shown in green. b) RNA:DNA hybrid duplex (1EFS; [44]) modelled into the ternary complex of Pfu (S. Wynne and A. Leslie, unpublished structure) showing the clash generated when nucleic acid intermediate between A- and B-form is synthesised by a DNA polymerase. c) As (b), except with the E664K mutation showing the charge reversal caused.

FIG. 49. RNA polymerase optimisation a) 664 position screen. TgoT Y409N position E664 was diversified by iPCR (using NNK codon) and 190 colonies screened by PAA. Active mutants were sequenced and 5× lystates normalised by dNTP activity were screened for NTP activity. b) Steric gate screen. The steric gate of TgoT E664K (Y409) was diversified and screened as for the E664 position.

Figure 50:
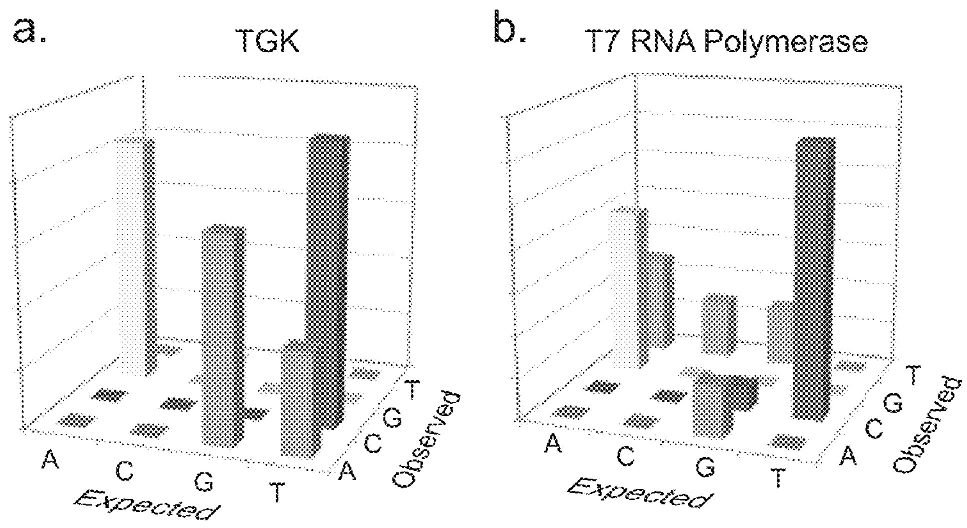
FIG. 50 shows error spectra of TGK RNA polymerase (a) and T7 RNA polymerase (b).

FIG. 50. Error spectra of TGK RNA polymerase and T7 RNA polymerase a) TGK b) T7

FIG. 51. Termination probability Analysis of the probability of termination at each NTP incorporation step demonstrates clearly the effect of the E664K mutation: TGE (TgoT Y409G) is able to incorporate 6 NTPs but 100% of primers chain terminate at +6. In contrast, TYK (TgoT E664K) and TGK (TgoT Y409G/E664K) can incorporate NTPs beyond +6 with little apparent change in termination probability.

REFERENCES TO EXAMPLE 25

1. Traut, T. W., *Physiological concentrations of purines and pyrimidines*. Mol Cell Biochem, 1994. 140(1): p. 1-22.
2. Nick McElhinny, S. A., et al., *Abundant ribonucleotide incorporation into DNA by yeast replicative polymerases*. PNAS, 2010. 107(11): p. 4949-54.
3. Bochner, B. R. and B. N. Ames, *Complete analysis of cellular nucleotides by two-dimensional thin layer chromatography*. J Biol Chem, 1982. 257(16): p. 9759-69.
4. Nick McElhinny, S. A., et al., *Genome instability due to ribonucleotide incorporation into DNA*. Nature Chemical Biology, 2010. 6(10): p. 774-81.
5. Clark, A. B., et al., *Mismatch repair-independent tandem repeat sequence instability resulting from ribonucleotide incorporation by DNA polymerase epsilon*. DNA Repair (Amst), 2011.
6. Evans, R. J., et al., *Structure of PolC reveals unique DNA binding and fidelity determinants*. Proc Natl Acad Sci USA, 2008. 105(52): p. 20695-700.
7. Bonnin, A., et al., *A single tyrosine prevents insertion of ribonucleotides in the eukaryotic-type phi29 DNA polymerase*. J Mol Biol, 1999. 290(1): p. 241-51.
8. Yang, G., et al., *A conserved Tyr residue is required for sugar selectivity in a Pol alpha DNA polymerase*. Biochemistry, 2002. 41(32): p. 10256-61.
9. Gardner, A. F. and W. E. Jack, *Determinants of nucleotide sugar recognition in an archaeon DNA polymerase*. Nucleic Acids Res, 1999. 27(12): p. 2545-53.
10. Astatke, M., et al., *A single side chain prevents Escherichia coli DNA polymerase I (Klenow fragment) from incorporating ribonucleotides*. Proc Natl Acad Sci USA, 1998. 95(7): p. 3402-7.
11. DeLucia, A. M., N. D. Grindley, and C. M. Joyce, *An error-prone family Y DNA polymerase (DinB homolog from Sulfolobus solfataricus) uses a 'steric gate' residue for discrimination against ribonucleotides*. Nucleic Acids Res, 2003. 31(14): p. 4129-37.
12. Jarosz, D. F., et al., *A single amino acid governs enhanced activity of DinB DNA polymerases on damaged templates*. Nature, 2006. 439(7073): p. 225-8.
13. Brown, J. A., et al., *A novel mechanism of sugar selection utilized by a human X-family DNA polymerase*. J Mol Biol, 2010. 395(2): p. 282-90.
14. Ruiz, J. F., et al., *Lack of sugar discrimination by human Pol mu requires a single glycine residue*. Nucleic Acids Res, 2003. 31(15): p. 4441-9.
15. Gao, G., et al., *Conferring RNA polymerase activity to a DNA polymerase: a single residue in reverse transcriptase controls substrate selection*. Proc Natl Acad Sci USA, 1997. 94(2): p. 407-11.
16. Cases-Gonzalez, C. E., M. Gutierrez-Rivas, and L. Menendez-Arias, *Coupling ribose selection to fidelity of DNA synthesis. The role of Tyr-115 of human immunodeficiency virus type 1 reverse transcriptase*. J Biol Chem, 2000. 275(26): p. 19759-67.
17. Entin-Meer, M., Z. Sevilya, and A. Hizi, *The role of phenylalanine-119 of the reverse transcriptase of mouse*

*mammary tumour virus in DNA synthesis, ribose selection and drug resistance*. Biochem J, 2002. 367(Pt 2): p. 381-91.

18. Boyer, P. L., et al., *Analysis of mutations at positions 115 and 116 in the dNTP binding site of HIV-1 reverse transcriptase*. Proc Natl Acad Sci USA, 2000. 97(7): p. 3056-61.
19. Astatke, M., N. D. Grindley, and C. M. Joyce, *How E. coli DNA polymerase I (Klenow fragment) distinguishes between deoxy-and dideoxynucleotides*. J Mol Biol, 1998. 278(1): p. 147-65.
20. Brown, J. A. and Z. Suo, *Unlocking the sugar "steric gate" of DNA polymerases*. Biochemistry, 2011. 50(7): p. 1135-42.
21. Patel, P. H. and L. A. Loeb, *Multiple amino acid substitutions allow DNA polymerases to synthesize RNA*. J Biol Chem, 2000. 275(51): p. 40266-72.
22. Staiger, N. and A. Marx, *A DNA polymerase with increased reactivity for ribonucleotides and C5-modified deoxyribonucleotides*. Chembiochem, 2010. 11(14): p. 1963-6.
23. Xia, G., et al., *Directed evolution of novel polymerase activities: mutation of a DNA polymerase into an efficient RNA polymerase*. Proc Natl Acad Sci USA, 2002. 99(10): p. 6597-602.
24. Ong, J. L., et al., *Directed evolution of DNA polymerase, RNA polymerase and reverse transcriptase activity in a single polypeptide*. J Mol Biol, 2006. 361(3): p. 537-50.
25. McCullum, E. O. and J. C. Chaput, *Transcription of an RNA aptamer by a DNA polymerase*. Chem Commun (Camb), 2009(20): p. 2938-40.
26. Shinkai, A., P. H. Patel, and L. A. Loeb, *The conserved active site motif A of Escherichia coli DNA polymerase I is highly mutable*. J Biol Chem, 2001. 276(22): p. 18836-42.
27. Delarue, M., et al., *An attempt to unify the structure of polymerases*. Protein Eng, 1990. 3(6): p. 461-7.
28. Moras, D., *Two sisters and their cousin*. Nature, 1993. 364(6438): p. 572-3.
29. Sousa, R., *Structural and mechanistic relationships between nucleic acid polymerases*. Trends Biochem Sci, 1996. 21(5): p. 186-90.
30. Cermakian, N., et al., *On the evolution of the single-subunit RNA polymerases*. J Mol Evol, 1997. 45(6): p. 671-81.
31. Herdewijn, P., *Nucleic acids with a six-membered 'carbohydrate' mimic in the backbone*. Chem Biodivers, 2010. 7(1): p. 1-59.
32. Lescrinier, E., et al., *Solution structure of a HNA-RNA hybrid*. Chem Biol, 2000. 7(9): p. 719-31.
33. Fogg, M. J., L. H. Pearl, and B. A. Connolly, *Structural basis for uracil recognition by archaeal family B DNA polymerases*. Nat Struct Biol, 2002. 9(12): p. 922-7.
34. Gardner, A. F. and W. E. Jack, *Acyclic and dideoxy terminator preferences denote divergent sugar recognition by archaeon and Taq DNA polymerases*. Nucleic Acids Res, 2002. 30(2): p. 605-13.
35. Blasco, M. A., et al., *Phi 29 DNA polymerase active site. Mutants in conserved residues Tyr254 and Tyr390 are affected in dNTP binding*. J Biol Chem, 1992. 267(27): p. 19427-34.
36. Yang, W., J. Y. Lee, and M. Nowotny, *Making and breaking nucleic acids: two-Mg2+-ion catalysis and substrate specificity*. Mol Cell, 2006. 22(1): p. 5-13.
37. Kirouac, K. N., Z. Suo, and H. Ling, *Structural mechanism of ribonucleotide discrimination by a Y-family DNA polymerase*. J Mol Biol, 2011. 407(3): p. 382-90.
38. Freisinger, E., et al., *Lesion (in)tolerance reveals insights into DNA replication fidelity*. EMBO J, 2004. 23(7): p. 1494-505.
39. Warren, L., et al., *Highly Efficient Reprogramming to Pluripotency and Directed Differentiation of Human Cells with Synthetic Modified mRNA*. Cell Stem Cell, 2010.
40. Kormann, M. S., et al., *Expression of therapeutic proteins after delivery of chemically modified mRNA in mice*. Nat Biotechnol, 2011. 29(2): p. 154-7.
41. Watts, J. K., et al., *Studies on the hydrolytic stability of 2' fluoroarabinonucleic acid (2'F-ANA)*. Org Biomol Chem, 2009. 7(9): p. 1904-10.
42. Ono, T., M. Scalf, and L. M. Smith, *2'-fluoro modified nucleic acids: polymerase-directed synthesis, properties and stability to analysis by matrix-assisted laser desorption/ionization mass spectrometry*. Nucleic Acids Research, 1997. 25(22): p. 4581-4588.
43. Swan, M. K., et al., *Structural basis of high-fidelity DNA synthesis by yeast DNA polymerase delta*. Nat Struct Mol Biol, 2009. 16(9): p. 979-86.
44. Wang, M., et al., *Insights into Base Selectivity from the 1.8 A Resolution Structure of an RB69 DNA Polymerase Ternary Complex*. Biochemistry, 2011. 50(4): p. 581-90.
45. Kirchner, J. M., H. Tran, and M. A. Resnick, *A DNA polymerase epsilon mutant that specifically causes +1 frameshift mutations within homonucleotide runs in yeast*. Genetics, 2000. 155(4): p. 1623-32.
46. Kokoska, R. J., et al., *Increased rates of genomic deletions generated by mutations in the yeast gene encoding DNA polymerase delta or by decreases in the cellular levels of DNA polymerase delta*. Mol Cell Biol, 2000. 20(20): p. 7490-504.
47. Stocki, S. A., R. L. Nonay, and L. J. Reha-Krantz, *Dynamics of bacteriophage T4 DNA polymerase function: identification of amino acid residues that affect switching between polymerase and 3'-->5' exonuclease activities*. J Mol Biol, 1995. 254(1): p. 15-28.
48. Kasiviswanathan, R., et al., *Disease mutations in the human mitochondrial DNA polymerase thumb subdomain impart severe defects in mitochondrial DNA replication*. J Biol Chem, 2009. 284(29): p. 19501-10.
49. Loh, E. and L. A. Loeb, *Mutability of DNA polymerase I: implications for the creation of mutant DNA polymerases*. DNA Repair (Amst), 2005. 4(12): p. 1390-8.
50. Franklin, M. C., J. Wang, and T. A. Steitz, *Structure of the replicating complex of a pol alpha family DNA polymerase*. Cell, 2001. 105(5): p. 657-67.
51. Wang, F. and W. Yang, *Structural insight into translesion synthesis by DNA Pol II*. Cell, 2009. 139(7): p. 1279-89.
52. Liu, S., et al., *Crystal structure of the herpes simplex virus 1 DNA polymerase*. J Biol Chem, 2006. 281(26): p. 18193-200.
53. Savino, C., et al., *Insights into DNA replication: the crystal structure of DNA polymerase B1 from the archaeon Sulfolobus solfataricus*. Structure, 2004. 12(11): p. 2001-8.
54. Hantz, E., et al., *Solution conformation of an RNA-DNA hybrid duplex containing a pyrimidine RNA strand and a purine DNA strand*. Int J Biol Macromol, 2001. 28(4): p. 273-84.
55. Kiefer, J. R., et al., *Visualizing DNA replication in a catalytically active Bacillus DNA polymerase crystal*. Nature, 1998. 391(6664): p. 304-7.
56. Pelletier, H., et al., *Structures of ternary complexes of rat DNA polymerase beta, a DNA template-primer, and ddCTP*. Science, 1994. 264(5167): p. 1891-903.

57. Li, Y., S. Korolev, and G. Waksman, *Crystal structures of open and closed forms of binary and ternary complexes of the large fragment of Thermus aquaticus DNA polymerase I: structural basis for nucleotide incorporation*. EMBO J, 1998. 17(24): p. 7514-25.

58. Johnson, S. J. and L. S. Beese, *Structures of mismatch replication errors observed in a DNA polymerase*. Cell, 2004. 116(6): p. 803-16.

59. Xiong, Y. and M. Sundaralingam, *Crystal structure of a DNA.RNA hybrid duplex with a polypurine RNA r(gaagaagag) and a complementary polypyrimidine DNA d(CTCTTCTTC)*. Nucleic Acids Res, 2000. 28(10): p. 2171-6.

60. Salazar, M., et al., *The DNA strand in DNA.RNA hybrid duplexes is neither B-form nor A-form in solution*. Biochemistry, 1993. 32(16): p. 4207-15.

61. Fedoroff, O. Y., Y. Ge, and B. R. Reid, *Solution structure of r(gaggacug):d(CAGTCCTC) hybrid: implications for the initiation of HIV-1 (+)-strand synthesis*. J Mol Biol, 1997. 269(2): p. 225-39.

62. Firbank, S. J., et al., *Uracil recognition in archaeal DNA polymerases captured by X-ray crystallography*. J Mol Biol, 2008. 381(3): p. 529-39.

63. Steitz, T. A., *The structural basis of the transition from initiation to elongation phases of transcription, as well as translocation and strand separation, by T7 RNA polymerase*. Curr Opin Struct Biol, 2004. 14(1): p. 4-9.

64. Plotch, S. J., et al., *A unique cap(m7 GpppXm)-dependent influenza virion endonuclease cleaves capped RNAs to generate the primers that initiate viral RNA transcription*. Cell, 1981. 23(3): p. 847-58.

65. Mir, M. A., et al., *Storage of cellular 5' mRNA caps in P bodies for viral cap-snatching*. Proc Natl Acad Sci USA, 2008. 105(49): p. 19294-9.

66. Rusakova, E. E., et al., *Mutant T7 RNA polymerase is capable of catalyzing DNA primer extension reaction*. FEBS Lett, 1998. 423(2): p. 189-92.

67. Ivanov, S. A., et al., *RNA synthesis by T7 RNA polymerase supported primer extension*. Mol Biol (Mosk), 2004. 38(5): p. 798-803.

68. Yin, Y. W. and T. A. Steitz, *Structural basis for the transition from initiation to elongation transcription in T7 RNA polymerase*. Science, 2002. 298(5597): p. 1387-95.

69. Ramsay, N., et al., *CyDNA: synthesis and replication of highly Cy-dye substituted DNA by an evolved polymerase*. J Am Chem Soc, 2010. 132(14): p. 5096-104.

70. Haseloff, J., *GFP variants for multispectral imaging of living cells*. Methods Cell Biol, 1999. 58: p. 139-51.

71. Kokoska, R. J., S. D. McCulloch, and T. A. Kunkel, *The efficiency and specificity of apurinic/apyrimidinic site bypass by human DNA polymerase eta and Sulfolobus solfataricus Dpo4*. J Biol Chem, 2003. 278(50): p. 50537-45

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

Sequence Listing

```
SEQ ID NO: 1
>Tgo_wt.fa - True Wild Type
MILDTDYITEDGKPVIRIFKKENGEFKIDYDRNFEPYIYALLKDDSAIEDVKKITAERHGTTVRVVRAEKVKKKFL
GRPIEVWKLYFTHPQDVPAIRDKIKEHPAVVDIYEYDIPFAKRYLIDKGLIPMEGDEELKMLAFDIETLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRAIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYEVPPEKLVIYEQITRDLKDYKATGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT

SEQ ID NO: 2
>TgoT.fa - 'wild type' with 4 mutations; therminator A485L, 2xexo D141A and
E143A; uracil read-ahead V93Q:
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYEVPPEKLVIYEQITRDLKDYKATGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT

SEQ ID NO: 3
>A1.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
```

-continued

Sequence Listing

GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYQVPPKKLVINQQITRELRDYKAKGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT

SEQ ID NO: 4
>C1.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYQVPPKELVIYAEITRPLQDYKARGPHVAVAK
RLAARGIKIRPGTVISYIVLKGSGRVGDRAIPFDEFDPAKHKYDAEYYIENQVLPAVERILRAFGYRKEDLRYQKT
RQVGLGAWLKPKT*

SEQ ID NO: 5
>C7.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYQVPPQQLAIYQPITRALQDYKAKGPHVAVAK
RLAARGIKIRPGTVISYIVLKGSGKIGDRAIPFDEFDPAKHKYDAEYYIENQVLPAVERILRAFGYRKEDLRYQKT
RQVGLGAWLKPKT

SEQ ID NO: 6
>D4.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYEVPTQHLVIHQQITRALNDYKAIGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT*

SEQ ID NO: 7
>E8.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYQVPPQQLVIYQKITKQLHEYKARGPHVAVAK
RLAARGIKIRPGTVISYIVLKGSGRIGDRAIPFDEFDPARHKYDAEYYIENQVLPAVERILRAFGYRKEDLRYQKT
RQVGLGAWLKPKT*

SEQ ID NO: 8
>G3.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYQVPSEQLVIYHQITRPLKEYRAMGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT*

-continued

Sequence Listing

SEQ ID NO: 9
>H2.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYEVSQQQLVIYQQITKELSEYKATGPHVAVAK
RLAARGVKIRPGTVISYIVLKGSGRIGDRAIPFDEFDPAKHKYDAEYYIENQVLPAVERILRAFGYRKEDLRYQKT
RQVGLGAWLKPKT

SEQ ID NO: 10
>NC11.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDCINAKLPGLLELEYEGFYKRGFFVTKKKYAVIDEEDKITTRGL
EIVRRDWSEIAKETQARVLEAILKHGDVEEAVRIVKEVTEKLSKYQVPPQPLVIYQKITKELNDYRAIGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT*

SEQ ID NO: 11
>G11.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYEVPPEKLVIYEQITRDLKDYKATGPHVAVAK
RLAARGIKIRPGTVISYIVLKGSGRIGDRAIPSDEFDPAKHKYDAEYYIENQVLPAVQSILGAFGYHRGDLKYQKS
QQMGLGAWLKPKT*

SEQ ID NO: 12
>6G12.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFATKKKYAVIDEEDKITTRGL
KMVRRDWSEIAKETQARVLEAILKHGDVEEAVRIVKEVTEKLSKYEVPPEQLVIYQPITKQLHDYRARGPHVSVAK
RLAARGIKIRPGTVISYIVPKGSGRIGDRAIPFDEFDPAKHKYDAGYYIENQVLPAVERILRAFGYRKEDLRYQKT
RQVGLGAWLKPKT

SEQ ID NO: 13
>E3.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKEYAVIDEEDKITTRGL
EIVRRDWSEIAKETQARVLEAILKHGDVEEAVRIVKEVTEKLSKYQVPTKQLVIYQEITKELRDYKARGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT

SEQ ID NO: 14
>E6.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG

-continued

Sequence Listing

LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDRSEIAKETQARVLEAILKHGDVEEAVRIVKEVTEKLSKYEVPPEKLVIYEQITRDLKDYKATGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT*

SEQ ID NO: 15
>H6.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYQVPPQQLVIYQPITKHLRDYKAKGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT*

SEQ ID NO: 16
>B11.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETLARVLEAILKHGDVEEAVRIVKEVTEKLSKYEVPPEKLVIYEQITRALKDYKATGPHVAVAK
RLAARGIKIRPGTVISYIVLKGSGRIGDRAIPFDEFDPAKHKYDAEYYIENQVLQDVQRILRAFGYKNGDLRCQKT
IRRAWGRG*

SEQ ID NO: 17
>B12.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYEVPPEKLVIYEQITRDLKDYKATGPHVAVAK
RLAARGIKIRPGTVISYIVLKGSGRIGDRAIPFDEFDPAKHKYDAEYYIENQVLPYVLDDSEGLWLQ*

SEQ ID NO: 18
>H12.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYEVPPEKLVIYEQITRDLKDYKATGPHVAVAK
RLAARGIKIRPGTVISYIVLKGSGRIGDRAIPFDEFDPAKHKYDAEYYIENQVLPAVQMILRAFGYQKDDLR*

>A1.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG

-continued

Sequence Listing

GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACCAGGTTCCACCGAAGAA
GCTGGTCATCAACCAGCAGATAACCAGAGAGCTGCGGGACTACAAGGCCAAGGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACA

>C1.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACCAGGTTCCACCGAAGGA
GCTGGTCATCTACGCGGAGATAACCAGACCCCTGCAGGACTACAAGGCCAGGGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGG
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACATAA

>C7.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG

-continued

Sequence Listing

GTGACGTTGAAGAAGCGGTAAGGATTGTCAAAGAGGTTACGGAGAAGCTGAGCAAGTACCAGGTTCCACCGCAGCA
ACTGGCCATCTACCAGCCGATAACCAGAGCCCTGCAGGACTACAAGGCCAAGGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAAGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACGTAA

>D4.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTCCAACGCAGCA
CCTGGTCATCCACCAGCAGATAACCAGAGCCCTGAACGACTACAAGGCCATCGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACATAA

>E8.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACCAGGTTCCACCGCAGCA
GCTGGTCATCTACCAAAAGATAACCAAACAGCTGCACGAGTACAAGGCCAGGGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAGGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACATAA

>G3.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA

-continued

Sequence Listing

```
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACCAGGTTCCATCGGAGCA
GCTGGTCATCTACCATCAGATAACCAGACCCCTGAAGGAGTACAGGGCCATGGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACATAA

>H2.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTTCACAGCAGCA
GCTGGTCATCTACCAGCAGATAACCAAAGAGCTGAGCGAGTACAAGGCCACCGGGCCGCATGTGGCTGTTGCAAAA
CGCCTCGCCGCAAGGGGGGTAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACA

>NC11.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
```

-continued

Sequence Listing

GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAGATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTGCATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACCAGGTTCCACCGCAGCC
GCTGGTCATCTACCAGAAGATAACCAAAGAGCTGAACGACTACAGGGCCATCGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACATAA

>G11.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTCCACCGGAGAA
GCTGGTCATCTACGAGCAGATAACCCGCGACCTGAAGGACTACAAGGCCACCGGGCCGCATGTGGCTGTTGCAAAA
CGCCTCGCCGCAAGGGGGATAAAAATCCGGCCCGGAACGGTCATAAGCTACATCGTGCTCAAAGGCTCAGGAAGGA
TTGGGGACAGGGCTATACCCTCTGACGAATTTGACCCGGCAAAGCACAAGTACGATGCAGAATACTACATCGAGAA
CCAGGTTCTTCCAGCTGTGCAGAGCATTCTGGGGGCCTTTGGTTACCATAGAGGTGATTTAAAGTACCAGAAGAGC
CAACAGATGGGCTTGGGGGCGTGGCTAAAACCTAAGACATAA

>6G12.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGCGACGAAGAAGAAGTACGCGGTTATAGACGAGGAGGACAAGATAACGACGCGCGGGCTT
AAAATGGTTAGGCGTGACTGGAGCGAGATAGCGAAGGAGACGCAGGCGAGGGTTCTTGAGGCGATACTAAAGCACG

-continued

Sequence Listing

GTGACGTTGAAGAAGCGGTAAGGATTGTCAAAGAGGTTACGGAGAAGCTGAGCAAGTACGAGGTTCCACCGGAGCA
GCTGGTCATCTACCAGCCGATAACCAAACAGTTGCACGACTACAGGGCCAGGGGGCCGCATGTGTCTGTTGCAAAA
CGCCTCGCCGCAAGGGGGATAAAAATCCGGCCCGGAACGGTCATAAGCTACATCGTGCCCAAAGGCTCGGGAAGGA
TTGGGGACAGGGCTATACCCTTTGACGAATTTGACCCGGCAAAGCACAAGTACGATGCAGGATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACA

>E3.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAGATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGGAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACCAGGTTCCAACGAAGCA
GCTGGTCATCTACCAGGAGATAACCAAAGAGCTGCGGGACTACAAGGCCAGGGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAGGATTTAAGGTATCAGAAAACG
CGGCAGGTTGGCTTGGGGGCGTGGCTAAAACCTAAGACA

>E6.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAGATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACCGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTCCACCGGAGAA
GCTGGTCATCTACGAGCAGATAACCCGCGACCTGAAGGACTACAAGGCCACCGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACATAA

>H6.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA

-continued

Sequence Listing

GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAGATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACCAGGTTCCACCGCAGCA
GCTGGTCATCTACCAGCCGATAACCAAACACCTGAGGGACTACAAGGCCAAGGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACATAA

>B11.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAGATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCTGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTCCACCGGAGAA
GCTGGTCATCTACGAGCAGATAACCCGCGCCCTGAAGGACTACAAGGCCACCGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCAAGATGTGCAGAGGATTCTGAGGGCCTTTGGTTACAAAAATGGAGATTTAAGGTGCCAGAAGACA
ATCAGACGGGCTTGGGGGCGTGGCTAA

>B12.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG

-continued

Sequence Listing

GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAGATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTCCACCGGAGAA
GCTGGTCATCTACGAGCAGATAACCCGCGACCTGAAGGACTACAAGGCCACCGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCATATGTGCTAGATGATTCTGAGGGCCTTTGGTTACAATAA

>H12.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTCCACCGGAGAA
GCTGGTCATCTACGAGCAGATAACCCGCGACCTGAAGGACTACAAGGCCACCGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGCAGATGATTTTGAGGGCCTTTGGTTACCAAAAAGATGATTTAAGGTAG

>Wildtype_TgoT.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTCCACCGGAGAA
GCTGGTCATCTACGAGCAGATAACCCGCGACCTGAAGGACTACAAGGCCACCGGGCCGCATGTGGCTGTTGCAAAA -continued Sequence Listing CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACA >DNA_D4.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCCGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAGATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTCCAACGCAGCA
CCTGGTCATCCACCAGCAGATAACCAGAGCCCTGAACGACTACAAGGCCATCGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACA >protein_D4.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYPDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYEVPTQHLVIHQQITRALNDYKAIGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT >DNA_D4N3.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCCGGACTTCC
GCTCCCTGAACCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAGATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG -continued Sequence Listing GTGACGTTGAAGAAGCGGTAAGGATTGTCAAAGAGGTTACGGAGAAGCTGAGCAAGTACGAGGTTCCAACGCAGCA
CCTGGTCATCCACCAGCAGATAACCAGAGCCCTGAACGACTACAAGGCCATCGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACA >protein_D4N3.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYPDFRSLNPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYEVPTQHLVIHQQITRALNDYKAIGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT >DNA_D4S.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCCGGACTTCC
GCTCCCTGAGCCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAGATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTCCAACGCAGCA
CCTGGTCATCCACCAGCAGATAACCAGAGCCCTGAACGACTACAAGGCCATCGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACA >protein_D4S.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYPDFRSLSPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYEVPTQHLVIHQQITRALNDYKAIGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT >DNA_TNQ.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG -continued Sequence Listing GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTCCACCGGAGAA
GCTGGTCATCTACCAGCAGATAACCCGCGACCTGAAGGACTACAAGGCCACCGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACA >protein_TNQ.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL
EIVRRDWSEIAKETQARVLEAILKHGDVEEAVRIVKEVTEKLSKYEVPPEKLVIYQQITRDLKDYKATGPHVAVAK
RLAARGIKIRPGTVISYIVLKGSGRIGDRAIPFDEFDPAKHKYDAEYYIENQVLPAVERILRAFGYRKEDLRYQKT
RQVGLGAWLKPKT >DNA_TNK.fa -
ATGATCCTCGATACAGACTACATAACTGAGGATGGAAAGCCCGTCATCAGGATCTTCAAGAAGGAGAACGGCGAGT
TCAAAATAGACTACGACAGAAACTTTGAGCCATACATCTACGCGCTCTTGAAGGACGACTCTGCGATTGAGGACGT
CAAGAAGATAACTGCCGAGAGGCACGGCACTACCGTTAGGGTTGTCAGGGCCGAGAAAGTGAAGAAGAAGTTCCTA
GGCAGGCCGATAGAGGTCTGGAAGCTCTACTTCACTCACCCCCAGGACCAGCCCGCAATCAGGGACAAGATAAAGG
AGCATCCTGCCGTTGTGGACATCTACGAGTACGACATCCCCTTCGCGAAGCGCTACCTCATAGACAAAGGCTTAAT
CCCGATGGAGGGCGACGAGGAACTTAAGATGCTCGCCTTCGCGATCGCGACGCTCTATCACGAGGGCGAGGAGTTC
GCCGAAGGGCCTATCCTGATGATAAGCTACGCCGACGAGGAAGGGGCGCGCGTTATTACCTGGAAGAATATCGACC
TTCCCTATGTTGACGTCGTTTCCACCGAGAAGGAGATGATAAAGCGCTTCCTCAAGGTCGTCAAGGAAAAGGATCC
CGACGTCCTCATAACCTACAACGGCGACAACTTCGACTTCGCCTACCTCAAGAAGCGCTCCGAGAAGCTCGGAGTC
AAGTTCATCCTCGGAAGGGAAGGGAGCGAGCCGAAAATCCAGCGCATGGGCGATCGCTTTGCGGTGGAGGTCAAGG
GAAGGATTCACTTCGACCTCTACCCCGTCATTAGGAGAACGATTAACCTCCCCACTTACACCCTTGAGGCAGTATA
TGAAGCCATCTTTGGACAGCCGAAGGAGAAGGTCTACGCTGAGGAGATAGCGCAGGCCTGGGAAACGGGCGAGGGA
TTAGAAAGGGTGGCCCGCTACTCGATGGAGGACGCAAAGGTAACCTATGAACTCGGAAAAGAATTCTTCCCTATGG
AAGCCCAGCTCTCGCGCCTCGTAGGCCAGAGCCTCTGGGATGTATCTCGCTCGAGTACCGGAAACCTCGTCGAGTG
GTTTTTGCTGAGGAAGGCCTACGAGAGGAATGAACTTGCACCAAACAAGCCGGACGAGAGGGAGCTGGCAAGAAGA
AGGGAGAGCTACGCGGGTGGATACGTCAAGGAGCCCGAAAGGGGACTGTGGGAGAACATCGTGTATCTGGACTTCC
GCTCCCTGTATCCTTCGATAATAATCACCCATAACGTCTCCCCTGATACACTCAACAGGGAGGGTTGTGAGGAGTA
CGACGTGGCTCCTCAGGTAGGCCATAAGTTCTGCAAGGACTTCCCCGGCTTCATCCCAAGCCTCCTCGGTGACCTC
TTGGAGGAGAGACAGAAGGTAAAGAAGAAGATGAAGGCCACTATAGACCCAATCGAGAAGAAACTCCTCGATTACA
GGCAACGACTGATCAAAATCCTTGCTAATAGCTTCTACGGTTACTACGGCTATGCAAAGGCCCGCTGGTACTGCAA
GGAGTGCGCCGAGAGCGTTACCGCTTGGGGCAGGCAGTACATCGAGACTACGATAAGGGAAATAGAGGAGAAATTT
GGCTTTAAAGTCCTCTACGCGGACACAGATGGATTTTTCGCAACAATACCTGGAGCGGACGCCGAAACCGTCAAAA
AGAAGGCAAAGGAGTTCCTGGACTACATCAACGCCAAACTGCCCGGCCTGCTCGAACTCGAATACGAGGGCTTCTA
CAAGCGCGGCTTCTTCGTGACGAAGAAGAAGTACGCGGTTATAGACGAGGAGGACAAGATAACGACGCGCGGGCTT
GAAATAGTTAGGCGTGACTGGAGCGAGATAGCGAAGGAGACGCAGGCGAGGGTTCTTGAGGCGATACTAAAGCACG
GTGACGTTGAAGAAGCGGTAAGGATTGTCAAAGAGGTTACGGAGAAGCTGAGCAAGTACGAGGTTCCACCGGAGAA
GCTGGTCATCTACAAGCAGATAACCCGCGACCTGAAGGACTACAAGGCCACCGGGCCGCATGTGGCTGTTGCAAAA
CGCCTCGCCGCAAGGGGGATAAAAATCCGGCCCGGAACGGTCATAAGCTACATCGTGCTCAAAGGCTCGGGAAGGA
TTGGGGACAGGGCTATACCCTTTGACGAATTTGACCCGGCAAAGCACAAGTACGATGCAGAATACTACATCGAGAA
CCAGGTTCTTCCAGCTGTGGAGAGGATTCTGAGGGCCTTTGGTTACCGTAAAGAAGATTTAAGGTATCAGAAAACG
CGGCAGGTTGGCTTGGGGGCGTGGCTAAAACCTAAGACA >protein_TNK.fa -
MILDTDYITEDGKPVIRIFKKENGEFKIDYDRNFEPYIYALLKDDSAIEDVKKITAERHGTTVRVVRAEKVKKKFL
GRPIEVWKLYFTHPQDQPAIRDKIKEHPAVVDIYEYDIPFAKRYLIDKGLIPMEGDEELKMLAFAIATLYHEGEEF
AEGPILMISYADEEGARVITWKNIDLPYVDVVSTEKEMIKRFLKVVKEKDPDVLITYNGDNFDFAYLKKRSEKLGV
KFILGREGSEPKIQRMGDRFAVEVKGRIHFDLYPVIRRTINLPTYTLEAVYEAIFGQPKEKVYAEEIAQAWETGEG
LERVARYSMEDAKVTYELGKEFFPMEAQLSRLVGQSLWDVSRSSTGNLVEWFLLRKAYERNELAPNKPDERELARR
RESYAGGYVKEPERGLWENIVYLDFRSLYPSIIITHNVSPDTLNREGCEEYDVAPQVGHKFCKDFPGFIPSLLGDL
LEERQKVKKKMKATIDPIEKKLLDYRQRLIKILANSFYGYYGYAKARWYCKECAESVTAWGRQYIETTIREIEEKF
GFKVLYADTDGFFATIPGADAETVKKKAKEFLDYINAKLPGLLELEYEGFYKRGFFVTKKKYAVIDEEDKITTRGL -continued

| Sequence Listing |
|---|
| EIVRRDWSEIAKETQARVLEAILKHGDVEEAVRIVKEVTEKLSKYEVPPEKLVIYKQITRDLKDYKATGPHVAVAK RLAARGIKIRPGTVISYIVLKGSGRIGDRAIPFDEFDPAKHKYDAEYYIENQVLPAVERILRAFGYRKEDLRYQKT RQVGLGAWLKPKT |

The invention claimed is:

1. A recombinant nucleic acid polymerase capable of producing a non-DNA nucleotide polymer from a DNA nucleotide polymer template, said polymerase comprising amino acid sequence having at least 85% identity to the amino acid sequence of SEQ ID NO:1, wherein said amino acid sequence is mutated relative to the amino acid sequence of SEQ ID NO:1 at one or more residues of the thumb region, said residues selected from: amino acids 651 to 679; and wherein said amino acid sequence is mutated relative to the amino acid sequence of SEQ ID NO:1 at residue E664.

2. A nucleic acid polymerase according to claim 1 wherein said non-DNA nucleotide polymer is a RNA polymer; and wherein said amino acid sequence is mutated relative to the amino acid sequence of SEQ ID NO:1 at residue Y409.

3. A nucleic acid polymerase according to claim 2 wherein said polymerase comprises the mutations Y409G and E664K.

4. A nucleic acid polymerase according to claim 1 wherein said polymerase is capable of producing a HNA nucleotide polymer from a DNA nucleotide polymer template and said polymerase comprises amino acid sequence corresponding to amino acids 651 to 679 of SEQ ID NO:12.

5. A nucleic acid polymerase according to claim 4 wherein said polymerase is capable of producing a HNA nucleotide polymer from a DNA nucleotide polymer template and said polymerase comprises amino acid sequence corresponding to SEQ ID NO:12.

6. A system comprising:

(i) a recombinant nucleic acid polymerase capable of producing a HNA nucleotide polymer from a DNA nucleotide polymer template, said polymerase comprising amino acid sequence having at least 85% identity to the amino acid sequence of SEQ 1D NO:1, wherein said amino acid sequence is mutated relative to the amino acid sequence of SEQ 1D NO:1 at one or more residues of the thumb region, said residues selected from: amino acids 651 to 679;

wherein said amino acid sequence is mutated relative to the amino acid sequence of SEQ ID NO:1 at residue E664; and (ii) a recombinant nucleic acid polymerase capable of reverse transcribing a HNA nucleotide polymer into a DNA nucleotide polymer, said polymerase comprising amino acid sequence having at least 85% identity to the amino acid sequence of SEQ 1D NO:1, wherein said amino acid sequence is mutated relative to the amino acid sequence of SEQ 1D NO:1 at residue I521.

* * * * *